US008609348B2

(12) United States Patent
Biebl et al.

(10) Patent No.: US 8,609,348 B2
(45) Date of Patent: Dec. 17, 2013

(54) BACTERIOPHAGE ADHESION PROTEINS

(75) Inventors: Manfred Biebl, Regensburg (DE);
Renate Grassl, Regensburg (DE);
Monika Walter, Regensburg (DE);
Stefan Miller, Regensburg (DE)

(73) Assignee: Biomerieux S.A., Marcy l'Etoile (FR)

( * ) Notice: Subject to any disclaimer, the term of this patent is extended or adjusted under 35 U.S.C. 154(b) by 0 days.

(21) Appl. No.: 13/002,465

(22) PCT Filed: Jul. 3, 2009

(86) PCT No.: PCT/EP2009/058453
§ 371 (c)(1),
(2), (4) Date: Jan. 25, 2012

(87) PCT Pub. No.: WO2010/000854
PCT Pub. Date: Jan. 7, 2010

(65) Prior Publication Data
US 2012/0122124 A1     May 17, 2012

(30) Foreign Application Priority Data
Jul. 4, 2008  (EP) .................................... 08012152

(51) Int. Cl.
*G01N 33/53*  (2006.01)
*C12P 21/06*  (2006.01)
*C07K 1/00*   (2006.01)
*C07K 14/00*  (2006.01)
*C07K 17/00*  (2006.01)

(52) U.S. Cl.
USPC ............................ 435/7.1; 435/69.1; 530/350

(58) Field of Classification Search
None
See application file for complete search history.

(56) References Cited

U.S. PATENT DOCUMENTS

| 7,700,729 B2 * | 4/2010 | Scholl et al. ................... 530/350 |
| 2004/0121403 A1 | 6/2004 | Miller ............................. 435/7.1 |
| 2004/0197833 A1 | 10/2004 | Loessner ........................ 435/7.2 |
| 2004/0248298 A1 | 12/2004 | Schutz et al. ................. 435/383 |

FOREIGN PATENT DOCUMENTS

| WO | WO 01/09370 | 2/2001 |
| WO | WO 02/061117 | 8/2002 |
| WO | WO 03/000888 | 1/2003 |
| WO | WO 2008/121830 | 10/2008 |

OTHER PUBLICATIONS

Baxa et al., "Interactions of phage P22 tails with their cellular receptor, Salmonella O-antigen polysaccharide," *Biophysical Journal* 71(4): 2040-2048. Oct. 1996.

Danner et al., "Folding and assembly of phage P22 tailspike endorhamnosidase lacking the N-terminal, head-binding domain," *European Journal of Biochemistry* 215(3): 653-661. Aug. 1993.

PCT International Preliminary Report on Patentability issued in International application No. PCT/EP2009/058453 dated Jul. 8, 2010.

(Continued)

*Primary Examiner* — Oluwatosin Ogunbiyi
(74) *Attorney, Agent, or Firm* — Parker Highlander PLLC

(57) ABSTRACT

Bacteriophage adhesion proteins binding to the O-antigen of gram negative bacteria, but lacking the ability of binding to a bacteriophage and of hydrolysing lipopolysaccharides, are described, as well as nucleic acid molecules encoding the proteins. In addition, methods for generating the bacteriophage adhesion proteins and their use in detection, purification and enrichment of bacteria are described.

7 Claims, 18 Drawing Sheets

(56) References Cited

OTHER PUBLICATIONS

Figure 1:
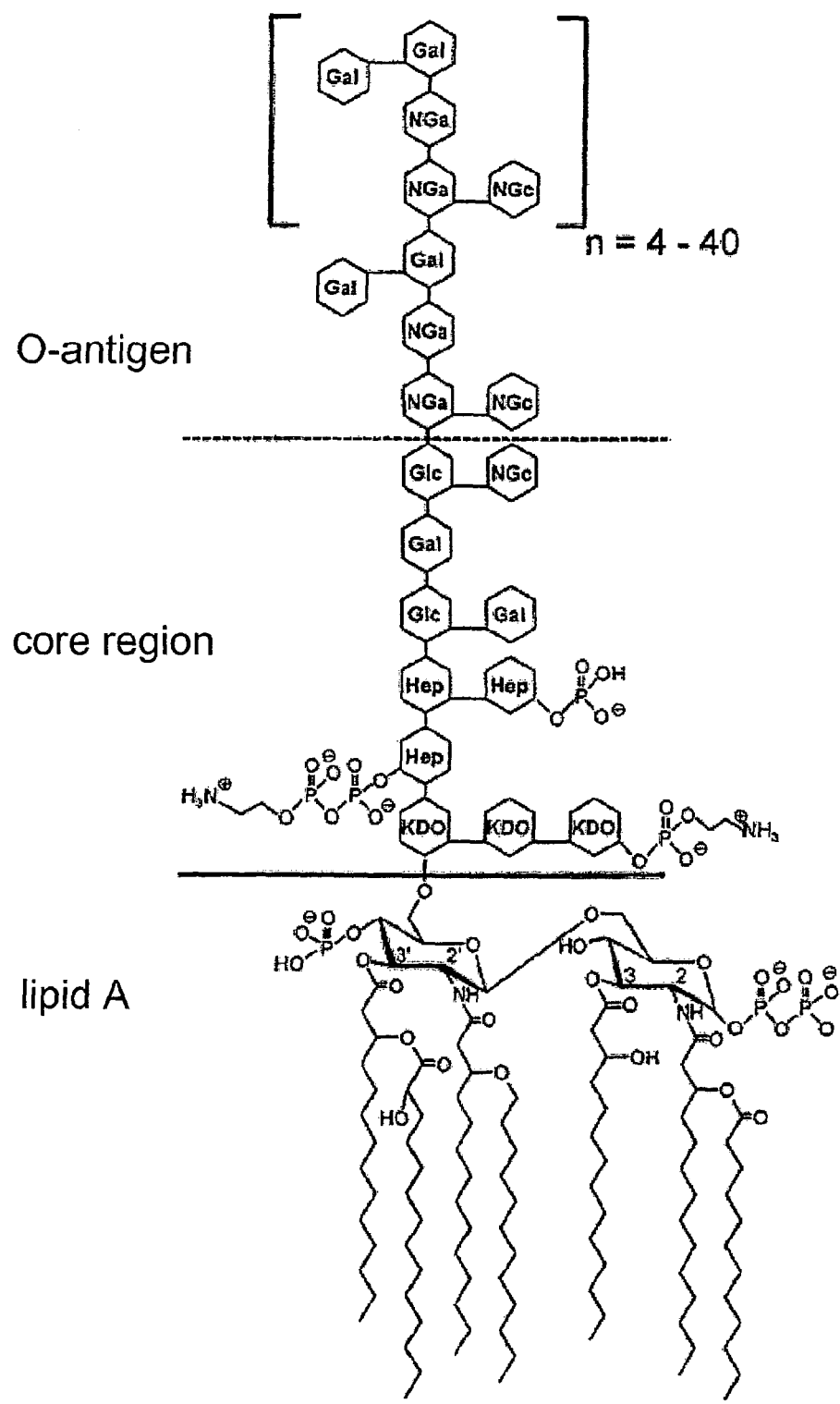

PCT International Search Report and Written Opinion issued in International application No. PCT/EP2009/058453 dated Mar. 2, 2010.

Samuel et al., "Relationships of the *Escherichia coli* O157, O111, and O55 O-Antigen Gene Clusters with Those of *Salmonella enterica* and *Citrobacter freundii*, Which Express Identical O Antigens," *J Bacteriology* 186(19): 6536-6543. Oct. 2004.

* cited by examiner

Fig. 2

```
P22-tailspike   MTDITANVVVSNPRPIFTE--SRSFKAVANGKIYIG---------QIDTDPVNPANQIPV 49
Det7-tailspike  MISQFNQPRGSTSIEVNKQSIARNFGVKEDEVVYFSSGIDLSGFKVIYDESTQRAYSLPS 60
                *  . :  *..  : .: :*.* .  . :*:.       *  ...: * ..:*

P22-tailspike   YIENEDGSHVQITCPLIINAAGKIVYNGQLVK---IVTVQG----------HSMAIYDA 95
Det7-tailspike  GIVSGTTAISLNEQAILTHSAGSVDLGELAVSREEYVTLPGSFNFGHIINVKNELLVHDD 120
                 *  .  :    *.::  ::**.:  .    *.   **: *         :. : ::*

P22-tailspike   N-------------GSQVDYIANV-----LKYDPDQYSIEADKKFKYSVKLSDYPTLQD 136
Det7-tailspike  KKYRWDGALPKVVPAGSTPASTGGVGLGAWVSVGDAAFRQEANKKFKYSVKLSDYSTLQD 180
                :             ** ..* :.. :     **:*************.****

P22-tailspike   AASAAVDGLLIDRDYNEYGGETVDFGGKVLTIECKAKFIGDGNLIFTKLGKGSRIAGVFM 196
Det7-tailspike  AVTDAVDGLLIDINYNFTDGESVDFGGKILTINCKAKFIGDGALIFNNMGPGSVINQPFM 240
                *.: ******** :*** .**:****** ***.********* :** *   **  **

P22-tailspike   ESTTTPWVIKPWTDDNQWLTDAAAVVATLKQSKTDGYQPTVSDYVKFPGIETLLPPNAKG 256
Det7-tailspike  ESKTTPWVIFPWDADGKWITDAALVAATLKQSKIEGYQPGVNDWVKFPGLEALLFQNVKD 300
                **.****** **  .:*:**** *.*******  :***.*::* :****:*:** *.*.

P22-tailspike   QNITSTLEIRECIGVEVHRASGLMACFLFRGCHFCKMVDANNPSGGKDGIITFENLSGDW 316
Det7-tailspike  QHIAATLDIRSASRVEIRNAGGLMAAYLFRSCHHCKVIDSDSIIGGKDGIITFENLSGDW 360
                *:*::**:**..:. **:. *****. ***.**.**::*::.  .**************

P22-tailspike   GKGNYVIGGRTSYGSVSSAQFLRNNGGFERDGGVIGFTSYRACESCVKTWQGTVGSTTSR 376
Det7-tailspike  GLGNYVIGGRVHYGSGSGVQFLRNNGGESHNGGVIGVTSWRAGESGFKTYQGSVGGGTAR 420
                * ********. ***.*..********.. .*****.** ***.** **.**.**..*:

P22-tailspike   NYNLQFRDSVVIYPVWDCFDLGADTDMNPELDRPGDYPITQYPLHQLPLNHLIDNLLVRG 436
Det7-tailspike  NYNLQFRDSVALSPVWDGFDLGSDPGMAPEPDRPGDLPVSEYPFHQLPNNHLVDNILVMN 480
                **********.: ****.****:*. *  * ***** *::.**:**** *** :** .

P22-tailspike   ALGVGFGMDGKGMYVSNITVEDCAGSGAYLLTHESVFTNIAIIDTNTKDFQANQIYISGA 496
Det7-tailspike  SLGVGLGMDGSGGYVSNVTVQDCAGAGMLAHTYNRVFSNITVIDCNYLNFDSDQIIIIGD 540
                :****:****.* ****:**:****:*  * * :.**:**::** * :.* :.:** *

P22-tailspike   CRVNGLRLIGIRSTDGQGLTIDAPNSTVSGITGMVDPSRINVANLAEEGLGNIRANSFGY 556
Det7-tailspike  CIVNGIRAAGIKPQPSNGLVISAPNSTISGLVGNVPPDKILVGNLLDPVLGQSRVIGFNS 600
                * ***:*  **:. *. :**.*****:**:.* *.*.:* *.**   .:** .. .*

P22-tailspike   DSAAIKLRIHKLSKTLDSGALYSHINGGAGSGSAYTQLTAISGSTPDAVSLKVNHKDCRG 616
Det7-tailspike  DTAELALRINKLSATLDSGALRSHLNGYAGSGSAWTELTALSGSTPNAVSLKVNRGDYKT 660
                *:* : ***:***.******* **:** ****** *:**:******:******:.* :

P22-tailspike   AEIPFVPDASDDFIKDSSCFLPYWENNSTSLKALVKKPNGELVRLTLATL 666
Det7-tailspike  TEIPISGTVLPDEGVLDINTMSLYLDAG--ALWALIRLPDGSKTRMKLSV- 708
                :***:     .*:  .*.. :  : .*  :* **:: *:*.  *:.*:.
```

Fig. 3

```
e15 tail fiber   ---------------MTVSTEVDHNDYTGNG------VTTSFPYTFRIFKKSDLVVQVVD  39
Det7_ORF790      MGYLQMTRNVESIFGAVVTAPHQIPYTYTATGGETFISLPFYPVTGFITINGGVQVPVDN  60
                                *  *  **.*       .:*  *   *   ::.:  *   *  :

e15 tail fiber   LNENITELILDTDYTVTGAGGYTCGDVVLSSPLAN----------GYQISISRELPVTQE  89
Det7_ORF790      YEIDGNTVNLGRALEADDVVYCLFDKILSPEDYENGIRIYKFQAVGNETTFTPDFTTYGV 120
                  :  :   :  . * .   ..:: ..   *         *  :  :: : ..

e15 tail fiber   TDLRNQGKFFAEVHENAFDKLTMLIQQVRSWLSLALRKPSFVANYYDALGNYIRNLRDPS 149
Det7_ORF790      QTLYIDGKFQVFGVDYNYNSATGVVSFLNGSPTAGVWVAEMSIKQNYLALSSDSGASLV  180
                   : :***  .   : ::. * ::. ..  :  : *   :     *.

e15 tail fiber   RPQDAATKNYVDNLSEGNNSYADNLFSRTLRVPEKINTLPSSLDRANKIPAFDSNGNAIV 209
Det7_ORF790      GTSSGNTVQEVLNSHSGSFQTGVKLLSSNDLIVDQSVIPNQLYRWDGAFPKTVAAGSSPA 240
                  .... *  :  :  .*.  .   :*:*    : :   *  * e15 tail fiber   IIPQSGSASDVLIELAKPS----GSGLVGFSHSNNYNPGMVGEKLQNVVYPTDAPFYAPT 265
Det7_ORF790      STGGVGNGSWVSVGDATLRGELNNEGVINFSHADTYGNDSVGAHLQNVVYPTDAPFNAAT 300
                  *:.* .*   *..* .   ..*::.:**.:*..   :.***********  *.* e15 tail fiber   DGTSDATTALQSAITHCEGKNAVLCINKSFSVSDSLSISSPLCVFAMNEQCGIVSSAPAG 325
Det7_ORF790      DGTTDTTVAIKSAIAHCISKGKKLVLNHLFMITDTLVISDGLHVECLTSDSGVKSDVPAG 360
                 ***:*:*.*:*:: *.: * : . * ::*:* :** .   .   :*.*  . *** e15 tail fiber   HAAVIFNGDNICWNGGFIRGLNQPSSSTIFQDGVLLNG--NDCVLDNVSINGFFAKGLHT 383
Det7_ORF790      KFAVKITGANSGWFGGKILGKNLPESTTVRQDGVLFDENAEYCFIIGTEVTGFFAKGLHT 420
                  :**  .*.* *.** * * * *..:*:*****:.:  . * : . ..:*********** e15 tail fiber   SNADGSGVGIRDYGTRNTISKCRVEYNKFGISLEGKDGWVLGNYVSNHYRMSSEAKPWDD 443
Det7_ORF790      SDADGVGYGIYDKGYGTLISKCYANS-KFCVALGGTEGRVLKNRITNNYLTSGEAKPWSW 479
                 *:***.* **:*  .:*.****  *  :*     :  *  ::* *   *.**** e15 tail fiber   TSNYWDGIVGGGEWLGVATGYLIDGNEFEDNGQSGIYAGGNGGIFAKNRITNNHIHGNWN 503
Det7_ORF790      ASNYWIGIVSEN------AHRYVIAFNDVSACGQSGIYFGGNGGYSTDNIIVNNTVYACWN 534
                 :*****.*::..       .*  :.* :.. .******.*****      .*.**   *:.**

e15 tail fiber   RGIDFGVVQR-LANSDVYENIITDNIVHNNRAANIWLAGVRDSIINNNNSWFTDDYRSME 562
Det7_ORF790      RGIDMGLFSEKSATNDVLRNIIKGNNSTYNNRENNIWLAGVSNCSVVGNTSWFDTNYDVIF 594
                 ****.*:..    * ***  ***..*. **** ***** .:*. ..::** * * *:

e15 tail fiber   AGNFDACVCLTLADGGEKAAPTGNQVNGNRCKTLESDDQISGFTLNITDTARGNQVRDNV 622
Det7_ORF790      AGYPGGHICISLASGANGEACVGNTIDSNTCIDPRGNAGITVPTGATGNVFGSG----NN 650
                 **    : .::. .*. *   **. .*. *  * .        **  ..      * e15 tail fiber   LSPIGEAYIPNPELYAVNNIDIPTEFAFTPQLIGGSG--VTLGNSSGKLTANGNVFSLSL 680
Det7_ORF790      LSQAGAIYIASPDLITSNREFLAVTGSFTFVLLPESGSITLSSSSTGVFRATGNRIDFSV 710
                 **   . ***.*:*: .* ::  *.*::*.:   .*.:: ..**  : * ***.:.:*:

e15 tail fiber   SISAQSVSSPSGSLTIGYIPGLSGTSVRHHNVRTEFYNNLNTTMQRAQPFYVNIGDSADQL 740
Det7_ORF790      TVNVSSISSPSGNLNIAYLPGMSGKTSSTSMFIIDYWNDLTLSSCVIPLASLNLENQDQI 770
                 ::...* ******.*.*. *.***.:. *  * : :      . :::*. :.    . **:

e15 tail fiber   RVYRLADGLSKDDLLEYFMSNSDLRMVGDIEIEPYNFSRSVTVVGESFCTSDVMSTELNR 800
Det7_ORF790      TVYRTDGGRVLYDFSSLMKSTSSFILKGFVDPN------------------------- 803
                  *** . *    *:  :*.*.*  :: * .* .  ::::

e15 tail fiber   LLGTDIYNFARGGASDVEVAMSQEAITRQYAPVGGSIPASGSVALTPTEVGIFWNGATGK 860
Det7_ORF790      ----------------------------------------------------------- e15 tail fiber   CIFGGIDGTFSTTLVNAGTGETQLVFTRDSAGSAVSVSTTATFAMRPYTRFNTNTIPAGR 920
Det7_ORF790      -----------------------------------------------------------
```

Fig. 3 (cont.)

```
e15 tail fiber    KHSLRRDDIYIVWGGRNSTDYTRYVSELHTMVANMHTQRFVICPEFPYDTETTGTTGATN 980
Det7_ORF790      ------------------------------------------------------------ e15 tail fiber    LAALNNNLKADFPDNYCQISGVDLLQNFKSKYNPAYAGDVTDIANGITPRSLREDNLHPS 1040
Det7_ORF790      ------------------------------------------------------------ e15 tail fiber    ETLQPNGLYIGAKVNADPIAQFIKSKGWGG 1070
Det7_ORF790      ------------------------------
```

Fig. 4

```
P22-tailspike     MTDITANVVVSNPRPIFTESRSFKAVANGKIYIGQIDTDPVNPANQIPVYIENEDGSHVQ  60
phage 14-tailspike MTDITANVVVSNPRPIFTESRSFKAVANGKIYIGKIDTDPVNPANQIPVYIENEDGSHVQ  60
                  *********************************:**************************

P22-tailspike     IAQPLIINAAGKIVYNGQLVKIVTVQGHSMAIYDANGSQVDYIANVLKYDPDQYSIEADK 120
phage 14-tailspike IAQPLIINSAGKIVYNGQLVKIVTVQGHSMAIYDAYGSQVDYIANVIKYDPDQFRQELAE 120
                  ********:*************************** ********* ***** *

P22-tailspike     KFKYSVKLSDYPTLQDAASAAVDGLLIDVDYHFYNGEKVDFGGKVLTIECKAKFIGDGNL 180
phage 14-tailspike --PDGSKKVGYKDSNVYDTLNKLELKFKSFQEMRDDNSNEIGDYALLTGWHTEHQGYGAG 178
                    . *  .*    :   *  :.   .: :..:. ::*. .*     :::. * *

P22-tailspike     IFTKLGKGSRIAGVFMESTTTPWVIKPWTDDNQWLTDAAAVVATLKQSKTDGYQPTVSDY 240
phage 14-tailspike VFQCVDKTGLTDDGGTIAVGSTYAWKRITG---------------PGDATEFGVVPNAG 222
                  :*   :.*  .    :.  :.:.  *  *.                 ..:  :  . .

P22-tailspike     VKFPGIETLLPPNAKGQNITSTLEIRECIGVEVHRASGLMAGFLFRGCHFCKMVDANNES 300
phage 14-tailspike SKFDNKAYILSAAATGALIFPAGDIYTTF--------------FTLTDTYLVRGNSTNIRE 269
                  **   : :*.. *.*  *  .: :*     :              * : . ::  ..:*  .

P22-tailspike     GGKDGIITFENLSGDWGKGNYVIGGRTSYGS-VSSAQFLRNNCGFERDGGVIGFTSYRAG 359
phage 14-tailspike IEAPNVTDFIVHCSRNGTWEGRIDGISWEGVNVYPVDEHRAFHTYFTTNGNMRDCRFRGG 329
                   .: *  ..  *.:    *.*.  : *  *  :..:   *         .*  :  :*.*

P22-tailspike     ESGVKTWQGTVGSTTSRNYNLQFRDSVVIYPVWDGFDLGADTDMNPELDRPGDYPITQYP 419
phage 14-tailspike ---VGSWFDGVSN-----------------WFIDSCEFSGSLGGENILNTPKVDPQGTIG 369
                      * :* . *..                  . *. ::... . : *: * *

P22-tailspike     LHQLPLNHLIDNLLVRGALGVGFGMDGKGMYVSNITVEDCAGSGAYLLTHESVFTNIAII 479
phage 14-tailspike TWVIFHKCFISRSACACARTIGLPS----VWFRDCIVYYNRDAGLLHYKDEDAYPNVEFG 425
                   :  :*..   **   :*:        ::.  :  *     .:*    .*...*: :

P22-tailspike     DTNTKDFQANQIYISGACRVNGLRLIGIRSTDCQGLTIDAPNSTVSGITGMVDPSRINVA 539
phage 14-tailspike VQKVTGCDIDSNDSSGVIMR---------------DVVYPDISNNWVSAGRVLNQAGVV 469
                  :... :  : .   **.            : *:   : . .. .:.        .: .*.

P22-tailspike     NLAEEGLGNIRANSFGYDSAAIKLRIHKLSKTLDSGALYSHINGGPGSGSAWTQLTAISG 599
phage 14-tailspike LIRCNDINVVENSAYFNGTHGISVEVCNFGTISNNNCSDNKNRG----------ISIQS 518
                  :  :.:.  :. .::   .:   :.*..: :  :   .  . :*           :*..

P22-tailspike     NTPDAVSLKVNHKDCRGAEIPFVPDIASDDFIKDSSCFLPYWENNS-TSLKALVKKPNGE 658
phage 14-tailspike DSGISSKLTVSGNTCCGTPLGSLPTAQEEGIHIEGDRIVSYGNVCAGNSSSQYINAASNK 578
                  ::   :.*.*. : * *:  *    :*  :* :. :..   :.* .  :  :  ...:

P22-tailspike     LVRLTLATL 667
phage 14-tailspike QEGLNITS- 586
                   *.:::
```

Fig. 5

```
e15 tail fiber   ---------------MTVSTEVDHNDYTGNG------VTTSFPYTFRIFKKSDLVVQVVD  39
Det7_ORF790      MGYLQMTRNVESIEGAVVTAPHQIPYTYTATGGETFISLPFYPVTGFITINGGVQVPVDN  60
                                *  *   *        *   * *       *   *  * * e15 tail fiber   LNENITELILDTDYTVTGAGGYTCGDVVLSSPLAN----------GYQISISRELPVTQE  89
Det7_ORF790      YEIDGNTVNLGRALEADDVVYCLFDKILSPEDYENGIRIYRFQAVGNETTFTPDFTTYGV 120
                  :  *     *         *           *        *  :  : :::

e15 tail fiber   TDLRNQGKFFAEVHENAFDKLTMLIQQVRSWLSLALRKPSFVANYYDALGNYIRNLRDPS 149
Det7_ORF790      QTLYIDGKFQVPGVDYNYNSATGVVSFLNGSPTAGVWVVAEMSIKQNYLALSSDSGASLV 180
                    *  **      :   ::  *  ::  :   :  :   ::    :   * e15 tail fiber   RPQDAATKNYVDNLSEGNNSYADNLFSRTLRVPEKINTLPSSLDRANKIPAFDSNGNAIV 209
Det7_ORF790      GTSSGNTVQEVLNSHSGSFQTGVKLLSSNDLIVDQSVIPNQLYRWDGAFPKTVAAGSSPA 240
                   :     *  *    :    :    :       ::           :

e15 tail fiber   IIPQSGSASDVLIELAKPS----GSGLVCFSHSNHYNPGMVGEKLQNVVYPTDAPFYAPT 265
Det7_ORF790      STGGVGNGSWVSVGDATLRGELNNEGVINFSHADTYGNDSVGAHLQNVVYPTDAPFNAAT 300
                   *  *     *   *         ::** ::*    *  *:**********:  * e15 tail fiber   DGTSDATTALQSAITHCEGKNAVLCINKSFSVSDSLSISSPLCVFAMNEQCGIVSSAPAG 325
Det7_ORF790      DGTTDTTVAIKSAIAHCISKGKRLVLNHLFMITDTLVISDGLHVECLTSDSGVKSDVPAG 360
                 ***:* *.  *   .  :   :  .*** * *                *** e15 tail fiber   KAAVIFNGDNICWNGGFIRGLNQPSSSTIRQDGVLLNG--NDCVLDNVSINGFFAKGLHT 383
Det7_ORF790      KFAVKITGANSGWFGGKILGKNLPESTTVRQDGVLFDENAEYCFITGTEVTGFFAKGLHT 420
                 : **  .     *.** : *:* *.::*:         .   :::.***** e15 tail fiber   SNADGSGVGIRDYGTRNTISKCRVEYNKFGISLEGKDGWVLGNYVSNRYRMSSEAKPWDD 443
Det7_ORF790      SDADGVGYGIYDKGYGTLISKCYANS-KFCVALGGTEGPVLKNRITNNYLTSGEAKPWSW 479
                 *:*** *.** *  * *****     ::*   :**   **.* ::* * :* ****.

e15 tail fiber   TSNYWDGIVGGGEWLGVATGYLIDGNEFEDNGQSGIYAGGNGGIFAKNRITNNHIHGNWN 503
Det7_ORF790      ASNYWDGIVSEN------AHRYVIAFNDVSACGQSGIYFGGNGGYSTDNIIVNNTVYACWN 534
                  ********:**      .   *   *    ****** **** . ***:**  .  **

e15 tail fiber   RGIDFGVVQR-LANSDVYENIITDNIVHNNRAANIWLAGVRDSIINNNNSWFTDDYRSMF 562
Det7_ORF790      RGIDMGLFSEKSATNDVLRNIIKGNNTYNNRENNIWLAGVSNCSVVGNTSWFDTNYDVIF 594
                 **  :      . :***   *  **  **.   :    ** :* ::* e15 tail fiber   AGNFDACVCLTLADCGEKAAFTGNQVNGNRCKTLESDDQISGFTLNITDTARGNQVRDNV 622
Det7_ORF790      AGYPGGHICISLASGANGEACVGNTIDSNTCIDPRGNAGITVPTGATGNVFGSG----NN 650
                 **     :* : *    :*.  ** ::.*** .  .    :  * :  .

e15 tail fiber   LSPIGEAYIFNFELYAVNNIDIPTEFAFTPQLIGGSG--VTLGNSSGKLTANGNVFSLSL 680
Det7_ORF790      LSQAGAIYIASFDLITSNRFELAVTGSFTPVLLPESGSITLSSSSTGVFRATGNRIDFSV 710
                 **  *  ** :*:*   *  ::  :  ***   *.  **.:.*.* ::.*** : :* e15 tail fiber   SISAQSVSSPSCSLTIGYIPGLSGTSVRHRNVRTEFYNNLNTTMQRAQPYVNIGDSADQL 740
Det7_ORF790      TVNVSSISSPSGNLNIAYLPGMSGKTSSTSMFIIDYWNDLTLSSGVIPLASLNLENQDQI 770
                   . *.:**** .* *.*:**:** :  .: :  :: *:*   :         :.**

e15 tail fiber   RVYRLADGLSKDDLLEYFMSNSDLRMVGDIKIEPYNFSRSVTVVGHSFCTSDVMSTELNR 800
Det7_ORF790      TVYRTDGCRVLYDFSSLMKSTSSFILKGFVDFN--------------------------- 803
                  ***  *  :  *    *.: *.:  :*. :::

e15 tail fiber   LLGTDIYNFARGGASDVEVAMSQEAITRQYAPVGGSIPASGSVALTPTEVGIFWNGATGK 860
Det7_ORF790      ------------------------------------------------------------ e15 tail fiber   CIFGCIDGTFSTTLVNAGTGETQLVFTRQSAGSAVSVSTTATFAMRPYTRFNTNTIPAGR 920
Det7_ORF790      ------------------------------------------------------------
```

Fig. 5 (cont.)

```
e15 tail fiber    KHSLHRDDIYIVWGGRNSTDYTRYVSELHTMVANMHTQRFVICPEFPYDTETTGTTGATN  980
Det7_ORF790       ------------------------------------------------------------ e15 tail fiber    LAALNNNLKADFPDNYCQISGVDLLQNFKSKYNPAYAGDVTDIAEGITPRSLREDNLHPS  1040
Det7_ORF790       ------------------------------------------------------------ e15 tail fiber    ETLQPNGLYIGAKVNADFIAQFIKSKGWGG  1070
Det7_ORF790       ------------------------------
```

Fig. 6

```
HK620 tailspike  MTDSINANVVVSMPSQLFTMARSFKAVANGKIYIGKIDTDPVNPENRIQVYVENEDGSHV 60
O111_BP1         -MTDITANVIVSMPSQLFTMARSFKAVANGKIYIGKIDTDPVNPENQIQVYVENEDGSHV 59
                  .*.***:*****************************************.**********

HK620 tailspike  PVSQPIIINAAGYPVYNGQIAKFVTVQGHSMAVYDAYGAQQFYFPNVLKYDPDQFRAIIE 120
O111_BP1         PVSQPIIINAAGYPVYNGQIAKFVTVQGHSMAVYDAYGAQQFYFPNVLKYDPDQLRQELA 119
                 ******************************************************:*  :

HK620 tailspike  SPEGAGHVGYQYRRNTGSTMRMVSDVLDERVSLW-DFHCDPSGNVIQPGPNVDSRQYLQA 179
O111_BP1         DPN-----GYLLIPSMDQHIKIQQWREEGDIRGWGAIDGEFNDAAVSAALDSESPSVKLG 174
                  .*:     **  .  . ...:::.   :  : *  :.:  ..  . :.... :  :*    .

HK620 tailspike  AIDYVSSNGGGTITIPAGYTWYLGSYGVGCIAGHSGIIQLRSNVNLNIFGRIHLSPFFDL 239
O111_BP1         GVGFVSKLR-SPINHKSNKVMHSGSLNFQFDGGTQ------QEKSGTLMANISNAKVIDV 227
                  .:.:**.   ..*. :. . :.  **  .. .*. :       .: . :...* : .:*:

HK620 tailspike  KPFQVFVGFDNGDPASSGNLENCHIYGHGVVDFGGYEFGASSQLRNGVAFG--RSYNCSV 297
O111_BP1         DITGTLDGGIRGYGGSNIVIDGVNVHDIGISMLSG-------ECGIGIWFGDYANYDVQT 280
                  .    ..: *   .*   .* .:  ::. :::.  *:   .*       *: **   .*: ..

HK620 tailspike  TGITFQNGDVTWAITLGWNGYGSNCYVRKCRFINLVNSSVNADHSTVYVNCPYSGVESCY 357
O111_BP1         DGLLIQNCNIKNIGGVGMQRGDGILVYNAKNFKVRENTIITTNRMGIAAGSDTRQFEIHG 340
                  *:  :**  ::.    :*  :     ..    .*      *:  :.::: :   ....      .*

HK620 tailspike  FSMSSSFARNIACSVELHQHDTFYRGSTVNGYCRGAYVVMHAAFAAGAGSYAYNMQVENN 417
O111_BP1         NYIGDTLLAGIDIEPDEGHTASNFKVYNNNIIGFAARYFIQGAGVG--QTFGIDTHANTS 398
                  :...::    .*    .:    :    : ::    .  *     .*    . .::.*  ..    ::. :  :..:..

HK620 tailspike  IAVIYGQFVILGSDVTATVSGHLNDVIVSGNIVSIGERAAFSAPFGAFIDIGPDNSGASN 477
O111_BP1         YGKVYKNILSAGQYGTEAFH-----IGNHADEIEITDNDLIGGAVVIPLFIKTYDGSGSK 453
                  . :* :::   *.   *  :.      :   .: :.*  :.   :.....  :  *  .  :...*:

HK620 tailspike  VQDIQRVLVTGNSFYAPANITDSAAITLRANLNGCTFIANNFDCRYMVYNAPGTTSPVVQ 537
O111_BP1         RIKINRNRAKG-TCKSFADVYMSEDVYISENVFSGNSSADSFFLRFSIISG----LNVDY 508
                  .*:*  ..:* ..* : :  *::  *   *  :  *:.  *:  .. *:. ..       *

HK620 tailspike  NLVWDKSNVIGGTHANQRAGQNLFDMQFASVVNSTIEVQLSCEDLSMFSCILFPASCQLS 597
O111_BP1         NRSSDTTNFIKAGDAGNTSNVKVTNNNISTLLDG--IDILTSGSLAGFIASGNTILCPAS 566
                  *   *.:*.*  . .*.: :. ::   :::::::.   *:. .*:  * .     *    *

HK620 tailspike  YSKITVDSAWTKSMSNTAVFEGNQQAGANVYVSYPATVNLTSYNTQGAVPFFSTDTNYAW 657
O111_BP1         NKGISLEVYGAGSISDLRLRGNIIYNATTKIYVSPAATGWDMLTTNTRFNLSGVQN---- 622
                  . *:::    : *:*:  :  .    .:..    **:..   .*: . : . ..::

HK620 tailspike  VTSAYSLSINENLDFSPPATYTNKANGQLVGVGYNEIGGVRSVSVRLMLQRQV 710
O111_BP1         GTQLFELSRNRVIQFLNNAWYDG----------------------------- 645
```

BACTERIOPHAGE ADHESION PROTEINS

This application is a national phase application under 35 U.S.C. §371 of International Patent Application No. PCT/EP 2009/058453 filed Jul. 3, 2009 claims priority to European Patent Application No. EP 08012152.8 filed Jul. 4, 2008. The entire text of each of the above-referenced disclosures are specifically incorporated herein by reference without disclaimer.

The present invention relates to bacteriophage adhesion proteins binding to the O-antigen of gram negative bacteria, lacking the ability of binding to a bacteriophage and of hydrolysing lipopolysaccharides. The invention further relates to nucleic acid molecules comprising a sequence encoding the proteins according to the present invention. In addition, the present invention relates to a method for generating bacteriophage adhesion proteins according to the present invention. The invention further relates to the use of said proteins and methods of detection, purification and enrichment of bacteria.

Bacteriophages are highly specific viruses that only infect bacteria. For infection bacteriophages use adhesion structures to bind to their bacterial hosts. The specificity of bacteriophages is defined over a line of their own proteins, which are important for the binding to the target cell. The phage-bacteria systems have evolved in nature over long periods of time so that the phages recognise their host bacteria in highly specific fashion and with a high level of binding affinity.

The specific binding of the bacteriophages to the bacteria is caused by bacteriophage adhesion proteins. The bacteriophage adhesion proteins specifically bind to a diverse group of receptors located on the surface of bacteria. These bacterial surface receptors can be components of the lipopolysaccharide, especially the O-antigen or the LPS core in gram negative bacteria as well as the K-antigen on the surface of gram negative bacteria which is a capsular polysaccharide, components of the peptidoglycan or teichoic or lipoteichoic acids in gram positive bacteria, membrane associated proteins of bacteria, special bacterial protrusions like flagella, pili or fimbria or extracellular components like capsules or slime layers, carbohydrates, polysaccharide matrices, surface protein layers or cell wall associated proteins. Some of the bacteriophage adhesion proteins are enzymatically active, e.g. O-antigen or K-antigen binding proteins, others are not, e.g. bacteriophage adhesion proteins binding to membrane associated bacterial proteins.

Lipopolysaccharide (LPS) is a part of the outer membrane of gram negative bacteria which is composed of lipid A, the core region, and the O-antigen. The O-antigen is the most surface exposed part of bacterial lipopolysaccharide which is composed of repetitive units of oligosaccharides, the lipid A is the region anchored within the outer membrane or gram negative bacteria. Compared to the lipid A and the core, the O-antigen is the most variable part in bacterial lipopolysaccharide. The huge variation in O-antigen structures (several hundred variants) provides one basis for bacteria detection down to the level of serogroups. Conventional bacterial detection uses antibodies to differentiate between closely related bacterial strains. For example, in the state of the art *Salmonella* has been classified by the use of different antisera into 46 serogroups with 67 different O-antigens (some serogroups are defined as a combination of more than one O-antigen). The *E. coli* database (ECODAB; Stenutz et al., 2006, FEMS Microbiol. Rev. 30, 382-403) lists 178 different O-antigens. The *E. coli* serotypes are conventionally identified on classical agglutinating methods using antisera against *E. coli*. Naturally occurring bacteriophages use different receptors on the bacterial surfaces for adsorption to the bacterial cell.

Bacteriophage adhesion proteins are composed of at least two functional domains, wherein the N-terminal domain binds to the bacteriophage and the C-terminal domain binds to a receptor on the bacterial surface. This C-terminal domain also comprises the active site, if the bacteriophage adhesion protein is enzymatically active, e.g. hydrolyzes bacterial O-antigen or K-antigen. However, as bacteriophage adhesion proteins are often composed of a modular arrangement of domains, a varying homology of the different functional parts is often observed.

After binding, the O-antigen binding bacteriophage adhesion proteins exhibiting a hydrolytic activity hydrolyse the O-antigen of the lipopolysaccharide. Said hydrolysis of the lipopolysaccaride is one part of the process of the polysaccharide layer's penetration during bacteriophage infection. Another process involved in bacteriophage infection is a so-called "surface walk". Said "surface walk" is performed by the infecting bacteriophage in order to find a site on the bacterial surface which is suitable for DNA injection. Both biological processes (polysaccharide penetration and "surface walk") comprise a repetitive binding and release of the bacteriophage. Consequently, the binding of said bacteriophage adhesion protein to the O-antigen on the bacterial surface is a reversible binding caused by the hydrolytic activity of said bacteriophage adhesion protein.

The high level of binding affinity qualifies bacteriophages adhesion proteins for the use as "biosorbents" for specific binding of bacteria even in complex environments as occur in nature but also in biological samples as e.g. in foodstuffs.

There are different applications for the use of bacteriophage adhesion proteins as biosorbents so far as e.g. the detection and identification of single bacterial strains or groups of bacteria or the purification of bacterial cells and cell components.

The rapid and exact detection of bacteria is the first essential step for the diagnosis and treatment of a bacterial infection in human and animals as well as to initiate preventive measures. Furthermore, the detection is useful to control hygienic and quality of raw materials and processed foodstuff and for monitoring the hygiene and quality aspect of drinking water and water for industrial uses and the water quality of public baths. Additionally, the detection is useful for process monitoring and optimization and for quality control in environmental analytics.

EP1198713A2 and EP1356080A1 describe methods for the detection and identification of single bacterial strains and groups of bacteria, in which whole bacteriophages or bacteriophage proteins are coupled to a support. After an incubation of the coupled bacteriophages or bacteriophage proteins with a test sample the bacteria of the sample bound to the bacteriophages or bacteriophage proteins can be detected.

Bacteriophage adhesion proteins offer a number of advantages over other biosorbents as e.g. antibodies for the detection and identification of bacteria, such as superior specificity and superior binding, when used in microbiological test systems. The higher specificity lowers the number of false-positives and false-negatives, whereas the better target binding gives a better signal to noise ratio. Furthermore, bacteriophage adhesion proteins can be immobilized on any surface and can easily be coupled to other molecules as e.g. fluorescent markers. Bacteriophage adhesion proteins have been proven to provide robust performance in many different applications, even when Challenged with the most demanding and complex food matrices.

In addition, the purification of bacterial cells and cell components is highly important for almost any further processing, analysis, or isolation of cell components. EP1399551A2 describes a method for the purification of bacterial cells and cell components, in which a sample containing bacterial cells or cell components is contacted with whole bacteriophages or bacteriophage proteins. Subsequently, said sample of bacterial cells or cell components and the bacteriophages or bacteriophage proteins are incubated with a solid support. After incubation the solid support can be separated from the sample and thereby the bacterial cells or cell components bound to the bacteriophages or bacteriophage proteins bound to the solid support as well.

The purification of bacterial cells and cell components by means of bacteriophages or bacteriophage proteins as described in EP1399551A2 offers amongst others the advantage that it can be automated and thus incorporated into an automated analysis or isolation method as e.g. plasmid purification.

However, there exist a binding equilibrium of naturally occurring bacteriophages or bacteriophage proteins and the bacteria due to the reversible binding of the bacteriophage adhesion proteins caused by its hydrolytic activity. This effect decreases the sensitivity of such phage-based bacteria assays.

The phage-based bacteria assays known in the art is that bacteriophage adhesion proteins are often very large proteins consisting of more than 1000 amino acids in the polypeptide chain, wherein said bacteriophage adhesion proteins are composed of several structural parts which confer different functions. The size and the several structural parts of said bacteriophage adhesion proteins make it difficult to express, purify, isolate and store said bacteriophage adhesion proteins. The modular domain arrangement of the bacteriophage adhesion proteins further bears the risk of proteolytic sensitivity in a way that the proteases digest the bacteriophage adhesion proteins between the different functional modules. Such a protease digestion causes a bacteriophage adhesion protein's property change coinciding e.g. with loss of activity of the protein.

Therefore, the object of the present invention is to provide bacteriophage adhesion proteins for the more efficient binding, enrichment, removing, capture and detection of gram-negative bacteria.

The object is solved by the subject matter as defined in the claims.

The following figures illustrate the present invention.

FIG. 1 shows a schematic representation of the chemical structure of LPS from *E. coli* O111:B4. The three parts representing the LPS, namely lipid A, core region, and O-antigen are marked. n=number of repeating units; Hep=L-glycero-D-manno-heptose; Gal=galactose; Glc=glucose; KDO=2-keto-3-desoxyoconic acid; NGa=N-acetyl-galactosamin; NGc=N-acetylglucosamin.

FIG. 2 shows an alignment of the ammo acid sequences of P22 tail spike and Det7 tail spike (SBP1). Identical amino acid residues are marked with an "*", amino acid residues closely related with respect to their side chains are marked with an ":" and less closely related amino acid residues with an ".". The part of the amino acid sequences showing high homology between both sequences is underlined. S152 of Det7 tail spike, which is the first amino acid residue of an N-terminally truncated variant, is printed in boldface, three amino acid residues involved in the active site are printed in bold face and italics.

FIG. 3 shows an alignment of the amino acid sequences of ∊15 tail fiber and Det7 ORF790 putative tail protein (SBP2). Identical amino acid residues are marked with an "*", amino acid residues closely related with respect to their side chains are marked with an ":" and less closely related amino acid residues with an ".". The part of the amino acid sequences showing high homology between both sequences is underlined. S252 of Det7 ORF790 putative tail protein, which is the first amino acid residue of an N-terminally truncated variant, is printed in boldface. D485 which is involved in the active site is printed in bold face and italics.

FIG. 4 shows an alignment of the amino acid sequences of P22 tail spike and phage 14 tail spike. Identical amino acid residues are marked with an "*", amino acid residues closely related with respect to their side chains are marked with an ":" and less closely related amino acid residues with an ".". The part of the amino acid sequences showing high homology between both sequences is underlined. K108 of phage 14 tail spike which is the first amino acid residue of an N-terminally truncated variant, is printed in boldface. E171, D433 and D435 which are acidic amino acid residues involved in inactivation are printed in bold face and italics.

FIG. 5 shows an alignment of the amino acid sequences of 615 tail fiber and O157_BP1. Identical amino acid residues are marked with an "*", amino acid residues closely related with respect to their side chains are marked with an ":" and less closely related amino acid residues with an ".". The part of the amino acid sequences showing high homology between both sequences is underlined. V163 of O157_BP1, which is the first amino acid residue of an N-terminally truncated variant, is printed in boldface. D463 which is involved in the active site is printed in bold face and italics.

FIG. 6 shows an alignment of the amino acid sequences of HK620 tail spike and O111_BP1. Identical amino acid residues are marked with an "*", amino acid residues closely related with respect to their side chains are marked with an ":" and less closely related amino acid residues with an ".". The part of the amino acid sequences showing high homology between both sequences is underlined. K108 of O111_BP1, which is the first amino acid residue of an N-terminally truncated variant, is printed in boldface. D204, D277, D302, D332, E337, D345, E354, E357, E415, D471, D476, D477, E482, and D492 which are relevant for inactivation of the enzyme, are printed in bold face and italics.

Figure 7:
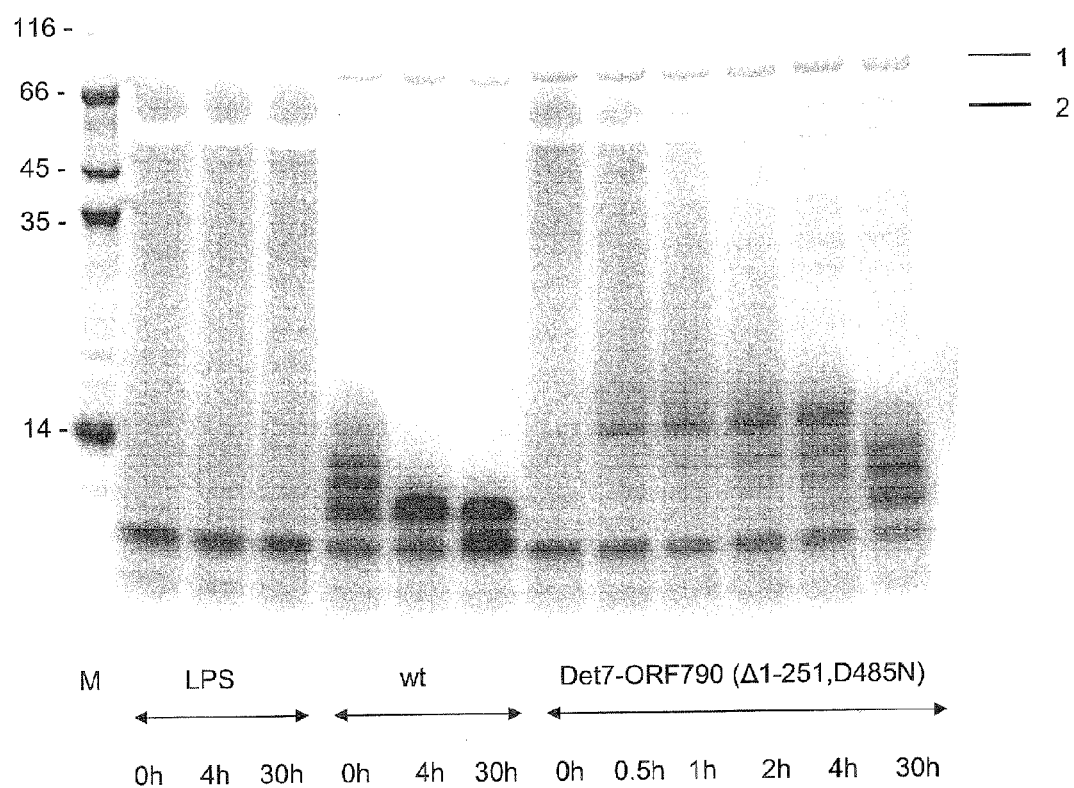

FIG. 7 depicts a silver-stained Tris-Tricin-gradient-gel showing the result of an LPS hydrolysis of *Salmonella* Lexington LPS by wt-Det7 ORF790 in comparison to the N-terminally truncated and inactivated variant Det7 ORF790 (Δ2-251, D485N). M is a polypeptide molecular weight marker, LPS means isolated lipopolysaccharide without addition of bacteriophage tail protein, wt means isolated lipopolysaccharide with addition of enzymatically active wild-type Det7 ORF790 tail spike, Det7 ORF790 (Δ2-251, D485N) means isolated lipopolysaccharide with addition of the N-terminally truncated variant bearing the inactivation mutation D485N. The respective incubation times in hours are indicated below. "1" marks the band of the bacteriophage adhesion protein, "2" marks the band of a proteinaceous impurity in the LPS-preparation.

Figure 8:
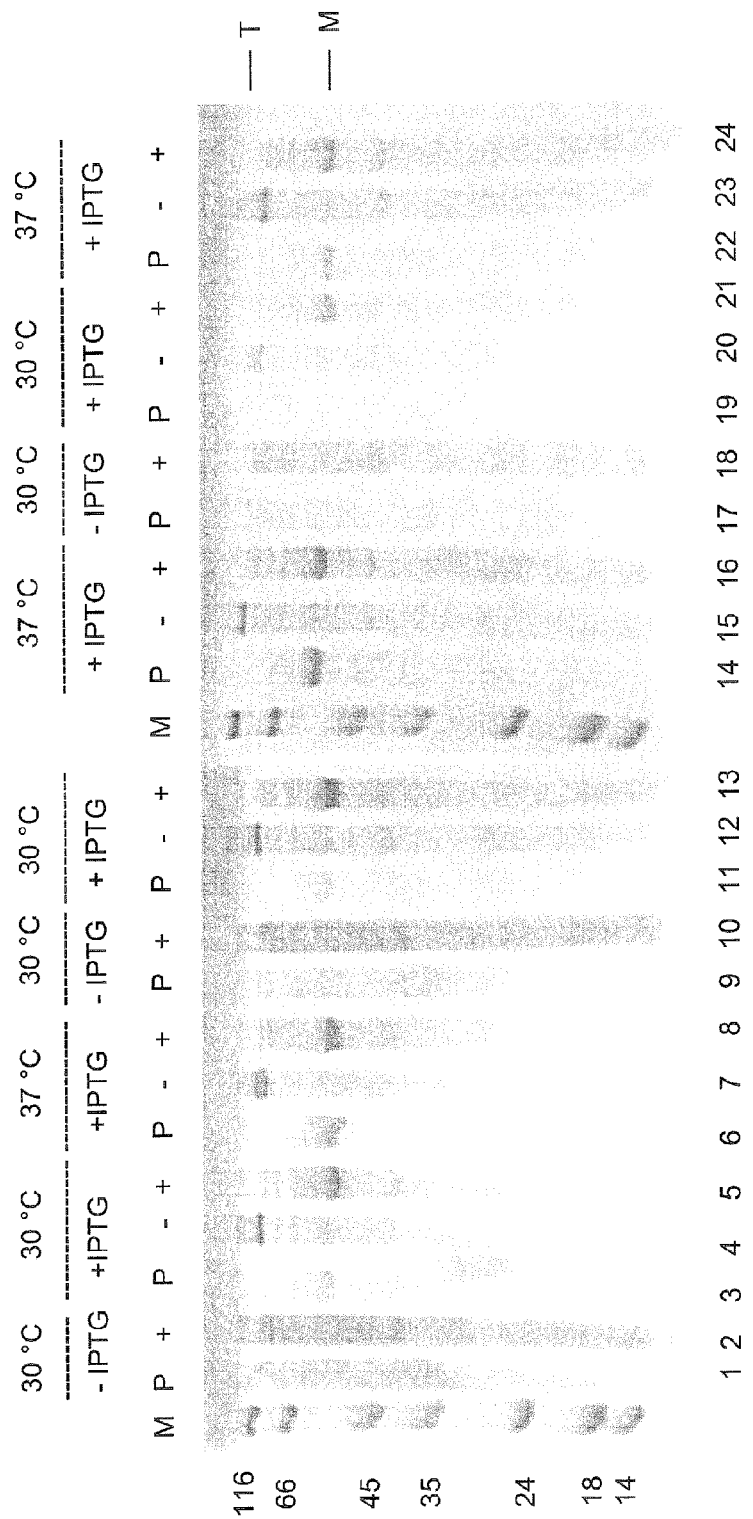

FIG. 8 depicts a Coomassie-stained SDS-gel showing three N-terminally truncated inactive mutants of Det7 tail spike SBP1 in a combined expression, solubility and SDS-stability test. "M" describes a lane with molecular weight markers, the sizes of which are indicated in the left margin. "P" describes the insoluble pellet fraction. "−" describes the part of the soluble protein fraction which was not boiled prior to sample application. "+" describes the part of the soluble protein fraction which was boiled prior to sample application. The expression temperatures of 30° C. or 37° C. are indicated above the gel as well as whether the samples were induced with IPTG (+IPTG) or not (−IPTG). The protein bands belonging to the monomer (−M) or SDS-resistant trimer (−T) are indicated in the right margin. Lanes 1 to 8 show the mutant SBP1(Δ2-151)E406Q, lanes 9 to 16 to SBP1(Δ2-151) D437N, and lanes 17 to 24 to SBP1(Δ2-151)D440N.

Figure 9:
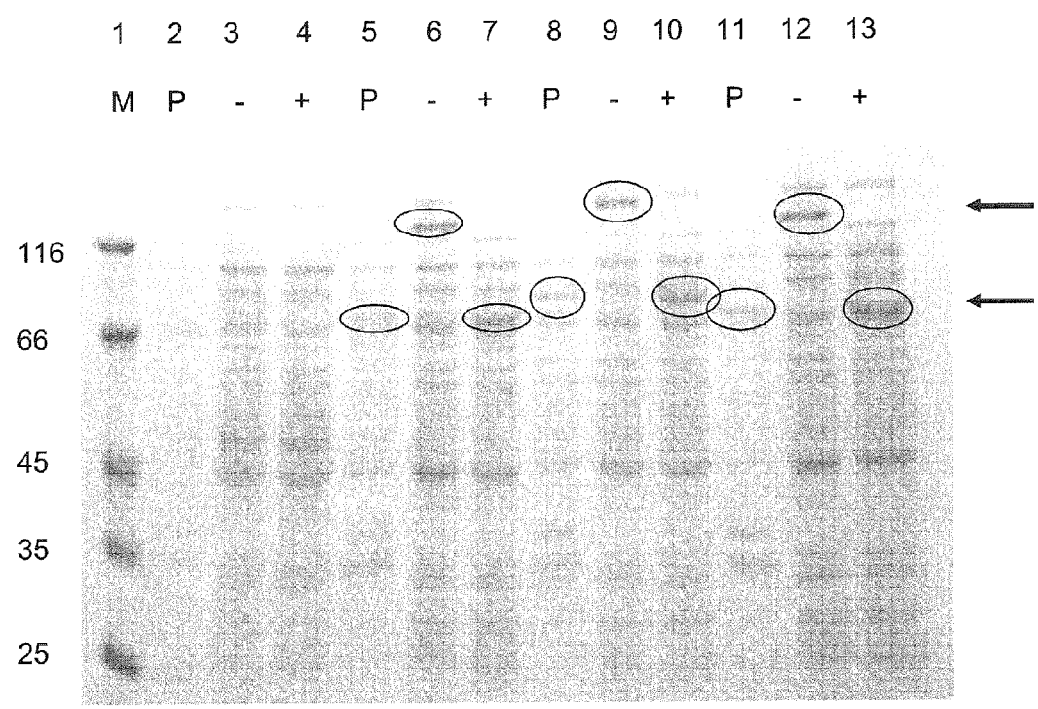

FIG. 9 depicts a Coomassie-stained SDS-gel showing truncated and inactivated forms of O157_BP1 fused to different N-terminal tags in a combined expression, solubility and SDS-stability test. "M" describes a lane with molecular weight markers, the sizes of which are indicated in the left margin. "P" describes the insoluble pellet fraction. "−" describes the part of the soluble protein fraction which was not boiled prior to sample application. "+" describes the part of the soluble protein fraction which was boiled prior to sample application. All proteins exhibit the truncation Δ2-162, and the amino acid mutation D463N. Lanes 2 to 4 show the background of E. coli proteins without induction, lanes 5 to 7 show O157BP1 with an N-terminal Strep-tag, lanes 8 to 10 O157_BP1 with an N-terminal JS-tag, and lanes 11 to 13 O157_BP1 with an N-terminal Cys-tag, all after induction with IPTG. The two arrows mark the position of the SDS-resistant oligomeric forms of the bacteriophage adhesion proteins (upper arrow), and the positions of the monomeric form (lower arrow).

Figure 10:
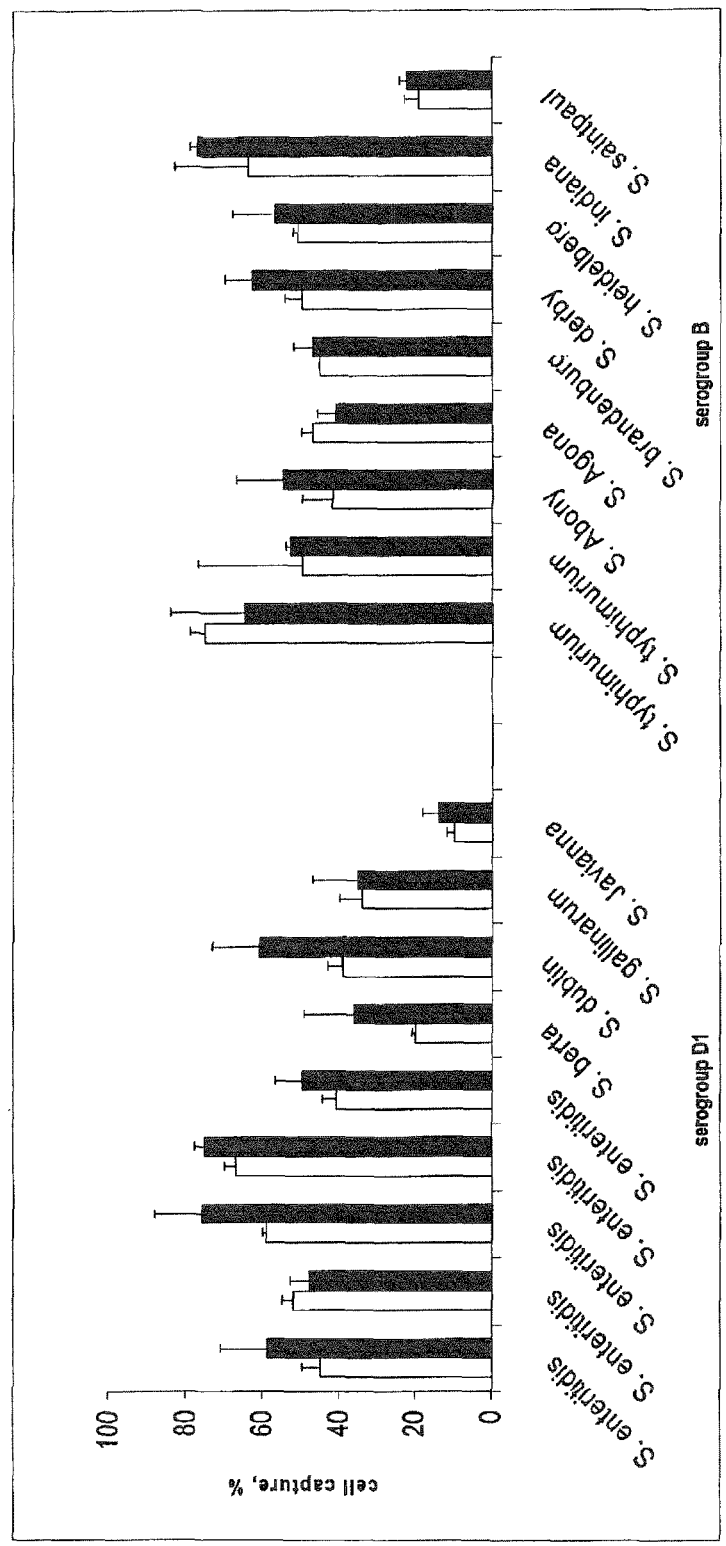

FIG. 10 is a schematic representation of the result of the specific capture of bacterial cells of Salmonella strains of the serogroups D1 and B using Det7 tail spike SBP1(Δ2-151; D437N). The bars indicate the percentage of cells captured from the sample using magnetic beads with epoxy-coupling of SBP1 (white bars) or tosyl-coupling of SBP1 (dark bars).

Figure 11:
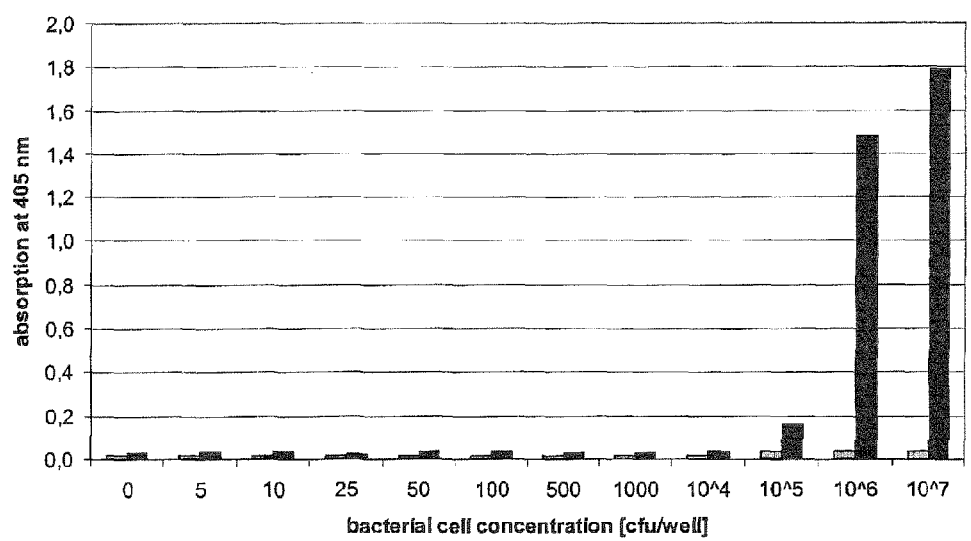

FIG. 11 is a schematic representation of the result of the detection of E. coli O157 cells in an assay analogous to an ELISA format using O157_BP1. Colorimetric detection (adsorption at 405 nm) of bacterial cells is plotted against the bacterial cell concentration in the sample (cfu per well of the microtiter plate). Color development after 90 min incubation is shown in samples with 1 μg O157_BP1 added as a specific bacteriophage adhesion protein (black bars) in reference to background absorption using microtiter plates without addition of O157_BP1 (grey bars).

Figure 12:
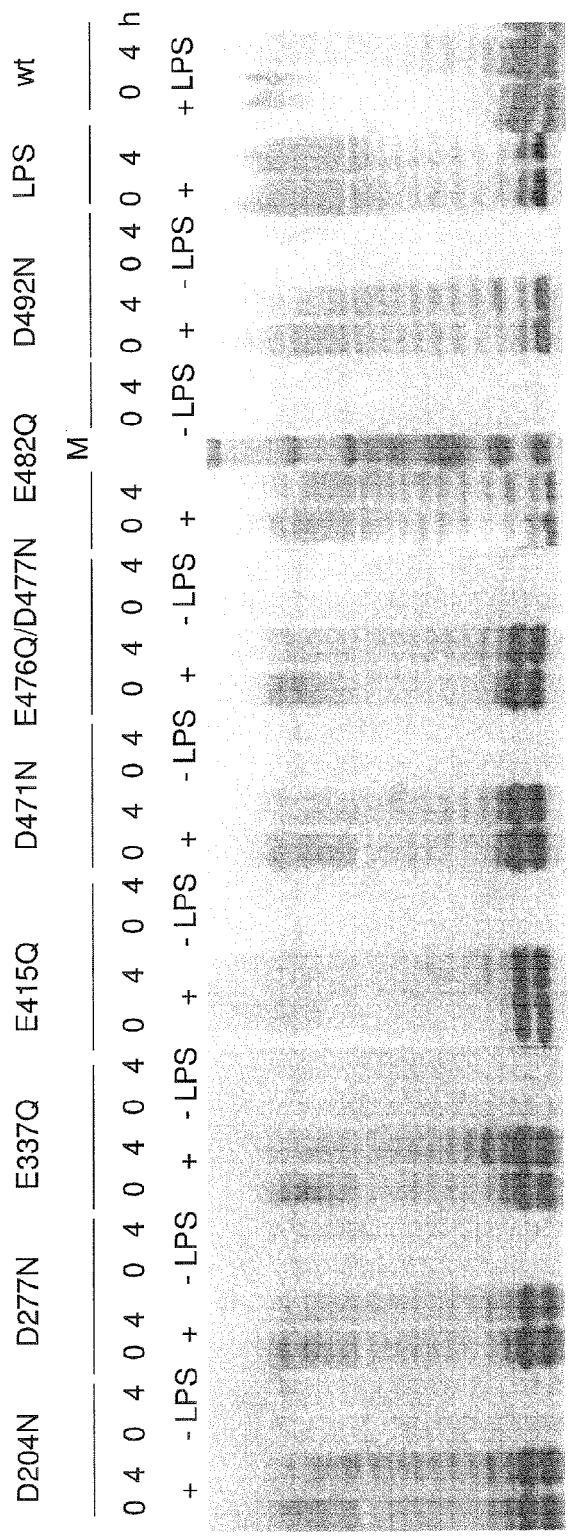

FIG. 12 depicts a silver-stained Tris-Tricin-gradient-gel showing the result of an LPS hydrolysis of E. coli O 111 LPS by wt-O111_BP1 in comparison to N-terminally truncated and inactivated variants of O111_BP1 (Δ2-107) comprising the mutations D204N or D277N or E337Q or E415Q or D471N or E482Q or D492N or the double mutation E476Q/ D477N. M is a polypeptide molecular weight marker, LPS means isolated lipopolysaccharide without addition of bacteriophage tail protein, wt means isolated lipopolysaccharide with addition of enzymatically active wild-type O111_BP1 "+LPS" means that isolated lipopolysaccharide and bacteriophage adhesion protein was present in the sample, "−LPS" means that only bacteriophage adhesion protein was present as a control. The respective incubation times in hours are also indicated.

Figure 13:
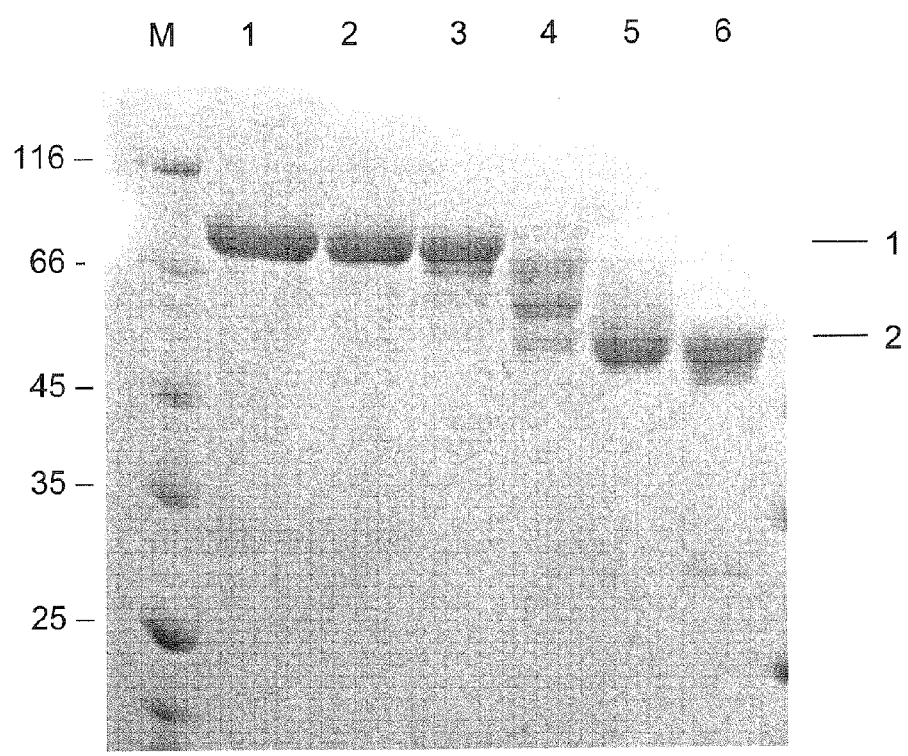

FIG. 13 depicts an SDS-polyacrylamide gel showing the result of a limited proteolysis of Det7 ORF790 (D485N) with proteinase K for 1 h at 37° C. "M" is a molecular weight marker. Lanes 1 to 6 belong to protease digests with proteinase K added in molar ratios of proteinase K to bacteriophage adhesion protein of $3\times10^{-5}$:1, $3\times10^{-4}$:1, $3\times10^{-2}$:1, 0.3:1 or 3:1. "−1" marks the position of the band of the full-length bacteriophage adhesion protein, "−2" marks the band of the N-terminally truncated variant generated by limited proteolysis which was determined by N-terminal sequencing to be Det7 ORF790 (Δ2-320; D485N).

Figure 14:
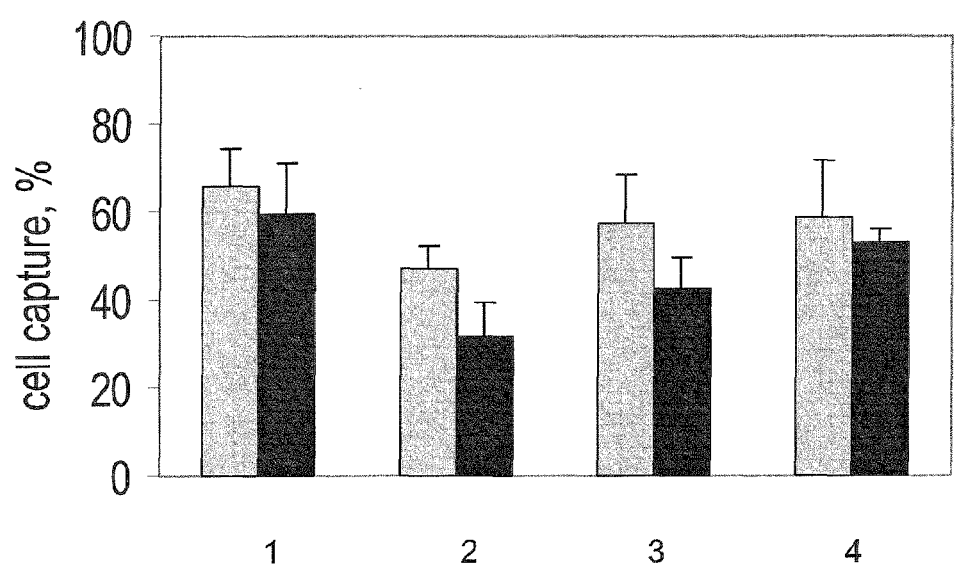

FIG. 14 is a schematic representation of the result of a comparison of capture efficiency of Salmonella cells using magnetic beads coated with bacteriophage adhesion protein or magnetic beads coated with antibodies. Depicted is the relative capture efficiency using Det7 tail spike SBP1 (Δ2- 151, D437N) (black bars) or using the antibody coated Dynabeads anti-Salmonella (grey bars). "1" marks Salmonella Typhimurium (serogroup B), "2" marks Salmonella Brandenburg (serogroup B), "3" marks Salmonella Heidelberg (serogroup B), and "4" marks Salmonella Enteritidis (serogroup $D_1$).

Figure 15:
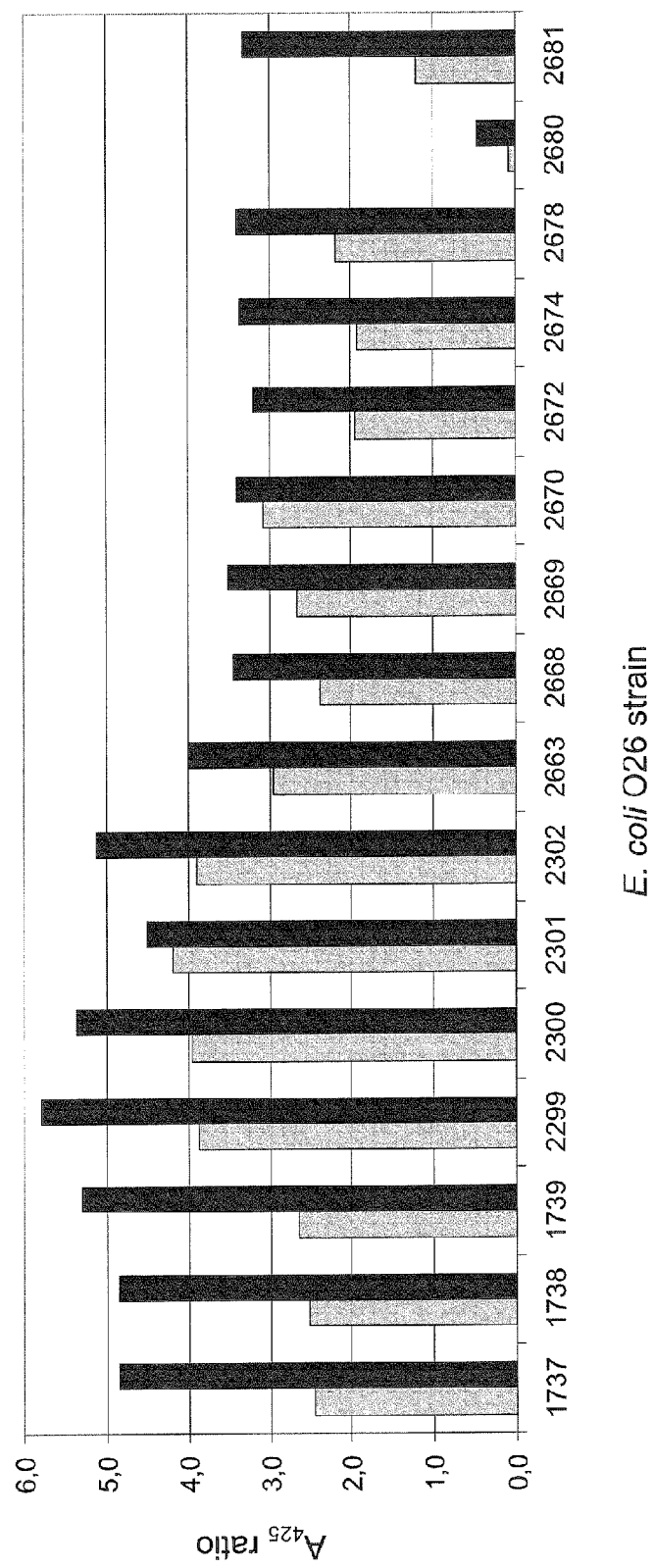

FIG. 15 is a schematic representation of the result of a colorimetric E. coli O26 detection assay using O111_BP1 wt and O111_BP1 (Δ2-107). This oNPG (ortho-nitrophenyl- βD-galactopyranoside)-test uses the E. coli own β-galactosidase activity for detection. Depicted is the signal ratio— measured as the absorption at 425 nm—of the signal resulting from cell capture using O111_BP1 coated magnetic beads divided by the signal resulting from cell capture using uncoated beads. Black bars stand for beads coated with O111_BP1 (Δ2-107), grey bars for beads coated with O111_BP1 wt. The numbers beneath the bars specify the strain numbers from the PROFOS culture collection for different E. coli O26 strains.

Figure 16:
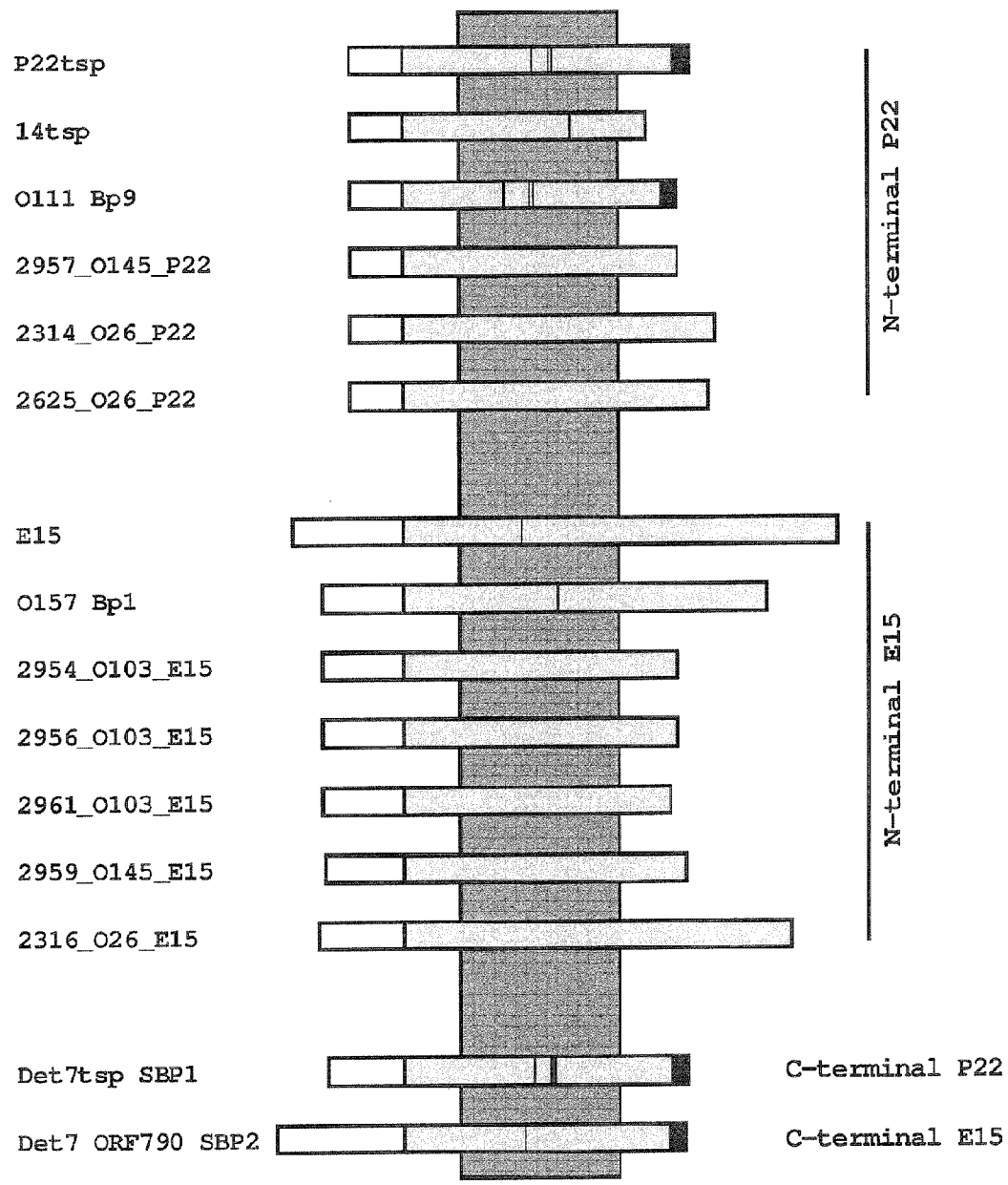

FIG. 16 shows an alignment of the various tail spike proteins related to groups P22, epsilon 15 and Det7. The white bars represent the homologous capsid binding domains which have been removed. The grey bars represent the LPS-binding domains (experimentally shown or predicted). The black bars are indicative for a trimerization domain. The black lines within the LPS-binding domains mark the mutated sites used to remove of the hydrolytic activity. Based on the homology and the location of the effective mutations in P22tsp, 14tsp, O111 Bp9, E15, O157 BP1, Det7tsp SBP1 and Det7 ORF790 SBP2 the area for mutations (dark grey area in the background) for the new family members O103, O26 and O145 is predicted.

The term "bacteriophage" or "phage" as used herein refers to viruses that can infect and multiply in a bacterium only.

The term "bacteriophage adhesion proteins" as used herein refers to bacteriophage proteins which specifically bind to bacterial surface receptors.

Bacteriophage adhesion proteins are composed of at least two functional domains, wherein one functional domain is the bacteriophage binding domain binding to the bacteriophage and the second domain binds to a bacterial surface receptor. Some of the bacteriophage adhesion proteins are enzymatically active, e.g. O-antigen or K-antigen binding proteins, others are not, e.g. bacteriophage adhesion proteins binding to membrane associated bacterial proteins. The enzymatic activity of bacteriophage adhesion proteins having an enzymatic activity is localized in the functional domain binding to a receptor on the bacterial surface. The enzymatic activity is preferentially a hydrolytic activity. Bacteriophage adhesion proteins include bacteriophage tail spikes, tail fibers (sometimes written in the literature tail fibres), tail pins and other tail proteins involved in binding to the bacterial surface. However, the term bacteriophage adhesion proteins does not include structural tail proteins not involved in bacterial binding e.g. tail sheath proteins, tail proteins in hinge regions, baseplate proteins, collar proteins.

The term "bacterial surface receptors" as used herein refers to components of the lipopolysaccharide, especially the O-antigen or the LPS core in gram negative bacteria, components of the peptidoglycan or teichoic or lipoteichoic acids in gram positive bacteria, membrane associated proteins of bacteria, special bacterial protrusions like flagella, pili or fimbria or extracellular components like capsules or slime layers, carbohydrates, polysaccharide matrices, surface protein layers or cell wall associated proteins. Some gram negative bacteria display also a K antigen on their surface which is a capsular polysaccharide, belongs to the term bacterial surface receptor also.

The term “O-antigen” as used herein refers to the somatic antigen on the cell surface of gram negative bacteria. The O-antigen is the most surface exposed part of the bacterial lipopolysaccharide. It is composed of repetitive units of oligosaccharides of different lengths with usually 2 to 7 sugar moieties per unit.

The term “wild-type” or “wt” as used herein refers to a naturally occurring form of a protein or nucleic acid which was not modified by human intervention. The term wild-type primarily refers to the polypeptide or nucleic acid sequence.

The term “bacteriophage binding domain” as used herein refers to the domain of a wild type bacteriophage adhesion protein, which is responsible for the binding of the bacteriophage adhesion protein to the bacteriophage.

The term “coliform” as used herein refers to a subgroup of the enterobacteria which are distinguished in that they utilise lactose and express the enzyme β-galactosidase, respectively.

The term “variants” as used herein refers to nucleotide or amino acid sequences which in relation to the wild type sequence exhibit modifications in the form of one or more deletions, substitutions, additions, inversions and/or chemical modifications of amino acids or nucleotides. For example the term “Δ2-107” in connection with a protein denotes a deletion of amino acids 2 to 107. Amino acid 108 of the original protein is the first amino acid of the protein variant after the obligatory methionine (start codon). In regard to substitutions and mutations, respectively, for example the term “D204N”, denotes an exchange of the original amino acid D at position 204 for an N at position 204 in the protein variant, wherein position 204 relates to the amino acid position in the wild type sequence unless otherwise stated.

The term “fragments” as used herein refers to parts of amino acid sequences and the nucleotide sequences coding for those amino acid sequence as long as they exhibit the biological function of the polypeptides according to the invention comprising amino acid sequences.

The term “specificity” as used herein refers to bacteriophage adhesion proteins recognising and binding only a single genus, species, or a sub-species, serotype or strain of bacterial cells or cell components.

The terms “capture”, “enrichment” or “purification” as used herein refers to specific separation of bacterial cells or cell components from aqueous solution, for example from the culture medium, in which the bacterial cells or cell components are located, or from environmental samples occurring in nature, or from biological samples as e.g. foodstuffs. The capture, purification or enrichment is carried out by means of solid supports, for example magnetic particles, glass particles, agarose particles, latex particles, reaction tubes, pipette tips, microtiter plates, membranes, filtration media, chromatographic media, or by centrifugation.

The term “bacterial cell components” as used herein refers to all components of a bacterium comprising bacterial lipopolysaccharides or bacterial O-antigen or fragments thereof as e.g. polysaccharides or oligosaccharides consisting of the repetitive units of the O-antigen.

The present invention refers to bacteriophage adhesion proteins binding specifically to the O-antigen of a gram negative bacterium, wherein the bacteriophage adhesion protein in comparison to its wild type form lacks the ability of binding to a bacteriophage and of hydrolysing lipopolysaccharides. Said bacteriophage adhesion protein may comprise a mutation and/or a deletion. Said deletion may comprise the bacteriophage binding domain and/or a mutation of acidic amino acids to non acidic amino acids, in particular a mutation of 1 to 7, 1 to 6, 1 to 5, 1 to 4, 1 to 3 or 1 to 2 acidic amino acids to non acidic amino acids and more particular of one acidic amino acids to a non acidic amino acid.

The present invention refers further to a bacteriophage adhesion protein comprising a marker moiety, preferably biotin or Streptavidin, or a tag, preferably a HA-tag, His-tag, Strep-tag, Avi-tag, Myc-tag, GST-tag, JS-tag or Cystein-tag. Preferably, the bacteriophage adhesion protein has an amino acid sequence according to SEQ ID NO:2, 4, 5, 7, 9, 11-14, 36-42, 56 or 58.

Bacteriophage Adhesion Proteins According to the Present Invention

Bacteriophage adhesion proteins according to the present invention preferably bind specifically to the O-antigen of a gram negative bacterium and in comparison to their wild type forms lack the ability of binding to a bacteriophage and exhibit a reduced ability of hydrolysing lipopolysaccharides.

Especially preferred are bacteriophage adhesion proteins binding specifically to gram negative bacteria of bacterial groups, families, genera or species comprising strains pathogenic for humans or animals like *Enterobacteriaceae* (*Escherichia*, especially *E. coli, Salmonella, Shigella, Citrobacter, Edwardsiella, Enterobacter, Hafnia, Klebsiella, Morganella, Proteus, Providencia, Serratia, Yersinia*), *Pseudomonadaceae* (*Pseudomonas, Burkholderia, Stenotrophomonas, Shewanella, Sphingomonas, Comamonas*), *Neisseria, Moraxella, Vibrio, Aeromonas, Brucella, Francisella, Bordetella, Legionella, Bartonella, Coxiella, Haemophilus, Pasteurella, Mannheimia, Actinobacillus, Gardnerella, Spirochaetaceae* (*Treponema* and *Borrelia*), *Leptospiraceae, Campylobacter, Helicobacter, Spirillum, Streptobacillus, Bacteroidaceae* (*Bacteroides, Fusobacterium, Prevotella, Porphyromonas*). Most preferred are bacteriophage adhesion proteins binding specifically to *E. coli* or *Salmonella*. Especially preferred are bacteriophage adhesion proteins binding specifically to *Salmonella* such as modified proteins of SEQ ID NO: 1, 3, 6 and 55. Preferred bacteriophage adhesion proteins binding specifically to *E. coli* are modified proteins of SEQ ID NO: 8, 10, 60, 62, 64, 66, 68, 70, 72 and 74.

Preferred are bacteriophage adhesion proteins deriving from wild type bacteriophage adhesion proteins of bacteriophages infecting the above mentioned gram negative bacteria, especially preferred from the bacteriophage groups of podoviridae, myoviridae and siphoviridae, more especially preferred are the bacteriophages related to P22, ϵ15, Sf6, HK620, T1, T5, T7, phage 14, gifsy, P2, phiV10, APSE-1, A1, A18a, ST104, ST64T, JK106 or Gifsy.

Further preferred are bacteriophage adhesion proteins deriving from wild type bacteriophage adhesion proteins of bacteriophages having an N-terminal homology, i.e. sequence identity in the N-terminal part of the amino acid sequence over an area of at least 50 consecutive amino acid residues of at least 30%, preferred 60%, more preferred 70%, 80%, 90%, 95%, 98% to the bacteriophage adhesion proteins of the phages P22, ϵ15, Sf6, HK620, T1, T7, phage 14, PhiV10, APSE-1, A1, A18a, ST104, ST64T, JK106, Det7, O157, O111 or Gifsy and an amino acid sequence identity of less than 30% to the respective bacteriophage adhesion proteins in the C-terminal part of the protein which is not involved in bacteriophage binding. Also preferred are bacteriophage adhesion proteins deriving from wild type bacteriophage adhesion proteins of bacteriophages having an C-terminal homology, i.e. sequence identity in the C-terminal part of the amino acid sequence over an area of at least 150 consecutive amino acid residues of at least 30%, preferred 60%, more preferred 70%, 80%, 90%, 95%, 98% to the bacteriophage adhesion proteins of the phages P22, ϵ15, Sf6, HK620, T1, T7, phage 14, PhiV10, APSE-1, A1, A18a, ST104, ST64T, JK106, Det7, O157, O111 or Gifsy and an amino acid sequence identity of less than 30% to the respective bacteriophage adhesion proteins in the N-terminal part of the protein which is involved in bacteriophage binding. Also preferred are bacteriophage adhesion proteins with a sequence identity of at least 30%, preferred 60% or more preferred 70%, 80%, 90%, 95%, 98% sequence identity over the complete amino acid sequence to the bacteriophage adhesion proteins of the phages P22, ϵ15, Sf6, HK620, T1, T7, phage 14, PhiV10, SPSE-1, A1, A18a, ST104, ST64T, JK106, Det7, O157, O111 or Gifsy.

In one embodiment of the present invention the bacteriophage adhesion proteins have a N-terminal homology as described above to the bacteriophage adhesion proteins of the phages P22 or ϵ15. Preferred are bacteriophage adhesion proteins having a N-terminal homology as described above to the wild type bacteriophage adhesion protein p22 tail spike according to SEQ ID NO: 53 or to the wild type bacteriophage adhesion protein ϵ15 side tail fiber according to SEQ ID NO: 55

Especially preferred are bacteriophage adhesion proteins deriving from a wild type bacteriophage adhesion protein as listed in Table 1.

age adhesion protein it is possible to reconstitute bacteriophage particles which lack the respective bacteriophage adhesion proteins with isolated bacteriophage adhesion proteins. Only bacteriophages reconstituted with bacteriophage adhesion proteins comprising functional bacteriophage binding domains build infectious phage particles, whereas bacteriophages reconstituted with bacteriophage adhesion proteins lacking the bacteriophage binding domain or with inactive bacteriophage binding domain build no infectious phage particles. A suitable assay using bacteriophage adhesion proteins under the control of suppressor tRNAs is described for P22 tail spike (Schwarz and Berget, 1989, J. Biol. Chem. 264 20112-20119, Schwarz and Berget, 1989, Genetics 121 635-649

Preferred is a truncation at the N-terminus or the C-terminus, especially preferred at the N-terminus. Further preferred is a truncation in the range of about 50 to about 400 amino acid residues, especially preferred is a truncation in the range of about 100 to about 350 amino acid residues. The exact length for the truncation depends on the bacteriophage binding domain in the respective bacteriophage adhesion protein.

One method to determine the length of the amino acid sequence to be truncated for the inactivation of the bacteriophage binding domain is to analyze the homology of the protein of interest to other bacteriophage adhesion proteins of which the sequences are known in the art. A suitable homology of the bacteriophage binding domain of a bacteriophage adhesion protein known in the art is a sequence identity of the amino acid sequence over an area of at least 50 consecutive amino acid residues of at least 30%, preferred about 60%,

TABLE 1

| Name | SEQ ID NO: (amino acid sequence) | SEQ ID NO: (nucleic acid sequence) | N-terminally homology as described above | Specifity |
|---|---|---|---|---|
| Det 7 tail spike SBP1 | 1 | | | Salmonella |
| Det7 ORF790 SBP2 | 3 | | | Salmonella |
| Phage 14 tail spike | 6 | | p22 tail spike | Salmonella |
| ϵ15 side tail fiber | 55 | 54 | | Salmonella |
| O157 BP1 | 8 | | ϵ15 side tail fiber | E. coli |
| EcoO111 tsp | 10 | 57 | p22 tail spike | E. coli |
| 2954_O103_E15 | 60 | 59 | ϵ15 side tail fiber | E. coli |
| 2956_O103_E15 | 62 | 61 | ϵ15 side tail fiber | E. coli |
| 2961_O103_E15 | 64 | 63 | ϵ15 side tail fiber | E. coli |
| 2959_O145_E15 | 66 | 65 | ϵ15 side tail fiber | E. coli |
| 2316_O26_E15 | 70 | 69 | ϵ15 side tail fiber | E. coli |
| 2314_O26_P22 | 72 | 71 | p22 tail spike | E. coli |
| 2625_O26_P22 | 74 | 73 | p22 tail spike | E. coli |

Truncation of the Bacteriophage Binding Domain

The bacteriophage adhesion proteins according to the present invention are preferably truncated in comparison to their wild type forms. In particular the bacteriophage adhesion proteins according to the present invention are N-terminally truncated. Preferably the amino acid residues responsible for the binding of the bacteriophage adhesion protein to the bacteriophage are truncated. Thus, a preferred bacteriophage adhesion protein lacks the bacteriophage binding domain. Another preferred bacteriophage adhesion protein lacks only a part of the bacteriophage binding domain, wherein the truncated part of the bacteriophage binding domain is responsible for the fact, that the bacteriophage adhesion protein according to the present invention is not able to bind to bacteriophages. Consequently, the bacteriophage binding domain of a bacteriophage adhesion protein according to the present invention is inactivated due to a truncation.

To determine, whether the bacteriophage binding domain has been inactivated by truncation of a wild type bacteriophage more preferred about 70%, 80%, 90%, 95%, 98%, preferably in the N-terminal part. Examples for bacteriophage adhesion proteins known in the art, which are suitable for a homology analysis are bacteriophage adhesion proteins of the phages P22, ϵ15, Sf6, HK620, T1, T7, phage 14, PhiV10, APSE-1, A1, A18a, ST104, ST64T, JK106, Det7, O157, O111 or Gifsy. For example, the sequence similarity can be investigated using the BLAST program (Basic Local Alignment Search Tool, Altschul et al., *Journal of Molecular Biology* 215, 403-410 (1990) at the NCBI with the blastp (protein-protein BLAST) algorithm using the BLOSUM62 scoring matrix.

Functional domains of proteins are coupled to each other by amino acid residues having no specific functions. Such amino acid sequences are called linker. To define the sequence for a truncation of a functional domain more precisely, it is possible to perform a linker prediction of the respective part of the sequence. The skilled artisan knows how to find and predict domain linker sequences as described e.g. in George and Heringa, 2003, Protein Eng. 15, 871-879 or Bae et al., 2005, Bioinformatics, 21, 2264-2270.

Another method to place a truncation according to the invention is a limited proteolysis of the bacteriophage adhesion proteins with subsequent sequencing of the respective more stable proteolysis products, preferably at the N-terminus. This is described for P22 tail spike in Danner et al., 1993, Eur. J. Biochem. 215, 653-661.

Preferred bacteriophage adhesion proteins according to the present invention are modified tail spike proteins of the wild type protein Det7 tail spike SBP1 (Det7 tail spike SBP1 (wild type); (SEQ ID NO:1)). The Det7 tail spike SBP1 (wild type) is a polypeptide of 708 amino acid residues length which is homolog to P22 tail spike in its C-terminal part whereas no homology is found in the N-terminal part. From an alignment of the two tail spike proteins it is evident that the C-terminal part showing high homology begins with amino acid residue E160 of Det7 tail spike. For N-terminal truncation, the maximal length for a truncation is therefore Δ2-159. The preferred bacteriophage adhesion protein Det7 tail spike SBP1 (Δ2-151, D437N) (SEQ ID NO:2) according to the present invention exhibits a truncation of the N-terminus from amino acid residue 2 to amino acid 151 (Δ2-151). Further bacteriophage adhesion proteins according to the present invention exhibit truncations from amino acid residue 2 to amino acid residues 138 up to 158 (Δ2-138 up to Δ2-158).

Further preferred bacteriophage adhesion proteins according to the present invention are modified proteins of the putative tail protein of ORF790 of Det7 phage (Det7 ORF790 SBP2 (wild type); SEQ ID NO:3). Det7 ORF790 SBP2 (wild type) is a polypeptide of 803 amino acid residues length which is homolog to the ε15 tail fiber in its C-terminal part whereas no homology is found in the N-terminal part. From an alignment of the two tail spike proteins it is evident that the C-terminal part showing high homology begins with amino acid residue N264 of Det7_ORF790 putative tail protein. The ε15 tail fiber additionally shows a C-terminal extension compared to the putative tail protein of Det7 ORF790 of around 300 amino acid residues. For N-terminal truncation, the maximal length for a truncation evident from a comparison of sequence homology is therefore Δ2-263. From limited proteolysis of Det7 ORF790 SBP2, however, an additional truncated, SDS-resistant and trimeric fragment beginning with amino acid residue G321 came up so that a deletion up to amino acid residue K320 is also possible. Preferred are bacteriophage adhesion proteins Det7 ORF790 (Δ2-251; D485N) (SEQ ID NO:4) and Det7 ORF790 (Δ2-320; D485N) (SEQ ID NO:5) exhibiting a truncation of the N-terminus from amino acid residue 2 to amino acid residue 251 (Δ2-251) or from amino acid residue 2 to amino acid residue 320 (Δ2-320). From linker prediction analysis additional preferred bacteriophage adhesion proteins according to the present invention exhibit truncations from amino acid residue 2 to amino acid residues 239 up to 262 (Δ2-239 up to Δ2-262).

Further preferred bacteriophage adhesion proteins according to the present invention are modified proteins of the phage 14 tail spike (phage 14 tail spike (wild type); SEQ ID NO:6). Phage 14 tail spike is a polypeptide of 586 amino acid residues length. Phage 14 tail spike specifically binds to *Salmonella* strains presenting O-antigen of serogroup C$_1$. The N-terminal part shows high homology to P22 tail spike whereas no homology is found in the C-terminal parts of the proteins. From an alignment of the two tail spike proteins it is evident that the N-terminal part showing high homology ends with amino acid residue R115 of phage 14 tail spike. For N-terminal truncation, the maximal length for a truncation is therefore Δ2-114. The preferred bacteriophage adhesion protein phage 14 tail spike (Δ2-107; D433N) (SEQ ID NO:7) according to the present invention exhibits a truncation of the N-terminus from amino acid residue 2 to amino acid residue 107 (Δ2-107).

Further preferred bacteriophage adhesion proteins according to the present invention are modified proteins of the O157 binding protein (O157_BP1 (wild type); SEQ ID NO:8). The O157 BP1 (wild type) is a polypeptide of 875 amino acid residues length which is homolog to the ε15 tail fiber in its N-terminal part whereas no homology is found in the C-terminal part. From an alignment of the two tail spike proteins it is evident that the N-terminal part showing high homology ends with amino acid residue A219 of O157_BP1. For N-terminal truncation, the maximal length for a truncation is therefore Δ2-219. The preferred bacteriophage adhesion protein O157 BP1 (Δ2-162; D463N) (SEQ ID NO:9) according to the present invention exhibits a truncation of the N-terminus from amino acid residue 2 to amino acid residue 162 (Δ2-162), which was found by linker prediction analysis. Further bacteriophage adhesion proteins according to the present invention exhibit truncation from amino acid residue 2 to amino acid residues 149 up to 191 (Δ2-149 up to Δ2-191).

Further preferred bacteriophage adhesion proteins according to the present invention are modified proteins of the O111 binding protein (O111_BP1 (wild type), SEQ ID NO:10). The O111 BP1 (wild type) is a polypeptide of 645 amino acid residues length which is homolog to the HK620 tail spike in its N-terminal part whereas no homology is found in the C-terminal part. From an alignment of the two tail spike proteins it is evident that the N-terminal part showing high homology ends with amino acid residue R115 of O111_BP1. For N-terminal truncation, the maximal length for a truncation is therefore Δ2-115. The preferred bacteriophage adhesion proteins O111 BP1 (Δ2-107; D204N) (SEQ ID NO:11) or O111 BP1 (Δ2-107; D277N) (SEQ ID NO:12) according to the present invention exhibit a truncation of the N-terminus from amino acid residue 2 to amino acid residue 107 (Δ2-107). Further bacteriophage adhesion proteins according to the present invention exhibit truncations from amino acid residue 2 to amino acid residues 70 up to 114 (Δ2-69 up to Δ2-114).

Further preferred bacteriophage adhesion proteins according to the present invention are modified proteins of the ε15 side tail fiber according to SEQ ID NO: 53. The ε15 side tail fiber (wild type) is a polypeptide of 1070 amino acid residues length. The preferred bacteriophage adhesion protein ΔN ε15 side tail fiber (Δ2-220; D449N) (SEQ ID NO:56) according to the present invention exhibits a truncation of the N-terminus from amino acid residue 2 to amino acid residue 220 (Δ2-107).

Further preferred bacteriophage adhesion proteins according to the present invention are modified proteins of the 2954_O103_E15 according to SEQ ID NO: 60. The 2954_O103_E15 (wild type) is a polypeptide of 697 amino acid residues length which is homolog to the ε15 side tail fiber in its N-terminal part. Preferably a modified protein of the 2954_O103_E15 according to the present invention exhibits a truncation of the N-terminus from amino acid residue 2 to amino acid residue 161 (Δ2-161).

Further preferred bacteriophage adhesion proteins according to the present invention are modified proteins of the 2956_O103_E15 according to SEQ ID NO: 62. The 2956_O103_E15 (wild type) is a polypeptide of 697 amino acid residues length which is homolog to the ε15 side tail fiber in its N-terminal part. Preferably a modified protein of the 2956_O103_E15 according to the present invention exhibits a truncation of the N-terminus from amino acid residue 2 to amino acid residue 161 (Δ2-161).

Further preferred bacteriophage adhesion proteins according to the present invention are modified proteins of the 2961_O103_E15 according to SEQ ID NO: 64. The 2961_O103_E15 (wild type) is a polypeptide of 684 amino acid residues length which is homolog to the ε15 side tail fiber in its N-terminal part. Preferably a modified protein of the 2961_O103_E15 according to the present invention exhibits a truncation of the N-terminus from amino acid residue 2 to amino acid residue 161 (Δ2-161).

Further preferred bacteriophage adhesion proteins according to the present invention are modified proteins of the 2959_O145_E15 according to SEQ ID NO: 66. The 2959_O145_E15 (wild type) is a polypeptide of 711 amino acid residues length which is homolog to the ε15 side tail fiber in its N-terminal part. Preferably a modified protein of the 2959_O145_E15 according to the present invention exhibits a truncation of the N-terminus from amino acid residue 2 to amino acid residue 156 (Δ2-156).

Further preferred bacteriophage adhesion proteins according to the present invention are modified proteins of the NS2957_O145_P22. The amino acid sequence of the NS2957_O145_P22 according to SEQ ID NO: 68 depicts the amino acid sequence of the already truncated wild type bacteriophage adhesion protein. The amino acid sequence according to SEQ ID NO:68 was obtained by truncating the N-terminus from amino acid residue 2 to amino acid residue 107 (Δ2-107). The respective full length wild type protein is homolog to the p22 tail spike in its N-terminal part.

Further preferred bacteriophage adhesion proteins according to the present invention are modified proteins of the 2316_O026_E15 according to SEQ ID NO: 70. The 2316_O026_E15 (wild type) is a polypeptide of 873 amino acid residues length which is homolog to the ε15 side tail fiber in its N-terminal part. Preferably a modified protein of the 2316_O026_E15 according to the present invention exhibits a truncation of the N-terminus from amino acid residue 2 to amino acid residue 169 (Δ2-169).

Further preferred bacteriophage adhesion proteins according to the present invention are modified proteins of the 2314_O026_P22 according to SEQ ID NO: 72. The 2314_O026_P22 (wild type) is a polypeptide of 718 amino acid residues length which is homolog to the p22 tail spike in its N-terminal part. Preferably a modified protein of the 2314_O026_P22 according to the present invention exhibits a truncation of the N-terminus from amino acid residue 2 to amino acid residue 107 (Δ2-107).

Further preferred bacteriophage adhesion proteins according to the present invention are modified proteins of the 2625_O026_P22 according to SEQ ID NO: 74. The 2625_O026_P22 (wild type) is a polypeptide of 707 amino acid residues length which is homolog to the p22 tail spike in its N-terminal part. Preferably a modified protein of the 2625_O026_P22 according to the present invention exhibits a truncation of the N-terminus from amino acid residue 2 to amino acid residue 107 (Δ2-107).

It turned out that bacteriophage adhesion proteins lacking the bacteriophage binding domain exhibit higher expression rate, a higher purification grade and can be stored for a longer period. Furthermore, the truncation of the bacteriophage binding domain provides the possibility to generate bacteriophage adhesion proteins, which can not be recombinantly expressed in their wild type form. For example the Det7 ORF790(Δ2-251; D485Q) (SEQ ID NO:4) lacking the bacteriophage binding domain can be expressed, whereas the respective full length wild type bacteriophage adhesion protein can not be expressed recombinantly.

Additionally, it turned out that the truncation of the bacteriophage binding domain induces an improved binding of the bacteriophage adhesion protein to the respective bacteria, as e.g. the Det7 ORF790(Δ2-251; D485Q) (SEQ ID NO:4) compared to Det7 ORF790(full length; D485Q) or the O111_BP1 (Δ2-107; D204N) (SEQ ID NO:11) compared to O111 BP1 (wild type), SEQ ID NO:10).

Further, it turned out that a truncation of the bacteriophage binding domain of the bacteriophage adhesion proteins according to the present invention has a positive effect on the stability and/or solubility of the respective bacteriophage adhesion proteins. Thus, bacteriophage adhesion proteins according to the present invention have a greater degree of long term stability. Additionally, their ability to aggregate is reduced. Since the aggregation of bacteriophage adhesion proteins known in the art decreases the active amount of bacteriophage adhesion proteins in technical applications, bacteriophage adhesion proteins according to the invention are more effective in technical applications.

Reduced Ability of Hydrolysing Lipopolysaccharides

Bacteriophage adhesion proteins according to the present invention exhibit a reduced preferably ability of inactivated hydrolysing lipopolysaccharides. Preferably, bacteriophage adhesion proteins exhibit a mutation. Said mutation is preferably a mutation of an acidic amino acid residue belonging to the active site of the wild type bacteriophage adhesion protein. Preferably, a bacteriophage adhesion protein according to the present invention comprises in comparison to its wild type form a mutation of 1 to 7 acidic amino acid residues (aspartic acid (D) or glutamic acid (E)) to non acidic amino acid residues, in particular a mutation of 1 to 6, 1 to 5, 1 to 4, 1 to 3 or 1 to 2 acidic amino acid residues to non acidic amino acid residues. Most preferred is a mutation of one acidic amino acid residue to a non acidic amino acid residue. The non acidic amino acid residues are preferably asparagine (N), alanine (A) or glutamine (Q). Especially preferred are mutations of aspartic acid (D) to asparagine (N) or alanine (A) and/or a mutation of glutamic acid (E) to glutamine (Q) or alanine (A).

The ability of hydrolysing lipopolysaccharides of a bacteriophage adhesion protein can be determined by an assay which shows the degradation of the respective LPS-variant which carries the O-antigen variant bound by the specific bacteriophage adhesion protein (LPS hydrolysis assay). Degradation of the LPS can be observed on silver stained SDS-gels where complete LPS molecules and fragments produced after hydrolysis of the O-antigen by an enzymatically active bacteriophage adhesion protein migrate with different mobility. A further assay is the quantification of reducing ends which arise from hydrolysis of the poly- and oligosaccharides by the bacteriophage adhesion proteins using the chromogenic substrate 3,5-dinitrosalicylic acid (Danner et al., 1993, Eur. J. Biochem. 215, 653-661). A further possibility to determine the enzymatic activity of O-antigen binding bacteriophage adhesion proteins is the quantification of fluorescently labelled oligosaccharides after analysis of substrate oligosaccharides and reaction products using reversed phase HPLC before and after enzymatic hydrolysis (Baxa et al. 1996, Biophysical Journal, 71, 2040-2048), The ability of hydrolysing lipopolysaccharides of different bacteriophage adhesion proteins can be compared in such an assay. The time span for hydrolysis ranges from seconds to several hours up to several days depending on the activity of the bacteriophage adhesion protein, and the temperature during the assay. Preferred time spans for the assays are 1 s up to 48 h and temperatures in the range of room temperature up to 37° C. Bacteriophage adhesion proteins according to the present invention exhibit a reduced ability of hydrolysing lipopolysaccharides with a residual activity of less than about 1%, preferably less than about 0.1% and most preferably of less than about 0.01% in comparison to their wild type form. For industrial application of the bacteriophage adhesion proteins showing reduced LPS hydrolysis it is important that LPS hydrolysis of the respective bacteriophage adhesion protein is low within the timespan of the incubation with bacterial cells or cell components in the bacterial detection of capture assay. Preferentially, LPS hydrolysis during assay time is less than about 50%, preferably less than about 10%, most preferably less than about 1%.

A functional assay is a comparison of the capture efficiency between wild-type bacteriophage adhesion protein and inactivated bacteriophage adhesion protein (cell binding assay). As inactive bacteriophage adhesion proteins bind to their respective bacterial host cells without releasing, the capture efficiency is better than with enzymatively active bacteriophage adhesion proteins.

If the bacteriophage binding domain resides at the N-terminus, the amino acid mutations are preferably performed within about the first 500 amino acid residues of the N-terminus subsequent to the truncation, especially preferred within the range of about the amino acid residues 50 to about 400. If the bacteriophage binding domain resides at the C-terminus, the amino acid residue mutations are preferably performed within the first 500 amino acid residues of the C-terminus subsequent to the truncation, especially preferred within the range of about the amino acid residues 50 to about 400. Preferably, the mutations are preformed within the LPS binding domain of the bacteriophage adhesion protein. The identification of suitable amino acid residues for mutation can for example be predicted on the basis of homology analysis (e.g. by means of alignments) and the location of the effective mutations in other bacteriophage adhesion proteins such as the p22 tail spike according to SEQ ID NO: 53, ϵ15 side tail fiber according to SEQ ID NO: 55, Det 7 tail spike SBP1 according to SEQ ID NO: 1, Det7 ORF790 SBP2 according to SEQ ID NO:3, Phage 14 tail spike according to SEQ ID NO: 6, O157BP1 according to SEQ ID NO: 8 or EcoO111 tsp according to SEQ ID NO: 10. The principle procedure for identifying suitable amino acid residues for mutation is exemplified in FIG. 16.

The bacteriophage adhesion protein Det7 tail spike SBP1 (Δ2-151, D437N) (SEQ ID NO:2) according to the present invention exhibits a mutation of D437 to N in comparison to Det7 tail spike SBP1 (wild type). Said mutation was found by a homology analysis in comparison to the P22 tail spike protein. The P22 tail spike protein exhibits three acidic amino acid residues belonging to the active site of the enzyme as kwon from the X-ray structure (Steinbacher et al., 1996). An alignment of P22 tail spike and Det7 tail spike SBP1 (wild type) identifies E404, D437 and D440 as corresponding active site amino acid residues in the Det7 tail spike SBP1 (wild type). Thus, further bacteriophage adhesion proteins according to the present invention exhibit a mutation of E404 to any other amino acid residue expect D, or a mutation of D437 or D440 to any non acidic amino acid residue, wherein mutations of E to Q and D to N are preferred. A preferred bacteriophage adhesion protein is depicted in SEQ ID NO:13.

The bacteriophage adhesion protein Det7-ORF790 SBP2 (Δ2-251; D485N) (SEQ ID NO:4) according to the present invention exhibit a mutation of D485 to N. Further bacteriophage adhesion proteins according to the present invention exhibit a mutation of D485 to any non acidic amino acid residue, in particular to alanine (A) or glutamine (Q).

A preferred bacteriophage adhesion protein phage 14 tail spike (Δ2-107; D433N) (SEQ ID NO:7) according to the present invention exhibits a mutation of D433 to N. Further bacteriophage adhesion proteins according to the present invention exhibit a mutation of D433 to any non acidic amino acid residue. Further preferred bacteriophage adhesion proteins phage 14 tail spike according to the present invention exhibit a mutation of E171 to Q or any other amino acid residue except D, or of D435 to N or any other amino acid residue except E, or a combination of two or three or the suggested mutations at positions E171, D433, and D435. A preferred bacteriophage adhesion protein is depicted in SEQ ID NO:14.

The bacteriophage adhesion protein O157_BP1 (Δ2-162; D463N) (SEQ ID NO:9) according to the present invention exhibit a mutation of D463 to N. Further bacteriophage adhesion proteins according to the present invention exhibit a mutation of D463 to any other non acidic amino acid residue, in particular to alanine (A) or glutamine (Q).

The bacteriophage adhesion protein O111_BP1 (Δ2-107; D204N) (SEQ ID NO:11) and O111_BP1 (Δ2-107; D277N) (SEQ ID NO:12) according to the present invention exhibit a mutation of D204 to N or D277 to N. It turned out that D204, D277, D302, D332, E337, D345, E354, E357, E415, D471, E476, D477, E482, D492 are putative active site amino acids of O111_BP1 (wild type). Thus, further bacteriophage adhesion proteins according to the present invention exhibit a mutation of D204 or D277 or D302 or D332 or D345 or D471 or D477 or D492 to any other amino acid residue expect E, preferably to N, or a mutation of E337 or E354 or E357 or E415 or E476 or E482 to any other amino acid residue expect D, preferably to Q. Further bacteriophage adhesion proteins according to the present invention exhibit a combinations of the above mentioned single amino acid residue exchanges from at least two amino acid residue exchanges up to all 7 amino acid residues exchanged. Especially preferred are the bacteriophage adhesion proteins according to the present invention with a mutation of D204N, and the bacteriophage adhesion protein according to the present invention with a mutation of D277 to N. A further preferred bacteriophage adhesion protein is the bacteriophage adhesion protein EcoO111 tsp (Δ2-107; D302N, E354Q, E357Q) according to SEQ ID NO: 58 which exhibits the mutations of D302 to N, of D354 to Q and of E357 to Q. Another further preferred bacteriophage adhesion protein is the bacteriophage adhesion protein EcoO111 tsp (Δ2-107; D302N, E354Q) which exhibits the mutations of D302 to N and of D354 to Q.

The bacteriophage adhesion protein ϵ15 side tail fiber (Δ2-220; D449N) (SEQ ID NO:56) according to the present invention exhibits a mutation of D449 to N. Further bacteriophage adhesion proteins according to the present invention exhibit a mutation of D449 to any other non acidic amino acid residue, in particular to alanine (A) or glutamine (Q).

Further preferred bacteriophage adhesion proteins according to the present invention are modified proteins of the 2954_O103_E15 according to SEQ ID NO: 60 exhibiting a truncation of the N-terminus from amino acid residue 2 to amino acid residue 161 (Δ2-161) and at least one mutation of an acidic amino acid residue to a non acidic amino acid residue in the range of amino acid residues 332 to 519. The putative active site amino acids of 2954_O103_E15, which can be identified by a person skilled in the art as e.g. described in FIG. 16, are D332, D341. D345, E365, D381, E392, D402, D405, E411, D417, E428, D431, E444, E456, D459, E483, E500, E518 and D519. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D332 to N, D341 to N, D345 to N, E365 to Q, D381 to N, E392 to Q, D402 to N, D405 to N, E411 to Q, D417 to N, D428 to N, D431 to N, E444 to Q, E456 to Q, D459 to N, E483 to Q, E500 to Q, E518 to Q or D519 to N. Further bacteriophage adhesion proteins according to the present invention exhibit a combinations of the above mentioned single amino acid residue exchanges from at least two amino acid residue exchanges up to all 19 amino acid residues exchanged. Especially preferred is a combination of 3, 4, 5, 6, 7, 8, 9, 10, 11, 12, 13, 14, 15, 16, 17, 18 of the above mentioned single amino acid residue exchanges.

Further preferred bacteriophage adhesion proteins according to the present invention are modified proteins of the 2956_O103_E15 according to SEQ ID NO: 62 exhibiting a truncation of the N-terminus from amino acid residue 2 to amino acid residue 161 (Δ2-161) and at least one mutation of an acidic amino acid residue to a non acidic amino acid residue in the range of amino acid residues 332 to 519. The putative active site amino acids of 2956_O103_E15, which can be identified by a person skilled in the art as e.g. described in FIG. 16, are D332, D341. D345, E365, D381, E392, D402, D405, E411, D417, D428, D431, E444, E456, D459, E483, E500, E518, D519. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D332 to N, D341 to N, D345 to N, E365 to Q, D381 to N, E392 to Q, D402 to N, D405 to N, E411 to Q, D417 to N, D428 to N, D431 to N, E444 to Q. E456 to Q, D459 to N, E483 to Q, E500 to Q, E518 to Q, D519 to N. Further bacteriophage adhesion proteins according to the present invention exhibit a combinations of the above mentioned single amino acid residue exchanges from at least two amino acid residue exchanges up to all 19 amino acid residues exchanged. Especially preferred is a combination of 3, 4, 5, 6, 7, 8, 9, 10, 11, 12, 13, 14, 15, 16, 17 or 18 of the above mentioned single amino acid residue exchanges.

Further preferred bacteriophage adhesion proteins according to the present invention are modified proteins of the 2961_O103_E15 according to SEQ ID NO: 64 exhibiting a truncation of the N-terminus from amino acid residue 2 to amino acid residue 161 (Δ2-161) and at least one mutation of an acidic amino acid residue to a non acidic amino acid residue in the range of amino acid residues 340 to 518. The putative active site amino acids of 2961_O103_E15, which can be identified by a person skilled in the art as e.g. described in FIG. 16, are D340, D344, E364, D380, E391, D401, D404, E410, D416, D427, D430, E443, E455, D458, E482, E499, E517 and D518. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D340 to N, D344 to N, E364 to Q, D380 to N, E391 to Q. D401 to N, D404 to N, E410 to Q, D416 to N, D427 to N, D430 to N, E443 to Q, E455 to Q, D458 to N, E482 to Q, E499 to Q, E517 to Q or D518 to N. Further bacteriophage adhesion proteins according to the present invention exhibit a combinations of the above mentioned single amino acid residue exchanges from at least two amino acid residue exchanges up to all 18 amino acid residues exchanged. Especially preferred is a combination of 3, 4, 5, 6, 7, 8, 9, 10, 11, 12, 13, 14, 15, 16 or 17 of the above mentioned single amino acid residue exchanges.

Further preferred bacteriophage adhesion proteins according to the present invention are modified proteins of the 2959_O145_E15 according to SEQ ID NO: 66 exhibiting a truncation of the N-terminus from amino acid residue 2 to amino acid residue 156 (Δ2-156) and at least one mutation of an acidic amino acid residue to a non acidic amino acid residue in the range of amino acid residues 329 to 523. The putative active site amino acids of 2959_O145E15, which can be identified by a person skilled in the art as e.g. described in FIG. 16, are E329, D351. D358, E375, E377, D383, D385, E393, E401, D446, E468, D487, E494, D495, D496, E503. E518 and D523. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of E329 to Q, D351 to N, D358 to N, E375 to Q, E377 to Q, D383 to N, D385 to N, E393 to Q, E401 to Q, D446 to N, E468 to Q, D487 to N, E494 to Q. D495 to N, D496 to N, E503 to Q, E518 to Q or D523 to N. However, further bacteriophage adhesion proteins according to the present invention exhibit a combinations of the above mentioned single amino acid residue exchanges from at least two amino acid residue exchanges up to all 18 amino acid residues exchanged. Especially preferred is a combination of 3, 4, 5, 6, 7, 8, 9, 10, 11, 12, 13, 14, 15, 16 or 17 of the above mentioned single amino acid residue exchanges.

Further preferred bacteriophage adhesion proteins according to the present invention are modified proteins of the NS2957_O145_P22 according to SEQ ID NO: 68 exhibiting at least one mutation of an acidic amino acid residue to a non acidic amino acid residue in the range of amino acid residues 180 to 357 of the amino acid sequence according to SEQ ID NO:68. The putative active site amino acids of NS2957_O145_P22, which can be identified by a person skilled in the art as e.g. described in FIG. 16, are D180, D186, D190, D211, D241, E246, D254, D261, D263, D265, E266, D301, E324, D333, E334, E336, D339 and D357. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D180 to N, D186 to N, D190 to N, D211 to N, D241 to N, E246 to Q, D254 to Q, D261 to N, D263 to N, D265 to N, E266 to Q, D301 to N, E324 to Q, D333 to N, E334 to Q, E336 to Q, D339 to Q or D357 to N. Further bacteriophage adhesion proteins according to the present invention exhibit a combinations of the above mentioned single amino acid residue exchanges from at least two amino acid residue exchanges up to all 18 amino acid residues exchanged. Especially preferred is a combination of 3, 4, 5, 6, 7, 8, 9, 10, 11, 12, 13, 14, 15, 16 or 17 of the above mentioned single amino acid residue exchanges.

Further preferred bacteriophage adhesion proteins according to the present invention are modified proteins of the 2316_026_E15 according to SEQ ID NO: 70 exhibiting a truncation of the N-terminus from amino acid residue 2 to amino acid residue 169 (Δ2-169) and at least one mutation of an acidic amino acid residue to a non acidic amino acid residue in the range of amino acid residues 344 to 636. The putative active site amino acids of 2316_026_E15, which can be identified by a person skilled in the art as e.g. described in FIG. 16, are D344, D345, E351, E356, D362, D398, E405, D408, D412, E425, E432, D435, E452, E498, D509, E511.

D529, E534, E538, E547, D554, D567, D573, D595, E609, D615 and D636. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D344 to N, D345 to N, E351 to Q, E356 to Q, D362 to N, D398 to N, E405 to Q, D408 to N, D412 to N, E425 to Q, E432 to Q, D435 to N, D452 to N, E498 to Q, D509 to N, E511 to Q, D529 to N, E534 to Q, E538 to Q, E547 to Q, D554 to N, D567 to N, D573 to N, D595 to N, E609 to Q, D615 to N or D636 to N. Further bacteriophage adhesion proteins according to the present invention exhibit a combinations of the above mentioned single amino acid residue exchanges from at least two amino acid residue exchanges up to all 27 amino acid residues exchanged. Especially preferred is a combination of 3, 4, 5, 6, 7, 8, 9, 10, 11, 12, 13, 14, 15, 16, 17, 18, 19, 20, 21, 22, 23, 24, 25 or 26 of the above mentioned single amino acid residue exchanges.

Further preferred bacteriophage adhesion proteins according to the present invention are modified proteins of the 2314_026_P22 according to SEQ ID NO: 72 exhibiting a truncation of the N-terminus from amino acid residue 2 to amino acid residue 107 (Δ2-107) and at least one mutation of an acidic amino acid residue to a non acidic amino acid residue in the range of amino acid residues 178 to 470. The putative active site amino acids of 2314_026_P22, which can be identified by a person skilled in the art as e.g. described in FIG. 16, are D178, D179, E185, E190, D196, D232, E239, D242, D246, E259, E266, D269, D286, E332, E345, D363, E368, E372, E381, D388, D401, D407, D429, E443, D449 and D470. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D178 to N, D179 to N, E185 to Q, E190 to Q, D196 to N, D232 to N, E239 to Q, D242 to N, D246 to N, E259 to Q, E266 to Q, D269 to N, D286 to N, E332 to Q, E345 to Q, D363 to N. E368 to Q, E372 to Q, E381 to Q, D388 to N, D401 to N, D407 to N, D429 to N, E443 to Q, D449 to N or D470 to N. Further bacteriophage adhesion proteins according to the present invention exhibit a combinations of the above mentioned single amino acid residue exchanges from at least two amino acid residue exchanges up to all 26 amino acid residues exchanged. Especially preferred is a combination of 3, 4, 5, 6, 7, 8, 9, 10, 11, 12, 13, 14, 15, 16, 17, 18, 19, 20, 21, 22, 23, 24 or 25 of the above mentioned single amino acid residue exchanges.

Further preferred bacteriophage adhesion proteins according to the present invention are modified proteins of the 23625_026_P22 according to SEQ ID NO: 74 exhibiting a truncation of the N-terminus from amino acid residue 2 to amino acid residue 107 (Δ2-107) and at least one mutation of a acidic amino acid residue to a non acidic amino acid residue in the range of amino acid residues 178 to 470. The putative active site amino acids of 23625_026_P22, which can be identified by a person skilled in the art as e.g. described in FIG. 16, are D178, D179, E185, E190, D196, D232, E239, D242, D246, E259, E266, D269, D286, E332, E345, D363, E368, E372, E381, D388, D401, D407, D429, E443, D449 and D470. Thus, further bacteriophage adhesion proteins according to the present invention exhibit a mutation of one of these putative active site amino acids to any non acidic amino acid residue, in particular to asparagine (N), alanine (A) or glutamine (Q). Especially preferred is at least one mutation of D178 to N, D179 to N, E185 to Q, E190 to Q, D196 to N, D232 to N, E239 to Q, D242 to N, D246 to N, E259 to Q, E266 to Q, D269 to N, D286 to N, E332 to Q, E345 to Q, D363 to N, E368 to Q, E372 to Q, E381 to Q, D388 to N, D401 to N, D407 to N, D429 to N, E443 to Q, D449 to N or D470 to N. Further bacteriophage adhesion proteins according to the present invention exhibit a combinations of the above mentioned single amino acid residue exchanges from at least two amino acid residue exchanges up to all 26 amino acid residues exchanged. Especially preferred is a combination of 3, 4, 5, 6, 7, 8, 9, 10, 11, 12, 13, 14, 15, 16, 17, 18, 19, 20, 21, 22, 23, 24 or 25 of the above mentioned single amino acid residue exchanges.

It turned out that the inactivation of the bacteriophage adhesion proteins according to the invention results in an improved or irreversible binding of the bacteriophage adhesion proteins to bacteria.

O-Antigen-Binding

The bacteriophage adhesion proteins according to the present invention bind to the O-antigen of gram-negative bacteria. To determine whether a bacteriophage adhesion protein binds to the O-antigen of gram-negative bacteria the LPS-degradation of respective bacteria strains is analyzed analogous to the assay as for the analysis of the ability to hydrolyse lipopolysaccharides as described above.

Compared to bacteriophage adhesion proteins binding in the more conserved LPS core, e.g. the short tail fibers T4 p12, K3 p12 or T2 p12, the O-Antigen binding bacteriophage adhesion proteins of the present invention exhibit a more narrow host specificity as O-antigen varies much more between more closely related bacterial species. For instance, there are more than 180 different O-antigens observed in *E. coli*, but only 5 core types. This increased specificity provides advantages for some applications of bacterial detection as well as for the purification of e.g. distinct cell components like the lipopolysaccharide bearing specific O-antigens. Within the bacterial species *E. coli*, for instance there are lots of harmless species like the *E colis* of the common human flora of the digestive tract. On the other hand, there are extremely harmful germs like the enterohemorrhagic *E. colis* (EHEC). These pathogenic strains often express specific O-antigens with *E. coli*: O157, *E. coli*: O111 or *E. coli*: O26 as well-known examples for the frequent occurrence of pathogenic species. Only O-antigen specific bacteriophages adhesion proteins can detect or capture these strains in a way analogous to specific antibodies, but not core binding bacteriophage adhesion proteins or bacteriophage adhesion proteins binding to other bacterial surface receptors like proteins or extracellular layers.

SDS-Resistance

Preferably, the bacteriophage adhesion proteins according to the invention are SDS-resistant. This means, bacteriophage adhesion proteins do not dissociate into monomers after the addition of SDS at ambient temperature. SDS-resistant proteins are stable against heating and proteases. Thus, they have greater long term stability than non SDS-resistant proteins. Furthermore, they can be used at higher temperatures than non SDS-resistant proteins and are thus suitable for processes, which require or are more effective at a higher temperature.

Oligomeric Structure

Bacteriophage adhesion proteins according to the invention are oligomers, preferably trimers, most preferably homotrimers. Preferably, the bacteriophage adhesion proteins according to the invention are folded into a trimeric, right-handed, parallel β-helix. The structure of bacteriophage adhesion proteins according to the invention can be analysed by analytic ultracentrifugation or analytic gel filtration chromatography as known by the person skilled in the art (see for example Seckler et al., 1989, J. Biol. Chem., 264 11750-11763).

Tags

In a further preferred embodiment the bacteriophage adhesion protein according to the invention comprises additional marker moieties such as biotin or Streptavidin or tags such as HA-tag, His-tag, Strep-tag, Avi-tag, Myc-tag, GST-tag, JS-tag, Cystein-tag or other tags known in the art. Preferably the tag is coupled to the C-terminus or the N-terminus of a bacteriophage adhesion protein according to the invention, most preferably to the N-terminus.

The coupling or linking of the tags with the bacteriophage adhesion proteins according to the present invention via recombinant DNA technology is preferred. The generation of the nucleic acid molecule, comprising the sequence of the bacteriophage adhesion proteins according to the present invention and the tag, and the production of the expression product are state of the art and there is no need to explain the production in detail at this point. A further aspect of the present invention is a the nucleic acid molecule comprising the nucleotide sequence coding the bacteriophage adhesion protein according to the present invention together with a HA-tag, His-tag, Strep-tag, Avi-tag, Myc-tag, GST-tag, JS-tag, Cystein-tag or other tags known in the art.

Preferred are bacteriophage adhesion proteins comprising a JS-tag. Said JS-tag refers to an amino acid sequence comprising a sequence as shown in SEQ ID NO:14-32 or derivatives thereof. The JS-tag derives from the biotin-aceptor-domain of the α-subunit of the *Klebsiella pneumoniae* oxalacetatdecarboxylase and comprises the consensus sequence MKM. The JS-Tag can be biotinylated in vivo by the biotinligase protein the amino acid residue K of the consensus sequence. The JS-tag is truncated in comparison to the complete α-subunit of the *Klebsiella pneumoniae* oxalacetatdecarboxylas. A possible minimal sequence for the JS-tag comprises 66 amino acids according to amino acids 529 to 594 of the *Klebsiella pneumoniae* oxalacetatdecarboxylase as set forth in SEQ ID NO: 15. Derivates of the JS-tag are sequences having a homology to SEQ ID NO:15 of at least about 80%, 90%, 95% or 98%. Examples for such derivates are shown in SEQ ID NO:16-32.

A further aspect of the present invention is bacteriophage adhesion proteins according to the present invention with a tag exhibiting a surface-exposed cysteine for the specific, directed biotinylation, e.g. the tags according to SEQ ID NO: 33-35. In addition, said directed biotinylation may be mediated by an appropriate spacer or linker.

| Sequence of the cyteine-tag | |
|---|---|
| MAC̲WSGA | SEQ ID NO: 33 |
| MAC̲WSHPQFEKGAS | SEQ ID NO: 34 |
| MASWSHPQFEKGAC̲ | SEQ ID NO: 35 |

The cyteines which can be modified, e.g. by biotinylation are underlined.

Preferred bacteriophage adhesion proteins comprising a tag are depicted in SEQ ID NO:36-42.

Modifications

Bacteriophage adhesion proteins according to the present invention may exhibit modifications. Bacteriophage adhesion proteins according to the present invention, their variants or fragments may be produced in easily recombinant fashion in large amounts and can be isolated as well. Thus, bacteriophage adhesion proteins according to the present invention are not limited to the specific embodiments of the SEQ ID NO: 2, 4, 5, 7, 9, 11-14, 36-42, 56 and 58 but also to their derivatives exhibiting modifications. Examples of modifications are posttranslational modifications of the amino acid residues like acetylation, biotinylation or other derivatization of functional groups of amino acid residues or PEGylation, carbohydrate attachment or the covalent attachment of fluorescent reporter groups and the attachment of GFP or enzymes suitable for detection like alkaline phosphatase or horse radish peroxidase.

Especially preferred are the following modified bacteriophage adhesion proteins exhibiting an amino acid sequence according to SEQ ID NO:2, 4, 5, 7, 9, 11-14, 36-42, 56 or 58.

Another aspect of the present invention is a nucleic acid molecule comprising a nucleotide sequence encoding a bacteriophage adhesion protein according to the present invention. Preferred are nucleic acid molecules comprising a nucleotide sequence according to SEQ ID NO: 43-51. Another aspect is a vector comprising said nucleotide sequence. Still another aspect of the present invention is a host cell transformed with said nucleic acid molecule or said vector.

Another aspect of the present invention is a method for generating bacteriophage adhesion proteins according to the present invention. Said method comprises the step of:
  (a) identifying the bacteriophage binding domain of a bacteriophage adhesion protein
  (b) deleting the identified bacteriophage binding domain of step (a) from a nucleic acid molecule comprising a sequence encoding the bacteriophage adhesion protein of step (a)
  (c) inactivating the hydrolysing activity of the bacteriophage adhesion protein by mutation.

The identification of the bacteriophage binding domain of a bacteriophage adhesion protein in step (a) is preferably carried out by a homology analysis of said bacteriophage adhesion protein with another bacteriophage adhesion protein. In particular, the identification of the bacteriophage binding domain is carried out by a homology analysis of both bacteriophage adhesion proteins as described above, in particular in regard of the N-terminus. Said homology analysis may comprise an amino acid alignment and subsequent determination of the N-terminus of said bacteriophage adhesion protein in comparison to another bacteriophage adhesion protein. In one embodiment of the present invention said other bacteriophage adhesion protein is a bacteriophage adhesion proteins of the phages P22 or ϵ15. Preferred are the bacteriophage adhesion protein p22 tail spike according to SEQ ID NO: 53 and the bacteriophage adhesion protein ϵ15 side tail fiber according to SEQ ID NO 55.

Alternatively, the identification of the bacteriophage binding domain of step (a) can be carried out by use of primers being suitable for homology fishing. Preferred are primers which are suitable for a homology fishing of the bacteriophage binding domain of bacteriophage adhesion proteins. Thereby, the bacteriophage binding domain is identified by the amplification of a nucleic acid sequence encoding a bacteriophage binding domain by primers generated by means of a known bacteriophage binding domain of another bacteriophage adhesion protein. Said other bacteriophage adhesion proteins may be any bacteriophage adhesion proteins as listed above in regard to the N-terminal homology of bacteriophage adhesion proteins according to the present invention. Especially preferred are primers designed in regard to the N-terminal bacteriophage binding domain of p22 tail spike according to SEQ ID NO: 53 or the bacteriophage binding domain of ϵ15 side tail fiber according to SEQ ID NO: 55. The design and generation of such primers being suitable for homology fishing are well known by a person skilled in the art.

The deletion of the identified bacteriophage binding domain of step (b) of the method according to the present invention is preformed as described above.

The inactivation of step c) occurs preferably by a mutation of a non acidic amino acid to non acidic amino acids as described above. In particular step c) can comprise the mutation of more than 1 acidic amino acid to a non acidic amino acid as a mutation of 1 to 7, 1 to 6, 1 to 5, 1 to 4, 1 to 3 or 1 to 2 acidic amino acids to non acidic amino acids.

In another embodiment of the method according to the present invention step (c) is carried out before step (a) or before step (b).

Another aspect of the present invention is the use of a bacteriophage adhesion protein according to the present invention for binding, enrichment, removing, capture and detection of gram negative bacteria.

Another aspect of the present invention is the provision of a method to detect bacteria, the method comprising the following steps (one-step method):
(a) coupling of bacteriophage adhesion proteins according to the present invention to a support,
(b) incubating the support coupled to said bacteriophage adhesion proteins with a sample,
(c) optionally removing the sample and the bacteria of the sample not bound to said bacteriophage adhesion proteins,
(d) optionally adding substances permeabilizing or destroying the bacterial membrane, and
(e) detecting the bacteria in the sample bound to said bacteriophage adhesion proteins.

Another aspect of the present invention is the provision of a method to detect bacteria, the method comprising the following steps (two-step method):
(a) contacting a sample containing bacterial cells or cell components with bacteriophage adhesion proteins according to the present invention, preferably with an incubation time of about 1 s to about 20 minutes
(b) subsequent incubation of said sample, containing the bacterial cells or cell components and said bacteriophage adhesion proteins with a solid support, preferably for about 1-60 minutes,
(c) optionally removing the sample and the bacteria of the sample not bound to said bacteriophage adhesion proteins,
(d) optional separation of the solid support with the bacterial cells or cell components bound via said bacteriophage adhesion proteins to said solid support from the sample
(e) optionally adding substances permeabilizing or destroying the bacterial membrane, and
(f) detecting the bacteria in the sample bound to said bacteriophage adhesion proteins.

Bacteriophage adhesion proteins according to the present invention specific for the bacteria to be detected desirably are employed for the detection methods according to the invention. The bacteria to be detected with the method according to the invention can originate for example from the family of enterobacteriaceae. Preferably bacteria are detected from the genus *Escherichia, Salmonella, Shigella, Klebsiella, Enterobacter, Citrobacter, Proteus, Serratia, Morganella, Providencia, Yersinia, Hafnia* and/or *Edwardsiella*, particularly preferably from *Escherichia, Salmonella, Shigella, Klebsiella, Enterobacter* and/or *Citrobacter*. Further preferably bacteria to be detected are the species *Escherichia* spec., *Salmonella* spec., *Shigella* spec., *Klebsiella* spec., *Enterobacter* spec., *Citrobacter* spec., *Proteus* spec., *Serratia* spec., *Morganella* spec., *Providencia* spec., *Yersinia* spec., *Hafnia* spec., *Edwardsiella* spec. and/or *Pseudomonas* spec. Preferably, the bacteriophage adhesion proteins according to the invention are specific for bacteria bearing a specific O-antigen or for serogroups of bacteria defined by their O-antigen like the serogroups of *Salmonella*.

Furthermore, two or more bacteriophage adhesion proteins according to the present invention may be used in a single detection method according to the present invention to simultaneously detect several types of bacteria.

A sample with regard to the methods according to the present invention is any material supposed to or containing bacteria, whereas the bacteria are a target for detection. Samples can be e.g. food or feed materials, surface materials or human or veterinary diagnostic probes.

For the methods according to the present invention the bacteriophage adhesion proteins according to the present invention are immobilised on suitable supporting structures, e.g., microtiter plates, test stripes, slides, wafers, filter materials, reaction tubes, magnetic, glass or latex particles, pipette tips or flow-through cell chambers. The supporting structures may consist of, e.g., polystyrene, polypropylene, polycarbonate, PMMA, cellulose acetate, nitrocellulose, glass, silicium wafer, latex. The immobilization may be accomplished by adsorption, by covalent binding or by further proteins, wherein the covalent binding is preferred. It is relevant that immobilization is a functional one, that is, said bacteriophage adhesion proteins exhibit structures accessible for bacteria although they are bound to the support material.

In order to suppress an unspecific reaction of the bacteria to be investigated with the support material a blocking with bovine serum albumin or Tween 20 or substances that are likewise employed in ELISAs, such as milk powder, may be performed. Furthermore, to increase the efficiency of the adsorption, the support systems may be pre-coated with suitable proteins (e.g., specific antibodies against bacteriophage adhesion proteins or unspecific proteins such as BSA) peptides, saccharides, (e.g., mono-, oligo-, or polysaccharides) or detergents (e.g., Tween 20 or octylglucoside). These coatings may occur overnight at a temperature ranging from about 4 to 20° C. or within a period of about 2 to 4 h at a temperature of about 30 to 65° C. Subsequently, the excess liquid is removed, and the supporting structure dried at about 60-70° C. The basic coating is to guarantee adsorption of functional bacteriophage adhesion proteins on the one hand and, on the other hand, to prevent an unspecific adsorption of the test bacteria to the supporting structure, thereby increasing the efficiency of the assay. Following the basic coating, the bacteriophage adhesion proteins according to the present invention are applied by applying an aqueous buffered solution of said bacteriophage adhesion proteins to the pre-treated supporting structure. After an adsorption at about 4-20° C. overnight or at about 30-65° C. for a period of about 2-4 hours the coating solution is removed and the supporting structure is dried as described above. In order to increase the coating efficiency, a covalent fixation of said bacteriophage adhesion proteins with chemical crosslinkers such as glutaric aldehyde may be performed subsequently.

Subsequently to the base coating the bacteriophage adhesion proteins according to the present invention are applied. For that purpose an aqueous buffered solution of said bacteriophage adhesion proteins is applied to the pretreated support structure. After adsorption for example at about 4-20° C.

overnight or at about 30-65° C. for about 2-4 h the coating solution is removed and the support structure dried as described above. In order to increase the level of coating efficiency it is possible subsequently to implement covalent fixing of said bacteriophage adhesion proteins with chemical crosslinkers such as for example glutaraldehyde.

Immobilisation of the bacteriophage adhesion proteins according to the present invention to the support material by means of adsorption can be effected by incubation of a bacteriophage adhesion protein solution in aqueous buffer, for example 100 mM Tris, pH 7.3 or 100 mM sodium phosphate, pH 7.5, over several hours or overnight at about 5° C. to 45° C., preferably at about 15° C. to 37° C., particularly preferably at about 20° C. to 37° C., particularly preferably at ambient temperature.

In addition the bacteriophage adhesion proteins according to the present invention do not have to be immobilised directly on the support but can bind to polypeptides which in turn were immobilised on the support. Those polypeptides can be, being specific for said bacteriophage adhesion proteins, antibodies, receptors or anticalins. In addition said bacteriophage adhesion proteins can be linked to low-molecular weight substances, for example biotin, which in turn can bind to other substances like polypeptides, for example streptavidin, which were immobilised on the support. In that respect, as described herein before, in regard to said bacteriophage adhesion proteins, the other polypeptides can bind to the support. In one embodiment of the methods according to the present invention, the bacteriophage adhesion proteins are biotinylated and bound via streptavidin or avidin variants.

With regard to covalent coupling the bacteriophage adhesion proteins according to the present invention can be coupled for example by way of primary amino groups or carboxyl groups to support materials already activated by the manufacturer, for example microtiter plates from Nunc, Xenobind or Costar, by way of standard conditions, for example $-NH_2$ by way of cyanuryl chloride (Russian Chemical Rev., 1964, 33: 92-103), or $-COO$ by way of EDC (1-ethyl-3'[3'-dimethylaminopropyl]carbodiimide) (Anal. Biochem. 1990, 185: 131-135), or by tosyl- or epoxy-coupling to activated surfaces. In addition the support materials can be directly activated with suitable procedures. One possibility which is preferred by virtue of the applicability for a wide spectrum of support materials is silanisation of the support material. For example silanisation in the case of polystyrene can be implemented by flame pyrolysis. Suitable bonding agents are then applied, which permit coupling by way of for example primary amino groups or carboxyl groups.

For binding of the bacteria to be investigated to the immobilised bacteriophage adhesion proteins according to the invention the sample being investigated is brought into contact in aqueous form with said bacteriophage adhesion proteins and incubated. Incubation is effected at a temperature in the range of about 4° to 90° C., preferably at a temperature in the range of about 4° to 45° C., particularly preferably at a temperature in the range of about 15' to 37° C., especially preferably at a temperature in the range of about 20° to 37° C., more particularly at ambient temperature, for up to 6 hours, preferably up to 4 hours, particularly preferably 2 hours, in particular 1 hour, particularly preferably at 1 to 20 minutes. For example incubation can be effected for about 2 to 120 minutes at about 4° to 37° C., preferably for about 20 to 30 minutes at about 25° C. to 37° C., particularly preferably for 35 minutes at 37° C.

After specific recognition and firm binding of the bacteria, non-specifically bound material can be removed by washing with aqueous buffer, for example with PBS or PBS-Tween, preferably at a neutral pH-value, for example with 50 mM sodium phosphate, pH 7.0. It is possible to add to the buffers used, optionally, for increasing the washing efficiency, detergents, for example Tween 20, Triton X 100 or chaotropic agents, for example guanidinium hydrochloride or urea. Said washing step can be repeated a plurality of times depending on the sample material.

After separation of non-specifically bound material the membrane of the bound bacteria can be permeabilised or if necessary (depending on the detection assay used) destroyed by the addition of detergents (for example sodium dodecylsulphate, octylglucoside, Triton-X-100), chemicals (for example Polymyxin B, chloroform), pore-forming polypeptides (for example nisin, holin, mellitin) or proteins (for example lysozyme, endolysins, autolysins). That membrane permeabilisation operation can be carried out for about 2 to 120 minutes at a temperature in the range of about 10° to 80° C. The bound bacteria are then detected.

In one embodiment of the methods according to the present invention the bacteria bound to the bacteriophage adhesion proteins according to the present invention are not subjected to any cultivation step.

In another embodiment of the detection methods of the present invention the methods to detect bacteria comprises a pre-cultivation step or a cultivation step after removing the sample and the bacteria of the sample not bound to the bacteriophage adhesion proteins. A pre-cultivation step or a cultivation step after removing the sample and the bacteria of the sample not bound to the bacteriophage adhesion proteins may be useful to increase sensitivity if the concentration of the bacteria to be detected or captured is very low. A pre-cultivation step prior to detection or capture of the bacteria can be performed by incubation of the sample at a temperature which is suitable for the growth of the respective bacterial species to be detected or captured. A pre-cultivation step can also be performed in selective or non-selective enrichment media suitable for the growth of the respective bacterial species to be detected or captured. Preferably, a pre-cultivation step is performed for about 1 h up to about 48 h, more preferably for about 2 h up to about 8 h. A cultivation step after removing the sample and the bacteria of the sample not bound to the bacteriophage adhesion proteins can also be performed in selective or non-selective enrichment media suitable for the growth of the respective bacterial species to be detected or captured. Preferably, this cultivation step is performed for about 1 h up to about 48 h, more preferably for about 2 h up to about 8 h. One example for a special cultivation step after removal of the bacterial cells from the sample by the bacterial adhesion proteins according to the invention is the plating of bacterial cells bound to bacterial adhesion proteins immobilized to magnetic beads in order to determine the capture efficiency of bacterial cell binding.

Is the sample contacted with the immobilized bacteriophage adhesion proteins according to the invention, e.g., in a flow-through chamber or on a filter, there is no stringent necessity to remove it after binding the bacteria to said bacteriophage adhesion proteins prior to carrying out the detection.

For detection of the bacteria bound to the bacteriophage adhesion proteins according to the present invention it is possible to use specific antibodies, polypeptides, bacteriophages, bacteriophage adhesion proteins or the bacteriophage adhesion proteins according to the present invention. Preferably bacteriophage adhesion proteins according to the present invention are used. The bacteriophage adhesion proteins used for the detection may be identical to the immobilized bacteriophage adhesion proteins according to the present invention or different than said immobilized bacteriophage adhesion proteins.

For the detection procedure, a marking, for example FITC, peroxidase or alkaline phosphatase, is coupled to the antibodies, polypeptides, bacteriophages, bacteriophage adhesion proteins or bacteriophage adhesion proteins according to the present invention, wherein signal development of the marking can be photometrically pursued after addition of a substrate. The genes for the bacteriophage proteins can be cloned in suitable expression vectors and in that way additionally modified according to the respective use involved, for example by fusion with a detection enzyme. Alternatively detection can be implemented by way of (bacterial) cellular enzymes (for example β-galactosidase in the case of coliforms or phosphatase in the case of *Salmonella*) or also other cell constituents such as nucleic acids, proteins, lipids or sugar components.

Depending on the requirement involved for example fluorescence, luminescence, absorption or circular dichroism, conductivity or capacitance variations in the respective probes are detected in the appropriate standard measuring apparatuses. A calibration straight line can be implemented with suitable standard molecules for exact determination of concentration of the bacteria.

Detection of the bacteria bound to bacteriophage adhesion proteins according to the present invention can also be implemented by the use of a colorimetric test. In that case for example NADH, β-galactosidase activity, phosphatase activity or inorganic phosphate is detected. Those tests permit the detection of at least $10^4$ cells per ml, by using fluorescence dyes the level of sensitivity can be improved to between $10^2$ and $10^3$ cells per nil. The colorimetric tests can generally be used for detection of the activity of intracellular, membraneous or periplasmatic enzymes or cell constituents.

The colorimetric tests can be the same for all bacteria to be investigated, but they can also be specific for given bacteria/bacteriophage adhesion protein combinations. The choice of the marking for example of the enzyme or fluorescence marker used can be adapted to the respective bacteria genus or bacteria species under test.

The detection of the bacteria bound to the bacteriophage adhesion proteins according to the invention may also occur by means of detecting DNA and/or RNA. For this purpose, substances may be used that bind to DNA and/or RNA. Binding to the DNA and/or RNA can occur directly on the basis of membrane diffusion or, in the alternative, on the basis of a membrane permeabilization. Commercially available fluorescence marker such as ethidium bromide, acridine orange, 4',6'-diamidino-2-phenylindole (DAPI) or SYBR green I and the respective detection protocols described in the literature may be used.

Preferred are methods according to the present invention, wherein the detections steps are carried out by means of a detection of DNA and/or RNA probes specific for the respective gram-negative bacterial cells to be detected (all types of PCR based assays, NASBA (nucleic acid sequence based amplification), hybridization techniques, Southern blot, Northern blot, dot blot).

Preferred are also methods according to the present invention, wherein the detection steps are performed in assay formats analogous to an immunoassay, the antibodies, however are substituted by specifically binding bacteriophage adhesion proteins according to the invention. Exemplary assay formats are the different types of ELISA, RIA, ELFA (enzyme linked fluorescence assay), IMS (immunomagnetic separation), Western blot or similar immunoassays known in the art. A preferentially preferred method is VIDAS® which is an automated immunoassay system working after the ELFA principle in the form of a sandwich ELISA. In the original assay format, capture antibodies are immobilized to specialized pipette tips, and detection antibodies are coupled in alkaline phosphatase conjugates. Bacterial samples are directly transferred to the VIDAS® instrument and immobilization, heating, washing and detection steps are directly performed within the instrument. It turned out that the capture antibodies as well as the detection antibodies or both of them can be replaced by bacteriophage adhesion proteins according to the invention leading to improved results with respect to sensitivity and detection of false positive results.

Another detection of the bacteria bound to bacteriophage adhesion proteins according to the invention the employment of lectins directed to cell surface structures of the bacteria, wherein signal development of a, e.g., peroxidase-coupled antibody is monitored photometrically. The cell surfaces of the bacteria recognised by the lectins may be, as an example, lipopolysaccharides or membrane proteins.

The methods according to the present invention allow a rapid and sensitive detection of bacteria. Coupling to suitable supporting structures described above enables a rapid and economic determination of numerous bacterial strains, a very exact determination of the bacterial genus and/or a quantification of bacteria in a single assay. Moreover, distinct cell components like the lipopolysaccharide bearing specific O-antigens can be detected by the methods according to the present invention. Amongst others, the exact determination of the bacterial species is important in the field of medical diagnostics as well as food industry and analytics, livestock breeding, fresh water or environmental analytics pertaining to the epidemiological characterization of the pathogens.

The method of the present invention can be used for a rapid, highly sensitive and economic detection of bacteria in any sample, in particular in the area of medicine, food industry and analytics, livestock breeding, fresh water or environmental analytics. The simple realization of the method enables both package solutions for the most important combinations of bacteria and system solutions adapted to the desire of clients and thus, a universal utilization of the method of the present invention. The present invention additionally allows a complete automatization of the method according to the present invention. Furthermore, the method is applicable to all bacteria for which suitable bacteriophages adhesion proteins according to the present invention are available or will be generated in future times. The method of the invention additionally qualifies for the use in kits to detect bacteria for "anyone" for the domestic use.

A further aspect of the invention refers to a kit for the detection of bacteria, including a support with immobilised bacteriophage adhesion proteins according to the present invention and the solutions, with the assay reagents, which are necessary for detection of the bound bacteria. The supports can be all the above-described supports to which the bacteriophage adhesion proteins according to the present invention are immobilised as described above. The solutions with the assay reagents also correspond to the substances which are described for the detection of the bacteria in the method according to the invention. The kit can also optionally include washing solutions and enzymes or detergents which are required for breaking up the bacterial membrane.

Another aspect of the present invention refers to methods for selective purification of bacterial cells or cell components comprising the following steps: (two-step method)

(a) contacting a sample containing bacterial cells or cell components with bacteriophage adhesion proteins according to the present invention, preferably with an incubation time of about 1 s to 20 minutes (b) subsequent incubation of said sample, containing the bacterial cells or cell components and said bacteriophage adhesion proteins with a solid support, preferably for about 1-60 minutes, (c) separation of the solid support with the bacterial cells or cell components bound via said bacteriophage adhesion proteins to said solid support from the sample.

Bacterial cells or cell components may be enriched selectively with methods according to the present invention, for example from mixed cultures of different species or from a culture of a single species. Enriched cell components may be, for example, lipopolysaccharide, endotoxines, complete O-antigen or fragments thereof like the oligosaccharides of the repeating units. The choice of appropriate bacteriophage adhesion proteins according to the present invention allows the selectivity of the method. Preferably, bacteriophage adhesion proteins according to the present invention are used for the methods of the present invention which are specific for the bacteria desired to be detected.

In a preferred embodiment of the present invention the sample is contacted with two or more distinct bacteriophage adhesion proteins according to the present invention. The two or more distinct bacteriophage adhesion proteins bind to two or more distinct types and/or genera of bacteria For binding purposes of the bacteria and/or cell components to be purified to the bacteriophage adhesion proteins according to the present invention in the two-step method, the sample, for example an overnight culture, is contacted with said bacteriophage adhesion proteins and is preferably incubated. The incubation occurs at a temperature in the range of about 4° C. to 90° C., preferably at a temperature in the range of about 4° C. to 45° C., more preferred at a temperature in the range of about 15° C. to 37° C., furthermore preferred at a temperature in the range of about 20° C. to 37° C., in particular at RT, for up to 6 hours, preferably up to 4 hours, more preferred 2 hours, in particular 1 hour, in particular preferred 1 s-20 minutes, exceptionally preferred 1-5 minutes. For example, the incubation can occur for about 2 to 120 minutes at about 4° C. to 37° C., preferably for about 20 to 30 minutes at about 25° C. to 37° C., preferably more preferred for about 10 s-5 minutes at about 37° C.

The sample is contacted with solid supports subsequently and incubated. Solid supports may be, for instance, magnetic particles (paramagnetic or ferromagnetic), glass particles, agarose particles, luminex particles, pipette tips, reactions tubes, membranes, filter materials or microtiter plates.

In case of using magnetic particles, they were subsequently added to the sample. The magnetic particles bind the bacteriophage adhesion protein-bacteria/cell component complex, which is then easily separated from the sample by using magnetic means, and which may then be purified. The magnetic means may be positioned at the outside of the container and either may be switched on for the enrichment so that the magnetic particles are collected at the container wall, or may slide along the outside wall of the container so that the magnetic particles are collected e.g. at the bottom of the container. The enrichment with a permanent magnet is preferred. The magnetic means may also immerse into the container and the sample so that the magnetic particles deposit at the magnetic means (the magnetic means may be covered by a pipette tip or a comparable disposable). In comparison to centrifugation or filtration techniques, the bacteria are subject to only minimal shear rates and therefore may be enriched with high yield in an active/living manner, if required. The easy handling facilitates easy and fast buffer/solution changes and may both easily be performed on a large scale, and well automated.

The magnetic particles exhibit a diameter allowing the binding of a sufficient amount of cells or cell components per particle. Preferably the magnetic particles exhibit a diameter in the range of about 0.5 to about 4 µm, in particular in the range of about 0.5 to about 2 µm, more preferred in the range of about 0.8 to about 1.8 µm, most preferred about 1 µm.

The binding of the bacteriophage adhesion protein-bacteria/cell component complexes to the solid supports, for example magnetic particles, preferably occurs via appropriate coupling groups, in particular polypeptides and/or low molecular substances. These polypeptides may also be antibodies, receptors or anticalins specific for the bacteriophage adhesion proteins according to the present invention.

For a binding of the complex the magnetic particles are contacted with the bacteriophage adhesion protein-bacteria/cell component complex and are preferably incubated. The incubation occurs at a temperature in the range of about 4° C. to 90° C., particularly in the range of about 4° C. to 45° C., more preferred at a temperature in the range of about 15° C. to 37° C., particularly preferred at a temperature in the range of about 20° C. to 37° C., in particular at RT, for up to 6 hours, preferably up to 4 hours, more preferred 2 hours, in particular 1 hour, in particular preferred 1 s-20 minutes, exceptionally preferred 10 s-5 minutes. For example, the incubation can occur for about 2 to 120 minutes at about 4° C. to 37° C., preferably for about 20 to 30 minutes at about 25° C. to 37° C., preferably more preferred for 10 s-5 minutes at 25° C.

The method of the present invention can be performed with other solid supports which may be added to the sample in an analogous manner. The single incubation conditions and separation steps have to be adapted for the different solid supports accordingly. This may easily be performed in test series and does not require any further explanation for the skilled artisan.

Alternatively, the two-step method may be performed in accordingly coated solid supports which may not be added to the sample, but wherein the sample is added onto or into the solid support, e.g. a reaction tube, pipette tip, magnetic particles, glass particles, agarose particles, latex particles, reaction tubes, microtiter plates, membranes, filtration media, or chromatographic media. For this purpose, the sample is added after step a), e.g. into the respective wells of the microtiter plate, and is incubated there, particularly for about 20-30 minutes with the other conditions remaining as described above. The wells of the microtiter plate or the inner walls of a reaction tube may exhibit the same coatings as described above for the solid support.

The enrichment and purification, respectively, of the bacterial cells and/or cell components may also be performed in a method comprising the following steps (one-step method):

a) contacting a sample containing bacterial cells and/or cell components with a solid support on the surface of which bacteriophage adhesion proteins according to the present invention are applied, preferably with an incubation of about 10 s-60 minutes, b) separating the magnetic support with the bacterial cells and/or cell components bound to it from the sample.

The bacteriophage adhesion proteins according to the present invention may be fixed to the magnetic support via covalent coupling. This allows a very tight binding to the magnetic support and thus the application of severe washing conditions for the washing of the cells which is possibly required for a further processing of the enriched cells. The coupling of said bacteriophage adhesion proteins via adsorption is a very simple and cost-effective method. One-step as well as two-step methods are possible by means of coupling said bacteriophage adhesion proteins via biotin/streptavidin or comparable ligand/receptor systems. The streptavidin used in this approach may be fixed via adsorption, as well as via chemical coupling. A functional immobilisation is important in the coating method, that means that despite their binding to the solid supports, said bacteriophage adhesion proteins exhibit structures which are accessible to bacteria.

The bacteriophage adhesion proteins according to the present invention may be coupled via covalent coupling to the magnetic support, which have already been activated by the manufacturers, for instance to magnetic particles by Merck, Estapor, etc. via standard conditions, for example —$NH_2$ via cyanuryl chloride (Russina Chemical Rev., 1964, 33: 92-103), or —COO— via EDC (1-Ethyl-3'[3'Dimethylaminopropyl]carbodiimid) (Anal. Biochem. 1990, 185: 131-135) or via tosyl- or epoxy-coupling. Moreover, the magnetic support may be activated directedly using appropriate methods. Furthermore, the coupling may occur via maleimide or iodoacetyl spacer to, for instance, a N-terminal introduced cystein.

The immobilisation of the bacteriophage adhesion proteins according to the present invention to the magnetic support via adsorption may be performed by incubation of a bacteriophage adhesion protein solution in aqueous buffer, for instance 100 mM Tris pH 7.3, or 100 mM sodium phosphate pH 7.5, PBS (10 mM sodium phosphate pH 7.4, 150 mM sodium chloride) for several hours or overnight at about 4° C. to 45° C., preferably at about 15° C. to 37° C., more preferred at about 20° C. to 37° C., in particular preferred at about 37° C. or RT, in particular preferred at about 30° C. to 65° C. for about 10 min-2 hours. The coating solution is discarded after the adsorption and the support structure is stored in aqueous, optionally in buffered solution.

A characteristic feature of the two-step method in comparison to the one-step method is that in the two-step method there is no preincubation of the bacteriophage adhesion proteins with the solid support before sample addition. As a difference, the bacteriophage adhesion proteins are not immobilised when getting into contact with the bacterial cells or cell components but act free in solution. In the two-step method, the complexes of bacteriophage adhesion protein and bacterial cells or cell components are immobilised to the solid support, whereas in the one-step method the bacterial cells or cell components are immobilised directly onto the bacterial adhesion proteins which are fixed to the solid support. Each method has its advantages or disadvantages depending on the exact assay format and the conditions to be used. The skilled person performing an assay may use both methods in order to decide which method performs better in the distinct assay he wants to use.

The methods according to the present invention (one-step and two-step method) may be used, for example, as an alternative for centrifugation in an automated purification of bacterial cells. This enables the automation of, e.g., the genome analysis, i.e. from the inoculation of the bacterial cultures to the determination of the sequence. Furthermore, the method of the present invention may be used, for example, to isolate cell components, particularly lipopolysaccharide, endotoxin, complete O-antigen or fragments thereof like the oligosaccharides of the repeating units.

A further aspect of the present invention relates to a kit for the enrichment of bacterial cells and/or cell components, comprising the solid supports according to the present invention, for example the magnetic particles, glass particles, agarose particles, latex particles, reaction tubes, pipette tips, microtiter plates, membranes, filtration media, or chromatographic media as well as the solutions including the test reagents necessary for the enrichment of the bacteria and/or cell components. Preferably, a kit according to the present invention may further comprises washing solutions and/or substances permeabilizing or destroying the bacterial membrane.

EXAMPLES

The following examples explain the present invention but are not considered to be limiting. Unless indicated differently, molecular biological standard methods were used, as e.g., described by Sambrock et al., 1989, Molecular Cloning: A Laboratory Manual, 2nd edition, Cold Spring Harbor Laboratory Press, Cold Spring Harbor, N.Y.

Example 1

Chemical Biotinylation of Bacteriophage Adhesion Proteins Using Sulfo-NHS-Biotin-Ester (NHS-Biotinylation)

Sulfo-NHS-LC-LC-biotin (sulfo-succinimidyl-6-(biotinamido)-6-hexanamido-hexanoate) forms stable amide components with primary amino group of the polypeptide amino acids (e.g. Lys) over the sulfo-NHS—(N-hydroxysuccinimide)-ester. Bacteriophage adhesion proteins at a concentration of around 1.5 mg/ml were incubated at room temperature for 15 min up to 120 min with a 1 to 20 times molar excess of sulfo-NHS-LC-LC-biotin over bacteriophage adhesion protein. 50 μl of the coupling reaction solution was stopped with 10 μl of 1 M Tris/HCL, pH 8.0 at different times. Coupled protein samples were dialyzes against 0.1 M sodium phosphate buffer, pH 7.4.

Example 2

Comparison of Cell Capture of *Salmonella* Cells of Serogroup E Using Inactivated Mutants of Full-Length and an N-Terminally Truncated Form of Det7 ORF790 Tail Spike

*Salmonella* cells of different serovars belonging to serogroups $E_1$ and $E_4$ were diluted 1:5 from an overnight culture in buffered peptone water and cultivated up to an $OD_{600}$ of 1. Cells were diluted to a concentration of $10^4$ cfu/ml in PBST buffer, pH 8.0. In a sample volume of 500 chemically biotinylated (by NHS-biotinylation) bacteriophage adhesion proteins of full-length-Det7 ORF790 (D485N) and N-terminally truncated Det7 ORF790 (Δ2-251, D485N) are added at a protein concentration of 5 μg/ml, mixed for 10 s, and RAS magnetic beads (streptavidin coated beads, Roche) added in a concentration of 50 Bacteriophage adhesion proteins, *Salmonella* cells and magnetic beads are incubated in a rollator for 20 min at room temperature. Beads-bacteriophage adhesion protein-bacterial cell-complexes are collected by magnetic separation and washed with 1 ml of PBST buffer. The beads-bacteriophage adhesion protein-bacterial cell-complexes are resuspended in the original sample volume and plated to XLD-agar plates which are incubated over night and the colonies counted. Captured cells are determined in comparison to the cells present in the sample. Cells bound unspecifically to the streptavidin coated beads are determined from controls without addition of bacteriophage adhesion protein.

Unspecific binding is observed in a range of up to 1.5%.

TABLE 1

Cell capture of *Salmonella* cells of serogroup E using inactivated mutants of full-length and N-terminally truncated form of Det7 ORF790 tail spike

| serovar | serogroup | Full-length-Det7 ORF790 (D485N) Specific cell capture, % | Det7 ORF790 (Δ2-251, D485N) |
|---|---|---|---|
| *Salmonella* Anatum | E1 | 46 | 97 |
| *Salmonella* Give | E1 | 56 | 96 |
| *Salmonella* Lexington | E1 | 55 | 97 |
| *Salmonella* Lexington | E1 | 53 | 98 |
| *Salmonella* Meleagridis | E1 | 25 | 94 |
| *Salmonella* Meleagridis | E1 | 61 | 96 |
| *Salmonella* Meleagridis | E1 | 50 | 95 |
| *Salmonella* Muenster | E1 | 52 | 94 |
| *Salmonella* Münster | E1 | 71 | 95 |
| *Salmonella* Newington | E1 | 68 | 96 |
| *Salmonella* Weltevreden | E1 | 56 | 96 |
| *Salmonella* Weltevreden | E1 | 38 | 95 |
| *Salmonella* Weltevreden | E1 | 57 | 97 |
| *Salmonella* Krefeld | E4 | 8 | 59 |
| *Salmonella* Krefeld | E4 | 7 | 65 |
| *Salmonella* Krefeld | E4 | 17 | 86 |
| *Salmonella* Liverpool | E4 | 12 | 78 |
| *Salmonella* Rideau | E4 | 11 | 91 |
| *Salmonella* Senftenberg | E4 | 3 | 80 |
| *Salmonella* Senftenberg | E4 | 15 | 65 |
| *Salmonella* Senftenberg | E4 | 14 | 55 |
| *Salmonella* Senftenberg | E4 | 15 | 78 |
| *Salmonella* Visby | E4 | 14 | 83 |

It is observed that Det7 ORF790 tail spike specifically binds *Salmonella* cells of strains belonging to serogroups $E_1$ and $E_4$. N-terminally truncated Det7 ORF790 (Δ2-251, D485N) according to the invention binds bacterial cells from serogroup $E_1$ with very high efficiency of specific binding of more than 90%, mostly more than 95% whereas full-length-Det7 ORF790 (D485N) binds with lower efficiency, mostly in the range of 50% binding. *Salmomella* cells from serogroup $E_4$ generally are bound with lower efficiency. But whereas N-terminally truncated Det7 ORF790 (Δ2-251, D485N) according to the invention binds serogroup $E_4$ with efficiencies in the range of 50 to 90%, full-length-Det7 ORF790 (D485N) binds with efficiencies lower than 20%. This shows that the truncated form of Det7 ORF790 according to the invention captures and detects the host cells with higher efficiency than the full-length form which is naturally observed.

Example 3

Preparation of LPS from Gram Negative Bacterial Cells (EDTA Extraction)

Bacterial cells (50 ml) from a culture growing in logarithmic phase are centrifuged (20 min, 4000 rpm, 4° C.), and the cell pellet is resuspended in 10 ml buffer including 10 mM Tris, 50 mM EDTA, pH 8. The suspension is incubated at room temperature for 10 min and vortexed several times. Cells are again centrifuged (20 min, 4000 rpm, 4° C.), and the supernatant containing extracted LPS is transferred into a fresh tube. Aceton is added up to a volume of 50 ml, and the tube is incubated at −20° C. for 30 min. The precipitate (extracted LPS) is centrifuged at 4000 rpm, 4° C. for 60 min in a table centrifuge. The supernatant is discarded and the precipitate is solubilized in 10 ml water in an ultrasonic bath. The precipitation with acetone repeated once, and the precipitate (extracted LPS) desiccated in a vacuum exsiccator for 2 h. The LPS-pellet is then resolved in 1 ml of water.

Example 4

LPS Hydrolysis Assay

The LPS hydrolysis assay is a test for enzymatic activity of bacteriophage adhesion proteins. LPS containing the O-antigen is isolated from gram negative bacterial cells by the EDTA extraction method. LPS is incubated with bacteriophage adhesion proteins (concentrations as indicated) in hydrolysis buffer (50 mM sodium phosphate, pH 7.5) at room temperature for several hours (as indicated in the figures). The enzymatic reaction is stopped by addition of SDS-sample buffer, and boiling of the samples before application to a Tris-Tricin-polyacrylamide gel. "0 h" means that the bacteriophage adhesion protein is added to isolated LPS, and the reaction is stopped immediately after mixing by adding SDS-sample buffer (this lasts less than 20 s) and boiling of the samples. As the bacteriophage adhesion proteins are SDS-resistant, LPS hydrolysis may be possible until the proteins are denatured by boiling. This may last for around 1 min (the sample volume is 20 μl). For separation of LPS and its hydrolysis products like O-antigen fragments of different lengths, Tris-Tricin gradient gels (4-12% acrylamide) are run in Tris-Tricin buffer. The gels are stained by a silver staining procedure which preferentially stains LPS and polysaccharides compared to proteins according to Hitchcock and Brown, 1983, J. Bacteriology, 154, 269-277. Non-hydrolyzed LPS is observed as a smear of bands beginning from high molecular weight fractions down to low molecular weight fractions as EDTA extracted LPS contains molecules of different sizes. Hydrolyzed LPS contains no high molecular weight fractions as the bacteriophage adhesion proteins successively hydrolyze the O-antigen at specific saccharide bonds of the repeating units resulting in a characteristic "ladder-motif" of bands.

In an LPS hydrolysis assay using isolated LPS of *Salmonella* Lexington (serogroup $E_1$), the activity of wt-Det7-ORF790 tail spike and a variant according to the invention, namely Det7-ORF790 (Δ2-251, D485N) was compared. Whereas isolated LPS without addition of bacteriophage adhesion protein appears as a continuous smear of polysaccharide bands of different length, the samples after addition of bacteriophage adhesion proteins (0.2 mg protein per sample) show hydrolysis of LPS resulting in a characteristic ladder band motif. It is seen, that after addition of wt-Det7-ORF790, most of the LPS is already hydrolyzed after a few seconds ("0 h") where no bands of higher molecular weight are seen, and hydrolysis proceeds so that only 2 prominent bands are observed after 4 h and 30 h of incubation. In contrast, using the inactivated mutant Det7-ORF790 (Δ2-251, D485N), the degree of hydrolysis which is already observed with wild-type protein after a few seconds needs 30 h of incubation with the inactivated mutant according to the invention. Up to 30 h of incubation there are still fragments of higher molecular weight. It can be stated that although the mutant Det7-ORF790 (Δ2-251, D485N) is not completely inactive, the hydrolysis rate is reduced by a factor of at least 1000.

In an analogous LPS hydrolysis assay using isolated LPS of an *E. coli* O111 strain, the activity of wt-O111_BP1 in comparison to N-terminally truncated and inactivated variants according to the invention, namely O111_BP1 (Δ2-107) comprising the mutations D204N or D277N or E337Q or E415Q or D471N or E482Q or D492N or the double mutation E476Q/D477N were compared. Isolated LPS of this bacterial strain without addition of bacteriophage adhesion protein shows a characteristic ladder motif of bands in the lower molecular weight region, and a smear of bands in the higher molecular weight region. Wt O111_BP1 shows almost complete LPS hydrolysis after 4 h incubation at room temperature with some low molecular weight bands persisting in the low molecular range, and also significant lysis after "0 h" incubation, where a smear or high molecular weight bands is still visible. LPS hydrolysis of the mutants according to the invention is significantly reduced compared to the wild-type, especially in the variants O111_BP1 ($\Delta$2-107, D204N), O111_BP1 ($\Delta$2-107, D277N), O111_BP1 ($\Delta$2-107, E337Q), but also in O111_BP1 ($\Delta$2-107, D471N), O111_BP1 ($\Delta$2-107, E482Q), O111_BP1 ($\Delta$2-107, D292N), and O111_BP1 ($\Delta$2-107, E476Q/D477N). The variant O111_BP1 ($\Delta$2-107, E415Q) shows a hydrolysis activity comparable to the wild-type, and is less preferred.

Example 5

Test for Expression, Solubility and Stability with Respect to SDS of Bacteriophage Adhesion Proteins 25 ml LB-medium (optionally containing antibiotics) were inoculated 1 to 100 with over night cultures of *E. coli* expression strains carrying the respective plasmids for the bacteriophage adhesion protein constructs to be expressed. The bacteria were cultivated up to an $OD_{600}$ of 0.5 to 0.7 at the expression temperatures indicated, and induced with 1 mM IPTG for 4 hours. A control sample was taken for protein expression without induction. After 4 h a 1 ml sample was taken, and the *E. coli* cells centrifuged for 10 min at 13000 rpm in a table centrifuge. The cell pellet was resuspended in 300 µl cell disruption buffer (50 mM Tris, 25 mM EDTA, pH 8.0). Ultrasonic cell disruption was performed for 2×20 s. The cell disruption sample was centrifuged for 15 min at 13000 rpm to obtain the insoluble pellet fraction which was resuspended in 300 µl cell disruption buffer, and a supernatant fraction containing soluble protein. 12 µl of the pellet fraction and the supernatant fraction were mixed with 3 µl 5× concentrated SDS-sample buffer (final concentrations 2% SDS, 10% glycerol, 10% 2-mercaptoethanol, 0.004% bromphenol blue, 0.125 M Tris, pH 6.8) each, and boiled for 5 min to denature the proteins and disrupt protein oligomers, before loading to an SDS-gel. Another 12 µl of the supernatant fraction was also mixed with 3 µl 5× concentrated SDS-sample buffer, but directly loaded to an SDS-gel without boiling. If the protein of interest is resistant to SDS, it is not dissociated to monomers, but migrates with the mobility of the oligomer also in an SDS-gel. With common, non SDS-resistant proteins, this behaviour is only observed using native gels which do not contain SDS.

Truncated ($\Delta$2-151) and inactivated forms (single amino acid mutations D437N, D440N, E406Q) of SBP1 exhibit soluble, SDS-resistant trimeric phage proteins after expression at 30° C. and 37° C. All variants of SBP1 according to the invention show good expression at 30° C. and 37° C., but the solubility of the proteins is significantly increased after expression at 30° C. Almost all of the protein migrates with the mobility of the trimer when the protein is not boiled prior to SDS-gel electrophoresis. This means that the phage adhesion proteins have adopted a native SDS-resistant, oligomeric form.

The truncated and inactivated form of O157BP1 ($\Delta$2-162, D463N) exhibits a soluble, SDS-resistant oligomeric phage protein after expression at 30° C. It is observed that in all constructs only a small fraction of O157BP1 is found in the insoluble pellet fraction, whereas most of the protein is expressed in a soluble form. After boiling in SDS-sample buffer, the protein migrates with the molecular mass of a monomer (around 70 to 85 kDa depending on the size of the tag). Without boiling, the protein is stable in SDS-sample buffer (2% SDS) and migrates with the molecular mass of an oligomer, probably a trimer.

Example 6

Capture of *Salmonella* Cells of Serovars B and D1 by Specific Binding to Det7 Tail Spike SBP1

The N-terminally truncated inactive variant Det7 tail spike SBP1($\Delta$2-151)D437N was covalently coupled to epoxy- or tosyl-activated magnetic polystyrene beads (Dynabeads M-270 Epoxy, Dynabeads M-280 Tosylactivated, Dynal) via the amino- or sulfhydryl groups present in proteins according to the manufacturers instructions. *Salmonella* cells from different strains from serogroup B and D1 (concentration ~$10^4$ cfu/ml) were incubated with SBP1 coated beads for 20 min at room temperature. Magnetic beads were collected in the magnetic separator and washed 2 times with PBST-buffer. The magnetic beads with the *Salmonella* cells bound are plated on *Salmonella* specific XLD-agar plates to determine the number of cells captured compared to the number of cells present in the sample.

The N-terminally truncated inactive variant of the Det7 tailspike ($\Delta$2-151)D437N specifically binds *Salmonella* cells from a multitude of *Salmonella* strains from the serogroups B and D1. According to the one-step method. Covalent coupling of the bacteriophage adhesion proteins about expoxy- or tosyl-groups functions equally well.

Example 7

Capture of *Salmonella* Cells of Serovars B and D1 by Specific Binding to Magnetic Beads Coated with Det7 Tail Spike SBP1($\Delta$2-151)D437N in Comparison to Dynabeads Anti-*Salmonella* (1-Step Procedure)

The N-terminally truncated inactive variant Det7 tail spike SBP1($\Delta$2-151)D437N was covalently coupled to tosyl-activated magnetic polystyrene beads (Dynabeads M-280 Tosylactivated, Dynal) via the amino- or sulfhydryl groups present in proteins according to the manufacturers instructions. Dynabeads anti-Salmonella (Dynal) are commercially available magnetic beads which are coated with antibodies against *Salmonella*. *Salmonella* cells from different strains from serogroup B and D1 (concentration ~$10^4$ cfu/ml) were incubated with SBP1 coated beads or Dynabeads anti-Salmonella (beads concentration 2.5 to 3.0×$10^7$ beads/ml) for 20 min at room temperature in PBST-buffer. Magnetic beads were collected in the magnetic separator and washed 2 times with PBST-buffer. The magnetic beads with the *Salmonella* cells bound are plated on *Salmonella* specific XLD-agar plates to determine the number of cells captured compared to the number of cells present in the sample.

It turned out that *Salmonella* cells of different strains belonging to serogroups B or $D_1$ could be captured with efficiencies between 50% and 70% using Det7 tail spike SBP1($\Delta$2-151)D437N covalently coupled to tosyl-activated magnetic polystyrene beads, and with efficiencies between 30% and 60% using Dynabeads anti-Salmonella. The capture efficiency was in each case better using the bacteriophage adhesion protein coated beads than using the antibody coated beads.

Example 8

Detection of *E. Coli* O157 Using O157_BP1 in an Assay Analogous to an ELISA Format An *E. coli* O157 overnight culture is diluted 1:5 with LB medium, and cultivated up to $OD_{600}=1$ (this relates to $5\times10^8$ cells per ml). Cells are centrifuged for 10 min at 4° C. at 13000 rpm. The bacterial cell pellet is resuspended in PBS buffer (10 mM sodium phosphate, 150 mM sodium chloride, pH 7.4) and serial dilutions of the cells are performed up to $10^7$ cfu/ml. 100 µA of bacterial cell solutions of different concentrations are given in each well of microtiter plates (Nunc, Maxi Sorb). Bacterial cell binding is allowed for 1 h at 37° C. The sample solution is removed, and the wells are washed three times with 200 µl of washing buffer (10 mM Tris, 171 mM NaCl, 0.1% Tween 20, pH 7.2). 200 µl of PBST-BSA buffer are added as a blocking solution and incubated for 1 h at 37° C. PBST-BSA solution is removed. Biotinylated O157_BP1 in 100 µl PBST-BSA buffer (10 mM sodium phosphate, 150 mM sodium chloride, 0.1% Tween 20, 0.5% BSA, pH 7.4) is added at a concentration of 1 µg protein per well. Binding of O157_BP1 to bacterial cells is allowed for 1 h at 37° C. The solution is removed with a pipette. The wells are washed three times with 200 µl of washing buffer to remove unbound O157_BP1. 100 µl of a streptactin-HRP (horse radish peroxidase)-conjugate (0.02%) is added as a detector molecule, and incubated for 1 h at room temperature. The solution is removed, and the wells are washed three times with 200 µl of washing buffer to remove unbound streptactin-HRP-conjugate. 100 µl ABTS-staining solution (0.085 M sodium phosphate, 0.048 M citrate, pH 4.6, 0.2% ABTS (2,2 azino-bis(3-ethyl)benzthiazoline 6-sulfonic acid), 5% $H_2O_2$) is added and development of color is monitored at room temperature by measuring the absorbance at 405 nm over a time period of 120 min. As a control, samples with addition of bacterial cells, but without addition of O157_BP1 are measured to monitor background signal without specific binding of the streptactin-HRP-conjugate to biotinylated O157_BP1. The develop the exact cell number of *E. coli* cells in the test, 100 µl of the serial dilutions are plated to agar plates, and the colonies counted on the following day.

An *E. coli* O157 detection assay using 1 µg of O157_BP1 in the described assay format analogous to an ELISA assay reliably detects bacterial concentrations of $10^5$ cfu or more in a colorimetric assay using specific binding of O157_BP1 to the bacterial cells, and specific binding of a streptactin-HRP-conjugate to biotinylated O157_BP1 in complex with bacterial cells.

Example 9

Inclusivity and Exclusivity Testing of the Specific Binding of Bacterial Cells by O157_BP1 (One-Step Procedure)

All test strains used were grown over night in pre-cultures at 37° C. Before bacteria capture, the pre-cultures were diluted 1:5 in mTSB-medium (modified TSB medium, Oxoid) and grown to an $OD_{600}$ of 1. Cells are diluted to bacterial cell concentration between $10^8$ and $10^4$ cfu/ml. Capture was performed at a bacteria concentration of $10^4$ cfu/ml in PBST buffer (2.25 mM $NaH_2PO_4$, 7.75 mM $Na_2HPO_4$, 150 mM NaCl, 0.05% Tween, pH 6.7) in a sample volume of 500 µl. 0.3 µg O157_BP1 were immobilized to 10 µl MCB45 magnetic beads (Microcoat, beads precoated with streptavidin, concentration 10 mg/ml) for 15 min, added to the bacterial sample, and incubated at room temperature in a rolling incubator. After 20 min incubation, the bacteria-O157_BP1-magnetic beads complexes were collected in a magnetic separator, and washed 2 times with PBST-buffer. After that, 100 µl of the sample including the bacteria-O157_BP1-magnetic beads complexes were plated to Caso-agar plates, and incubated at 37° C. over night. Samples using streptavidin coated beads without addition of O157_BP1 were used as a control for unspecific binding. The fraction of specifically bound bacteria was calculated in relation to the bacterial cell number used in the test, which was also plated on Caso-agar plates directly after bacterial dilution, for comparison.

TABLE 2

Specific capture with O157_BP1 of *E. coli* O157 strains.

| *E. coli* strain | | % specific capture |
|---|---|---|
| EHEC | | |
| O157:H7 | S1716 | 100 |
| | S1717 | 99 |
| | S1718 | 99 |
| | S1719 | 100 |
| | S1720 | 99 |
| | S1721 | 96 |
| | S1722 | 99 |
| | S1723 | 90 |
| | S1724 | 90 |
| | S1725 | 91 |
| | S2405 | 98 |
| | S2406 | 99 |
| | S2407 | 99 |
| | S2409 | 99 |
| | S2410 | 99 |
| | S2411 | 96 |
| | S757 | 98 |
| | S600 | 99 |
| O157:H− | S1726 | 98 |
| | S1727 | 98 |
| | S1728 | 99 |
| | S1729 | 100 |
| | S1730 | 99 |
| | S2404 | 100 |
| | S2408 | 99 |
| | S597 | 98 |
| Non-EHEC | | |
| O157:H7 | S755 | 99 |
| | S756 | 99 |
| | S2370 | 97 |
| | S2372 | 96 |
| | S2374 | 94 |
| | S2376 | 96 |
| | S2395 | 99 |
| O157:H− | S504 | 98 |
| | S2371 | 98 |
| | S2373 | 98 |
| | S2375 | 94 |
| | S2377 | 97 |
| | S2378 | 97 |
| | S2379 | 94 |
| | S2380 | 90 |
| | S2384 | 96 |
| | S2385 | 96 |
| | S2386 | 96 |
| | S2389 | 98 |
| | S2390 | 97 |
| | S2391 | 96 |
| | S2392 | 97 |
| | S2393 | 96 |

TABLE 2-continued

Specific capture with O157_BP1 of *E. coli* O157 strains.

| *E. coli* strain | % specific capture |
|---|---|
| S2394 | 100 |
| S2396 | 99 |
| S2397 | 99 |
| S2398 | 98 |

The numbers of the *E. coli* strains are from the PROFOS culture collection.

O157_BP1 is capable of binding, all 26 *E. coli* O157 EHEC strains tested, and the 27 *E. coli* O157 non-EHEC strains tested with a very high efficiency of specific binding of higher or equal 90% of the cells in the sample, mostly even with an efficiency higher than 95%. There is no difference in binding efficiency between EHEC strains and non-EHEC strains, and also between strains presenting the H7-antigen or not (H7 versus H—) as long as the O157 antigen is present. This suggests that O157_BP1 is specific for the O157 antigen.

TABLE 3

Specific capture with O157_BP1 of non-O157 *E. coli* strains.

| Serotype | *E. coli* strain | % specific capture |
|---|---|---|
| O(rough):H20 | 686 | 0 |
| O6:H10 | 693 | 0 |
| O8:H45 | 689 | 0 |
| O26:H– | S2318 | 1 |
| O26:H11 | S2320 | 1 |
| O26:H11 | S2316 | 0 |
| O26:H11 | S2314 | 0 |
| O38:H8 | 506 | 5 |
| O55:H7 | 719 | 0 |
| O56:K+:H– | S2497 | 0 |
| O63:H6 | 503 | 0 |
| O73:H31 | 507 | 0 |
| O86:H2 | 690 | 0 |
| O86:H35 | 505 | 0 |
| O87:H32 | 684 | 0 |
| O91:H– | S2306 | 0 |
| O99:H33 | 508 | 0 |
| O103:H– | S2311 | 0 |
| O103:H2 | S2303 | 0 |
| O103:H3 | S2308 | 2 |
| O111:H– | S2303 | 0 |
| O118:H8 | 502 | 1 |
| O144:H4 | 683 | 0 |
| O145:H– | S2313 | 0 |
| O145:H34 | S2315 | 3 |
| O149:H– | 511 | 0 |
| O159:H21 | 510 | 0 |
| O167:H5(rough) | 512 | 0 |
| O9:H– | 509 | 4 |
| O145:H– | S2317 | 1 |
| O145:H34 | S2322 | 0 |

The numbers of the *E. coli* strains are from the PROFOS culture collection.

From the 31 non-O157 *E. coli* strains tested, none was bound with a specific capture efficiency of more than 5%, mostly capture efficiency was even 0% specific. This means that O157_BP1 does not bind to surface receptors specific for *E. coli* bacterial cells in general, but specifically binds to the O157 antigen.

TABLE 4

Specific capture with O157_BP1 of non *E. coli* strains

| Bacteria genus | Species - serotype in *Salmonella* strains, serogroup in brackets | % specific |
|---|---|---|
| *Citrobacter* | *braakii* | 0 |
| | *freundii* | 0 |
| | *freundii* | 0 |
| | *freundii* F90 | 99 |
| | *amalonaticus* | 8 |
| | *diversus* | 5 |
| | *alvei* | 0 |
| | *oxytoca* | 0 |
| *Hafnia* | *pneumoniae* | 0 |
| *Klebsiella* | *vulgaris* | 0 |
| | *mirabilis* | 0 |
| *Proteus* | *tarda* | 1 |
| | *cloacae* | 8 |
| *Escherichia* | *agglomerans* | 1 |
| *Enterobacter* | *hermannii* | 0 |
| | *fluorescens* | 1 |
| *Escherichia* | *putida* | 0 |
| *Pseudomonas* | *liquefaciens* | 0 |
| | *dysenteria* SV9 | 0 |
| *Serratia* | *morganii* | 0 |
| *Shigella* | *Choleraesuis* (C1) | 0 |
| *Morganella* | *Enteritidis* (D1) | 0 |
| *Salmonella* | *Agona* (B) | 0 |
| | *Urbana* (N) | 78 |
| | *Nijmegen* (N) | 64 |
| | *Morehead* (N) | 61 |
| | *Matopeni* (N) | 59 |
| | *Urbana* (N) | 81 |
| | *Urbana* (N) | 79 |
| | *Urbana* (N) | 85 |
| | *Zehlendorf* (N) | 87 |
| | *Kentucky* (C2-C3) | 3 |
| | *Bovismorbificans* (C2-C3) | 0 |
| *Staphylococcus* | *aureus* | 0 |

In was also tested whether O157_BP1 specifically binds to bacteria other than *E. coli* O157. From the 33 species tested mainly from other gram negative bacterial genera and one from a gram positive (*Staphylococcus aureus*), only the *Citrobacter* strain with the O157 antigen and the *Salmonella* strains belonging to serogroup N show significant binding to O157_BP1. From the art it is known (Samuel et al., 2004, J. Bacteriology 186, 6536-6543) that *Salmonella* serogroup N with its main antigen O:30 exhibits the same antigen as *E. coli* O157, and that there are some representatives in the genus *Citrobacter* which also possess an O-antigen identical to the O157 antigen in *E. coli*, and also lead to cross contamination in immunological tests using antibodies. The O157 antigen repeating unit has the chemical structure →2)αDPer4NAc(1→3)αLFuc(1→4)βDG1c(1→3)αDGalNAc(1→, which is also observed in *Salmonella enterica* O-antigen O30 and *Citrobacter freundii* F90 O-antigen. These *Citrobacter* and *Salmonella* bacterial strains have a rare incidence, but they are also potential pathogens like the *E. coli* O157 strains. Therefore, in assays where it is desired to capture all potential pathogens exhibiting the O157 antigen or in assays where it is desirable to purify the O157 antigen, these non-*E. coli* O157 bacterial strains do not disturb. For specific detection of *E. coli* O157 or *Citrobacter* O157 or *Salmonella* serogroup N one has to use a succeeding assay for strain specific detection like PCR or a precultivation medium favouring one bacterial species over the other.

Example 10

Generation of a Truncated Variant of Det7 ORF790 (D485N) by Limited Proteolysis 30 μl of a protein solution of Det7 ORF790 (D485N) with a concentration of ca. 1 mg/ml was mixed with 30 μl of a solution of proteinase K in buffer 0.1 M sodium phosphate, pH 7.4. Proteinase K was added in molar ratios of proteinase K to bacteriophage adhesion protein of $3\times10^{-5}$:1, $3\times10^{-4}$:1, $3\times10^{-2}$:1, 0.3:1 or 3:1. The protease digest samples were incubated at 37° C. for 1 h. Protease digests were stopped by addition of SDS sample buffer and boiling of the samples. Samples were run on 12% SDS-polyacrylamide gels and stained with Coomassie blue. N-terminal sequencing of the band belonging to the protein fragment resulting from a threefold molar excess of proteinase K over bacteriophage adhesion protein resulted in a protein starting with the sequence GKKLVLN which is from amino acid G321 of full-length Det7 ORF790 tail protein. The same proteolytically generated variant Det7 ORF790 (Δ2-320; D485N) resulted from a limited protease digest of the already truncated variant Det7 ORF790 (Δ2-251; D485N) showing that this is probably the shortest stable variant with N-terminal truncation. It came out that several fragments with a length between full-length Det7 ORF790 tail protein and the variant Det7 ORF790 (Δ2-320) were populated as intermediates so that also other truncated variants as suggested by homology comparison are structurally sensible.

Example 11 oNPG (ortho-nitrophenyl-βD-galactopyranoside)-Test Using the *E. coli* Own β-Galactosidase Activity For Detection (Two-Step Method)

*E. coli* cells from overnight cultures which were induced by 1 mM IPTG were diluted 1:10 in LB medium. 5 μg bacteriophage adhesion protein comprising a strep-tag or a biotin were pipetted into one well of a microtiter plate. 200 μl of the diluted bacterial cell suspension was added and incubated for 15 min at room temperature. Streptavidin coated magnetic beads (Merck) were diluted 1:1 with PBST-buffer, and 5 μl of the beads suspension were added per well. The solution containing bacteriophage adhesion protein, bacterial cells and magnetic beads was incubated at room temperature for 20 min up to 45 min. Magnetic beads were collected at the bottom of the wells using a magnetic block, the supernatant including unbound cells removed and washed two times with 200 μl PBST buffer. The pellet containing the magnetic beads-bacteriophage adhesion protein-bacterial cell complexes was resuspended in 200 μl oNPG-reaction solution and incubated at 37° C. for 1 h. 40 ml oNPG-reaction solution contains 5 ml of 0.5 M sodium phosphate, pH 7.0, 2.5 ml of Ringer's solution (NaCl 8 g/l, $CaCl_2$ 0.2 g/l, KCl 0.2 g/l, $NaHCO_3$ 1 g/l), 27.5 ml $H_2O$, and 5 ml oNPG standard solution. oNPG standard solution has the following composition: 15 mg oNPG in 1 ml $H_2O$, 4 μl 1 M Tris/HCl, pH 9.5, 13 μl 0.1 N HCl, 0.08% Triton X-100, 5 μl/ml polmyxin B solution with 10 mg/ml. The β-galactosidase reaction was stopped by adding 50 μl carbonate buffer (di-sodium carbonate 28 g/l, mono-sodium carbonate 12 g/l, sodium citrate 100 g/l) and cooling down to 4° C. Magnetic beads complexes were again collected at the bottom of the wells and 150 μl of the supernatant per well were transferred into a polystyrol microtiter plate for measurement of the absorption at 425 nm. The colorimetric signal was corrected for the background absorption measured at 620 nm. Samples without addition of bacteriophage adhesion protein were taken as a control for unspecific adsorption of the bacterial cells to the magnetic beads or to the microtiter plate. The ratio of the absorption measured in samples with bacteriophage adhesion protein to samples without protein added was taken as a signal for specific binding of bacterial cells by the respective bacteriophage adhesion protein.

The oNPG-test was used for colorimetric detection of *E. coli* O26 using O111_BP1 wt and the truncated variant O111_BP1 (Δ2-107). Both bacteriophage adhesion proteins exhibited an N-terminal strep-tag for efficient binding to streptavidin coated beads. An A425 signal ratio of around two or more signalizes specific cell capture of the respective bacterial cells. It turned out that both bacteriophage adhesion proteins were suitable to specifically detect a variety of *E. coli* O26 strains. Only strain number 2680 gave a weaker signal. It also turned out that specific cell binding was always better using the N-terminally shortened variant O111_BP1 (Δ2-107) than using the wild type protein containing the bacteriophage head binding domain.

Example 12

Specific Cell Binding of *Salmonella* Cells of Serogroups B and D₁ by P22 Tsp (Δ2-108; D392N) and Det7 tsp (Δ2-151; D437N)

Both bacteriophage adhesion proteins, P22 tsp (Δ2-108; D392N) and Det7 tail spike SBP1(Δ2-151; D437N) were chemically biotinylated using the NHS-biotinylation protocol. Cell capture was performed using the 2-step-method with a concentration of 30 μg/ml bacteriophage adhesion proteins, $10^4$ *Salmonella* cells per nil, and 50 μg/ml RAS magnetic beads (streptavidin coated beads, Roche). The binding time for bacterial cells and bacteriophage adhesion proteins was 1 min, and the binding time for the beads was 20 min at room temperature. The collected complexes of magnetic beads, bacterial cells and bacteriophage adhesion proteins were washed once with double the sample volume. Cell capture was determined as percentage of the cells introduced in the assay. As a control for unspecific binding, RAS beads without protein coating were used. Unspecific cell binding by uncoated beads ranged between 0% and 2%. The values for cell capture presented in table 5 are mean values between 4 determinations using two bacteriophage adhesion proteins from two different protein purifications, and double determinations of the capture efficiencies.

TABLE 5

Specific cell binding of *Salmonella* cells of serogroups B and D₁ by P22 tsp (Δ2-108; D392N) and Det7 tsp (Δ2-151; D437N)

| *Salmonella* serovar | serogroup | P22 tsp (Δ2-108; D392N) cell capture, % | Det7 tsp (Δ2-151; D437N) |
|---|---|---|---|
| S. Abony | B | 40.4 | 77.0 |
| S. Agona | B | 81.3 | 89.2 |
| S. Brandenburg | B | 48.7 | 89.9 |
| S. Bredeney | B | 0.5 | 0.6 |
| S. Derby | B | 87.3 | 92.3 |
| S. Heidelberg | B | 65.7 | 94.6 |
| S. Indiana | B | 44.2 | 84.6 |
| S. Paratyphi B | B | 74.4 | 93.6 |
| S. Paratyphi B | B | 51.2 | 94.4 |

TABLE 5-continued

Specific cell binding of Salmonella cells of serogroups B and D₁ by P22 tsp (Δ2-108; D392N) and Det7 tsp (Δ2-151; D437N)

| Salmonella serovar | serogroup | P22 tsp (Δ2-108; D392N) cell capture, % | Det7 tsp (Δ2-151; D437N) cell capture, % |
|---|---|---|---|
| S. Paratyphi B | B | 70.6 | 88.4 |
| S. Paratyphi B | B | 64.3 | 89.7 |
| S. Paratyphi B | B | 8.9 | 29.2 |
| S. Paratyphi B | B | 64.6 | 93.6 |
| S. Paratyphi B | B | 71.4 | 94.7 |
| S. Paratyphi B | B | 77.5 | 96.1 |
| S. Paratyphi B | B | 59.6 | 90.4 |
| S. Paratyphi B | B | 64.6 | 97.4 |
| S. Reading | B | 52.3 | 41.8 |
| S. Saintpaul | B | 30.2 | 91.3 |
| S. Saintpaul | B | 87.4 | 81.3 |
| S. Saintpaul | B | 88.2 | 81.8 |
| S. Saintpaul | B | 64.7 | 55.5 |
| S. Schwarzengrund | B | 0.3 | 0.4 |
| S. Stanley | B | 57.5 | 83.2 |
| S. Typhimurium | B | 65.6 | 93.7 |
| S. Typhimurium | B | 69.8 | 91.5 |
| S. Typhimurium | B | 55.9 | 89.3 |
| S. Typhimurium | B | 62.2 | 90.5 |
| S. Typhimurium | B | 36.8 | 83.3 |
| S. Typhimurium | B | 47.4 | 72.9 |
| S. Berta | D1 | 56.2 | 83.3 |
| S. Berta | D1 | 62.5 | 91.7 |
| S. Berta | D1 | 63.8 | 92.8 |
| S. Dublin | D1 | 28.0 | 89.8 |
| S. Enteritidis | D1 | 35.8 | 93.2 |
| S. Enteritidis | D1 | 53.0 | 86.2 |
| S. Enteritidis | D1 | 36.3 | 83.5 |
| S. Enteritidis | D1 | 35.4 | 95.0 |
| S. Enteritidis | D1 | 29.9 | 90.2 |
| S. Enteritidis | D1 | 37.1 | 87.4 |
| S. Gallinarum | D1 | 34.6 | 71.3 |
| S. Javiana | D1 | 25.9 | 21.9 |
| S. Javiana | D1 | 90.0 | 77.3 |
| S. Javiana | D1 | 13.6 | 13.0 |
| S. Javiana | D1 | 27.0 | 21.6 |
| S. Moscow | D1 | 51.5 | 78.5 |
| S. Panama | D1 | 46.81 | 85.8 |
| S. Typhi | D1 | 9.6 | 72.7 |
| S. Typhi | D1 | 8.7 | 43.0 |
| S. Typhi | D1 | 2.5 | 13.9 |
| S. Typhi | D1 | 0.4 | 2.0 |
| S. Typhi | D1 | 5.1 | 44.6 |
| S. Typhi | D1 | 3.6 | 22.3 |
| S. Typhi | D1 | 12.4 | 65.6 |
| S. Typhi | D1 | 3.2 | 21.6 |
| S. Typhi | D1 | 10.2 | 60.6 |
| S. Baildon | D2 | 0.8 | 0.9 |
| S. Wernigerode | D2 | 0.5 | 0.7 |
| S. Mayday | D2 | 1.0 | 0.5 |
| Salmonella SII | D3 | 1.8 | 2.0 |
| Salmonella SII | D3 | 0.6 | 0.4 |

Both bacteriophage adhesion proteins preferentially bind to Salmonella cells belonging to serogroups B and D₁, but not to cells belonging to serogroups D₂ or D₃. Serogroup B is characterized by O-antigens 1, 4 and 12 as main antigens whereas serogroup D₁ characterized by O-antigens 1, 9 and 12 as main antigens. Thus, is assumed that both bacteriophage adhesion proteins bind to Salmonella O-antigens 1 or 12 or both. As Salmonella Typhi which exhibits O-antigens 9 and 12, but lacks O-antigen 1 is generally bound with lower efficiency, especially from P22 tsp (Δ2-108; D392N), O-antigen 1 is likely to play an important role, but is not the only O-antigen bound. From the 56 Salmonella serovars tested belonging to serogroups B and D₁ only 3 were bound by Det7 tsp (Δ2-151; D437N) with an efficiency of less than 10%, whereas 10 serovars were bound by P22 tsp (Δ2-108; D392N) with an efficiency of less than 10%. In almost all of the serovars tested, Det7 tsp (Δ2-151; D437N) binds with significantly higher efficiency than P22 tsp (Δ2-108; D392N) so that is seems that Det7 tsp (Δ2-151; D437N) is more suitable in applications according to the invention than P22 tsp (Δ2-108; D392N).

The invention claimed is:

1. A bacteriophage adhesion protein, comprising the amino acid sequence according to SEQ ID NO: 9 but lacking residues 2-162 of SEQ ID NO: 8, SEQ ID NO: 11, SEQ ID NO: 12, or SEQ ID NO: 58;

or a bacteriophage adhesion protein exhibiting a truncation of the N-terminus from amino acid residue 2 to amino acid residue 161 and at least one mutation of D332 to N, D341 to N, D345 to N, E365 to Q, D381 to N, E392 to Q, D402 to N, D405 to N, E411 to Q, D417 to N, D428 to N, D431 to N, E444 to Q, E456 to Q, D459 to N, E483 to Q, E500 to Q, E518 to Q or D519 to N relating to SEQ ID NO: 60;

or a bacteriophage adhesion protein exhibiting a truncation of the N-terminus from amino acid residue 2 to amino acid residue 161 and at least one mutation of D332 to N, D341 to N, D345 to N, E365 to Q, D381 to N, E392 to Q, D402 to N, D405 to N, E411 to Q, D417 to N, D428 to N, D431 to N, E444 to Q, E456 to Q, D459 to N, E483 to Q, E500 to Q, E518 to Q or D519 to N relating to SEQ ID NO: 62;

or a bacteriophage adhesion protein exhibiting a truncation of the N-terminus from amino acid residue 2 to amino acid residue 161 and at least one mutation of D340 to N, D344 to N, E364 to Q, D380 to N, E391 to Q, D401 to N, D404 to N, E410 to Q, D416 to N, D427 to N, D430 to N, E443 to Q, E455 to Q, D458 to N, E482 to Q, E499 to Q, E517 to Q or D518 to N relating to SEQ ID NO: 64;

or bacteriophage adhesion protein exhibiting a truncation of the N-terminus from amino acid residue 2 to amino acid residue 156 and at least one mutation of E329 to Q, D351 to N, D358 to N, E375 to Q, E377 to Q, D383 to N, D385 to N, E393 to Q, E401 to Q, D446 to N, E468 to Q, D487 to N, E494 to Q, D495 to N, D496 to N, E503 to Q, E518 to Q or D523 to N relating to SEQ ID NO: 66;

or a bacteriophage adhesion protein exhibiting at least one mutation of D180 to N, D186 to N, D190 to N, D211 to N, D241 to N, E246 to Q, D254 to Q, D261 to N, D263 to N, D265 to N, E266 to Q, D301 to N, E324 to Q, D333 to N, E334 to Q, E336 to Q, D339 to Q or D357 to N relating to SEQ ID NO: 68;

or a bacteriophage adhesion protein exhibiting a truncation of the N-terminus from amino acid residue 2 to amino acid residue 169 and at least one mutation of D344 to N, D345 to N, E351 to Q, E356 to Q, D362 to N, D398 to N, E405 to Q, D408 to N, D412 to N, E425 to Q, E432 to Q, D435 to N, D452 to N, E498 to Q, D509 to N, E511 to Q, D529 to N, E534 to Q, E538 to Q, E547 to Q, D554 to N, D567 to N, D573 to N, D595 to N, E609 to Q, D615 to N or D636 to N relating to SEQ ID NO: 70;

or a bacteriophage adhesion protein exhibiting a truncation of the N-terminus from amino acid residue 2 to amino acid residue 107 and at least one mutation of D178 to N, D179 to N, E185 to Q, E190 to Q, D196 to N, D232 to N, E239 to Q, D242 to N, D246 to N, E259 to Q, E266 to Q, D269 to N, D286 to N, E332 to Q, E345 to Q, D363 to N, E368 to Q, E372 to Q, E381 to Q, D388 to N, D401 to N, D407 to N, D429 to N, E443 to Q, D449 to N or D470 to N relating to SEQ ID NO: 72;

or a bacteriophage adhesion protein exhibiting a truncation of the N-terminus from amino acid residue 2 to amino acid residue 107 and at least one mutation of D178 to N, D179 to N, E185 to Q, E190 to Q, D196 to N, D232 to N, E239 to Q, D242 to N, D246 to N, E259 to Q, E266 to Q, D269 to N, D286 to N, E332 to Q, E345 to Q, D363 to N, E368 to Q, E372 to Q, E381 to Q, D388 to N, D401 to N, D407 to N, D429 to N, E443 to Q, D449 to N or D470 to N relating to SEQ ID NO: 74.

2. A kit comprising bacteriophage adhesion proteins according to claim 1, a support and assay reagents for the detection, purification or enrichment of gram negative bacteria and/or cell components.

3. A method to detect gram negative bacteria, the method comprising the following steps:
 (a) coupling of bacteriophage adhesion proteins according to claim 1 to a support,
 (b) incubating the support coupled to said bacteriophage adhesion proteins with a sample,
 (c) optionally removing the sample and the bacteria of the sample not bound to said bacteriophage adhesion proteins,
 d) optionally adding substances permeabilizing or destroying the bacterial membrane and
 (e) detecting the gram negative bacteria in the sample bound to said bacteriophage adhesion proteins.

4. A method to detect gram negative bacteria, the method comprising the following steps:
 (a) contacting a sample containing bacterial cells or cell components with bacteriophage adhesion proteins according to claim 1, with an incubation time of 1 s to 20 minutes
 (b) Subsequent Incubation Of Said Sample, Containing The Bacterial Cells Or Cell Components and said bacteriophage adhesion proteins with a solid support, for 1-60 minutes,
 (c) optionally removing the sample and the bacteria of the sample not bound to said bacteriophage adhesion proteins,
 (d) optionally adding substances permeabilizing or destroying the bacterial membrane, and
 (e) detecting the gram negative bacteria in the sample bound to said bacteriophage adhesion proteins.

5. The method according to claim 4, wherein the sample is a medicine, a food, livestock material, water or an environmental sample.

6. A method for selective purification of gram negative bacterial cells or cell components comprising the following steps:
 (a) contacting a sample containing bacterial cells or cell components with bacteriophage adhesion proteins according to claim 1, with an incubation time of 1 s to 20 minutes,
 b) subsequent incubation of said sample, containing the bacterial cells or cell components and said bacteriophage adhesion proteins with a solid support, for 1-60 minutes, and
 (c) separation of the solid support with the gram negative bacterial cells or cell components bound via said bacteriophage adhesion proteins to said solid support from the sample.

7. A method for the enrichment or purification of gram negative bacterial cells and/or cell components comprising the following steps:
 (a) contacting a sample containing bacterial cells and/or cell components with a magnetic support on the surface of which bacteriophage adhesion proteins according to claim 1 are applied, with an incubation of 60 minutes, and
 (b) separating the magnetic support with the gram negative bacterial cells and/or cell components bound to it from the sample.

* * * * *

UNITED STATES PATENT AND TRADEMARK OFFICE
CERTIFICATE OF CORRECTION

PATENT NO. : 8,609,348 B2
APPLICATION NO. : 13/002465
DATED : December 17, 2013
INVENTOR(S) : Manfred Biebl et al.

It is certified that error appears in the above-identified patent and that said Letters Patent is hereby corrected as shown below:

In the Claims:

In claim 4, column 205, lines 31-32, delete "Subsequent Incubation Of Said Sample, Containing The Bacterial Cells Or Cell Components" and insert --subsequent incubation of said sample, containing the bacterial cells or cell components-- therefor.

In claim 7, column 206, line 29, before "60", insert --1 - --.

Signed and Sealed this
Eleventh Day of March, 2014

Michelle K. Lee
*Deputy Director of the United States Patent and Trademark Office*

SEQUENCE LISTING

```
<160> NUMBER OF SEQ ID NOS: 74

<210> SEQ ID NO 1
<211> LENGTH: 708
<212> TYPE: PRT
<213> ORGANISM: Bacteriophage

<400> SEQUENCE: 1

Met Ile Ser Gln Phe Asn Gln Pro Arg Gly Ser Thr Ser Ile Glu Val
1               5                   10                  15

Asn Lys Gln Ser Ile Ala Arg Asn Phe Gly Val Lys Glu Asp Glu Val
            20                  25                  30

Val Tyr Phe Ser Ser Gly Ile Asp Leu Ser Gly Phe Lys Val Ile Tyr
        35                  40                  45

Asp Glu Ser Thr Gln Arg Ala Tyr Ser Leu Pro Ser Gly Ile Val Ser
    50                  55                  60

Gly Thr Thr Ala Ile Ser Leu Asn Glu Gln Ala Ile Leu Thr His Ser
65                  70                  75                  80

Ala Gly Ser Val Asp Leu Gly Glu Leu Ala Val Ser Arg Glu Glu Tyr
```

-continued

```
                85                  90                  95
Val Thr Leu Pro Gly Ser Phe Asn Phe Gly His Ile Ile Asn Val Lys
            100                 105                 110

Asn Glu Leu Leu Val His Asp Asp Lys Lys Tyr Arg Trp Asp Gly Ala
            115                 120                 125

Leu Pro Lys Val Val Pro Ala Gly Ser Thr Pro Ala Ser Thr Gly Gly
            130                 135                 140

Val Gly Leu Gly Ala Trp Val Ser Val Gly Asp Ala Ala Phe Arg Gln
145                 150                 155                 160

Glu Ala Asn Lys Lys Phe Lys Tyr Ser Val Lys Leu Ser Asp Tyr Ser
                165                 170                 175

Thr Leu Gln Asp Ala Val Thr Asp Ala Val Asp Gly Leu Leu Ile Asp
            180                 185                 190

Ile Asn Tyr Asn Phe Thr Asp Gly Glu Ser Val Asp Phe Gly Gly Lys
            195                 200                 205

Ile Leu Thr Ile Asn Cys Lys Ala Lys Phe Ile Gly Asp Gly Ala Leu
            210                 215                 220

Ile Phe Asn Asn Met Gly Pro Gly Ser Val Ile Asn Gln Pro Phe Met
225                 230                 235                 240

Glu Ser Lys Thr Thr Pro Trp Val Ile Phe Pro Trp Asp Ala Asp Gly
                245                 250                 255

Lys Trp Ile Thr Asp Ala Ala Leu Val Ala Ala Thr Leu Lys Gln Ser
                260                 265                 270

Lys Ile Glu Gly Tyr Gln Pro Gly Val Asn Asp Trp Val Lys Phe Pro
            275                 280                 285

Gly Leu Glu Ala Leu Leu Pro Gln Asn Val Lys Asp Gln His Ile Ala
            290                 295                 300

Ala Thr Leu Asp Ile Arg Ser Ala Ser Arg Val Glu Ile Arg Asn Ala
305                 310                 315                 320

Gly Gly Leu Met Ala Ala Tyr Leu Phe Arg Ser Cys His His Cys Lys
                325                 330                 335

Val Ile Asp Ser Asp Ser Ile Ile Gly Gly Lys Asp Gly Ile Ile Thr
            340                 345                 350

Phe Glu Asn Leu Ser Gly Asp Trp Gly Leu Gly Asn Tyr Val Ile Gly
            355                 360                 365

Gly Arg Val His Tyr Gly Ser Gly Val Gln Phe Leu Arg Asn
            370                 375                 380

Asn Gly Gly Glu Ser His Asn Gly Gly Val Ile Gly Val Thr Ser Trp
385                 390                 395                 400

Arg Ala Gly Glu Ser Gly Phe Lys Thr Tyr Gln Gly Ser Val Gly Gly
                405                 410                 415

Gly Thr Ala Arg Asn Tyr Asn Leu Gln Phe Arg Asp Ser Val Ala Leu
            420                 425                 430

Ser Pro Val Trp Asp Gly Phe Asp Leu Gly Ser Asp Pro Gly Met Ala
            435                 440                 445

Pro Glu Pro Asp Arg Pro Gly Asp Leu Pro Val Ser Glu Tyr Pro Phe
450                 455                 460

His Gln Leu Pro Asn Asn His Leu Val Asp Asn Ile Leu Val Met Asn
465                 470                 475                 480

Ser Leu Gly Val Gly Leu Gly Met Asp Gly Ser Gly Tyr Val Ser
                485                 490                 495

Asn Val Thr Val Gln Asp Cys Ala Gly Ala Gly Met Leu Ala His Thr
            500                 505                 510
```

```
Tyr Asn Arg Val Phe Ser Asn Ile Thr Val Ile Asp Cys Asn Tyr Leu
            515                 520                 525

Asn Phe Asp Ser Asp Gln Ile Ile Ile Gly Asp Cys Ile Val Asn
530                 535                 540

Gly Ile Arg Ala Ala Gly Ile Lys Pro Gln Pro Ser Asn Gly Leu Val
545                 550                 555                 560

Ile Ser Ala Pro Asn Ser Thr Ile Ser Gly Leu Val Gly Asn Val Pro
                565                 570                 575

Pro Asp Lys Ile Leu Val Gly Asn Leu Leu Asp Pro Val Leu Gly Gln
                580                 585                 590

Ser Arg Val Ile Gly Phe Asn Ser Asp Thr Ala Glu Leu Ala Leu Arg
            595                 600                 605

Ile Asn Lys Leu Ser Ala Thr Leu Asp Ser Gly Ala Leu Arg Ser His
        610                 615                 620

Leu Asn Gly Tyr Ala Gly Ser Gly Ser Ala Trp Thr Glu Leu Thr Ala
625                 630                 635                 640

Leu Ser Gly Ser Thr Pro Asn Ala Val Ser Leu Lys Val Asn Arg Gly
                645                 650                 655

Asp Tyr Lys Thr Thr Glu Ile Pro Ile Ser Gly Thr Val Leu Pro Asp
                660                 665                 670

Glu Gly Val Leu Asp Ile Asn Thr Met Ser Leu Tyr Leu Asp Ala Gly
            675                 680                 685

Ala Leu Trp Ala Leu Ile Arg Leu Pro Asp Gly Ser Lys Thr Arg Met
690                 695                 700

Lys Leu Ser Val
705

<210> SEQ ID NO 2
<211> LENGTH: 558
<212> TYPE: PRT
<213> ORGANISM: Artificial sequence
<220> FEATURE:
<223> OTHER INFORMATION: Det7 tail spike SBP1

<400> SEQUENCE: 2

Met Ser Val Gly Asp Ala Ala Phe Arg Gln Glu Ala Asn Lys Lys Phe
1               5                   10                  15

Lys Tyr Ser Val Lys Leu Ser Asp Tyr Ser Thr Leu Gln Asp Ala Val
            20                  25                  30

Thr Asp Ala Val Asp Gly Leu Leu Ile Asp Ile Asn Tyr Asn Phe Thr
        35                  40                  45

Asp Gly Glu Ser Val Asp Phe Gly Gly Lys Ile Leu Thr Ile Asn Cys
    50                  55                  60

Lys Ala Lys Phe Ile Gly Asp Gly Ala Leu Ile Phe Asn Asn Met Gly
65                  70                  75                  80

Pro Gly Ser Val Ile Asn Gln Pro Phe Met Glu Ser Lys Thr Thr Pro
                85                  90                  95

Trp Val Ile Phe Pro Trp Asp Ala Asp Gly Lys Trp Ile Thr Asp Ala
            100                 105                 110

Ala Leu Val Ala Ala Thr Leu Lys Gln Ser Lys Ile Glu Gly Tyr Gln
        115                 120                 125

Pro Gly Val Asn Asp Trp Val Lys Phe Pro Gly Leu Glu Ala Leu Leu
    130                 135                 140

Pro Gln Asn Val Lys Asp Gln His Ile Ala Ala Thr Leu Asp Ile Arg
145                 150                 155                 160

Ser Ala Ser Arg Val Glu Ile Arg Asn Ala Gly Gly Leu Met Ala Ala
```

```
                        165                 170                 175
Tyr Leu Phe Arg Ser Cys His His Cys Lys Val Ile Asp Ser Asp Ser
                    180                 185                 190
Ile Ile Gly Gly Lys Asp Gly Ile Ile Thr Phe Glu Asn Leu Ser Gly
                195                 200                 205
Asp Trp Gly Leu Gly Asn Tyr Val Ile Gly Gly Arg Val His Tyr Gly
            210                 215                 220
Ser Gly Ser Gly Val Gln Phe Leu Arg Asn Asn Gly Gly Glu Ser His
225                 230                 235                 240
Asn Gly Gly Val Ile Gly Val Thr Ser Trp Arg Ala Gly Glu Ser Gly
                245                 250                 255
Phe Lys Thr Tyr Gln Gly Ser Val Gly Gly Thr Ala Arg Asn Tyr
                260                 265                 270
Asn Leu Gln Phe Arg Asp Ser Val Ala Leu Ser Pro Val Trp Asn Gly
                275                 280                 285
Phe Asp Leu Gly Ser Asp Pro Gly Met Ala Pro Glu Pro Asp Arg Pro
            290                 295                 300
Gly Asp Leu Pro Val Ser Glu Tyr Pro Phe His Gln Leu Pro Asn Asn
305                 310                 315                 320
His Leu Val Asp Asn Ile Leu Val Met Asn Ser Leu Gly Val Gly Leu
                325                 330                 335
Gly Met Asp Gly Ser Gly Gly Tyr Val Ser Asn Val Thr Val Gln Asp
                340                 345                 350
Cys Ala Gly Ala Gly Met Leu Ala His Thr Tyr Asn Arg Val Phe Ser
                355                 360                 365
Asn Ile Thr Val Ile Asp Cys Asn Tyr Leu Asn Phe Asp Ser Asp Gln
                370                 375                 380
Ile Ile Ile Ile Gly Asp Cys Ile Val Asn Gly Ile Arg Ala Ala Gly
385                 390                 395                 400
Ile Lys Pro Gln Pro Ser Asn Gly Leu Val Ile Ser Ala Pro Asn Ser
                405                 410                 415
Thr Ile Ser Gly Leu Val Gly Asn Val Pro Pro Asp Lys Ile Leu Val
                420                 425                 430
Gly Asn Leu Leu Asp Pro Val Leu Gly Gln Ser Arg Val Ile Gly Phe
                435                 440                 445
Asn Ser Asp Thr Ala Glu Leu Ala Leu Arg Ile Asn Lys Leu Ser Ala
                450                 455                 460
Thr Leu Asp Ser Gly Ala Leu Arg Ser His Leu Asn Gly Tyr Ala Gly
465                 470                 475                 480
Ser Gly Ser Ala Trp Thr Glu Leu Thr Ala Leu Ser Gly Ser Thr Pro
                485                 490                 495
Asn Ala Val Ser Leu Lys Val Asn Arg Gly Asp Tyr Lys Thr Thr Glu
                500                 505                 510
Ile Pro Ile Ser Gly Thr Val Leu Pro Asp Glu Gly Val Leu Asp Ile
                515                 520                 525
Asn Thr Met Ser Leu Tyr Leu Asp Ala Gly Ala Leu Trp Ala Leu Ile
                530                 535                 540
Arg Leu Pro Asp Gly Ser Lys Thr Arg Met Lys Leu Ser Val
545                 550                 555

<210> SEQ ID NO 3
<211> LENGTH: 803
<212> TYPE: PRT
<213> ORGANISM: Bacteriophage
```

-continued

```
<400> SEQUENCE: 3

Met Gly Tyr Leu Gln Met Thr Arg Asn Val Glu Ser Ile Phe Gly Ala
1               5                   10                  15

Val Val Thr Ala Pro His Gln Ile Pro Tyr Thr Tyr Thr Ala Thr Gly
            20                  25                  30

Gly Glu Thr Phe Ile Ser Leu Pro Phe Tyr Pro Val Thr Gly Phe Ile
        35                  40                  45

Thr Ile Asn Gly Gly Val Gln Val Pro Val Asp Asn Tyr Glu Ile Asp
    50                  55                  60

Gly Asn Thr Val Asn Leu Gly Arg Ala Leu Glu Ala Asp Asp Val Val
65                  70                  75                  80

Tyr Cys Leu Phe Asp Lys Ile Leu Ser Pro Glu Asp Tyr Glu Asn Gly
                85                  90                  95

Ile Arg Ile Tyr Lys Phe Gln Ala Val Gly Asn Glu Thr Thr Phe Thr
            100                 105                 110

Pro Asp Phe Thr Thr Tyr Gly Val Gln Thr Leu Tyr Ile Asp Gly Lys
        115                 120                 125

Phe Gln Val Pro Gly Val Asp Tyr Asn Tyr Asn Ser Ala Thr Gly Val
    130                 135                 140

Val Ser Phe Leu Asn Gly Ser Pro Thr Ala Gly Val Trp Val Val Ala
145                 150                 155                 160

Glu Met Ser Ile Lys Gln Asn Tyr Leu Ala Leu Ser Ser Asp Ser Gly
                165                 170                 175

Ala Ser Leu Val Gly Thr Ser Ser Gly Asn Thr Val Gln Glu Val Leu
            180                 185                 190

Asn Ser His Ser Gly Ser Phe Gln Thr Gly Val Lys Leu Leu Ser Ser
        195                 200                 205

Asn Asp Leu Ile Val Asp Gln Ser Val Ile Pro Asn Gln Leu Tyr Arg
    210                 215                 220

Trp Asp Gly Ala Phe Pro Lys Thr Val Ala Ala Gly Ser Ser Pro Ala
225                 230                 235                 240

Ser Thr Gly Gly Val Gly Asn Gly Ser Trp Val Ser Val Gly Asp Ala
                245                 250                 255

Thr Leu Arg Gly Glu Leu Asn Asn Glu Gly Val Ile Asn Phe Ser His
            260                 265                 270

Ala Asp Thr Tyr Gly Asn Asp Ser Val Gly Ala His Leu Gln Asn Val
        275                 280                 285

Val Tyr Pro Thr Asp Ala Pro Phe Asn Ala Ala Thr Asp Gly Thr Thr
    290                 295                 300

Asp Thr Thr Val Ala Ile Lys Ser Ala Ile Ala His Cys Ile Ser Lys
305                 310                 315                 320

Gly Lys Lys Leu Val Leu Asn His Leu Phe Met Ile Thr Asp Thr Leu
                325                 330                 335

Val Ile Ser Asp Gly Leu His Val Glu Cys Leu Thr Ser Asp Ser Gly
            340                 345                 350

Val Lys Ser Asp Val Pro Ala Gly Lys Phe Ala Val Lys Ile Thr Gly
        355                 360                 365

Ala Asn Ser Gly Trp Phe Gly Gly Lys Ile Leu Gly Lys Asn Leu Pro
    370                 375                 380

Glu Ser Thr Thr Val Arg Gln Asp Gly Val Leu Phe Asp Glu Asn Ala
385                 390                 395                 400

Glu Tyr Cys Phe Ile Thr Gly Thr Glu Val Thr Gly Phe Phe Ala Lys
                405                 410                 415
```

```
Gly Leu His Thr Ser Asp Ala Asp Gly Val Gly Tyr Gly Ile Tyr Asp
                420                 425                 430

Lys Gly Tyr Gly Thr Leu Ile Ser Lys Cys Tyr Ala Asn Ser Lys Phe
                435                 440                 445

Cys Val Ala Leu Gly Gly Thr Glu Gly Arg Val Leu Lys Asn Arg Ile
450                 455                 460

Thr Asn Asn Tyr Leu Thr Ser Gly Glu Ala Lys Pro Trp Ser Trp Ala
465                 470                 475                 480

Ser Asn Tyr Trp Asp Gly Ile Val Ser Glu Asn Ala His Arg Tyr Val
                485                 490                 495

Ile Ala Phe Asn Asp Val Ser Ala Cys Gly Gln Ser Gly Ile Tyr Phe
                500                 505                 510

Gly Gly Asn Gly Gly Tyr Ser Thr Asp Asn Ile Ile Val Asn Asn Thr
                515                 520                 525

Val Tyr Ala Cys Trp Asn Arg Gly Ile Asp Met Gly Leu Phe Ser Glu
                530                 535                 540

Lys Ser Ala Thr Asn Asp Val Leu Arg Asn Ile Ile Lys Gly Asn Asn
545                 550                 555                 560

Thr Tyr Asn Asn Arg Glu Asn Asn Ile Trp Leu Ala Gly Val Ser Asn
                565                 570                 575

Cys Ser Val Val Gly Asn Thr Ser Trp Phe Asp Thr Asn Tyr Asp Val
                580                 585                 590

Ile Phe Ala Gly Tyr Pro Gly Gly His Ile Cys Ile Ser Leu Ala Ser
                595                 600                 605

Gly Ala Asn Gly Glu Ala Cys Val Gly Asn Thr Ile Asp Ser Asn Thr
                610                 615                 620

Cys Ile Asp Pro Arg Gly Asn Ala Gly Ile Thr Val Pro Thr Gly Ala
625                 630                 635                 640

Thr Gly Asn Val Phe Gly Ser Gly Asn Asn Leu Ser Gln Ala Gly Ala
                645                 650                 655

Ile Tyr Ile Ala Ser Pro Asp Leu Ile Thr Ser Asn Arg Phe Glu Leu
                660                 665                 670

Ala Val Thr Gly Ser Phe Thr Pro Val Leu Leu Pro Glu Ser Gly Ser
                675                 680                 685

Ile Thr Leu Ser Ser Ser Thr Gly Val Phe Arg Ala Thr Gly Asn
                690                 695                 700

Arg Ile Asp Phe Ser Val Thr Val Asn Val Ser Ser Ile Ser Ser Pro
705                 710                 715                 720

Ser Gly Asn Leu Asn Ile Ala Tyr Leu Pro Gly Met Ser Gly Lys Thr
                725                 730                 735

Ser Ser Thr Ser Met Phe Ile Ile Asp Tyr Trp Asn Asp Leu Thr Leu
                740                 745                 750

Ser Ser Gly Val Ile Pro Leu Ala Ser Leu Asn Leu Glu Asn Gln Asp
                755                 760                 765

Gln Ile Thr Val Tyr Arg Thr Asp Gly Gly Arg Val Leu Tyr Asp Phe
                770                 775                 780

Ser Ser Leu Met Lys Ser Thr Ser Ser Phe Ile Leu Lys Gly Phe Val
785                 790                 795                 800

Asp Phe Asn

<210> SEQ ID NO 4
<211> LENGTH: 553
<212> TYPE: PRT
<213> ORGANISM: Artificial sequence
<220> FEATURE:
```

<223> OTHER INFORMATION: Det7 ORF790 SBP2

<400> SEQUENCE: 4

```
Met Ser Val Gly Asp Ala Thr Leu Arg Gly Glu Leu Asn Asn Glu Gly
1               5                   10                  15

Val Ile Asn Phe Ser His Ala Asp Thr Tyr Gly Asn Asp Ser Val Gly
            20                  25                  30

Ala His Leu Gln Asn Val Val Tyr Pro Thr Asp Ala Pro Phe Asn Ala
        35                  40                  45

Ala Thr Asp Gly Thr Thr Asp Thr Thr Val Ala Ile Lys Ser Ala Ile
    50                  55                  60

Ala His Cys Ile Ser Lys Gly Lys Lys Leu Val Leu Asn His Leu Phe
65                  70                  75                  80

Met Ile Thr Asp Thr Leu Val Ile Ser Asp Gly Leu His Val Glu Cys
                85                  90                  95

Leu Thr Ser Asp Ser Gly Val Lys Ser Asp Val Pro Ala Gly Lys Phe
            100                 105                 110

Ala Val Lys Ile Thr Gly Ala Asn Ser Gly Trp Phe Gly Gly Lys Ile
        115                 120                 125

Leu Gly Lys Asn Leu Pro Glu Ser Thr Thr Val Arg Gln Asp Gly Val
    130                 135                 140

Leu Phe Asp Glu Asn Ala Glu Tyr Cys Phe Ile Thr Gly Thr Glu Val
145                 150                 155                 160

Thr Gly Phe Phe Ala Lys Gly Leu His Thr Ser Asp Ala Asp Gly Val
                165                 170                 175

Gly Tyr Gly Ile Tyr Asp Lys Gly Tyr Gly Thr Leu Ile Ser Lys Cys
            180                 185                 190

Tyr Ala Asn Ser Lys Phe Cys Val Ala Leu Gly Gly Thr Glu Gly Arg
        195                 200                 205

Val Leu Lys Asn Arg Ile Thr Asn Asn Tyr Leu Thr Ser Gly Glu Ala
    210                 215                 220

Lys Pro Trp Ser Trp Ala Ser Asn Tyr Trp Asn Gly Ile Val Ser Glu
225                 230                 235                 240

Asn Ala His Arg Tyr Val Ile Ala Phe Asn Asp Val Ser Ala Cys Gly
                245                 250                 255

Gln Ser Gly Ile Tyr Phe Gly Asn Gly Gly Tyr Ser Thr Asp Asn
            260                 265                 270

Ile Ile Val Asn Asn Thr Val Tyr Ala Cys Trp Asn Arg Gly Ile Asp
    275                 280                 285

Met Gly Leu Phe Ser Glu Lys Ser Ala Thr Asn Asp Val Leu Arg Asn
290                 295                 300

Ile Ile Lys Gly Asn Asn Thr Tyr Asn Asn Arg Glu Asn Asn Ile Trp
305                 310                 315                 320

Leu Ala Gly Val Ser Asn Cys Ser Val Val Gly Asn Thr Ser Trp Phe
                325                 330                 335

Asp Thr Asn Tyr Asp Val Ile Phe Ala Gly Tyr Pro Gly Gly His Ile
            340                 345                 350

Cys Ile Ser Leu Ala Ser Gly Ala Asn Gly Glu Ala Cys Val Gly Asn
        355                 360                 365

Thr Ile Asp Ser Asn Thr Cys Ile Asp Pro Arg Gly Asn Ala Gly Ile
    370                 375                 380

Thr Val Pro Thr Gly Ala Thr Gly Asn Val Phe Gly Ser Gly Asn Asn
385                 390                 395                 400

Leu Ser Gln Ala Gly Ala Ile Tyr Ile Ala Ser Pro Asp Leu Ile Thr
```

```
                     405                 410                 415
Ser Asn Arg Phe Glu Leu Ala Val Thr Gly Ser Phe Thr Pro Val Leu
                420                 425                 430

Leu Pro Glu Ser Gly Ser Ile Thr Leu Ser Ser Ser Thr Gly Val
            435                 440                 445

Phe Arg Ala Thr Gly Asn Arg Ile Asp Phe Ser Val Thr Asn Val
        450                 455                 460

Ser Ser Ile Ser Ser Pro Ser Gly Asn Leu Asn Ile Ala Tyr Leu Pro
465                 470                 475                 480

Gly Met Ser Gly Lys Thr Ser Ser Thr Ser Met Phe Ile Ile Asp Tyr
                485                 490                 495

Trp Asn Asp Leu Thr Leu Ser Ser Gly Val Ile Pro Leu Ala Ser Leu
                500                 505                 510

Asn Leu Glu Asn Gln Asp Gln Ile Thr Val Tyr Arg Thr Asp Gly Gly
            515                 520                 525

Arg Val Leu Tyr Asp Phe Ser Ser Leu Met Lys Ser Thr Ser Ser Phe
        530                 535                 540

Ile Leu Lys Gly Phe Val Asp Phe Asn
545                 550

<210> SEQ ID NO 5
<211> LENGTH: 484
<212> TYPE: PRT
<213> ORGANISM: Artificial sequence
<220> FEATURE:
<223> OTHER INFORMATION: Det7 ORF790 SBP2

<400> SEQUENCE: 5

Met Gly Lys Lys Leu Val Leu Asn His Leu Phe Met Ile Thr Asp Thr
1               5                   10                  15

Leu Val Ile Ser Asp Gly Leu His Val Glu Cys Leu Thr Ser Asp Ser
            20                  25                  30

Gly Val Lys Ser Asp Val Pro Ala Gly Lys Phe Ala Val Lys Ile Thr
        35                  40                  45

Gly Ala Asn Ser Gly Trp Phe Gly Gly Lys Ile Leu Gly Lys Asn Leu
    50                  55                  60

Pro Glu Ser Thr Thr Val Arg Gln Asp Gly Val Leu Phe Asp Glu Asn
65                  70                  75                  80

Ala Glu Tyr Cys Phe Ile Thr Gly Thr Glu Val Thr Gly Phe Phe Ala
                85                  90                  95

Lys Gly Leu His Thr Ser Asp Ala Asp Gly Val Gly Tyr Gly Ile Tyr
            100                 105                 110

Asp Lys Gly Tyr Gly Thr Leu Ile Ser Lys Cys Tyr Ala Asn Ser Lys
        115                 120                 125

Phe Cys Val Ala Leu Gly Gly Thr Glu Gly Arg Val Leu Lys Asn Arg
    130                 135                 140

Ile Thr Asn Asn Tyr Leu Thr Ser Gly Glu Ala Lys Pro Trp Ser Trp
145                 150                 155                 160

Ala Ser Asn Tyr Trp Asn Gly Ile Val Ser Glu Asn Ala His Arg Tyr
                165                 170                 175

Val Ile Ala Phe Asn Asp Val Ser Ala Cys Gly Gln Ser Gly Ile Tyr
            180                 185                 190

Phe Gly Gly Asn Gly Gly Tyr Ser Thr Asp Asn Ile Ile Val Asn Asn
        195                 200                 205

Thr Val Tyr Ala Cys Trp Asn Arg Gly Ile Asp Met Gly Leu Phe Ser
    210                 215                 220
```

Glu Lys Ser Ala Thr Asn Asp Val Leu Arg Asn Ile Ile Lys Gly Asn
225                 230                 235                 240

Asn Thr Tyr Asn Asn Arg Glu Asn Asn Ile Trp Leu Ala Gly Val Ser
            245                 250                 255

Asn Cys Ser Val Val Gly Asn Thr Ser Trp Phe Asp Thr Asn Tyr Asp
        260                 265                 270

Val Ile Phe Ala Gly Tyr Pro Gly Gly His Ile Cys Ile Ser Leu Ala
    275                 280                 285

Ser Gly Ala Asn Gly Glu Ala Cys Val Gly Asn Thr Ile Asp Ser Asn
290                 295                 300

Thr Cys Ile Asp Pro Arg Gly Asn Ala Gly Ile Thr Val Pro Thr Gly
305                 310                 315                 320

Ala Thr Gly Asn Val Phe Gly Ser Gly Asn Asn Leu Ser Gln Ala Gly
            325                 330                 335

Ala Ile Tyr Ile Ala Ser Pro Asp Leu Ile Thr Ser Asn Arg Phe Glu
        340                 345                 350

Leu Ala Val Thr Gly Ser Phe Thr Pro Val Leu Leu Pro Glu Ser Gly
    355                 360                 365

Ser Ile Thr Leu Ser Ser Ser Thr Gly Val Phe Arg Ala Thr Gly
370                 375                 380

Asn Arg Ile Asp Phe Ser Val Thr Val Asn Val Ser Ser Ile Ser Ser
385                 390                 395                 400

Pro Ser Gly Asn Leu Asn Ile Ala Tyr Leu Pro Gly Met Ser Gly Lys
            405                 410                 415

Thr Ser Ser Thr Ser Met Phe Ile Ile Asp Tyr Trp Asn Asp Leu Thr
        420                 425                 430

Leu Ser Ser Gly Val Ile Pro Leu Ala Ser Leu Asn Leu Glu Asn Gln
    435                 440                 445

Asp Gln Ile Thr Val Tyr Arg Thr Asp Gly Gly Arg Val Leu Tyr Asp
    450                 455                 460

Phe Ser Ser Leu Met Lys Ser Thr Ser Ser Phe Ile Leu Lys Gly Phe
465                 470                 475                 480

Val Asp Phe Asn

<210> SEQ ID NO 6
<211> LENGTH: 586
<212> TYPE: PRT
<213> ORGANISM: Bacteriophage

<400> SEQUENCE: 6

Met Thr Asp Ile Thr Ala Asn Val Val Ser Asn Pro Arg Pro Ile
1               5                   10                  15

Phe Thr Glu Ser Arg Ser Phe Lys Ala Val Ala Asn Gly Lys Ile Tyr
            20                  25                  30

Ile Gly Lys Ile Asp Thr Asp Pro Val Asn Pro Ala Asn Gln Ile Pro
        35                  40                  45

Val Tyr Ile Glu Asn Glu Asp Gly Ser His Val Gln Ile Ala Gln Pro
    50                  55                  60

Leu Ile Ile Asn Ser Ala Gly Lys Ile Val Tyr Asn Gly Gln Leu Val
65                  70                  75                  80

Lys Ile Val Thr Val Gln Gly His Ser Met Ala Ile Tyr Asp Ala Tyr
            85                  90                  95

Gly Ser Gln Val Asp Tyr Ile Ala Asn Val Leu Lys Tyr Asp Pro Asp
        100                 105                 110

-continued

```
Gln Phe Arg Gln Glu Leu Ala Glu Pro Asp Gly Ser Lys Lys Val Gly
    115                 120                 125

Tyr Lys Asp Ser Asn Val Tyr Asp Thr Leu Asn Lys Leu Glu Leu Lys
130                 135                 140

Phe Lys Ser Phe Gln Glu Met Arg Asp Asn Ser Asn Glu Ile Gly
145                 150                 155                 160

Asp Tyr Ala Leu Leu Thr Gly Trp His Thr Glu His Gln Gly Tyr Gly
                165                 170                 175

Ala Gly Val Phe Gln Cys Val Asp Lys Thr Gly Leu Thr Asp Asp Gly
            180                 185                 190

Gly Thr Ile Ala Val Gly Ser Thr Tyr Ala Trp Lys Arg Ile Thr Gly
        195                 200                 205

Pro Gly Asp Ala Thr Glu Phe Gly Val Val Pro Asn Ala Gly Ser Lys
    210                 215                 220

Phe Asp Asn Lys Ala Tyr Ile Leu Ser Ala Ala Thr Gly Ala Leu
225                 230                 235                 240

Ile Phe Pro Ala Gly Asp Ile Tyr Thr Thr Phe Phe Thr Leu Thr Asp
                245                 250                 255

Thr Tyr Leu Val Arg Gly Asn Ser Thr Asn Ile Arg Glu Ile Glu Ala
            260                 265                 270

Pro Asn Val Thr Asp Phe Ile Val His Cys Ser Arg Asn Gly Thr Trp
        275                 280                 285

Glu Gly Arg Ile Asp Gly Ile Ser Trp Glu Gly Val Asn Val Tyr Pro
    290                 295                 300

Val Asp Glu His Arg Ala Phe His Thr Tyr Phe Thr Thr Asn Gly Asn
305                 310                 315                 320

Met Arg Asp Cys Arg Phe Arg Gly Gly Val Gly Ser Trp Phe Asp Gly
                325                 330                 335

Val Ser Asn Trp Phe Ile Asp Ser Cys Glu Phe Ser Gly Ser Leu Gly
            340                 345                 350

Gly Glu Asn Ile Leu Asn Thr Pro Lys Val Asp Pro Gln Gly Thr Ile
        355                 360                 365

Gly Thr Trp Val Ile Phe His Lys Cys Phe Ile Ser Arg Ser Ala Gly
    370                 375                 380

Ala Gly Ala Arg Thr Ile Gly Leu Pro Ser Val Trp Phe Arg Asp Cys
385                 390                 395                 400

Ile Val Tyr Tyr Asn Arg Asp Ala Gly Leu Leu His Tyr Lys Asp Glu
                405                 410                 415

Asp Ala Tyr Pro Asn Val Glu Phe Gly Val Gln Lys Val Thr Gly Cys
            420                 425                 430

Asp Ile Asp Ser Asn Asp Ser Ser Gly Val Ile Met Arg Asp Val Val
        435                 440                 445

Tyr Pro Asp Ile Ser Asn Asn Trp Val Ser Ala Gly Arg Val Leu Asn
    450                 455                 460

Gln Ala Gly Val Val Leu Ile Arg Cys Asn Asp Ile Asn Val Val Glu
465                 470                 475                 480

Asn Ser Ala Tyr Phe Asn Gly Thr His Gly Ile Ser Glu Val Cys
                485                 490                 495

Asn Phe Gly Thr Ile Ser Asn Asn Cys Ser Asp Asn Lys Asn Arg
            500                 505                 510

Gly Ile Ser Ile Gln Ser Asp Ser Gly Ile Ser Ser Lys Leu Thr Val
        515                 520                 525

Ser Gly Asn Thr Cys Cys Gly Thr Pro Leu Gly Ser Leu Pro Thr Ala
    530                 535                 540
```

Gln Glu Glu Gly Ile His Ile Glu Gly Asp Arg Ile Val Ser Tyr Gly
            545                 550                 555                 560

Asn Val Cys Ala Gly Asn Ser Ser Gln Tyr Ile Asn Ala Ala Ser
                565                 570                 575

Asn Lys Gln Glu Gly Leu Asn Ile Thr Ser
            580                 585

<210> SEQ ID NO 7
<211> LENGTH: 480
<212> TYPE: PRT
<213> ORGANISM: Artificial sequence
<220> FEATURE:
<223> OTHER INFORMATION: Phage 14 tail spike

<400> SEQUENCE: 7

Met Lys Tyr Asp Pro Asp Gln Phe Arg Gln Glu Leu Ala Glu Pro Asp
1               5                   10                  15

Gly Ser Lys Lys Val Gly Tyr Lys Asp Ser Asn Val Tyr Asp Thr Leu
            20                  25                  30

Asn Lys Leu Glu Leu Lys Phe Lys Ser Phe Gln Glu Met Arg Asp Asp
        35                  40                  45

Asn Ser Asn Glu Ile Gly Asp Tyr Ala Leu Leu Thr Gly Trp His Thr
50                  55                  60

Glu His Gln Gly Tyr Gly Ala Gly Val Phe Gln Cys Val Asp Lys Thr
65                  70                  75                  80

Gly Leu Thr Asp Asp Gly Gly Thr Ile Ala Val Gly Ser Thr Tyr Ala
                85                  90                  95

Trp Lys Arg Ile Thr Gly Pro Gly Asp Ala Thr Glu Phe Gly Val Val
            100                 105                 110

Pro Asn Ala Gly Ser Lys Phe Asp Asn Lys Ala Tyr Ile Leu Ser Ala
        115                 120                 125

Ala Ala Thr Gly Ala Leu Ile Phe Pro Ala Gly Asp Ile Tyr Thr Thr
    130                 135                 140

Phe Phe Thr Leu Thr Asp Thr Tyr Leu Val Arg Gly Asn Ser Thr Asn
145                 150                 155                 160

Ile Arg Glu Ile Glu Ala Pro Asn Val Thr Asp Phe Ile Val His Cys
                165                 170                 175

Ser Arg Asn Gly Thr Trp Glu Gly Arg Ile Asp Gly Ile Ser Trp Glu
            180                 185                 190

Gly Val Asn Val Tyr Pro Val Asp Glu His Arg Ala Phe His Thr Tyr
        195                 200                 205

Phe Thr Thr Asn Gly Asn Met Arg Asp Cys Arg Phe Arg Gly Gly Val
    210                 215                 220

Gly Ser Trp Phe Asp Gly Val Ser Asn Trp Phe Ile Asp Ser Cys Glu
225                 230                 235                 240

Phe Ser Gly Ser Leu Gly Gly Asn Ile Leu Asn Thr Pro Lys Val
                245                 250                 255

Asp Pro Gln Gly Thr Ile Gly Thr Trp Val Ile Phe His Lys Cys Phe
            260                 265                 270

Ile Ser Arg Ser Ala Gly Ala Gly Ala Arg Thr Ile Gly Leu Pro Ser
        275                 280                 285

Val Trp Phe Arg Asp Cys Ile Val Tyr Tyr Asn Arg Asp Ala Gly Leu
    290                 295                 300

Leu His Tyr Lys Asp Glu Asp Ala Tyr Pro Asn Val Glu Phe Gly Val
305                 310                 315                 320

```
Gln Lys Val Thr Gly Cys Asn Ile Asp Ser Asn Asp Ser Ser Gly Val
            325                 330                 335

Ile Met Arg Asp Val Val Tyr Pro Asp Ile Ser Asn Asn Trp Val Ser
        340                 345                 350

Ala Gly Arg Val Leu Asn Gln Ala Gly Val Val Leu Ile Arg Cys Asn
        355                 360                 365

Asp Ile Asn Val Val Glu Asn Ser Ala Tyr Phe Asn Gly Thr His Gly
        370                 375                 380

Ile Ser Val Glu Val Cys Asn Phe Gly Thr Ile Ser Asn Asn Asn Cys
385                 390                 395                 400

Ser Asp Asn Lys Asn Arg Gly Ile Ser Ile Gln Ser Asp Ser Gly Ile
            405                 410                 415

Ser Ser Lys Leu Thr Val Ser Gly Asn Thr Cys Cys Gly Thr Pro Leu
            420                 425                 430

Gly Ser Leu Pro Thr Ala Gln Glu Glu Gly Ile His Ile Glu Gly Asp
            435                 440                 445

Arg Ile Val Ser Tyr Gly Asn Val Cys Ala Gly Asn Ser Ser Ser Gln
            450                 455                 460

Tyr Ile Asn Ala Ala Ser Asn Lys Gln Glu Gly Leu Asn Ile Thr Ser
465                 470                 475                 480

<210> SEQ ID NO 8
<211> LENGTH: 875
<212> TYPE: PRT
<213> ORGANISM: Bacteriophage

<400> SEQUENCE: 8

Met Thr Val Ser Thr Glu Val Asn His Asn Glu Tyr Thr Gly Asn Gly
1               5                   10                  15

Val Thr Thr Ser Phe Pro Tyr Thr Phe Arg Val Phe Lys Glu Ser Asp
                20                  25                  30

Leu Val Val Gln Val Val Asp Leu Asn Asp Asn Ile Thr Val Leu Thr
            35                  40                  45

Leu Asp Thr Asp Tyr Thr Val Thr Gly Ala Gly Gly Tyr Glu Gly Gly
50                  55                  60

Asn Val Ile Leu Ala Thr Ala Leu Ala Asn Gly Tyr Gln Ile Ser Ile
65                  70                  75                  80

Ser Arg Glu Leu Ser Val Thr Gln Glu Thr Asp Leu Arg Asn Gln Gly
                85                  90                  95

Lys Phe Phe Ala Glu Val His Gly Asp Ala Phe Asp Lys Leu Thr Met
                100                 105                 110

Leu Ile Gln Gln Val Arg Ser Trp Phe Ser Leu Ala Leu Arg Lys Pro
            115                 120                 125

Ser Phe Val Ala Asn Tyr Tyr Asp Ala Met Asp Asn Tyr Ile Arg Asn
130                 135                 140

Leu Arg Asp Pro Val Arg Pro Gln Asp Ala Ala Thr Lys Lys Tyr Val
145                 150                 155                 160

Asp Gly Val Ala Glu Thr Asn Leu Ser Arg Thr Leu Arg Thr Pro Glu
                165                 170                 175

Pro Ile Pro Ala Leu Pro Gly Ile Glu Gln Arg Lys Asn Lys Ile Val
                180                 185                 190

Ala Met Asp Asp Thr Gly Asn Pro Ile Met Val Leu Pro Glu Ser Gly
            195                 200                 205

Ser Ala Thr Asp Val Met Ile Gln Leu Ala Ala Asn Asp Gly Phe Lys
210                 215                 220
```

-continued

```
Phe Ile Gly Gln Cys Pro Asp Ile Leu Thr Leu Arg Thr Ile Glu Pro
225                 230                 235                 240

Glu Lys Asn Gly Gln Arg Ile Thr Leu Arg Gln His Thr Ile Gly Thr
            245                 250                 255

Gly Leu Gly Gly Gly Val Phe Arg Ala Val Leu Asp Gly Thr Gly Tyr
        260                 265                 270

Thr Asp Asp Asp Gly Val Val Ile Lys Thr Ala Gly Ser Val Trp
    275                 280                 285

Leu Arg Val Asn Ala Asp Lys Val Asn Pro Phe Met Phe Gly Ala Thr
    290                 295                 300

Gly Val Ala Asp Asp Thr Ala Ala Leu Gln Lys Met Leu Glu Cys Gly
305                 310                 315                 320

Arg Ala Ala Glu Leu Gly Thr Asn Val Trp Lys Ala Ser Asn Leu Glu
            325                 330                 335

Leu Asn Asn Lys Ser Cys Ser Leu Ser Gly Ser Gly Leu His Val Ser
            340                 345                 350

Arg Ile Glu Gln Ile Ser Gly Ala Thr Gly Ala Leu Leu Thr Ile Thr
        355                 360                 365

Gln Asp Cys Ser Leu Ile Tyr Leu Ser Asp Cys Gly Leu Tyr Gly Asp
    370                 375                 380

Gly Ile Thr Ala Gly Thr Ser Val Thr Met Glu Thr Gly Asn Pro
385                 390                 395                 400

Gly Gly Ala Pro Ser Tyr Pro Phe Asn Thr Ala Pro Asp Val Arg Arg
            405                 410                 415

Asp Leu Tyr Ile Ser Asn Val His Ile Thr Gly Phe Asp Glu Leu Gly
        420                 425                 430

Phe Asp Tyr Pro Glu Thr Asn Phe Ser Val Ser Thr His Gly Leu Phe
    435                 440                 445

Ile Arg Asn Ile Lys Lys Thr Gly Ala Lys Ile Gly Thr Thr Asp Phe
    450                 455                 460

Thr Trp Thr Asn Leu Gln Ile Asp Thr Cys Gly Gln Glu Cys Leu Val
465                 470                 475                 480

Leu Asp Gly Ala Gly Asn Cys Arg Ile Ile Gly Ala Lys Leu Ile Trp
            485                 490                 495

Ala Gly Ser Glu Asn Glu Thr Pro Tyr Ser Gly Leu Arg Ile Ser Asn
        500                 505                 510

Ser Gln Asn Val Asn Met Thr Gly Val Glu Leu Gln Asp Cys Ala Tyr
    515                 520                 525

Asp Gly Leu Tyr Ile Lys Asn Ser Thr Val Ala Ile Ser Gly Leu Asn
    530                 535                 540

Thr Asn Arg Asn Ser Ala Ser Ser Asn Leu Ser Tyr His Asn Met Val
545                 550                 555                 560

Phe Glu Asn Ser Ile Val Thr Val Asp Gly Tyr Val Cys Arg Asn Tyr
            565                 570                 575

Ala Ala Thr Ser Leu Tyr Asp Leu Asn Ser Gln Ala Gly Asn Val Arg
        580                 585                 590

Cys Ile Gly Ser Asp Ser Thr Val Leu Ile Asn Gly Ile Tyr Glu Ser
    595                 600                 605

Glu Val Asn Ser Glu Arg Leu Met Gly Asp Asn Leu Ile Gln Pro
610                 615                 620

Tyr Ser Gly Asp Leu Ile Ile Asn Gly Leu Lys Asn Tyr Tyr Thr Tyr
625                 630                 635                 640

Thr Gly Ser Val Lys Asn Asn Ile Pro Thr Phe Asp Gly Val Val Thr
            645                 650                 655
```

-continued

```
Thr Ala Thr Tyr Val Ser Ala Pro Ser Ile Leu Gly Gln Gly Asn Met
            660                 665                 670

Leu Lys Leu Thr Gln Ser Asn Lys Asp Lys Leu Leu Phe Ser Asp Lys
        675                 680                 685

Val Ser Arg His Gly Cys Thr Ile Gly Leu Val Leu Ile Pro Ser Phe
    690                 695                 700

Thr Gly Ala Thr Thr Met Thr Ala Phe Thr Leu Gly Ser Gly Tyr Ser
705                 710                 715                 720

Pro Ser Gly Asn Ser Ala Val Met Gln Phe Ile Val Asn Ser Ser Gly
                725                 730                 735

Val Gln Thr Ile Ala Ile Leu Leu Ser Gly Asp Gly Ile Thr Gln Thr
            740                 745                 750

Leu Thr Ser Asp Leu Thr Thr Glu Gln Ala Leu Ala Ser Gly Gly Val
        755                 760                 765

Tyr His Phe Ala Met Gly Phe Ala Pro Gly Arg Leu Trp Trp Ser Ile
    770                 775                 780

Ile Asp Ile Asn Thr Gly Arg Arg Ile Arg Arg Ala Tyr Arg Gln Pro
785                 790                 795                 800

Asp Leu His Ala Ala Phe Asn Ser Ile Phe Asn Ser Gly Thr Ser Ser
                805                 810                 815

Ile Thr Ala Phe Ser Gly Pro Leu Ala Gly Asp Ile Ala Cys Glu Gly
            820                 825                 830

Ala Gly Ser His Val Tyr Val Gly Gly Phe Ser Glu Ser Asp Tyr
        835                 840                 845

Ala Ala Ser Arg Met Tyr Gly Leu Phe Thr Pro Val Asp Leu Asp Lys
    850                 855                 860

Gln Tyr Ser Phe Arg Thr Leu Asn Gly Asn Ile
865                 870                 875

<210> SEQ ID NO 9
<211> LENGTH: 714
<212> TYPE: PRT
<213> ORGANISM: Artificial sequence
<220> FEATURE:
<223> OTHER INFORMATION: O157 BP1

<400> SEQUENCE: 9

Met Val Ala Glu Thr Asn Leu Ser Arg Thr Leu Arg Thr Pro Glu Pro
1               5                   10                  15

Ile Pro Ala Leu Pro Gly Ile Glu Gln Arg Lys Asn Lys Ile Val Ala
            20                  25                  30

Met Asp Asp Thr Gly Asn Pro Ile Met Val Leu Pro Glu Ser Gly Ser
        35                  40                  45

Ala Thr Asp Val Met Ile Gln Leu Ala Ala Asn Asp Gly Phe Lys Phe
    50                  55                  60

Ile Gly Gln Cys Pro Asp Ile Leu Thr Leu Arg Thr Ile Glu Pro Glu
65                  70                  75                  80

Lys Asn Gly Gln Arg Ile Thr Leu Arg Gln His Thr Ile Gly Thr Gly
                85                  90                  95

Leu Gly Gly Gly Val Phe Arg Ala Val Leu Asp Gly Thr Gly Tyr Thr
            100                 105                 110

Asp Asp Asp Gly Val Val Ile Lys Thr Ala Gly Gly Ser Val Trp Leu
        115                 120                 125

Arg Val Asn Ala Asp Lys Val Asn Pro Phe Met Phe Gly Ala Thr Gly
    130                 135                 140
```

```
Val Ala Asp Asp Thr Ala Ala Leu Gln Lys Met Leu Glu Cys Gly Arg
145                 150                 155                 160

Ala Ala Glu Leu Gly Thr Asn Val Trp Lys Ala Ser Asn Leu Glu Leu
                165                 170                 175

Asn Asn Lys Ser Cys Ser Leu Ser Gly Ser Gly Leu His Val Ser Arg
            180                 185                 190

Ile Glu Gln Ile Ser Gly Ala Thr Gly Ala Leu Leu Thr Ile Thr Gln
        195                 200                 205

Asp Cys Ser Leu Ile Tyr Leu Ser Asp Cys Gly Leu Tyr Gly Asp Gly
    210                 215                 220

Ile Thr Ala Gly Thr Ser Gly Val Thr Met Glu Thr Gly Asn Pro Gly
225                 230                 235                 240

Gly Ala Pro Ser Tyr Pro Phe Asn Thr Ala Pro Asp Val Arg Arg Asp
                245                 250                 255

Leu Tyr Ile Ser Asn Val His Ile Thr Gly Phe Asp Glu Leu Gly Phe
            260                 265                 270

Asp Tyr Pro Glu Thr Asn Phe Ser Val Ser Thr His Gly Leu Phe Ile
        275                 280                 285

Arg Asn Ile Lys Lys Thr Gly Ala Lys Ile Gly Thr Thr Asn Phe Thr
    290                 295                 300

Trp Thr Asn Leu Gln Ile Asp Thr Cys Gly Gln Glu Cys Leu Val Leu
305                 310                 315                 320

Asp Gly Ala Gly Asn Cys Arg Ile Ile Gly Ala Lys Leu Ile Trp Ala
                325                 330                 335

Gly Ser Glu Asn Glu Thr Pro Tyr Ser Gly Leu Arg Ile Ser Asn Ser
            340                 345                 350

Gln Asn Val Asn Met Thr Gly Val Glu Leu Gln Asp Cys Ala Tyr Asp
        355                 360                 365

Gly Leu Tyr Ile Lys Asn Ser Thr Val Ala Ile Ser Gly Leu Asn Thr
    370                 375                 380

Asn Arg Asn Ser Ala Ser Ser Asn Leu Ser Tyr His Asn Met Val Phe
385                 390                 395                 400

Glu Asn Ser Ile Val Thr Val Asp Gly Tyr Val Cys Arg Asn Tyr Ala
                405                 410                 415

Ala Thr Ser Leu Tyr Asp Leu Asn Ser Gln Ala Gly Asn Val Arg Cys
            420                 425                 430

Ile Gly Ser Asp Ser Thr Val Leu Ile Asn Gly Ile Tyr Glu Ser Glu
        435                 440                 445

Val Asn Ser Glu Arg Leu Met Gly Asp Asn Asn Leu Ile Gln Pro Tyr
    450                 455                 460

Ser Gly Asp Leu Ile Ile Asn Gly Leu Lys Asn Tyr Tyr Thr Tyr Thr
465                 470                 475                 480

Gly Ser Val Lys Asn Asn Ile Pro Thr Phe Asp Gly Val Val Thr Thr
                485                 490                 495

Ala Thr Tyr Val Ser Ala Pro Ser Ile Leu Gly Gln Gly Asn Met Leu
            500                 505                 510

Lys Leu Thr Gln Ser Asn Lys Asp Lys Leu Leu Phe Ser Asp Lys Val
        515                 520                 525

Ser Arg His Gly Cys Thr Ile Gly Leu Val Leu Ile Pro Ser Phe Thr
    530                 535                 540

Gly Ala Thr Thr Met Thr Ala Phe Thr Leu Gly Ser Gly Tyr Ser Pro
545                 550                 555                 560

Ser Gly Asn Ser Ala Val Met Gln Phe Ile Val Asn Ser Ser Gly Val
                565                 570                 575
```

-continued

```
Gln Thr Ile Ala Ile Leu Leu Ser Gly Asp Gly Ile Thr Gln Thr Leu
                580                 585                 590
Thr Ser Asp Leu Thr Thr Glu Gln Ala Leu Ala Ser Gly Gly Val Tyr
            595                 600                 605
His Phe Ala Met Gly Phe Ala Pro Gly Arg Leu Trp Trp Ser Ile Ile
        610                 615                 620
Asp Ile Asn Thr Gly Arg Arg Ile Arg Arg Ala Tyr Arg Gln Pro Asp
625                 630                 635                 640
Leu His Ala Ala Phe Asn Ser Ile Phe Asn Ser Gly Thr Ser Ser Ile
                645                 650                 655
Thr Ala Phe Ser Gly Pro Leu Ala Gly Asp Ile Ala Cys Glu Gly Ala
            660                 665                 670
Gly Ser His Val Tyr Val Gly Phe Ser Ser Glu Ser Asp Tyr Ala
        675                 680                 685
Ala Ser Arg Met Tyr Gly Leu Phe Thr Pro Val Asp Leu Asp Lys Gln
        690                 695                 700
Tyr Ser Phe Arg Thr Leu Asn Gly Asn Ile
705                 710

<210> SEQ ID NO 10
<211> LENGTH: 645
<212> TYPE: PRT
<213> ORGANISM: Bacteriophage

<400> SEQUENCE: 10

Met Thr Asp Ile Thr Ala Asn Val Ile Val Ser Met Pro Ser Gln Leu
1               5                   10                  15
Phe Thr Met Ala Arg Ser Phe Lys Ala Val Ala Asn Gly Lys Ile Tyr
            20                  25                  30
Ile Gly Lys Ile Asp Thr Asp Pro Val Asn Pro Glu Asn Gln Ile Gln
        35                  40                  45
Val Tyr Val Glu Asn Glu Asp Gly Ser His Val Pro Val Ser Gln Pro
    50                  55                  60
Ile Ile Ile Asn Ala Ala Gly Tyr Pro Val Tyr Asn Gly Gln Ile Ala
65                  70                  75                  80
Lys Phe Val Thr Val Gln Gly His Ser Met Ala Val Tyr Asp Ala Tyr
                85                  90                  95
Gly Ala Gln Gln Phe Tyr Phe Pro Asn Val Leu Lys Tyr Asp Pro Asp
            100                 105                 110
Gln Leu Arg Gln Glu Leu Ala Asp Pro Asn Gly Tyr Leu Leu Ile Pro
        115                 120                 125
Ser Met Asp Gln His Ile Lys Ile Gln Gln Trp Arg Glu Glu Gly Asp
    130                 135                 140
Ile Arg Gly Trp Gly Ala Ile Asp Gly Glu Phe Asn Asp Ala Ala Val
145                 150                 155                 160
Ser Ala Ala Leu Asp Ser Glu Ser Pro Ser Val Lys Leu Gly Gly Val
                165                 170                 175
Gly Phe Val Ser Lys Leu Arg Ser Pro Ile Asn His Lys Ser Asn Lys
            180                 185                 190
Val Met His Ser Gly Ser Leu Asn Phe Gln Phe Asp Gly Gly Thr Gln
        195                 200                 205
Gln Glu Lys Ser Gly Ile Leu Met Ala Asn Ile Ser Asn Ala Lys Val
    210                 215                 220
Ile Asp Val Asp Ile Thr Gly Thr Leu Asp Gly Gly Ile Arg Gly Tyr
225                 230                 235                 240
```

-continued

```
Gly Gly Ser Asn Ile Val Ile Asp Gly Val Asn Val His Asp Ile Gly
            245                 250                 255
Ile Ser Met Leu Ser Gly Glu Cys Gly Ile Gly Ile Trp Phe Gly Asp
        260                 265                 270
Tyr Ala Asn Tyr Asp Val Gln Thr Asp Gly Leu Leu Ile Gln Asn Cys
            275                 280                 285
Asn Ile Lys Asn Ile Gly Gly Val Gly Met Gln Arg Gly Asp Gly Ile
    290                 295                 300
Leu Val Tyr Asn Ala Lys Asn Phe Lys Val Arg His Asn Thr Ile Ile
305                 310                 315                 320
Thr Thr Asn Arg Met Gly Ile Ala Ala Gly Ser Asp Thr Arg Gln Phe
                325                 330                 335
Glu Ile His Gly Asn Tyr Ile Gly Asp Thr Leu Leu Ala Gly Ile Asp
            340                 345                 350
Ile Glu Pro Asp Glu Gly His Thr Ala Ser Asn Phe Lys Val Tyr Asn
        355                 360                 365
Asn Asn Ile Ile Gly Phe Ala Ala Arg Tyr Phe Ile Gln Gly Ala Gly
    370                 375                 380
Val Gly Gln Thr Phe Gly Ile Asp Thr His Ala Asn Thr Ser Tyr Gly
385                 390                 395                 400
Lys Val Tyr Lys Asn Ile Leu Ser Ala Gly Gln Tyr Gly Thr Glu Ala
                405                 410                 415
Phe His Ile Gly Asn His Ala Asp Glu Ile Glu Ile Thr Asp Asn Asp
            420                 425                 430
Leu Ile Gly Gly Ala Val Val Ile Pro Leu Phe Ile Lys Thr Tyr Asp
        435                 440                 445
Gly Ser Gly Ser Lys Arg Ile Lys Ile Asn Arg Asn Arg Ala Lys Gly
    450                 455                 460
Thr Cys Lys Ser Phe Ala Asp Val Tyr Met Ser Glu Asp Val Tyr Ile
465                 470                 475                 480
Ser Glu Asn Val Phe Ser Gly Asn Ser Ser Ala Asp Ser Phe Phe Leu
                485                 490                 495
Arg Phe Ser Ile Ile Ser Gly Leu Asn Val Asp Tyr Asn Arg Ser Ser
            500                 505                 510
Asp Thr Thr Asn Phe Ile Lys Ala Gly Asp Ala Gly Asn Thr Ser Asn
        515                 520                 525
Val Lys Val Thr Asn Asn Ile Ser Thr Leu Leu Asp Gly Ile Asp
    530                 535                 540
Ile Leu Thr Ser Gly Ser Leu Ala Gly Phe Ile Ala Ser Gly Asn Thr
545                 550                 555                 560
Ile Leu Cys Pro Ala Ser Asn Lys Gly Ile Ser Leu Glu Val Tyr Gly
                565                 570                 575
Ala Gly Ser Ile Ser Asp Leu Arg Leu Arg Gly Asn Ile Ile Tyr Asn
            580                 585                 590
Ala Thr Thr Lys Ile Tyr Val Ser Pro Ala Ala Thr Gly Trp Asp Met
        595                 600                 605
Leu Thr Thr Asn Thr Arg Phe Asn Leu Ser Gly Val Gln Asn Gly Thr
    610                 615                 620
Gln Leu Phe Glu Leu Ser Arg Asn Arg Val Thr Gln Phe Leu Asn Asn
625                 630                 635                 640
Ala Trp Tyr Asp Gly
                645
```

```
<210> SEQ ID NO 11
<211> LENGTH: 539
<212> TYPE: PRT
<213> ORGANISM: Artificial sequence
<220> FEATURE:
<223> OTHER INFORMATION: O111 BP1

<400> SEQUENCE: 11

Met Lys Tyr Asp Pro Asp Gln Leu Arg Gln Glu Leu Ala Asp Pro Asn
1               5                   10                  15

Gly Tyr Leu Leu Ile Pro Ser Met Asp Gln His Ile Lys Ile Gln Gln
            20                  25                  30

Trp Arg Glu Glu Gly Asp Ile Arg Gly Trp Gly Ala Ile Asp Gly Glu
        35                  40                  45

Phe Asn Asp Ala Ala Val Ser Ala Ala Leu Asp Ser Glu Ser Pro Ser
    50                  55                  60

Val Lys Leu Gly Gly Val Gly Phe Val Ser Lys Leu Arg Ser Pro Ile
65                  70                  75                  80

Asn His Lys Ser Asn Lys Val Met His Ser Gly Ser Leu Asn Phe Gln
                85                  90                  95

Phe Asn Gly Gly Thr Gln Gln Glu Lys Ser Gly Ile Leu Met Ala Asn
            100                 105                 110

Ile Ser Asn Ala Lys Val Ile Asp Val Asp Ile Thr Gly Thr Leu Asp
        115                 120                 125

Gly Gly Ile Arg Gly Tyr Gly Gly Ser Asn Ile Val Ile Asp Gly Val
    130                 135                 140

Asn Val His Asp Ile Gly Ile Ser Met Leu Ser Gly Glu Cys Gly Ile
145                 150                 155                 160

Gly Ile Trp Phe Gly Asp Tyr Ala Asn Tyr Asp Val Gln Thr Asp Gly
                165                 170                 175

Leu Leu Ile Gln Asn Cys Asn Ile Lys Asn Ile Gly Gly Val Gly Met
            180                 185                 190

Gln Arg Gly Asp Gly Ile Leu Val Tyr Asn Ala Lys Asn Phe Lys Val
        195                 200                 205

Arg His Asn Thr Ile Ile Thr Thr Asn Arg Met Gly Ile Ala Ala Gly
    210                 215                 220

Ser Asp Thr Arg Gln Phe Glu Ile His Gly Asn Tyr Ile Gly Asp Thr
225                 230                 235                 240

Leu Leu Ala Gly Ile Asp Ile Glu Pro Asp Glu Gly His Thr Ala Ser
                245                 250                 255

Asn Phe Lys Val Tyr Asn Asn Ile Ile Gly Phe Ala Ala Arg Tyr
            260                 265                 270

Phe Ile Gln Gly Ala Gly Val Gly Gln Thr Phe Gly Ile Asp Thr His
        275                 280                 285

Ala Asn Thr Ser Tyr Gly Lys Val Tyr Lys Asn Ile Leu Ser Ala Gly
    290                 295                 300

Gln Tyr Gly Thr Glu Ala Phe His Ile Gly Asn His Ala Asp Glu Ile
305                 310                 315                 320

Glu Ile Thr Asp Asn Asp Leu Ile Gly Gly Ala Val Val Ile Pro Leu
                325                 330                 335

Phe Ile Lys Thr Tyr Asp Gly Ser Gly Ser Lys Arg Ile Lys Ile Asn
            340                 345                 350

Arg Asn Arg Ala Lys Gly Thr Cys Lys Ser Phe Ala Asp Val Tyr Met
        355                 360                 365

Ser Glu Asp Val Tyr Ile Ser Glu Asn Val Phe Ser Gly Asn Ser Ser
    370                 375                 380
```

```
Ala Asp Ser Phe Phe Leu Arg Phe Ser Ile Ile Ser Gly Leu Asn Val
385                 390                 395                 400

Asp Tyr Asn Arg Ser Ser Asp Thr Thr Asn Phe Ile Lys Ala Gly Asp
            405                 410                 415

Ala Gly Asn Thr Ser Asn Val Lys Val Thr Asn Asn Asn Ile Ser Thr
            420                 425                 430

Leu Leu Asp Gly Ile Asp Ile Leu Thr Ser Gly Ser Leu Ala Gly Phe
            435                 440                 445

Ile Ala Ser Gly Asn Thr Ile Leu Cys Pro Ala Ser Asn Lys Gly Ile
        450                 455                 460

Ser Leu Glu Val Tyr Gly Ala Gly Ser Ile Ser Asp Leu Arg Leu Arg
465                 470                 475                 480

Gly Asn Ile Ile Tyr Asn Ala Thr Thr Lys Ile Tyr Val Ser Pro Ala
                485                 490                 495

Ala Thr Gly Trp Asp Met Leu Thr Thr Asn Thr Arg Phe Asn Leu Ser
                500                 505                 510

Gly Val Gln Asn Gly Thr Gln Leu Phe Glu Leu Ser Arg Asn Arg Val
            515                 520                 525

Thr Gln Phe Leu Asn Asn Ala Trp Tyr Asp Gly
    530                 535
```

<210> SEQ ID NO 12
<211> LENGTH: 539
<212> TYPE: PRT
<213> ORGANISM: Artificial sequence
<220> FEATURE:
<223> OTHER INFORMATION: O111 BP1

<400> SEQUENCE: 12

```
Met Lys Tyr Asp Pro Asp Gln Leu Arg Gln Glu Leu Ala Asp Pro Asn
1               5                   10                  15

Gly Tyr Leu Leu Ile Pro Ser Met Asp Gln His Ile Lys Ile Gln Gln
            20                  25                  30

Trp Arg Glu Glu Gly Asp Ile Arg Gly Trp Gly Ala Ile Asp Gly Glu
        35                  40                  45

Phe Asn Asp Ala Ala Val Ser Ala Ala Leu Asp Ser Glu Ser Pro Ser
    50                  55                  60

Val Lys Leu Gly Gly Val Gly Phe Val Ser Lys Leu Arg Ser Pro Ile
65                  70                  75                  80

Asn His Lys Ser Asn Lys Val Met His Ser Gly Ser Leu Asn Phe Gln
                85                  90                  95

Phe Asp Gly Gly Thr Gln Gln Glu Lys Ser Gly Ile Leu Met Ala Asn
            100                 105                 110

Ile Ser Asn Ala Lys Val Ile Asp Val Asp Ile Thr Gly Thr Leu Asp
        115                 120                 125

Gly Gly Ile Arg Gly Tyr Gly Gly Ser Asn Ile Val Ile Asp Gly Val
    130                 135                 140

Asn Val His Asp Ile Gly Ile Ser Met Leu Ser Gly Glu Cys Gly Ile
145                 150                 155                 160

Gly Ile Trp Phe Gly Asp Tyr Ala Asn Tyr Asn Val Gln Thr Asp Gly
                165                 170                 175

Leu Leu Ile Gln Asn Cys Asn Ile Lys Asn Ile Gly Val Gly Met
            180                 185                 190

Gln Arg Gly Asp Gly Ile Leu Val Tyr Asn Ala Lys Asn Phe Lys Val
        195                 200                 205
```

```
Arg His Asn Thr Ile Ile Thr Thr Asn Arg Met Gly Ile Ala Ala Gly
    210                 215                 220

Ser Asp Thr Arg Gln Phe Glu Ile His Gly Asn Tyr Ile Gly Asp Thr
225                 230                 235                 240

Leu Leu Ala Gly Ile Asp Ile Glu Pro Asp Glu Gly His Thr Ala Ser
                245                 250                 255

Asn Phe Lys Val Tyr Asn Asn Asn Ile Ile Gly Phe Ala Ala Arg Tyr
            260                 265                 270

Phe Ile Gln Gly Ala Gly Val Gly Gln Thr Phe Gly Ile Asp Thr His
        275                 280                 285

Ala Asn Thr Ser Tyr Gly Lys Val Tyr Lys Asn Ile Leu Ser Ala Gly
    290                 295                 300

Gln Tyr Gly Thr Glu Ala Phe His Ile Gly Asn His Ala Asp Glu Ile
305                 310                 315                 320

Glu Ile Thr Asp Asn Asp Leu Ile Gly Gly Ala Val Val Ile Pro Leu
                325                 330                 335

Phe Ile Lys Thr Tyr Asp Gly Ser Gly Ser Lys Arg Ile Lys Ile Asn
            340                 345                 350

Arg Asn Arg Ala Lys Gly Thr Cys Lys Ser Phe Ala Asp Val Tyr Met
        355                 360                 365

Ser Glu Asp Val Tyr Ile Ser Glu Asn Val Phe Ser Gly Asn Ser Ser
370                 375                 380

Ala Asp Ser Phe Phe Leu Arg Phe Ser Ile Ile Ser Gly Leu Asn Val
385                 390                 395                 400

Asp Tyr Asn Arg Ser Ser Asp Thr Thr Asn Phe Ile Lys Ala Gly Asp
                405                 410                 415

Ala Gly Asn Thr Ser Asn Val Lys Val Thr Asn Asn Asn Ile Ser Thr
            420                 425                 430

Leu Leu Asp Gly Ile Asp Ile Leu Thr Ser Gly Ser Leu Ala Gly Phe
        435                 440                 445

Ile Ala Ser Gly Asn Thr Ile Leu Cys Pro Ala Ser Asn Lys Gly Ile
    450                 455                 460

Ser Leu Glu Val Tyr Gly Ala Gly Ser Ile Ser Asp Leu Arg Leu Arg
465                 470                 475                 480

Gly Asn Ile Ile Tyr Asn Ala Thr Thr Lys Ile Tyr Val Ser Pro Ala
                485                 490                 495

Ala Thr Gly Trp Asp Met Leu Thr Thr Asn Thr Arg Phe Asn Leu Ser
            500                 505                 510

Gly Val Gln Asn Gly Thr Gln Leu Phe Glu Leu Ser Arg Asn Arg Val
        515                 520                 525

Thr Gln Phe Leu Asn Asn Ala Trp Tyr Asp Gly
    530                 535

<210> SEQ ID NO 13
<211> LENGTH: 558
<212> TYPE: PRT
<213> ORGANISM: Artificial sequence
<220> FEATURE:
<223> OTHER INFORMATION: Det7 tail spike SBP1

<400> SEQUENCE: 13

Met Ser Val Gly Asp Ala Ala Phe Arg Gln Glu Ala Asn Lys Lys Phe
1               5                   10                  15

Lys Tyr Ser Val Lys Leu Ser Asp Tyr Ser Thr Leu Gln Asp Ala Val
            20                  25                  30

Thr Asp Ala Val Asp Gly Leu Leu Ile Asp Ile Asn Tyr Asn Phe Thr
```

```
                35                  40                  45
Asp Gly Glu Ser Val Asp Phe Gly Gly Lys Ile Leu Thr Ile Asn Cys
 50                  55                  60

Lys Ala Lys Phe Ile Gly Asp Gly Ala Leu Ile Phe Asn Asn Met Gly
65                   70                  75                  80

Pro Gly Ser Val Ile Asn Gln Pro Phe Met Glu Ser Lys Thr Thr Pro
                 85                  90                  95

Trp Val Ile Phe Pro Trp Asp Ala Asp Gly Lys Trp Ile Thr Asp Ala
                100                 105                 110

Ala Leu Val Ala Ala Thr Leu Lys Gln Ser Lys Ile Glu Gly Tyr Gln
            115                 120                 125

Pro Gly Val Asn Asp Trp Val Lys Phe Pro Gly Leu Glu Ala Leu Leu
            130                 135                 140

Pro Gln Asn Val Lys Asp Gln His Ile Ala Ala Thr Leu Asp Ile Arg
145                 150                 155                 160

Ser Ala Ser Arg Val Glu Ile Arg Asn Ala Gly Gly Leu Met Ala Ala
                165                 170                 175

Tyr Leu Phe Arg Ser Cys His His Cys Lys Val Ile Asp Ser Asp Ser
            180                 185                 190

Ile Ile Gly Gly Lys Asp Gly Ile Ile Thr Phe Glu Asn Leu Ser Gly
            195                 200                 205

Asp Trp Gly Leu Gly Asn Tyr Val Ile Gly Gly Arg Val His Tyr Gly
210                 215                 220

Ser Gly Ser Gly Val Gln Phe Leu Arg Asn Asn Gly Gly Glu Ser His
225                 230                 235                 240

Asn Gly Gly Val Ile Gly Val Thr Ser Trp Arg Ala Gly Gln Ser Gly
                245                 250                 255

Phe Lys Thr Tyr Gln Gly Ser Val Gly Gly Thr Ala Arg Asn Tyr
            260                 265                 270

Asn Leu Gln Phe Arg Asp Ser Val Ala Leu Ser Pro Val Trp Asn Gly
            275                 280                 285

Phe Asn Leu Gly Ser Asp Pro Gly Met Ala Pro Glu Pro Asp Arg Pro
290                 295                 300

Gly Asp Leu Pro Val Ser Glu Tyr Pro Phe His Gln Leu Pro Asn Asn
305                 310                 315                 320

His Leu Val Asp Asn Ile Leu Val Met Asn Ser Leu Gly Val Gly Leu
                325                 330                 335

Gly Met Asp Gly Ser Gly Gly Tyr Val Ser Asn Val Thr Val Gln Asp
            340                 345                 350

Cys Ala Gly Ala Gly Met Leu Ala His Thr Tyr Asn Arg Val Phe Ser
            355                 360                 365

Asn Ile Thr Val Ile Asp Cys Asn Tyr Leu Asn Phe Asp Ser Asp Gln
            370                 375                 380

Ile Ile Ile Ile Gly Asp Cys Ile Val Asn Gly Ile Arg Ala Ala Gly
385                 390                 395                 400

Ile Lys Pro Gln Pro Ser Asn Gly Leu Val Ile Ser Ala Pro Asn Ser
                405                 410                 415

Thr Ile Ser Gly Leu Val Gly Asn Val Pro Pro Asp Lys Ile Leu Val
            420                 425                 430

Gly Asn Leu Leu Asp Pro Val Leu Gly Gln Ser Arg Val Ile Gly Phe
            435                 440                 445

Asn Ser Asp Thr Ala Glu Leu Ala Leu Arg Ile Asn Lys Leu Ser Ala
450                 455                 460
```

```
Thr Leu Asp Ser Gly Ala Leu Arg Ser His Leu Asn Gly Tyr Ala Gly
465                 470                 475                 480

Ser Gly Ser Ala Trp Thr Glu Leu Thr Ala Leu Ser Gly Ser Thr Pro
                485                 490                 495

Asn Ala Val Ser Leu Lys Val Asn Arg Gly Asp Tyr Lys Thr Thr Glu
            500                 505                 510

Ile Pro Ile Ser Gly Thr Val Leu Pro Asp Glu Gly Val Leu Asp Ile
        515                 520                 525

Asn Thr Met Ser Leu Tyr Leu Asp Ala Gly Ala Leu Trp Ala Leu Ile
    530                 535                 540

Arg Leu Pro Asp Gly Ser Lys Thr Arg Met Lys Leu Ser Val
545                 550                 555

<210> SEQ ID NO 14
<211> LENGTH: 480
<212> TYPE: PRT
<213> ORGANISM: Artificial sequence
<220> FEATURE:
<223> OTHER INFORMATION: Phage 14 tail spike

<400> SEQUENCE: 14

Met Lys Tyr Asp Pro Asp Gln Phe Arg Gln Glu Leu Ala Glu Pro Asp
1               5                   10                  15

Gly Ser Lys Lys Val Gly Tyr Lys Asp Ser Asn Val Tyr Asp Thr Leu
            20                  25                  30

Asn Lys Leu Glu Leu Lys Phe Lys Ser Phe Gln Glu Met Arg Asp Asp
        35                  40                  45

Asn Ser Asn Glu Ile Gly Asp Tyr Ala Leu Leu Thr Gly Trp His Thr
    50                  55                  60

Gln His Gln Gly Tyr Gly Ala Gly Val Phe Gln Cys Val Asp Lys Thr
65                  70                  75                  80

Gly Leu Thr Asp Asp Gly Gly Thr Ile Ala Val Gly Ser Thr Tyr Ala
                85                  90                  95

Trp Lys Arg Ile Thr Gly Pro Gly Asp Ala Thr Glu Phe Gly Val Val
            100                 105                 110

Pro Asn Ala Gly Ser Lys Phe Asp Asn Lys Ala Tyr Ile Leu Ser Ala
        115                 120                 125

Ala Ala Thr Gly Ala Leu Ile Phe Pro Ala Gly Asp Ile Tyr Thr Thr
    130                 135                 140

Phe Phe Thr Leu Thr Asp Thr Tyr Leu Val Arg Gly Asn Ser Thr Asn
145                 150                 155                 160

Ile Arg Glu Ile Glu Ala Pro Asn Val Thr Asp Phe Ile Val His Cys
                165                 170                 175

Ser Arg Asn Gly Thr Trp Glu Gly Arg Ile Asp Gly Ile Ser Trp Glu
            180                 185                 190

Gly Val Asn Val Tyr Pro Val Asp Glu His Arg Ala Phe His Thr Tyr
        195                 200                 205

Phe Thr Thr Asn Gly Asn Met Arg Asp Cys Arg Phe Arg Gly Gly Val
    210                 215                 220

Gly Ser Trp Phe Asp Gly Val Ser Asn Trp Phe Ile Asp Ser Cys Glu
225                 230                 235                 240

Phe Ser Gly Ser Leu Gly Gly Glu Asn Ile Leu Asn Thr Pro Lys Val
                245                 250                 255

Asp Pro Gln Gly Thr Ile Gly Thr Trp Val Ile Phe His Lys Cys Phe
            260                 265                 270

Ile Ser Arg Ser Ala Gly Ala Gly Ala Arg Thr Ile Gly Leu Pro Ser
```

```
                   275                 280                 285
Val Trp Phe Arg Asp Cys Ile Val Tyr Tyr Asn Arg Asp Ala Gly Leu
290                 295                 300
Leu His Tyr Lys Asp Glu Asp Ala Tyr Pro Asn Val Glu Phe Gly Val
305                 310                 315                 320
Gln Lys Val Thr Gly Cys Asn Ile Asn Ser Asn Asp Ser Ser Gly Val
            325                 330                 335
Ile Met Arg Asp Val Val Tyr Pro Asp Ile Ser Asn Asn Trp Val Ser
        340                 345                 350
Ala Gly Arg Val Leu Asn Gln Ala Gly Val Val Leu Ile Arg Cys Asn
    355                 360                 365
Asp Ile Asn Val Val Glu Asn Ser Ala Tyr Phe Asn Gly Thr His Gly
370                 375                 380
Ile Ser Val Glu Val Cys Asn Phe Gly Thr Ile Ser Asn Asn Asn Cys
385                 390                 395                 400
Ser Asp Asn Lys Asn Arg Gly Ile Ser Ile Gln Ser Asp Ser Gly Ile
            405                 410                 415
Ser Ser Lys Leu Thr Val Ser Gly Asn Thr Cys Cys Gly Thr Pro Leu
        420                 425                 430
Gly Ser Leu Pro Thr Ala Gln Glu Glu Gly Ile His Ile Glu Gly Asp
    435                 440                 445
Arg Ile Val Ser Tyr Gly Asn Val Cys Ala Gly Asn Ser Ser Ser Gln
450                 455                 460
Tyr Ile Asn Ala Ala Ser Asn Lys Gln Glu Gly Leu Asn Ile Thr Ser
465                 470                 475                 480

<210> SEQ ID NO 15
<211> LENGTH: 66
<212> TYPE: PRT
<213> ORGANISM: Artificial sequence
<220> FEATURE:
<223> OTHER INFORMATION: JS-Tag

<400> SEQUENCE: 15

Val Thr Ala Pro Leu Ala Gly Thr Ile Trp Lys Val Leu Ala Ser Glu
1               5                   10                  15
Gly Gln Thr Val Ala Ala Gly Glu Val Leu Leu Ile Leu Glu Ala Met
            20                  25                  30
Lys Met Glu Thr Glu Ile Arg Ala Ala Gln Ala Gly Thr Val Arg Gly
        35                  40                  45
Ile Ala Val Lys Ala Gly Asp Ala Val Ala Val Gly Glu Thr Leu Met
    50                  55                  60
Thr Leu
65

<210> SEQ ID NO 16
<211> LENGTH: 66
<212> TYPE: PRT
<213> ORGANISM: Artificial sequence
<220> FEATURE:
<223> OTHER INFORMATION: JS-Tag

<400> SEQUENCE: 16

Val Thr Ala Pro Leu Ala Gly Thr Ile Trp Lys Val Leu Ala Ser Glu
1               5                   10                  15
Gly Gln Thr Val Ala Ala Gly Glu Val Leu Leu Ile Leu Glu Ala Met
            20                  25                  30
Lys Met Glu Thr Glu Ile Arg Ala Ala Gln Ala Gly Thr Val Arg Gly
```

```
                  35                  40                  45

Ile Ala Val Lys Ala Gly Asp Ala Val Ala Val Gly Asp Thr Leu Met
 50                  55                  60

Thr Leu
 65

<210> SEQ ID NO 17
<211> LENGTH: 67
<212> TYPE: PRT
<213> ORGANISM: Artificial sequence
<220> FEATURE:
<223> OTHER INFORMATION: JS-Tag

<400> SEQUENCE: 17

Val Thr Ala Pro Leu Ala Gly Thr Ile Trp Lys Val Leu Ala Ser Glu
 1               5                  10                  15

Gly Gln Thr Val Ala Ala Gly Glu Val Leu Leu Ile Leu Glu Ala Met
                20                  25                  30

Lys Met Glu Thr Glu Ile Arg Ala Ala Gln Ala Gly Thr Val Arg Gly
             35                  40                  45

Ile Ala Val Lys Ala Gly Asp Ala Val Ala Val Gly Glu Thr Leu Met
 50                  55                  60

Thr Leu Val
 65

<210> SEQ ID NO 18
<211> LENGTH: 68
<212> TYPE: PRT
<213> ORGANISM: Artificial sequence
<220> FEATURE:
<223> OTHER INFORMATION: JS-Tag

<400> SEQUENCE: 18

Val Thr Ala Pro Leu Ala Gly Thr Ile Trp Lys Val Leu Ala Ser Glu
 1               5                  10                  15

Gly Gln Thr Val Ala Ala Gly Glu Val Leu Leu Ile Leu Glu Ala Met
                20                  25                  30

Lys Met Glu Thr Glu Ile Arg Ala Ala Gln Ala Gly Thr Val Arg Gly
             35                  40                  45

Ile Ala Val Lys Ala Gly Asp Ala Val Ala Val Gly Glu Thr Leu Met
 50                  55                  60

Thr Leu Val Asp
 65

<210> SEQ ID NO 19
<211> LENGTH: 67
<212> TYPE: PRT
<213> ORGANISM: Artificial sequence
<220> FEATURE:
<223> OTHER INFORMATION: JS-Tag

<400> SEQUENCE: 19

Met Val Thr Ala Pro Leu Ala Gly Thr Ile Trp Lys Val Leu Ala Ser
 1               5                  10                  15

Glu Gly Gln Thr Val Ala Ala Gly Glu Val Leu Leu Ile Leu Glu Ala
                20                  25                  30

Met Lys Met Glu Thr Glu Ile Arg Ala Ala Gln Ala Gly Thr Val Arg
             35                  40                  45

Gly Ile Ala Val Lys Ala Gly Asp Ala Val Ala Val Gly Glu Thr Leu
 50                  55                  60
```

Met Thr Leu
65

<210> SEQ ID NO 20
<211> LENGTH: 68
<212> TYPE: PRT
<213> ORGANISM: Artificial sequence
<220> FEATURE:
<223> OTHER INFORMATION: JS-Tag

<400> SEQUENCE: 20

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
                20                  25                  30

Met Lys Met Glu Thr Glu Ile Arg Ala Ala Gln Ala Gly Thr Val Arg
            35                  40                  45

Gly Ile Ala Val Lys Ala Gly Asp Ala Val Ala Val Gly Glu Thr Leu
        50                  55                  60

Met Thr Leu Val
65

<210> SEQ ID NO 21
<211> LENGTH: 69
<212> TYPE: PRT
<213> ORGANISM: Artificial sequence
<220> FEATURE:
<223> OTHER INFORMATION: JS-Tag

<400> SEQUENCE: 21

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
                20                  25                  30

Met Lys Met Glu Thr Glu Ile Arg Ala Ala Gln Ala Gly Thr Val Arg
            35                  40                  45

Gly Ile Ala Val Lys Ala Gly Asp Ala Val Ala Val Gly Glu Thr Leu
        50                  55                  60

Met Thr Leu Val Asp
65

<210> SEQ ID NO 22
<211> LENGTH: 70
<212> TYPE: PRT
<213> ORGANISM: Artificial sequence
<220> FEATURE:
<223> OTHER INFORMATION: JS-Tag

<400> SEQUENCE: 22

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
                20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
        50                  55                  60

Glu Thr Leu Met Thr Leu
65                  70

<210> SEQ ID NO 23

```
<211> LENGTH: 71
<212> TYPE: PRT
<213> ORGANISM: Artificial sequence
<220> FEATURE:
<223> OTHER INFORMATION: JS-Tag

<400> SEQUENCE: 23

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Val
65                  70

<210> SEQ ID NO 24
<211> LENGTH: 72
<212> TYPE: PRT
<213> ORGANISM: Artificial sequence
<220> FEATURE:
<223> OTHER INFORMATION: JS-Tag

<400> SEQUENCE: 24

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Glu Thr Leu Met Thr Leu Val Asp
65                  70

<210> SEQ ID NO 25
<211> LENGTH: 67
<212> TYPE: PRT
<213> ORGANISM: Artificial sequence
<220> FEATURE:
<223> OTHER INFORMATION: JS-Tag

<400> SEQUENCE: 25

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Asp Thr Leu Met
    50                  55                  60

Thr Leu Val
65

<210> SEQ ID NO 26
<211> LENGTH: 68
<212> TYPE: PRT
<213> ORGANISM: Artificial sequence
<220> FEATURE:
<223> OTHER INFORMATION: JS-Tag
```

<400> SEQUENCE: 26

Val Thr Ala Pro Leu Ala Gly Thr Ile Trp Lys Val Leu Ala Ser Glu
1               5                   10                  15

Gly Gln Thr Val Ala Ala Gly Glu Val Leu Leu Ile Leu Glu Ala Met
            20                  25                  30

Lys Met Glu Thr Glu Ile Arg Ala Ala Gln Ala Gly Thr Val Arg Gly
        35                  40                  45

Ile Ala Val Lys Ala Gly Asp Ala Val Ala Val Gly Asp Thr Leu Met
    50                  55                  60

Thr Leu Val Asp
65

<210> SEQ ID NO 27
<211> LENGTH: 67
<212> TYPE: PRT
<213> ORGANISM: Artificial sequence
<220> FEATURE:
<223> OTHER INFORMATION: JS-Tag

<400> SEQUENCE: 27

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
            20                  25                  30

Met Lys Met Glu Thr Glu Ile Arg Ala Ala Gln Ala Gly Thr Val Arg
        35                  40                  45

Gly Ile Ala Val Lys Ala Gly Asp Ala Val Ala Val Gly Asp Thr Leu
    50                  55                  60

Met Thr Leu
65

<210> SEQ ID NO 28
<211> LENGTH: 68
<212> TYPE: PRT
<213> ORGANISM: Artificial sequence
<220> FEATURE:
<223> OTHER INFORMATION: JS-Tag

<400> SEQUENCE: 28

Met Val Thr Ala Pro Leu Ala Gly Thr Ile Trp Lys Val Leu Ala Ser
1               5                   10                  15

Glu Gly Gln Thr Val Ala Ala Gly Glu Val Leu Leu Ile Leu Glu Ala
            20                  25                  30

Met Lys Met Glu Thr Glu Ile Arg Ala Ala Gln Ala Gly Thr Val Arg
        35                  40                  45

Gly Ile Ala Val Lys Ala Gly Asp Ala Val Ala Val Gly Asp Thr Leu
    50                  55                  60

Met Thr Leu Val
65

<210> SEQ ID NO 29
<211> LENGTH: 69
<212> TYPE: PRT
<213> ORGANISM: Artificial sequence
<220> FEATURE:
<223> OTHER INFORMATION: JS-Tag

<400> SEQUENCE: 29

Met Val Thr Ala Pro Leu Ala Gly Thr Ile Trp Lys Val Leu Ala Ser
1               5                   10                  15

```
Glu Gly Gln Thr Val Ala Ala Gly Glu Val Leu Leu Ile Leu Glu Ala
        20                  25                  30

Met Lys Met Glu Thr Glu Ile Arg Ala Ala Gln Ala Gly Thr Val Arg
        35                  40                  45

Gly Ile Ala Val Lys Ala Gly Asp Ala Val Ala Val Gly Asp Thr Leu
    50                  55                  60

Met Thr Leu Val Asp
65

<210> SEQ ID NO 30
<211> LENGTH: 70
<212> TYPE: PRT
<213> ORGANISM: Artificial sequence
<220> FEATURE:
<223> OTHER INFORMATION: JS-Tag

<400> SEQUENCE: 30

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Asp Thr Leu Met Thr Leu
65                  70

<210> SEQ ID NO 31
<211> LENGTH: 70
<212> TYPE: PRT
<213> ORGANISM: Artificial sequence
<220> FEATURE:
<223> OTHER INFORMATION: JS-Tag

<400> SEQUENCE: 31

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Asp Thr Leu Met Thr Leu
65                  70

<210> SEQ ID NO 32
<211> LENGTH: 70
<212> TYPE: PRT
<213> ORGANISM: Artificial sequence
<220> FEATURE:
<223> OTHER INFORMATION: JS-Tag

<400> SEQUENCE: 32

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
```

```
            35                  40                  45
Thr Val Arg Gly Ile Ala Val Lys Ala Gly Asp Ala Val Ala Val Gly
    50                  55                  60

Asp Thr Leu Met Thr Leu
65                  70

<210> SEQ ID NO 33
<211> LENGTH: 7
<212> TYPE: PRT
<213> ORGANISM: Artificial sequence
<220> FEATURE:
<223> OTHER INFORMATION: Cysteine-tag

<400> SEQUENCE: 33

Met Ala Cys Trp Ser Gly Ala
1               5

<210> SEQ ID NO 34
<211> LENGTH: 14
<212> TYPE: PRT
<213> ORGANISM: Artificial sequence
<220> FEATURE:
<223> OTHER INFORMATION: Cysteine-tag

<400> SEQUENCE: 34

Met Ala Cys Trp Ser His Pro Gln Phe Glu Lys Gly Ala Ser
1               5                   10

<210> SEQ ID NO 35
<211> LENGTH: 14
<212> TYPE: PRT
<213> ORGANISM: Artificial sequence
<220> FEATURE:
<223> OTHER INFORMATION: Cysteine-tag

<400> SEQUENCE: 35

Met Ala Ser Trp Ser His Pro Gln Phe Glu Lys Gly Ala Cys
1               5                   10

<210> SEQ ID NO 36
<211> LENGTH: 570
<212> TYPE: PRT
<213> ORGANISM: Artificial sequence
<220> FEATURE:
<223> OTHER INFORMATION: Det7 tail spike SBP1

<400> SEQUENCE: 36

Met Ala Ser Trp Ser His Pro Gln Phe Glu Lys Gly Ala Ser Val Gly
1               5                   10                  15

Asp Ala Ala Phe Arg Gln Glu Ala Asn Lys Lys Phe Lys Tyr Ser Val
            20                  25                  30

Lys Leu Ser Asp Tyr Ser Thr Leu Gln Asp Ala Val Thr Asp Ala Val
        35                  40                  45

Asp Gly Leu Leu Ile Asp Ile Asn Tyr Asn Phe Thr Asp Gly Glu Ser
    50                  55                  60

Val Asp Phe Gly Gly Lys Ile Leu Thr Ile Asn Cys Lys Ala Lys Phe
65                  70                  75                  80

Ile Gly Asp Gly Ala Leu Ile Phe Asn Asn Met Gly Pro Gly Ser Val
                85                  90                  95

Ile Asn Gln Pro Phe Met Glu Ser Lys Thr Thr Pro Trp Val Ile Phe
            100                 105                 110

Pro Trp Asp Ala Asp Gly Lys Trp Ile Thr Asp Ala Ala Leu Val Ala
        115                 120                 125
```

-continued

```
Ala Thr Leu Lys Gln Ser Lys Ile Glu Gly Tyr Gln Pro Gly Val Asn
    130                 135                 140
Asp Trp Val Lys Phe Pro Gly Leu Glu Ala Leu Leu Pro Gln Asn Val
145                 150                 155                 160
Lys Asp Gln His Ile Ala Ala Thr Leu Asp Ile Arg Ser Ala Ser Arg
                165                 170                 175
Val Glu Ile Arg Asn Ala Gly Gly Leu Met Ala Ala Tyr Leu Phe Arg
            180                 185                 190
Ser Cys His His Cys Lys Val Ile Asp Ser Asp Ser Ile Ile Gly Gly
        195                 200                 205
Lys Asp Gly Ile Ile Thr Phe Glu Asn Leu Ser Gly Asp Trp Gly Leu
    210                 215                 220
Gly Asn Tyr Val Ile Gly Gly Arg Val His Tyr Gly Ser Gly Ser Gly
225                 230                 235                 240
Val Gln Phe Leu Arg Asn Asn Gly Gly Glu Ser His Asn Gly Gly Val
                245                 250                 255
Ile Gly Val Thr Ser Trp Arg Ala Gly Glu Ser Gly Phe Lys Thr Tyr
            260                 265                 270
Gln Gly Ser Val Gly Gly Gly Thr Ala Arg Asn Tyr Asn Leu Gln Phe
        275                 280                 285
Arg Asp Ser Val Ala Leu Ser Pro Val Trp Asn Gly Phe Asp Leu Gly
    290                 295                 300
Ser Asp Pro Gly Met Ala Pro Glu Pro Asp Arg Pro Gly Asp Leu Pro
305                 310                 315                 320
Val Ser Glu Tyr Pro Phe His Gln Leu Pro Asn Asn His Leu Val Asp
                325                 330                 335
Asn Ile Leu Val Met Asn Ser Leu Gly Val Gly Leu Gly Met Asp Gly
            340                 345                 350
Ser Gly Gly Tyr Val Ser Asn Val Thr Val Gln Asp Cys Ala Gly Ala
        355                 360                 365
Gly Met Leu Ala His Thr Tyr Asn Arg Val Phe Ser Asn Ile Thr Val
    370                 375                 380
Ile Asp Cys Asn Tyr Leu Asn Phe Asp Ser Asp Gln Ile Ile Ile Ile
385                 390                 395                 400
Gly Asp Cys Ile Val Asn Gly Ile Arg Ala Ala Gly Ile Lys Pro Gln
                405                 410                 415
Pro Ser Asn Gly Leu Val Ile Ser Ala Pro Asn Ser Thr Ile Ser Gly
            420                 425                 430
Leu Val Gly Asn Val Pro Pro Asp Lys Ile Leu Val Gly Asn Leu Leu
        435                 440                 445
Asp Pro Val Leu Gly Gln Ser Arg Val Ile Gly Phe Asn Ser Asp Thr
    450                 455                 460
Ala Glu Leu Ala Leu Arg Ile Asn Lys Leu Ser Ala Thr Leu Asp Ser
465                 470                 475                 480
Gly Ala Leu Arg Ser His Leu Asn Gly Tyr Ala Gly Ser Gly Ser Ala
                485                 490                 495
Trp Thr Glu Leu Thr Ala Leu Ser Gly Ser Thr Pro Asn Ala Val Ser
            500                 505                 510
Leu Lys Val Asn Arg Gly Asp Tyr Lys Thr Thr Glu Ile Pro Ile Ser
        515                 520                 525
Gly Thr Val Leu Pro Asp Glu Gly Val Leu Asp Ile Asn Thr Met Ser
    530                 535                 540
Leu Tyr Leu Asp Ala Gly Ala Leu Trp Ala Leu Ile Arg Leu Pro Asp
```

```
                545                 550                 555                 560

Gly Ser Lys Thr Arg Met Lys Leu Ser Val
                565                 570

<210> SEQ ID NO 37
<211> LENGTH: 579
<212> TYPE: PRT
<213> ORGANISM: Artificial sequence
<220> FEATURE:
<223> OTHER INFORMATION: Det7 tail spike SBP1

<400> SEQUENCE: 37

Met Ser Gly Leu Asn Asp Ile Phe Glu Ala Gln Lys Ile Glu Trp His
1               5                   10                  15

Glu Gly Ala Pro Gly Ser Ser Val Gly Asp Ala Ala Phe Arg Gln Glu
            20                  25                  30

Ala Asn Lys Lys Phe Lys Tyr Ser Val Lys Leu Ser Asp Tyr Ser Thr
        35                  40                  45

Leu Gln Asp Ala Val Thr Asp Ala Val Asp Gly Leu Leu Ile Asp Ile
    50                  55                  60

Asn Tyr Asn Phe Thr Asp Gly Glu Ser Val Asp Phe Gly Gly Lys Ile
65                  70                  75                  80

Leu Thr Ile Asn Cys Lys Ala Lys Phe Ile Gly Asp Gly Ala Leu Ile
                85                  90                  95

Phe Asn Asn Met Gly Pro Gly Ser Val Ile Asn Gln Pro Phe Met Glu
            100                 105                 110

Ser Lys Thr Thr Pro Trp Val Ile Phe Pro Trp Asp Ala Asp Gly Lys
        115                 120                 125

Trp Ile Thr Asp Ala Ala Leu Val Ala Ala Thr Leu Lys Gln Ser Lys
    130                 135                 140

Ile Glu Gly Tyr Gln Pro Gly Val Asn Asp Trp Val Lys Phe Pro Gly
145                 150                 155                 160

Leu Glu Ala Leu Leu Pro Gln Asn Val Lys Asp Gln His Ile Ala Ala
                165                 170                 175

Thr Leu Asp Ile Arg Ser Ala Ser Arg Val Glu Ile Arg Asn Ala Gly
            180                 185                 190

Gly Leu Met Ala Ala Tyr Leu Phe Arg Ser Cys His His Cys Lys Val
        195                 200                 205

Ile Asp Ser Asp Ser Ile Ile Gly Gly Lys Asp Gly Ile Ile Thr Phe
    210                 215                 220

Glu Asn Leu Ser Gly Asp Trp Gly Leu Gly Asn Tyr Val Ile Gly Gly
225                 230                 235                 240

Arg Val His Tyr Gly Ser Gly Ser Gly Val Gln Phe Leu Arg Asn Asn
                245                 250                 255

Gly Gly Glu Ser His Asn Gly Gly Val Ile Gly Val Thr Ser Trp Arg
            260                 265                 270

Ala Gly Glu Ser Gly Phe Lys Thr Tyr Gln Gly Ser Val Gly Gly Gly
        275                 280                 285

Thr Ala Arg Asn Tyr Asn Leu Gln Phe Arg Asp Ser Val Ala Leu Ser
    290                 295                 300

Pro Val Trp Asn Gly Phe Asp Leu Gly Ser Asp Pro Gly Met Ala Pro
305                 310                 315                 320

Glu Pro Asp Arg Pro Gly Asp Leu Pro Val Ser Glu Tyr Pro Phe His
                325                 330                 335

Gln Leu Pro Asn Asn His Leu Val Asp Asn Ile Leu Val Met Asn Ser
            340                 345                 350
```

```
Leu Gly Val Gly Leu Gly Met Asp Gly Ser Gly Gly Tyr Val Ser Asn
            355                 360                 365
Val Thr Val Gln Asp Cys Ala Gly Ala Gly Met Leu Ala His Thr Tyr
    370                 375                 380
Asn Arg Val Phe Ser Asn Ile Thr Val Ile Asp Cys Asn Tyr Leu Asn
385                 390                 395                 400
Phe Asp Ser Asp Gln Ile Ile Ile Gly Asp Cys Ile Val Asn Gly
                405                 410                 415
Ile Arg Ala Ala Gly Ile Lys Pro Gln Pro Ser Asn Gly Leu Val Ile
                420                 425                 430
Ser Ala Pro Asn Ser Thr Ile Ser Gly Leu Val Gly Asn Val Pro Pro
                435                 440                 445
Asp Lys Ile Leu Val Gly Asn Leu Leu Asp Pro Val Leu Gly Gln Ser
            450                 455                 460
Arg Val Ile Gly Phe Asn Ser Asp Thr Ala Glu Leu Ala Leu Arg Ile
465                 470                 475                 480
Asn Lys Leu Ser Ala Thr Leu Asp Ser Gly Ala Leu Arg Ser His Leu
                485                 490                 495
Asn Gly Tyr Ala Gly Ser Gly Ser Ala Trp Thr Glu Leu Thr Ala Leu
            500                 505                 510
Ser Gly Ser Thr Pro Asn Ala Val Ser Leu Lys Val Asn Arg Gly Asp
        515                 520                 525
Tyr Lys Thr Thr Glu Ile Pro Ile Ser Gly Thr Val Leu Pro Asp Glu
        530                 535                 540
Gly Val Leu Asp Ile Asn Thr Met Ser Leu Tyr Leu Asp Ala Gly Ala
545                 550                 555                 560
Leu Trp Ala Leu Ile Arg Leu Pro Asp Gly Ser Lys Thr Arg Met Lys
                565                 570                 575
Leu Ser Val

<210> SEQ ID NO 38
<211> LENGTH: 582
<212> TYPE: PRT
<213> ORGANISM: Artificial sequence
<220> FEATURE:
<223> OTHER INFORMATION: Det7 tail spike SBP1

<400> SEQUENCE: 38

Met Ser Gly Leu Asn Asp Ile Phe Glu Ala Gln Lys Ile Glu Trp His
1               5                   10                  15
Glu Gly Ala Pro Gly Ala Arg Gly Ser Ser Val Gly Asp Ala Ala Phe
                20                  25                  30
Arg Gln Glu Ala Asn Lys Lys Phe Lys Tyr Ser Val Lys Leu Ser Asp
            35                  40                  45
Tyr Ser Thr Leu Gln Asp Ala Val Thr Asp Ala Val Asp Gly Leu Leu
        50                  55                  60
Ile Asp Ile Asn Tyr Asn Phe Thr Asp Gly Glu Ser Val Asp Phe Gly
65              70                  75                  80
Gly Lys Ile Leu Thr Ile Asn Cys Lys Ala Lys Phe Ile Gly Asp Gly
                85                  90                  95
Ala Leu Ile Phe Asn Asn Met Gly Pro Gly Ser Val Ile Asn Gln Pro
            100                 105                 110
Phe Met Glu Ser Lys Thr Thr Pro Trp Val Ile Phe Pro Trp Asp Ala
        115                 120                 125
Asp Gly Lys Trp Ile Thr Asp Ala Ala Leu Val Ala Ala Thr Leu Lys
```

```
            130                 135                 140
Gln Ser Lys Ile Glu Gly Tyr Gln Pro Gly Val Asn Asp Trp Val Lys
145                 150                 155                 160

Phe Pro Gly Leu Glu Ala Leu Leu Pro Gln Asn Val Lys Asp Gln His
                165                 170                 175

Ile Ala Ala Thr Leu Asp Ile Arg Ser Ala Ser Arg Val Glu Ile Arg
            180                 185                 190

Asn Ala Gly Gly Leu Met Ala Ala Tyr Leu Phe Arg Ser Cys His His
                195                 200                 205

Cys Lys Val Ile Asp Ser Asp Ser Ile Ile Gly Gly Lys Asp Gly Ile
210                 215                 220

Ile Thr Phe Glu Asn Leu Ser Gly Asp Trp Gly Leu Gly Asn Tyr Val
225                 230                 235                 240

Ile Gly Gly Arg Val His Tyr Gly Ser Gly Ser Val Gln Phe Leu
                245                 250                 255

Arg Asn Asn Gly Gly Glu Ser His Asn Gly Val Ile Gly Val Thr
                260                 265                 270

Ser Trp Arg Ala Gly Glu Ser Gly Phe Lys Thr Tyr Gln Gly Ser Val
    275                 280                 285

Gly Gly Gly Thr Ala Arg Asn Tyr Asn Leu Gln Phe Arg Asp Ser Val
290                 295                 300

Ala Leu Ser Pro Val Trp Asn Gly Phe Asp Leu Gly Ser Asp Pro Gly
305                 310                 315                 320

Met Ala Pro Glu Pro Asp Arg Pro Gly Asp Leu Pro Val Ser Glu Tyr
                325                 330                 335

Pro Phe His Gln Leu Pro Asn Asn His Leu Val Asp Asn Ile Leu Val
                340                 345                 350

Met Asn Ser Leu Gly Val Gly Leu Gly Met Asp Gly Ser Gly Gly Tyr
                355                 360                 365

Val Ser Asn Val Thr Val Gln Asp Cys Ala Gly Ala Gly Met Leu Ala
                370                 375                 380

His Thr Tyr Asn Arg Val Phe Ser Asn Ile Thr Val Ile Asp Cys Asn
385                 390                 395                 400

Tyr Leu Asn Phe Asp Ser Asp Gln Ile Ile Ile Gly Asp Cys Ile
                405                 410                 415

Val Asn Gly Ile Arg Ala Ala Gly Ile Lys Pro Gln Pro Ser Asn Gly
                420                 425                 430

Leu Val Ile Ser Ala Pro Asn Ser Thr Ile Ser Gly Leu Val Gly Asn
                435                 440                 445

Val Pro Pro Asp Lys Ile Leu Val Gly Asn Leu Leu Asp Pro Val Leu
450                 455                 460

Gly Gln Ser Arg Val Ile Gly Phe Asn Ser Asp Thr Ala Glu Leu Ala
465                 470                 475                 480

Leu Arg Ile Asn Lys Leu Ser Ala Thr Leu Asp Ser Gly Ala Leu Arg
                485                 490                 495

Ser His Leu Asn Gly Tyr Ala Gly Ser Gly Ser Ala Trp Thr Glu Leu
                500                 505                 510

Thr Ala Leu Ser Gly Ser Thr Pro Asn Ala Val Ser Leu Lys Val Asn
                515                 520                 525

Arg Gly Asp Tyr Lys Thr Thr Glu Ile Pro Ile Ser Gly Thr Val Leu
                530                 535                 540

Pro Asp Glu Gly Val Leu Asp Ile Asn Thr Met Ser Leu Tyr Leu Asp
545                 550                 555                 560
```

```
Ala Gly Ala Leu Trp Ala Leu Ile Arg Leu Pro Asp Gly Ser Lys Thr
            565                 570                 575

Arg Met Lys Leu Ser Val
            580

<210> SEQ ID NO 39
<211> LENGTH: 636
<212> TYPE: PRT
<213> ORGANISM: Artificial sequence
<220> FEATURE:
<223> OTHER INFORMATION: Det7 tail spike SBP1

<400> SEQUENCE: 39

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
        35                  40                  45

Thr Val Arg Gly Ile Ala Val Lys Ala Gly Asp Ala Val Ala Val Gly
    50                  55                  60

Asp Thr Leu Met Thr Leu Ala Gly Ala Gly Ala Gly Ala Gly Ser Ser
65                  70                  75                  80

Val Gly Asp Ala Ala Phe Arg Gln Glu Ala Asn Lys Lys Phe Lys Tyr
                85                  90                  95

Ser Val Lys Leu Ser Asp Tyr Ser Thr Leu Gln Asp Ala Val Thr Asp
            100                 105                 110

Ala Val Asp Gly Leu Leu Ile Asp Ile Asn Tyr Asn Phe Thr Asp Gly
        115                 120                 125

Glu Ser Val Asp Phe Gly Gly Lys Ile Leu Thr Ile Asn Cys Lys Ala
    130                 135                 140

Lys Phe Ile Gly Asp Gly Ala Leu Ile Phe Asn Asn Met Gly Pro Gly
145                 150                 155                 160

Ser Val Ile Asn Gln Pro Phe Met Glu Ser Lys Thr Thr Pro Trp Val
                165                 170                 175

Ile Phe Pro Trp Asp Ala Asp Gly Lys Trp Ile Thr Asp Ala Ala Leu
            180                 185                 190

Val Ala Ala Thr Leu Lys Gln Ser Lys Ile Glu Gly Tyr Gln Pro Gly
        195                 200                 205

Val Asn Asp Trp Val Lys Phe Pro Gly Leu Glu Ala Leu Leu Pro Gln
    210                 215                 220

Asn Val Lys Asp Gln His Ile Ala Ala Thr Leu Asp Ile Arg Ser Ala
225                 230                 235                 240

Ser Arg Val Glu Ile Arg Asn Ala Gly Gly Leu Met Ala Ala Tyr Leu
                245                 250                 255

Phe Arg Ser Cys His His Cys Lys Val Ile Asp Ser Asp Ser Ile Ile
            260                 265                 270

Gly Gly Lys Asp Gly Ile Ile Thr Phe Glu Asn Leu Ser Gly Asp Trp
        275                 280                 285

Gly Leu Gly Asn Tyr Val Ile Gly Gly Arg Val His Tyr Gly Ser Gly
    290                 295                 300

Ser Gly Val Gln Phe Leu Arg Asn Asn Gly Gly Glu Ser His Asn Gly
305                 310                 315                 320

Gly Val Ile Gly Val Thr Ser Trp Arg Ala Gly Glu Ser Gly Phe Lys
                325                 330                 335

Thr Tyr Gln Gly Ser Val Gly Gly Gly Thr Ala Arg Asn Tyr Asn Leu
```

340                 345                 350
Gln Phe Arg Asp Ser Val Ala Leu Ser Pro Val Trp Asn Gly Phe Asp
            355                 360                 365

Leu Gly Ser Asp Pro Gly Met Ala Pro Glu Pro Asp Arg Pro Gly Asp
        370                 375                 380

Leu Pro Val Ser Glu Tyr Pro Phe His Gln Leu Pro Asn Asn His Leu
385                 390                 395                 400

Val Asp Asn Ile Leu Val Met Asn Ser Leu Gly Val Gly Leu Gly Met
                405                 410                 415

Asp Gly Ser Gly Gly Tyr Val Ser Asn Val Thr Val Gln Asp Cys Ala
            420                 425                 430

Gly Ala Gly Met Leu Ala His Thr Tyr Asn Arg Val Phe Ser Asn Ile
        435                 440                 445

Thr Val Ile Asp Cys Asn Tyr Leu Asn Phe Asp Ser Asp Gln Ile Ile
    450                 455                 460

Ile Ile Gly Asp Cys Ile Val Asn Gly Ile Arg Ala Ala Gly Ile Lys
465                 470                 475                 480

Pro Gln Pro Ser Asn Gly Leu Val Ile Ser Ala Pro Asn Ser Thr Ile
                485                 490                 495

Ser Gly Leu Val Gly Asn Val Pro Pro Asp Lys Ile Leu Val Gly Asn
            500                 505                 510

Leu Leu Asp Pro Val Leu Gly Gln Ser Arg Val Ile Gly Phe Asn Ser
        515                 520                 525

Asp Thr Ala Glu Leu Ala Leu Arg Ile Asn Lys Leu Ser Ala Thr Leu
    530                 535                 540

Asp Ser Gly Ala Leu Arg Ser His Leu Asn Gly Tyr Ala Gly Ser Gly
545                 550                 555                 560

Ser Ala Trp Thr Glu Leu Thr Ala Leu Ser Gly Ser Thr Pro Asn Ala
                565                 570                 575

Val Ser Leu Lys Val Asn Arg Gly Asp Tyr Lys Thr Thr Glu Ile Pro
            580                 585                 590

Ile Ser Gly Thr Val Leu Pro Asp Glu Gly Val Leu Asp Ile Asn Thr
        595                 600                 605

Met Ser Leu Tyr Leu Asp Ala Gly Ala Leu Trp Ala Leu Ile Arg Leu
    610                 615                 620

Pro Asp Gly Ser Lys Thr Arg Met Lys Leu Ser Val
625                 630                 635

<210> SEQ ID NO 40
<211> LENGTH: 559
<212> TYPE: PRT
<213> ORGANISM: Artificial sequence
<220> FEATURE:
<223> OTHER INFORMATION: Det7 ORF790 SBP2

<400> SEQUENCE: 40

Met Ala Cys Trp Ser Gly Ala Ser Val Gly Asp Ala Thr Leu Arg Gly
1               5                   10                  15

Glu Leu Asn Asn Glu Gly Val Ile Asn Phe Ser His Ala Asp Thr Tyr
            20                  25                  30

Gly Asn Asp Ser Val Gly Ala His Leu Gln Asn Val Val Tyr Pro Thr
        35                  40                  45

Asp Ala Pro Phe Asn Ala Ala Thr Asp Gly Thr Thr Asp Thr Thr Val
    50                  55                  60

Ala Ile Lys Ser Ala Ile Ala His Cys Ile Ser Lys Gly Lys Lys Leu
65                  70                  75                  80

-continued

```
Val Leu Asn His Leu Phe Met Ile Thr Asp Thr Leu Val Ile Ser Asp
             85                  90                  95
Gly Leu His Val Glu Cys Leu Thr Ser Asp Ser Gly Val Lys Ser Asp
            100                 105                 110
Val Pro Ala Gly Lys Phe Ala Val Lys Ile Thr Gly Ala Asn Ser Gly
            115                 120                 125
Trp Phe Gly Gly Lys Ile Leu Gly Lys Asn Leu Pro Glu Ser Thr Thr
            130                 135                 140
Val Arg Gln Asp Gly Val Leu Phe Asp Glu Asn Ala Glu Tyr Cys Phe
145                 150                 155                 160
Ile Thr Gly Thr Glu Val Thr Gly Phe Phe Ala Lys Gly Leu His Thr
                165                 170                 175
Ser Asp Ala Asp Gly Val Gly Tyr Gly Ile Tyr Asp Lys Gly Tyr Gly
            180                 185                 190
Thr Leu Ile Ser Lys Cys Tyr Ala Asn Ser Lys Phe Cys Val Ala Leu
            195                 200                 205
Gly Gly Thr Glu Gly Arg Val Leu Lys Asn Arg Ile Thr Asn Asn Tyr
            210                 215                 220
Leu Thr Ser Gly Glu Ala Lys Pro Trp Ser Trp Ala Ser Asn Tyr Trp
225                 230                 235                 240
Asn Gly Ile Val Ser Glu Asn Ala His Arg Tyr Val Ile Ala Phe Asn
                245                 250                 255
Asp Val Ser Ala Cys Gly Gln Ser Gly Ile Tyr Phe Gly Gly Asn Gly
            260                 265                 270
Gly Tyr Ser Thr Asp Asn Ile Ile Val Asn Asn Thr Val Tyr Ala Cys
            275                 280                 285
Trp Asn Arg Gly Ile Asp Met Gly Leu Phe Ser Glu Lys Ser Ala Thr
            290                 295                 300
Asn Asp Val Leu Arg Asn Ile Ile Lys Gly Asn Asn Thr Tyr Asn Asn
305                 310                 315                 320
Arg Glu Asn Asn Ile Trp Leu Ala Gly Val Ser Asn Cys Ser Val Val
                325                 330                 335
Gly Asn Thr Ser Trp Phe Asp Thr Asn Tyr Asp Val Ile Phe Ala Gly
            340                 345                 350
Tyr Pro Gly Gly His Ile Cys Ile Ser Leu Ala Ser Gly Ala Asn Gly
            355                 360                 365
Glu Ala Cys Val Gly Asn Thr Ile Asp Ser Asn Thr Cys Ile Asp Pro
            370                 375                 380
Arg Gly Asn Ala Gly Ile Thr Val Pro Thr Gly Ala Thr Gly Asn Val
385                 390                 395                 400
Phe Gly Ser Gly Asn Asn Leu Ser Gln Ala Gly Ala Ile Tyr Ile Ala
                405                 410                 415
Ser Pro Asp Leu Ile Thr Ser Asn Arg Phe Glu Leu Ala Val Thr Gly
            420                 425                 430
Ser Phe Thr Pro Val Leu Leu Pro Glu Ser Gly Ser Ile Thr Leu Ser
            435                 440                 445
Ser Ser Ser Thr Gly Val Phe Arg Ala Thr Gly Asn Arg Ile Asp Phe
            450                 455                 460
Ser Val Thr Val Asn Val Ser Ser Ile Ser Ser Pro Ser Gly Asn Leu
465                 470                 475                 480
Asn Ile Ala Tyr Leu Pro Gly Met Ser Gly Lys Thr Ser Ser Thr Ser
                485                 490                 495
Met Phe Ile Ile Asp Tyr Trp Asn Asp Leu Thr Leu Ser Ser Gly Val
```

```
                500              505              510
Ile Pro Leu Ala Ser Leu Asn Leu Glu Asn Gln Asp Gln Ile Thr Val
            515                  520                  525

Tyr Arg Thr Asp Gly Gly Arg Val Leu Tyr Asp Phe Ser Ser Leu Met
    530                  535                  540

Lys Ser Thr Ser Ser Phe Ile Leu Lys Gly Phe Val Asp Phe Asn
545                  550                  555
```

<210> SEQ ID NO 41
<211> LENGTH: 509
<212> TYPE: PRT
<213> ORGANISM: Artificial sequence
<220> FEATURE:
<223> OTHER INFORMATION: Phage 14 tail spike

<400> SEQUENCE: 41

```
Met Ala Ser Trp Ser His Pro Gln Phe Glu Lys Gly Ala Thr Met Gly
1               5                   10                  15

Thr Arg Ser Arg Gly Ser His His His His His Gly Ser Lys Tyr
            20                  25                  30

Asp Pro Asp Gln Phe Arg Gln Glu Leu Ala Glu Pro Asp Gly Ser Lys
        35                  40                  45

Lys Val Gly Tyr Lys Asp Ser Asn Val Tyr Asp Thr Leu Asn Lys Leu
    50                  55                  60

Glu Leu Lys Phe Lys Ser Phe Gln Glu Met Arg Asp Asp Asn Ser Asn
65                  70                  75                  80

Glu Ile Gly Asp Tyr Ala Leu Leu Thr Gly Trp His Thr Glu His Gln
                85                  90                  95

Gly Tyr Gly Ala Gly Val Phe Gln Cys Val Asp Lys Thr Gly Leu Thr
            100                 105                 110

Asp Asp Gly Gly Thr Ile Ala Val Gly Ser Thr Tyr Ala Trp Lys Arg
        115                 120                 125

Ile Thr Gly Pro Gly Asp Ala Thr Glu Phe Gly Val Val Pro Asn Ala
130                 135                 140

Gly Ser Lys Phe Asp Asn Lys Ala Tyr Ile Leu Ser Ala Ala Ala Thr
145                 150                 155                 160

Gly Ala Leu Ile Phe Pro Ala Gly Asp Ile Tyr Thr Thr Phe Thr
                165                 170                 175

Leu Thr Asp Thr Tyr Leu Val Arg Gly Asn Ser Thr Asn Ile Arg Glu
            180                 185                 190

Ile Glu Ala Pro Asn Val Thr Asp Phe Ile Val His Cys Ser Arg Asn
        195                 200                 205

Gly Thr Trp Glu Gly Arg Ile Asp Gly Ile Ser Trp Glu Gly Val Asn
210                 215                 220

Val Tyr Pro Val Asp Glu His Arg Ala Phe His Thr Tyr Phe Thr Thr
225                 230                 235                 240

Asn Gly Asn Met Arg Asp Cys Arg Phe Arg Gly Val Gly Ser Trp
                245                 250                 255

Phe Asp Gly Val Ser Asn Trp Phe Ile Asp Ser Cys Glu Phe Ser Gly
            260                 265                 270

Ser Leu Gly Gly Glu Asn Ile Leu Asn Thr Pro Lys Val Asp Pro Gln
        275                 280                 285

Gly Thr Ile Gly Thr Trp Val Ile Phe His Lys Cys Phe Ile Ser Arg
290                 295                 300

Ser Ala Gly Ala Gly Ala Arg Thr Ile Gly Leu Pro Ser Val Trp Phe
305                 310                 315                 320
```

```
Arg Asp Cys Ile Val Tyr Tyr Asn Arg Asp Ala Gly Leu Leu His Tyr
            325                 330                 335

Lys Asp Glu Asp Ala Tyr Pro Asn Val Glu Phe Gly Val Gln Lys Val
            340                 345                 350

Thr Gly Cys Asn Ile Asp Ser Asn Asp Ser Ser Gly Val Ile Met Arg
            355                 360                 365

Asp Val Val Tyr Pro Asp Ile Ser Asn Asn Trp Val Ser Ala Gly Arg
            370                 375                 380

Val Leu Asn Gln Ala Gly Val Leu Ile Arg Cys Asn Asp Ile Asn
385                 390                 395                 400

Val Val Glu Asn Ser Ala Tyr Phe Asn Gly Thr His Gly Ile Ser Val
            405                 410                 415

Glu Val Cys Asn Phe Gly Thr Ile Ser Asn Asn Cys Ser Asp Asn
            420                 425                 430

Lys Asn Arg Gly Ile Ser Ile Gln Ser Asp Ser Gly Ile Ser Ser Lys
            435                 440                 445

Leu Thr Val Ser Gly Asn Thr Cys Cys Gly Thr Pro Leu Gly Ser Leu
450                 455                 460

Pro Thr Ala Gln Glu Glu Gly Ile His Ile Glu Gly Asp Arg Ile Val
465                 470                 475                 480

Ser Tyr Gly Asn Val Cys Ala Gly Asn Ser Ser Ser Gln Tyr Ile Asn
            485                 490                 495

Ala Ala Ser Asn Lys Gln Glu Gly Leu Asn Ile Thr Ser
            500                 505

<210> SEQ ID NO 42
<211> LENGTH: 795
<212> TYPE: PRT
<213> ORGANISM: Artificial sequence
<220> FEATURE:
<223> OTHER INFORMATION: O157 BP1

<400> SEQUENCE: 42

Met Val Gly Ala Val Thr Ala Pro Leu Ala Gly Thr Ile Trp Lys Val
1               5                   10                  15

Leu Ala Ser Glu Gly Gln Thr Val Ala Ala Gly Glu Val Leu Leu Ile
            20                  25                  30

Leu Glu Ala Met Lys Met Glu Thr Glu Ile Arg Ala Ala Gln Ala Gly
            35                  40                  45

Thr Val Arg Gly Ile Ala Val Lys Ala Gly Asp Ala Val Ala Val Gly
            50                  55                  60

Glu Thr Leu Met Thr Leu Ala Gly Ala Gly Ala Gly Ala Gly Ser Glu
65                  70                  75                  80

Leu Met Val Ala Glu Thr Asn Leu Ser Arg Thr Leu Arg Thr Pro Glu
            85                  90                  95

Pro Ile Pro Ala Leu Pro Gly Ile Glu Gln Arg Lys Asn Lys Ile Val
            100                 105                 110

Ala Met Asp Asp Thr Gly Asn Pro Ile Met Val Leu Pro Glu Ser Gly
            115                 120                 125

Ser Ala Thr Asp Val Met Ile Gln Leu Ala Ala Asn Asp Gly Phe Lys
            130                 135                 140

Phe Ile Gly Gln Cys Pro Asp Ile Leu Thr Leu Arg Thr Ile Glu Pro
145                 150                 155                 160

Glu Lys Asn Gly Gln Arg Ile Thr Leu Arg Gln His Thr Ile Gly Thr
            165                 170                 175
```

```
Gly Leu Gly Gly Gly Val Phe Arg Ala Val Leu Asp Gly Thr Gly Tyr
                180                 185                 190
Thr Asp Asp Gly Val Val Ile Lys Thr Ala Gly Ser Val Trp
        195                 200                 205
Leu Arg Val Asn Ala Asp Lys Val Asn Pro Phe Met Phe Gly Ala Thr
210                 215                 220
Gly Val Ala Asp Asp Thr Ala Ala Leu Gln Lys Met Leu Glu Cys Gly
225                 230                 235                 240
Arg Ala Ala Glu Leu Gly Thr Asn Val Trp Lys Ala Ser Asn Leu Glu
                245                 250                 255
Leu Asn Asn Lys Ser Cys Ser Leu Ser Gly Ser Gly Leu His Val Ser
                260                 265                 270
Arg Ile Glu Gln Ile Ser Gly Ala Thr Gly Ala Leu Leu Thr Ile Thr
                275                 280                 285
Gln Asp Cys Ser Leu Ile Tyr Leu Ser Asp Cys Gly Leu Tyr Gly Asp
                290                 295                 300
Gly Ile Thr Ala Gly Thr Ser Gly Val Thr Met Glu Thr Gly Asn Pro
305                 310                 315                 320
Gly Gly Ala Pro Ser Tyr Pro Phe Asn Thr Ala Pro Asp Val Arg Arg
                325                 330                 335
Asp Leu Tyr Ile Ser Asn Val His Ile Thr Gly Phe Asp Glu Leu Gly
                340                 345                 350
Phe Asp Tyr Pro Glu Thr Asn Phe Ser Val Ser Thr His Gly Leu Phe
                355                 360                 365
Ile Arg Asn Ile Lys Lys Thr Gly Ala Lys Ile Gly Thr Thr Asn Phe
                370                 375                 380
Thr Trp Thr Asn Leu Gln Ile Asp Thr Cys Gly Gln Glu Cys Leu Val
385                 390                 395                 400
Leu Asp Gly Ala Gly Asn Cys Arg Ile Ile Gly Ala Lys Leu Ile Trp
                405                 410                 415
Ala Gly Ser Glu Asn Glu Thr Pro Tyr Ser Gly Leu Arg Ile Ser Asn
                420                 425                 430
Ser Gln Asn Val Asn Met Thr Gly Val Glu Leu Gln Asp Cys Ala Tyr
                435                 440                 445
Asp Gly Leu Tyr Ile Lys Asn Ser Thr Val Ala Ile Ser Gly Leu Asn
                450                 455                 460
Thr Asn Arg Asn Ser Ala Ser Ser Asn Leu Ser Tyr His Asn Met Val
465                 470                 475                 480
Phe Glu Asn Ser Ile Val Thr Val Asp Gly Tyr Val Cys Arg Asn Tyr
                485                 490                 495
Ala Ala Thr Ser Leu Tyr Asp Leu Asn Ser Gln Ala Gly Asn Val Arg
                500                 505                 510
Cys Ile Gly Ser Asp Ser Thr Val Leu Ile Asn Gly Ile Tyr Glu Ser
                515                 520                 525
Glu Val Asn Ser Glu Arg Leu Met Gly Asp Asn Asn Leu Ile Gln Pro
                530                 535                 540
Tyr Ser Gly Asp Leu Ile Ile Asn Gly Leu Lys Asn Tyr Tyr Thr Tyr
545                 550                 555                 560
Thr Gly Ser Val Lys Asn Asn Ile Pro Thr Phe Asp Gly Val Val Thr
                565                 570                 575
Thr Ala Thr Tyr Val Ser Ala Pro Ser Ile Leu Gly Gln Gly Asn Met
                580                 585                 590
Leu Lys Leu Thr Gln Ser Asn Lys Asp Lys Leu Leu Phe Ser Asp Lys
                595                 600                 605
```

```
Val Ser Arg His Gly Cys Thr Ile Gly Leu Val Leu Ile Pro Ser Phe
    610                 615                 620

Thr Gly Ala Thr Thr Met Thr Ala Phe Thr Leu Gly Ser Gly Tyr Ser
625                 630                 635                 640

Pro Ser Gly Asn Ser Ala Val Met Gln Phe Ile Val Asn Ser Ser Gly
                645                 650                 655

Val Gln Thr Ile Ala Ile Leu Leu Ser Gly Asp Gly Ile Thr Gln Thr
            660                 665                 670

Leu Thr Ser Asp Leu Thr Thr Glu Gln Ala Leu Ala Ser Gly Gly Val
        675                 680                 685

Tyr His Phe Ala Met Gly Phe Ala Pro Gly Arg Leu Trp Trp Ser Ile
    690                 695                 700

Ile Asp Ile Asn Thr Gly Arg Arg Ile Arg Arg Ala Tyr Arg Gln Pro
705                 710                 715                 720

Asp Leu His Ala Ala Phe Asn Ser Ile Phe Asn Ser Gly Thr Ser Ser
                725                 730                 735

Ile Thr Ala Phe Ser Gly Pro Leu Ala Gly Asp Ile Ala Cys Glu Gly
            740                 745                 750

Ala Gly Ser His Val Tyr Val Gly Gly Phe Ser Ser Glu Ser Asp Tyr
        755                 760                 765

Ala Ala Ser Arg Met Tyr Gly Leu Phe Thr Pro Val Asp Leu Asp Lys
    770                 775                 780

Gln Tyr Ser Phe Arg Thr Leu Asn Gly Asn Ile
785                 790                 795

<210> SEQ ID NO 43
<211> LENGTH: 1677
<212> TYPE: DNA
<213> ORGANISM: Artificial sequence
<220> FEATURE:
<223> OTHER INFORMATION: Det7 tail spike SBP1

<400> SEQUENCE: 43
atgagtgttg gtgatgctgc atttaggcag gaagctaata agaaattcaa atattcagta      60
aagttatctg attattctac attacaggat gcagttactg atgccgttga tggattgctt     120
attgatatca attacaactt cacggatggt gagtctgtag attttggtgg taagatttta     180
accattaact gtaaggctaa gtttattgga gatgggcttt aatctttaa taatatgggg      240
ccaggctcgg taattaatca accattcatg gagagcaaga ctactccatg ggtcattttc     300
ccgtgggatg ctgatggtaa atggattaca gatgctgccc ttgttgctgc aacgctgaag     360
caatcaaaga ttgaaggcta tcaacctggg gtaaatgact gggttaaatt ccctggatta     420
gaagcattac tcccacagaa cgttaaagac caacatattg cagccactct agatattcgc     480
agtgccagcc gagtagaaat aagaaatgct ggtggtctta tggctgctta ccttttccgt     540
agttgtcatc actgcaaggt aattgattca gatagcatca ttggtggtaa agatggaatc     600
attacctttg agaaccttag tggtgattgg ggactaggta attatgttat tggtggacgt     660
gttcattatg gttctggtag tggtgttcag ttcctgagaa ataatggtgg tgaatcccac     720
aatggtggag ttattggtgt tacatcatgg cgagcgggtg agtctggttt caagacttat     780
cagggttccg ttggtggtgg tactgcacgt aactataatc tacagttcag ggattctgtt     840
gcattgtctc ctgtttggaa tggttttgac ttgggttctg acccaggtat ggcaccagaa     900
ccggatagac ctgggggattt acctgtatct gaatacccat tccaccaact gcctaataac     960
catttggttg ataatattct tgttatgaac tcacttggtg ttggtttagg tatggatggt    1020
```

```
agtggtgggt atgtttctaa cgttaccgta caggattgtg ctggtgcagg tatgcttgca    1080
catacttaca accgtgtatt ttctaacatt acagttattg attgtaacta ccttaatttt    1140
gattctgacc aaattatcat tataggtgat tgtattgtta atgggattag ggctgctggg    1200
attaaaccac aaccatcaaa tggtctggtt atcagtgcac caaactccac aataagtggg    1260
ttggtcggta atgttcctcc agataaaatt cttgttggta acttacttga cccagtatta    1320
ggtcagtcta gagtcatcgg gttcaatagt gatactgctg agttggctct acgtattaac    1380
aagctgtcag ctactctgga tagtggtgct ttacgttccc atctgaacgg ttatgctggt    1440
tctggttcag catggactga gttaactgca ctctctggtt caacccctaa tgctgtatct    1500
ctcaaggtta accgaggaga ttataagaca actgagatac ctatttctgg tacagtatta    1560
ccggatgaag gtgtgttgga tattaataca atgtccttgt acttagatgc gggtgcactg    1620
tgggctttga tacgactccc tgatggaagt aaaacacgta tgaagttatc tgtgtaa      1677
```

<210> SEQ ID NO 44
<211> LENGTH: 1662
<212> TYPE: DNA
<213> ORGANISM: Artificial sequence
<220> FEATURE:
<223> OTHER INFORMATION: Det7 ORF790 SBP2

<400> SEQUENCE: 44

```
atgagtgttg gtgatgcgac attaagaggt gagttaaata tgaaggggt aatcaatttc    60 tcccatgctg atacgtatgg taatgacagt gtaggagcgc atcttcaaaa tgtcgtatac    120
ccaacagacg ccccttttcaa tgccgctaca gatggtacta cagacacaac agtagctatt    180
aaaagtgcaa tagcgcactg tatatcaaag ggtaaaaaat tagtattaaa tcatttgttc    240
atgattacag atactctggt aatcagtgat gggttgcatg ttgagtgtct tactagtgac    300
tcaggtgtta agtctgatgt accagcaggt aaatttgcag taaaaataac gggggccaat    360
tctggttggt ttgggggtaa aatcctgggt aaaaacttac cagaatctac aacagtaagg    420
caggatggcg tactctttga tgagaatgct gaatactgct ttattactgg tacagaggtt    480
actggcttct ttgcaaaagg tttgcatacc tcagatgctg atggtgtagg ctatggtatt    540
tacgataaag ggtatggtac tctcatctct aaatgttatg caaactcaaa gttctgtgta    600
gctctgggtg gtactgaggg tcgcgtactt aagaaccgta taaccaataa ctaccttaca    660
tccggggagg ctaaaccatg gagctgggct agcaactatt ggaatgggat agtatccgag    720
aatgctcaca gatatgtcat cgcttttaat gatgtatcag cctgtggaca gagtggaatt    780
tactttggtg ggaatggtgg ttattcaaca gataacatca tcgtaaataa cactgtttac    840
gcctgctgga accgtggtat tgatatgggt ttgttttctg aaaaatcggc aacaaatgac    900
gtactcagaa atatcatcaa gggtaacaat acctataaca accgagaaaa taatatctgg    960
cttgcaggtg ttagtaactg ctcagtagtt ggtaatacat cgtggtttga caccaattat    1020
gatgtaattt ttgcaggtta tccaggcggt catatttgta ttagtctagc ttctggtgca    1080
aatggggaag cttgtgtagg gaacacaatc gactctaata cttgtattga ccctagaggt    1140
aatgcaggta taacagtacc tactggggca actggtaatg tttttggatc aggtaataat    1200
ctatctcaag ctggggctat ttatatagct tcacctgact tgattacgtc taacagattt    1260
gaactggcag tcactggttc gttcacaccg gtcctgcttc ctgaaagcgg aagtataacc    1320
ctgtcgtcat caagtacagg agtctttagg gcaaccggca atagaataga tttttccgta    1380
acagtaaatg tatcttcaat atcatcgcca agtgggaatt taaatatcgc ctatcttcca    1440
```

```
ggaatgagtg ggaaaacaag ctcaacatca atgtttatta ttgactattg gaatgattta    1500
acgttatcaa gtggtgtaat tccattggca tcattaaatt tagaaaatca agatcaaata    1560
acagtctacc gaactgatgg gggaagggtt ctctatgact tttcttcatt gatgaaatca    1620
acatcatcgt ttatattaaa aggttttgtt gattttaact aa                      1662

<210> SEQ ID NO 45
<211> LENGTH: 1680
<212> TYPE: DNA
<213> ORGANISM: Artificial sequence
<220> FEATURE:
<223> OTHER INFORMATION: Det7 ORF790 SBP2

<400> SEQUENCE: 45
atggcttgct ggagcggcgc cagtgttggt gatgcgacat taagaggtga gttaaataat      60 gaagggtaa tcaatttctc ccatgctgat acgtatggta atgacagtgt aggagcgcat      120
cttcaaaatg tcgtataccc aacagacgcc cctttcaatg ccgctacaga tggtactaca     180
gacacaacag tagctattaa aagtgcaata gcgcactgta tatcaaaggg taaaaaatta     240
gtattaaatc atttgttcat gattacagat actctggtaa tcagtgatgg gttgcatgtt     300
gagtgtctta ctagtgactc aggtgttaag tctgatgtac cagcaggtaa atttgcagta     360
aaaataacgg gggccaattc tggttggttt ggggtaaaa tcctgggtaa aaacttacca     420
gaatctacaa cagtaaggca ggatggcgta ctctttgatg agaatgctga atactgcttt     480
attactggta cagaggttac tggcttcttt gcaaaaggtt tgcatacctc agatgctgat     540
ggtgtaggct atggtattta cgataaaggg tatggtactc tcatctctaa atgttatgca     600
aactcaaagt tctgtgtagc tctgggtggt actgagggtc gcgtacttaa gaaccgtata     660
accaataact accttacatc cggggaggct aaaccatgga gctgggctag caactattgg    720
aatgggatag tatccgagaa tgctcacaga tatgtcatcg cttttaatga tgtatcagcc     780
tgtggacaga gtggaattta cttttggtggg aatggtggtt attcaacaga taacatcatc    840
gtaaataaca ctgtttacgc ctgctggaac cgtggtattg atatgggttt gttttctgaa    900
aaatcggcaa caaatgacgt actcagaaat atcatcaagg gtaacaatac ctataacaac    960
cgagaaaata tatctggcta tgcaggtgtt agtaactgct cagtagttgg taatacatcg   1020
tggtttgaca ccaattatga tgtaattttt gcaggttatc caggcggtca tatttgtatt   1080
agtctagctt ctggtgcaaa tggggaagct tgtgtaggga acacaatcga ctctaatact   1140
tgtattgacc ctagaggtaa tgcaggtata acagtaccta ctggggcaac tggtaatgtt   1200
tttggatcag gtaataatct atctcaagct gggctatt tatatagctt acctgacttg    1260
attacgtcta acagatttga actggcagtc actggttcgt tcacaccggt cctgcttcct   1320
gaaagcggaa gtataacccct gtcgtcatca agtacaggag tctttagggc aaccggcaat   1380
agaatagatt tttccgtaac agtaaatgta tcttcaatat catcgccaag tgggaattta   1440
aatatcgcct atcttccagg aatgagtggg aaaacaagct caacatcaat gtttattatt   1500
gactattgga atgatttaac gttatcaagt ggtgtaattc cattggcatc attaaatta   1560 gaaaatcaag atcaaataac agtctaccga actgatgggg aagggttct ctatgacttt    1620 tcttcattga tgaaatcaac atcatcgttt atattaaaag gttttgttga ttttaactaa   1680

<210> SEQ ID NO 46
<211> LENGTH: 1443
<212> TYPE: DNA
<213> ORGANISM: Artificial sequence
```

<220> FEATURE:
<223> OTHER INFORMATION: Phage 14 tail spike

<400> SEQUENCE: 46

```
atgaagtatg acccagatca gttccgacaa gaactggctg agccggatgg atctaaaaaa      60
gtagggtata aagacagtaa cgtatatgac acattgaaca agctagaatt aaaattcaaa     120
tcattccagg aaatgcgtga tgataattca aatgagatag gcgattacgc cctactcaca     180
ggctggcata cagagcatca gggttatggt gctggcgtat tcagtgcgt cgataaaact      240
ggcttaacgg acgatggtgg cactattgcg gttggctcta cgtatgcgtg aaacgtatc      300
acgggtccgg gtgatgctac tgaatttggt gttgtgccga acgccgggag taagtttgat     360
aataaagcgt atattttatc cgctgcggct acggggcgc ttatctttcc agcaggtgat      420
atttatacaa cattctttac ccttactgat acctaccttg tgagagggaa ttcaaccaat     480
attcgcgaaa ttgaagcgcc aaatgtaaca gactttattg tccactgctc cagaaacggg     540
acatgggaag ggcgaattga cggaatttcg tgggaaggag ttaatgttta cccagtagac     600
gagcatcgcg cattccatac gtatttcacc actaacggca atatgcggga ttgtcgattc     660
cgtggcgggg ttggctcatg gtttgatggt gtttcaaact ggtttattga ttcctgtgaa     720
ttctctggct cattaggagg agagaatatc cttaatacac ctaaagtcga tcctcaagga     780
acaattggga catgggtgat attccacaaa tgctttatat cacgaagcgc tggagcagga     840
gccagaacta ttggccttcc ttctgtatgg ttcagggatt gtattgtata ttacaaccgt     900
gatgctggtc tcttgcatta taagatgaa acgcttatc ccaatgtaga gtttggagtt       960
cagaaggtaa cgggatgtaa cattgattca aatgattcct ccggagtaat tatgcgggat    1020
gtggtttacc ctgatatatc taacaattgg gtcagcgcag aagggttct taatcaggct     1080
ggagtagtgc tcattaggtg taatgacata aatgttgtag agaacagtgc gtattttaat    1140
ggaactcacg gcatatcagt tgaggtgtgc aattttggaa cgatttctaa caacaactgc    1200
agcgataaca aaacagagg aattagcatc cagagtgact cagggataag cagcaaacta     1260
actgtgtctg gcaataccct ctgtggaact ccactaggtt cgctcccgac agcacaggaa    1320
gagggcattc atatcgaggg agatcgcata gtttcgtatg gtaacgtatg tgccggaaac    1380
tcatcaagtc aatatattaa cgctgcatct aataagcaag agggacttaa tataacctca    1440
tag                                                                   1443
```

<210> SEQ ID NO 47
<211> LENGTH: 1530
<212> TYPE: DNA
<213> ORGANISM: Artificial sequence
<220> FEATURE:
<223> OTHER INFORMATION: Phage 14 tail spike

<400> SEQUENCE: 47

```
atggctagct ggagccaccc gcagttcgaa aaaggcgcca ccatgggtac cagatctcgc      60
ggatcgcatc accatcacca tcacggatcc aagtatgacc cagatcagtt ccgacaagaa     120
ctggctgagc cggatggatc taaaaaagta gggtataaag acagtaacgt atatgacaca     180
ttgaacaagc tagaattaaa attcaaatca ttccaggaaa tgcgtgatga taattcaaat     240
gagataggcg attacgccct actcacaggc tggcatacag agcatcaggg ttatggtgct     300
ggcgtatttc agtgcgtcga taaaactggc ttaacggacg atggtggcac tattgcggtt     360
ggctctacgt atgcgtggaa acgtatcacg gtccgggtg atgctactga atttggtgtt      420
gtgccgaacg ccgggagtaa gtttgataat aaagcgtata ttttatccgc tgcggctacg     480
```

| | |
|---|---|
| ggggcgctta tctttccagc aggtgatatt tatacaacat tctttaccct tactgatacc | 540 |
| taccttgtga gagggaattc aaccaatatt cgcgaaattg aagcgccaaa tgtaacagac | 600 |
| tttattgtcc actgctccag aaacgggaca tgggaagggc gaattgacgg aatttcgtgg | 660 |
| gaaggagtta atgtttaccc agtagacgag catcgcgcat tccatacgta tttcaccact | 720 |
| aacggcaata tgcgggattg tcgattccgt ggcggggttg gctcatggtt tgatggtgtt | 780 |
| tcaaactggt ttattgattc ctgtgaattc tctggctcat taggaggaga gaatatcctt | 840 |
| aatacaccta aagtcgatcc tcaaggaaca attgggacat gggtgatatt ccacaaatgc | 900 |
| tttatatcac gaagcgctgg agcaggagcc agaactattg gccttccttc tgtatggttc | 960 |
| agggattgta ttgtatatta caaccgtgat gctggtctct tgcattataa agatgaagac | 1020 |
| gcttatccca atgtagagtt tggagttcag aaggtaacgg gatgtaacat tgattcaaat | 1080 |
| gattcctccg gagtaattat gcgggatgtg gtttaccctg atatatctaa caattgggtc | 1140 |
| agcgcaggaa gggttcttaa tcaggctgga gtagtgctca ttaggtgtaa tgacataaat | 1200 |
| gttgtagaga acagtgcgta ttttaatgga actcacggca tatcagttga ggtgtgcaat | 1260 |
| tttggaacga tttctaacaa caactgcagc gataacaaaa acagaggaat tagcatccag | 1320 |
| agtgactcag ggataagcag caaactaact gtgtctggca ataccgctg tggaactcca | 1380 |
| ctaggttcgc tcccgacagc acaggaagag ggcattcata tcgagggaga tcgcatagtt | 1440 |
| tcgtatggta acgtatgtgc cggaaactca tcaagtcaat atattaacgc tgcatctaat | 1500 |
| aagcaagagg gacttaatat aacctcatag | 1530 |

<210> SEQ ID NO 48
<211> LENGTH: 2148
<212> TYPE: DNA
<213> ORGANISM: Artificial sequence
<220> FEATURE:
<223> OTHER INFORMATION: O157 BP1

<400> SEQUENCE: 48

| | |
|---|---|
| atggtcgcag aaacaaacct gagcagaacg ctacgaaccc ctgagccgat accagcattg | 60 |
| ccgggaattg agcaacgtaa gaataagatt gttgcaatgg atgatactgg aaatccgata | 120 |
| atggttttgc ctgaatctgg ttcggctact gatgtaatga tccagttagc ggcaaatgat | 180 |
| ggatttaagt ttattggtca gtgccctgat atattgacac taagaacaat agaacctgaa | 240 |
| aaaaatggtc aaaggatcac gttgcgacag catacgatcg gaactgggct tggtggaggg | 300 |
| gtattcagag ctgtacttga tggaactggc tataccgatg atgatggtgt tgtaataaaa | 360 |
| acagcaggtg gttctgtatg gttacgggtt aatgcagata aggttaatcc gtttatgttt | 420 |
| ggggccactg gcgtggctga tgatacagca gcactgcaaa agatgcttga atgtggcagg | 480 |
| gcggctgagc ttggcacaaa tgtctggaaa gcatctaatc ttgagctaaa taacaagtcg | 540 |
| tgttcactat ctgggtctgg tctacacgtt tccaggatag agcaaatatc tggggcaaca | 600 |
| ggcgcgttac tgacaattac tcaggattgc agcctgattt atttgtccga ttgtggcctg | 660 |
| tatggggatg gaataactgc gggaacaagc ggggtaacga tggagacagg aaacccaggt | 720 |
| ggggcaccaa gctatccatt caataccgcc cctgacgttc gtagggatct ttacattagc | 780 |
| aatgttcaca ttacaggatt tgacgagtta ggatttgatt atcctgaaac gaattttttcc | 840 |
| gtctcaacgc atggattatt cataagaaac attaaaaaaa ccggggctaa gatcggaact | 900 |
| accaattta catggacaaa ccttcaaatt gatacgtgtg gcaggaatg cttagtgctt | 960 |
| gatggtgctg gtaattgcag aattataggt gccaaattaa tttgggctgg ttcagaaaat | 1020 |

```
gaaacaccat attcaggatt acgtatttct aattcacaaa atgtaaacat gacaggagtt    1080
gagttacagg actgtgcata cgatggattg tatattaaaa attcaactgt tgctatcagt    1140
gggttgaata ctaacagaaa tagtgcatca tcaaatctgt cataccataa tatggttttt    1200
gaaaacagta tagtaactgt agatggttat gtttgccgta actatgctgc tacatcgcta    1260
tatgatctaa attcacaagc cggaaatgtg aggtgtattg gttccgatag taccgtattg    1320
ataaatggta tttacgagtc agaagtaaac agcgaacgac tcatgggtga caataatctt    1380
attcagccat attctggtga tttaataata aatggcctaa aaaactatta tacatataca    1440
ggaagcgtaa aaaacaatat tcctacattt gacggagtcg ttacaaccgc aacatatgta    1500
agcgctcctt cgatactagg gcaaggaaac atgcttaagt taacgcaatc aaacaaggat    1560
aagttattat tttctgataa agtatcgaga catgggtgta caatcggcct tgttctaatc    1620
ccgtcattta cgggtgcaac aactatgaca gctttcactc tggggagtgg atattcgccc    1680
tctgaaaact ctgctgttat gcaatttata gttaactcca gtggtgtgca gactatagca    1740
atattattat ccggtgatgg tataactcaa acgttaacaa gcgatctgac aacggagcaa    1800
gcgttagctt caggaggcgt atatcatttt gcgatggat tcgctccagg ccgattatgg    1860
tggtctatta ttgatataaa taccggaagg cgtatacgac gggcgtacag acaaccagat    1920
cttcacgccg catttaatag catattcaac agcggaacat cttctatcac cgcatttca    1980 ggaccattag caggtgatat tgcatgtgaa ggggcaggtt cgcatgttta tgttggcggt    2040
ttctcatctg agtcagacta cgcagcgagc agaatgtacg gattatttac cccagtagac    2100
ctggataaac aatactcatt ccgcacgctg aacggaaata tttaataa                  2148

<210> SEQ ID NO 49
<211> LENGTH: 2391
<212> TYPE: DNA
<213> ORGANISM: Artificial sequence
<220> FEATURE:
<223> OTHER INFORMATION: O157 BP1

<400> SEQUENCE: 49
atggtaggtg cagttacagc tccgctggcg ggcactatct ggaaggtgct ggccagcgaa      60
ggccagacgg tggccgcagg cgaggtgctg ctgattctgg aagccatgaa gatgaaaacc     120
gaaatccgcg ccgcgcaggc cgggaccgtg cgcggtatcg cggtgaaagc cggcgacgcg     180
gtggcggtcg gcgaaaccct gatgaccctg gctggagcag gcgccggtgc aggatccgag     240
ctcatggtcg cagaaacaaa cctgagcaga acgctacgaa ccctgagcc gataccagca     300 ttgccgggaa ttgagcaacg taagaataag attgttgcaa tggatgatac tggaaatccg     360
ataatggttt tgcctgaatc tggttcggct actgatgtaa tgatccagtt agcggcaaat     420
gatggattta agtttattgg tcagtgccct gatatattga cactaagaac aatagaacct     480
gaaaaaaatg gtcaaaggat cacgttgcga cagcatacga tcggaactgg gcttggtgga     540
ggggtattca gagctgtact tgatggaact ggctataccg atgatgatgg tgttgtaata     600
aaaacagcag gtggttctgt atggttacgg gttaatgcag ataaggttaa tccgtttatg     660
tttggggcca ctggcgtggc tgatgataca gcagcactgc aaaagatgct tgaatgtggc     720
agggcggctg agcttggcac aaatgtctgg aaagcatcta atcttgagct aaataacaag     780
tcgtgttcac tatctgggtc tggtctacac gtttccagga tagagcaaat atctggggca     840
acaggcgcgt tactgacaat tactcaggat tgcagcctga tttatttgtc cgattgtggc     900
ctgtatgggg atggaataac tgcgggaaca agcggggtaa cgatggagac aggaaaccca     960
```

```
ggtggggcac caagctatcc attcaatacc gcccctgacg ttcgtaggga tctttacatt    1020
agcaatgttc acattacagg atttgacgag ttaggatttg attatcctga aacgaatttt    1080
tccgtctcaa cgcatggatt attcataaga aacattaaaa aaaccggggc taagatcgga    1140
actaccaatt ttacatggac aaaccttcaa attgatacgt gtgggcagga atgcttagtg    1200
cttgatggtg ctggtaattg cagaattata ggtgccaaat taatttgggc tggttcagaa    1260
aatgaaacac catattcagg attacgtatt tctaattcac aaaatgtaaa catgacagga    1320
gttgagttac aggactgtgc atacgatgga ttgtatatta aaaattcaac tgttgctatc    1380
agtgggttga atactaacag aaatagtgca tcatcaaatc tgtcatacca taatatggtt    1440
tttgaaaaca gtatagtaac tgtagatggt tatgtttgcc gtaactatgc tgctacatcg    1500
ctatatgatc taaattcaca agccggaaat gtgaggtgta ttggttccga tagtaccgta    1560
ttgataaatg gtatttacga gtcagaagta aacagcgaac gactcatggg tgacaataat    1620
cttattcagc catattctgg tgatttaata ataaatggcc taaaaaacta ttatacatat    1680
acaggaagcg taaaaaacaa tattcctaca tttgacggag tcgttacaac cgcaacatat    1740
gtaagcgctc cttcgatact agggcaagga acatgctta agttaacgca atcaaacaag    1800
gataagttat tattttctga taaagtatcg agacatgggt gtacaatcgg ccttgttcta    1860
atcccgtcat ttacgggtgc aacaactatg acagctttca ctctggggag tggatattcg    1920
ccctctggaa actctgctgt tatgcaattt atagttaact ccagtggtgt gcagactata    1980
gcaatattat tatccggtga tggtataact caaacgttaa caagcgatct gacaacggag    2040
caagcgttag cttcaggagg cgtatatcat tttgcgatgg gattcgctcc aggccgatta    2100
tggtggtcta ttattgatat aaataccgga aggcgtatac gacgggcgta cagacaacca    2160
gatcttcacg ccgcatttaa tagcatattc aacagcggaa catcttctat caccgcattt    2220
tcaggaccat tagcaggtga tattgcatgt gaaggggcag gttcgcatgt ttatgttggc    2280
ggtttctcat ctgagtcaga ctacgcagcg agcagaatgt acggattatt taccccagta    2340
gacctggata acaatactc attccgcacg ctgaacggaa atatttaata a              2391
```

<210> SEQ ID NO 50
<211> LENGTH: 1623
<212> TYPE: DNA
<213> ORGANISM: Artificial sequence
<220> FEATURE:
<223> OTHER INFORMATION: O111 BP1

<400> SEQUENCE: 50

```
atgaagtacg accctgacca attaagacaa gagctagcgg atccaaatgg atatcttcta      60
atcccatcga tggatcagca tattaaaatt cagcagtgga gagaagaggg tgacattcgc     120
ggatggggtg ctattgatgg agagttcaac gatgctgctg tatccgctgc attagactct     180
gaatctccta gcgttaaact tggtggcgtc ggattcgttt caaaacttcg ctcacctatt     240
aaccacaaaa gtaataaagt gatgcatagc gggtcattaa actttcaatt taatggcgga     300
actcagcaag agaaatccgg gatacttatg gctaacatct ccaacgccaa agtgattgat     360
gttgatataa caggcaccct ggatggagga attcgtgggt acggtggcag caatatcgtt     420
atagacggcg tgaatgttca cgatattgga atttcaatgc tatccggtga gtgcggcata     480
ggaatatggt tcggtgatta tgcaaactac gatgtacaga cggatgggct gttaattcaa     540
aattgtaata tcaaaatat tggtggtgta gggatgcagc gtggtgatgg catcctggtt     600
tataacgcga aaaatttcaa ggtaaggcat aacaccatca ttacaaccaa taggatgggt     660
```

```
attgcagccg aagtgatac taggcagttt gagattcatg gaaactacat aggtgatacg     720
ctattagctg gtatagatat tgaacccgac gaaggtcaca ccgcttcaaa tttcaaggta    780
tataataaca atattatcgg atttgctgca cgatacttca ttcaaggcgc tggtgttggt    840
caaacctttg gcatagatac tcatgccaat acctcgtatg gcaaagtgta caagaacata    900
ttgtcggcag gtcagtatgg aacagaagca tttcatatag gaaaccatgc ggatgagatt    960
gaaattacgg ataacgacct gatcggcggt gctgttgtaa tcccattatt catcaagaca   1020
tatgatggta gcggtagtaa gcgcatcaaa ataaaccgca acagggcaaa gggaacatgt   1080
aaatcatttg cagatgtata tatgtctgaa gatgtttata tttctgaaaa tgtattctct   1140
ggtaacagct ctgctgatag ttttttccta agattttcaa taatatcagg gcttaatgtt   1200
gactacaacc ggtccagtga cacaacaaac ttcattaagg caggtgacgc tggaaacaca   1260
tcaaacgtga aggtcactaa taataacatc tctactcttt tagatggtat agacatacta   1320
acttctggtt ccctggctgg ttttattgct tctggcaaca ctattttatg tccagcatcc   1380
aacaaaggaa tttcacttga agtgtatggc gcaggttcta tttcagacct taggcttcgc   1440
ggaaacataa tttataatgc tacaaccaaa atatatgtgt caccagctgc cacgggatgg   1500
gatatgttaa ccacaaatac caggtttaat ctgtctggag ttcaaaatgg cactcagcta   1560
tttgaactat caagaaatag agttacacag tttcttaaca atgcttggta tgatggttag   1620
taa                                                                 1623

<210> SEQ ID NO 51
<211> LENGTH: 1620
<212> TYPE: DNA
<213> ORGANISM: Artificial sequence
<220> FEATURE:
<223> OTHER INFORMATION: O111 BP1

<400> SEQUENCE: 51
atgaagtacg accctgacca attaagacaa gagctagcgg atccaaatgg atatcttcta     60
atcccatcga tggatcagca tattaaaatt cagcagtgga gagaagaggg tgacattcgc    120
ggatggggtg ctattgatgg agagttcaac gatgctgctg tatccgctgc attagactct    180
gaatctccta gcgttaaact tggtggcgtc ggattcgttt caaaacttcg ctcacctatt    240
aaccacaaaa gtaataaagt gatgcatagc gggtcattaa actttcaatt tgatggcgga    300
actcagcaag agaaatccgg gatacttatg gctaacatct ccaacgccaa agtgattgat    360
gttgatataa caggcaccct ggatggagga attcgtgggt acggtggcag caatatcgtt    420
atagacggcg tgaatgttca cgatattgga atttcaatgc tatccggtga gtgcggcata    480
ggaatatggt tcggtgatta tgcaaactac aatgtacaga cggatgggct gttaattcaa    540
aattgtaata tcaaaaatat tggtggtgta gggatgcagc gtggtgatgg catcctggtt    600
tataacgcga aaaatttcaa ggtaaggcat aacaccatca ttacaaccaa taggatgggg    660
attgcagccg aagtgatac taggcagttt gagattcatg gaaactacat aggtgatacg     720
ctattagctg gtatagatat tgaacccgac gaaggtcaca ccgcttcaaa tttcaaggta    780
tataataaca atattatcgg atttgctgca cgatacttca ttcaaggcgc tggtgttggt    840
caaacctttg gcatagatac tcatgccaat acctcgtatg gcaaagtgta caagaacata    900
ttgtcggcag gtcagtatgg aacagaagca tttcatatag gaaaccatgc ggatgagatt    960
gaaattacgg ataacgacct gatcggcggt gctgttgtaa tcccattatt catcaagaca   1020
tatgatggta gcggtagtaa gcgcatcaaa ataaaccgca acagggcaaa gggaacatgt   1080
```

| | |
|---|---:|
| aaatcatttg cagatgtata tatgtctgaa gatgtttata tttctgaaaa tgtattctct | 1140 |
| ggtaacagct ctgctgatag ttttttccta agattttcaa taatatcagg gcttaatgtt | 1200 |
| gactacaacc ggtccagtga cacaacaaac ttcattaagg caggtgacgc tggaaacaca | 1260 |
| tcaaacgtga aggtcactaa taataacatc tctactcttt tagatggtat agacatacta | 1320 |
| acttctggtt ccctggctgg ttttattgct tctggcaaca ctattttatg tccagcatcc | 1380 |
| aacaaaggaa tttcacttga agtgtatggc gcaggttcta tttcagacct taggcttcgc | 1440 |
| ggaaacataa tttataatgc tacaaccaaa atatatgtgt caccagctgc cacgggatgg | 1500 |
| gatatgttaa ccacaaatac caggtttaat ctgtctggag ttcaaaatgg cactcagcta | 1560 |
| tttgaactat caagaaatag agttacacag tttcttaaca atgcttggta tgatggttag | 1620 |

<210> SEQ ID NO 52
<211> LENGTH: 2004
<212> TYPE: DNA
<213> ORGANISM: Bacteriophage

<400> SEQUENCE: 52

| | |
|---|---:|
| atgacagaca tcactgcaaa cgtagttgtt tctaaccctc gtccaatctt cactgaatcc | 60 |
| cgttcgttta agctgttgc taatgggaaa atttacattg gtcagattga taccgatccg | 120 |
| gttaatcctg ccaatcagat acccgtatac attgaaaatg aggatggctc tcacgtccag | 180 |
| attactcagc cgctaattat caacgcagcc ggtaaaatcg tatacaacgg ccaactggtg | 240 |
| aaaattgtca ccgttcaggg tcatagcatg gctatctatg atgccaatgg ttctcaggtt | 300 |
| gactatattg ctaacgtatt gaagtacgat ccagatcaat attcaataga agctgataaa | 360 |
| aaatttaagt attcagtaaa attatcagat tatccaacat gcaggatgc agcatctgct | 420 |
| gcggttgatg gccttcttat cgatcgagat tataattttt atggtggaga gacagttgat | 480 |
| tttggcggaa aggttctgac tatagaatgt aaagctaaat ttataggaga tggaaatctt | 540 |
| attttttacga aattaggcaa aggttcccgc attgccgggg tttttatgga aagcactaca | 600 |
| acaccatggg ttatcaagcc ttggacggat gacaatcagt ggctaacgga tgccgcagcg | 660 |
| gtcgttgcca cttaaaaca atctaaaact gatgggtatc agccaaccgt aagcgattac | 720 |
| gttaaattcc caggaataga aacgttactc ccacctaatg caaaagggca aaacataacg | 780 |
| tctacgttag aaattagaga atgtataggg gtcgaagttc atcgggctag cggtctaatg | 840 |
| gctggttttt tgtttagagg gtgtcacttc tgcaagatgg tagacgccaa taatccaagc | 900 |
| ggaggtaaag atggcattat aaccttcgaa aaccttagcg gcgattgggg aagggtaac | 960 |
| tatgtcattg gcggacgaac cagctatggg tcagtaagta gcgcccagtt tttacgtaat | 1020 |
| aatggtggct ttgaacgtga tggtggagtt attgggttta cttcatatcg cgctggggag | 1080 |
| agtggcgtta aaacttggca aggtactgtg ggctcgacaa cctctcgcaa ctataatctg | 1140 |
| caattccgcg actcggtcgt tatttacccc gtatgggacg gattcgattt aggtgctgac | 1200 |
| actgacatga atccggagtt ggacaggcca gggactacc ctataaccca atacccactg | 1260 |
| catcagttac ccctaaatca cctgattgat aatcttctgg ttcgcggggc gttaggtgta | 1320 |
| ggttttggta tggatggtaa gggcatgtat gtgtctaata ttaccgtaga agattgcgct | 1380 |
| ggctctggcg cgtacctact cacccatgaa tcagtattta ccaatatagc cataattgat | 1440 |
| accaatacta aggatttcca ggctaatcag atttatatat ctggggcttg ccgtgtgaac | 1500 |
| ggtttacgtt taattgggat ccgctcaacc gatgggcagg gtctaaccat agacgcccct | 1560 |
| aactctaccg taagcggtat caccggggatg gtagacccct ctagaattaa tgttgctaat | 1620 |

-continued

```
ttggcagaag aagggttagg taatatccgc gctaatagtt tcggctatga tagcgcagcg    1680
attaaactgc ggattcataa gttatcaaag accttagata gcggagcatt gtactcccac    1740
attaacgtgg ggcccggttc tggctcagcg tggactcaac ttactgctat ttcaggtaac    1800
acacctgacg ctgtatcatt aaaagttaac cacaaagatt gcaggggggc agagatacca    1860
tttgtccctg acatcgcgtc agatgatttt ataaaggatt cctcatgttt tttgccatat    1920
tgggaaaata attctacttc tttaaaggct ttagtgaaaa aacccaatgg agaattagtt    1980
agattaacct tagcaacact ttag                                           2004
```

<210> SEQ ID NO 53
<211> LENGTH: 667
<212> TYPE: PRT
<213> ORGANISM: Bacteriophage

<400> SEQUENCE: 53

```
Met Thr Asp Ile Thr Ala Asn Val Val Ser Asn Pro Arg Pro Ile
 1               5                  10                  15

Phe Thr Glu Ser Arg Ser Phe Lys Ala Val Ala Asn Gly Lys Ile Tyr
                20                  25                  30

Ile Gly Gln Ile Asp Thr Asp Pro Val Asn Pro Ala Asn Gln Ile Pro
            35                  40                  45

Val Tyr Ile Glu Asn Glu Asp Gly Ser His Val Gln Ile Thr Gln Pro
        50                  55                  60

Leu Ile Ile Asn Ala Ala Gly Lys Ile Val Tyr Asn Gly Gln Leu Val
65                  70                  75                  80

Lys Ile Val Thr Val Gln Gly His Ser Met Ala Ile Tyr Asp Ala Asn
                85                  90                  95

Gly Ser Gln Val Asp Tyr Ile Ala Asn Val Leu Lys Tyr Asp Pro Asp
            100                 105                 110

Gln Tyr Ser Ile Glu Ala Asp Lys Lys Phe Lys Tyr Ser Val Lys Leu
        115                 120                 125

Ser Asp Tyr Pro Thr Leu Gln Asp Ala Ala Ser Ala Ala Val Asp Gly
130                 135                 140

Leu Leu Ile Asp Arg Asp Tyr Asn Phe Tyr Gly Gly Glu Thr Val Asp
145                 150                 155                 160

Phe Gly Gly Lys Val Leu Thr Ile Glu Cys Lys Ala Lys Phe Ile Gly
                165                 170                 175

Asp Gly Asn Leu Ile Phe Thr Lys Leu Gly Lys Gly Ser Arg Ile Ala
            180                 185                 190

Gly Val Phe Met Glu Ser Thr Thr Thr Pro Trp Val Ile Lys Pro Trp
        195                 200                 205

Thr Asp Asp Asn Gln Trp Leu Thr Asp Ala Ala Ala Val Val Ala Thr
    210                 215                 220

Leu Lys Gln Ser Lys Thr Asp Gly Tyr Gln Pro Thr Val Ser Asp Tyr
225                 230                 235                 240

Val Lys Phe Pro Gly Ile Glu Thr Leu Leu Pro Pro Asn Ala Lys Gly
                245                 250                 255

Gln Asn Ile Thr Ser Thr Leu Glu Ile Arg Glu Cys Ile Gly Val Glu
            260                 265                 270

Val His Arg Ala Ser Gly Leu Met Ala Gly Phe Leu Phe Arg Gly Cys
        275                 280                 285

His Phe Cys Lys Met Val Asp Ala Asn Asn Pro Ser Gly Gly Lys Asp
    290                 295                 300
```

```
Gly Ile Ile Thr Phe Glu Asn Leu Ser Gly Asp Trp Gly Lys Gly Asn
305                 310                 315                 320

Tyr Val Ile Gly Gly Arg Thr Ser Tyr Gly Ser Val Ser Ser Ala Gln
            325                 330                 335

Phe Leu Arg Asn Asn Gly Gly Phe Glu Arg Asp Gly Val Ile Gly
        340                 345                 350

Phe Thr Ser Tyr Arg Ala Gly Glu Ser Gly Val Lys Thr Trp Gln Gly
        355                 360                 365

Thr Val Gly Ser Thr Thr Ser Arg Asn Tyr Asn Leu Gln Phe Arg Asp
        370                 375                 380

Ser Val Val Ile Tyr Pro Val Trp Asp Gly Phe Asp Leu Gly Ala Asp
385                 390                 395                 400

Thr Asp Met Asn Pro Glu Leu Asp Arg Pro Gly Asp Tyr Pro Ile Thr
                405                 410                 415

Gln Tyr Pro Leu His Gln Leu Pro Leu Asn His Leu Ile Asp Asn Leu
                420                 425                 430

Leu Val Arg Gly Ala Leu Gly Val Gly Phe Gly Met Asp Gly Lys Gly
            435                 440                 445

Met Tyr Val Ser Asn Ile Thr Val Glu Asp Cys Ala Gly Ser Gly Ala
450                 455                 460

Tyr Leu Leu Thr His Glu Ser Val Phe Thr Asn Ile Ala Ile Asp
465                 470                 475                 480

Thr Asn Thr Lys Asp Phe Gln Ala Asn Gln Ile Tyr Ile Ser Gly Ala
                485                 490                 495

Cys Arg Val Asn Gly Leu Arg Leu Ile Gly Ile Arg Ser Thr Asp Gly
            500                 505                 510

Gln Gly Leu Thr Ile Asp Ala Pro Asn Ser Thr Val Ser Gly Ile Thr
        515                 520                 525

Gly Met Val Asp Pro Ser Arg Ile Asn Val Ala Asn Leu Ala Glu Glu
530                 535                 540

Gly Leu Gly Asn Ile Arg Ala Asn Ser Phe Gly Tyr Asp Ser Ala Ala
545                 550                 555                 560

Ile Lys Leu Arg Ile His Lys Leu Ser Lys Thr Leu Asp Ser Gly Ala
                565                 570                 575

Leu Tyr Ser His Ile Asn Gly Gly Ala Gly Ser Gly Ser Ala Tyr Thr
            580                 585                 590

Gln Leu Thr Ala Ile Ser Gly Ser Thr Pro Asp Ala Val Ser Leu Lys
        595                 600                 605

Val Asn His Lys Asp Cys Arg Gly Ala Glu Ile Pro Phe Val Pro Asp
610                 615                 620

Ile Ala Ser Asp Asp Phe Ile Lys Asp Ser Ser Cys Phe Leu Pro Tyr
625                 630                 635                 640

Trp Glu Asn Asn Ser Thr Ser Leu Lys Ala Leu Val Lys Lys Pro Asn
                645                 650                 655

Gly Glu Leu Val Arg Leu Thr Leu Ala Thr Leu
            660                 665

<210> SEQ ID NO 54
<211> LENGTH: 3213
<212> TYPE: DNA
<213> ORGANISM: Bacteriophage

<400> SEQUENCE: 54
atgacggttt caaccgaagt tgaccacaat gactacacag ggaacggggt cacgacatca        60
ttcccctata cctttcgaat ttttaagaag tctgatctgg ttgtgcaggt tgttgacctg       120
```

```
aacgagaaca tcacagaact gattcttgac actgattaca ccgtgactgg tgccggtgga      180
tacacttgcg gggatgttgt cttatcatct cctcttgcca atggttatca gatttcaatt      240
tcacgtgaac ttcctgttac tcaggaaaca gatctacgaa atcaggggaa gttcttcgca      300
gaagtgcatg agaatgcttt tgataaactg acgatgctga ttcagcaggt acgcagttgg      360
ttaagtctgg ccctgcgtaa gccatcattt gtcgccaact actatgatgc acttggcaac      420
tacatccgca atcttcgcga cccgtctcgg cctcaggacg ccgcaacgaa aaattatgtt      480 gataaccta gtgaaggtaa taattcctat gcggataatc ttttagtag aacgcttaga       540 gttcctgaga aaataaacac tctaccatca tcgctggatc gggctaacaa atccctgct      600 tttgatagta atggaaatgc aattgttatc atcccgcaat ctggctcagc atcagatgta      660
ttgatcgaac ttgctaaacc atctgggtct ggtttagtcg gattctcaca cagcaataat      720
tacaacccag ggatggttgg tgaaaagctt caaaacgttg tttatccaac tgacgcccca      780
ttttatgcac caaccgatgg gactagcgat gcaacgactg cgcttcaaag cgccattacc      840
cactgcgagg gaaaaaatgc agttttatgc atcaataaaa gttttcggt ctctgacagt       900 ctttcaattt catcaccgct atgtgtattt gccatgaatg agcagtgcgg gattgtatca      960
tccgctccag ccgggcatgc tgctgttatt tttaatggag ataatatttg ctggaatggt     1020
ggttttattc gtggtttaaa tcaaccaagt agttccacta taagacaaga tggcgtcctg     1080
cttaatggga atgattgtgt tttagataat gtctctatca atggtttctt cgctaaaggg     1140
ttacatacct ctaatgcaga tgggagcggg gttggcatcc gggactatgg tacgcgaaat     1200
accatcagta agtgccgggt agagtataat aaattcggca tatctctcga agggaaagac     1260
ggttgggtac tcggaaacta tgtgagtaac cattaccgga tgtcttctga agccaagccg     1320
tgggacgata ccagtaacta ctgggatggt attgttggcg gcggtgaatg gcttggcgtt     1380
gcaaccggat atctgattga tggtaatgag tttgaggata atggtcagag cggtatctat     1440
gctggtggca acgggggtat tttcgccaag aacaggatta ctaataacca catacatgga     1500
aactggaatc gcggtataga ttttgggggtt gtacagcgtc ttgctaatag tgatgtttat     1560
gaaaatataa tcaccgacaa catagtgcat aacaaccgag cagctaacat atggttagct     1620
ggcgttcggg atagcataat aaataacaat aactcctggt ttactgatga ttatcggtct     1680
atgttcgctg ggaattttga tgcctgcgtg tgcctgacgt tagcagacgg cggtgaaaaa     1740
gcagcgccaa ccggtaatca ggtaaacggt aaccggtgta agaccttgga atctgatgat     1800
cagatcagcg gttttacgtt aaatattaca gacaccgcca gaggaaacca ggtacgggat     1860
aatgtgttgt cccctatagg ggaggcatat attccaaatc cagaactata tgctgttaat     1920
aatatcgata tccctactga gttcgcattc acaccgcaac tcataggcgg gtcaggtgtg     1980
acactgggta acagttctgg caagttaacc gctaacggaa atgtgtttag cctaagtttg     2040
tctatctctg cccagtctgt ctcatcccca agcggcagcc tgacaatcgg gtatataccg     2100
gggcttagtg gtactagtgt tcgccatcac aacgtacgaa cggaattcta taacaacctg     2160
aatactacaa tgcaacgggc gcagccgtac gtaaatatcg tgatagcgc ggaccaattg      2220 cgtgtataca gactggctga tggattatct aaagatgatt tactagagta ttttatgtct     2280
aattcagatc tacgtatggt tggcgatatt gaaatagagc catataactt tagccgttca     2340
gttaccgtgg ttgggcatag cttctgtacc agtgatgtta tgagcacaga gttgaaccgg     2400
ctgcttggta ccgatatata caacttcgcc aggggcgggg ctagtgatgt tgaagttgcc     2460
atgtcgcaag aggcaataac acgacaatat gcgcctgtag gcgggtcaat acctgcgtct     2520
```

-continued

```
ggttcagtag ctcttacgcc tacggaagta ggtatattct ggaacggcgc tacggggaaa      2580
tgtatctttg gaggtatcga cggtacattt tcaacaacgc tggtaaacgc gggaactggt      2640
gagactcagc ttgtattcac gcgtgattct gctggtagtg cggtaagtgt gtcaacaact      2700
gcaacatttg ctatgcggcc gtatacaaga tttaatacaa atactatccc agcagggcga      2760
aagcactctc tgcatagggâ tgatatctat atcgtttggg gcggtcgtaa ctcaactgac      2820
tatactagat atgtgtcaga gttgcatacc atggttgcta atatgcatac tcagcgcttt      2880
gttatttgcc ctgagtttcc ttatgatacg gagacaacgg gaactactgg agctacaaat      2940
ttagcagctc tcaataacaa cctgaaagcc gattttccag ataactattg ccaaattagc      3000
ggcgttgatt tattgcagaa ctttaaaagc aaatataacc cagcctatgc aggagatgta      3060
actgatattg caaacggtat aacccctcgc tctctgcgag aagataacct gcacccatct      3120
gaaacactac agccaaatgg cttgtatata ggtgcaaaag taaacgctga ttttattgct      3180
cagtttatta agtcgaaggg gtggggtggg taa                                   3213
```

<210> SEQ ID NO 55
<211> LENGTH: 1070
<212> TYPE: PRT
<213> ORGANISM: Bacteriophage

<400> SEQUENCE: 55

```
Met Thr Val Ser Thr Glu Val Asp His Asn Asp Tyr Thr Gly Asn Gly
1               5                   10                  15

Val Thr Thr Ser Phe Pro Tyr Thr Phe Arg Ile Phe Lys Lys Ser Asp
            20                  25                  30

Leu Val Val Gln Val Val Asp Leu Asn Glu Asn Ile Thr Glu Leu Ile
        35                  40                  45

Leu Asp Thr Asp Tyr Thr Val Thr Gly Ala Gly Tyr Thr Cys Gly
    50                  55                  60

Asp Val Val Leu Ser Ser Pro Leu Ala Asn Gly Tyr Gln Ile Ser Ile
65                  70                  75                  80

Ser Arg Glu Leu Pro Val Thr Gln Glu Thr Asp Leu Arg Asn Gln Gly
                85                  90                  95

Lys Phe Phe Ala Glu Val His Glu Asn Ala Phe Asp Lys Leu Thr Met
            100                 105                 110

Leu Ile Gln Gln Val Arg Ser Trp Leu Ser Leu Ala Leu Arg Lys Pro
        115                 120                 125

Ser Phe Val Ala Asn Tyr Tyr Asp Ala Leu Gly Asn Tyr Ile Arg Asn
    130                 135                 140

Leu Arg Asp Pro Ser Arg Pro Gln Asp Ala Ala Thr Lys Asn Tyr Val
145                 150                 155                 160

Asp Asn Leu Ser Glu Gly Asn Asn Ser Tyr Ala Asp Asn Leu Phe Ser
                165                 170                 175

Arg Thr Leu Arg Val Pro Glu Lys Ile Asn Thr Leu Pro Ser Ser Leu
            180                 185                 190

Asp Arg Ala Asn Lys Ile Pro Ala Phe Asp Ser Asn Gly Asn Ala Ile
        195                 200                 205

Val Ile Ile Pro Gln Ser Gly Ser Ala Ser Asp Val Leu Ile Glu Leu
    210                 215                 220

Ala Lys Pro Ser Gly Ser Gly Leu Val Gly Phe Ser His Ser Asn Asn
225                 230                 235                 240

Tyr Asn Pro Gly Met Val Gly Glu Lys Leu Gln Asn Val Val Tyr Pro
                245                 250                 255
```

```
Thr Asp Ala Pro Phe Tyr Ala Pro Thr Asp Gly Thr Ser Asp Ala Thr
            260                 265                 270

Thr Ala Leu Gln Ser Ala Ile Thr His Cys Glu Gly Lys Asn Ala Val
            275                 280                 285

Leu Cys Ile Asn Lys Ser Phe Ser Val Ser Asp Ser Leu Ser Ile Ser
            290                 295                 300

Ser Pro Leu Cys Val Phe Ala Met Asn Glu Gln Cys Gly Ile Val Ser
305                 310                 315                 320

Ser Ala Pro Ala Gly His Ala Ala Val Ile Phe Asn Gly Asp Asn Ile
                325                 330                 335

Cys Trp Asn Gly Gly Phe Ile Arg Gly Leu Asn Gln Pro Ser Ser Ser
                340                 345                 350

Thr Ile Arg Gln Asp Gly Val Leu Leu Asn Gly Asn Asp Cys Val Leu
            355                 360                 365

Asp Asn Val Ser Ile Asn Gly Phe Phe Ala Lys Gly Leu His Thr Ser
    370                 375                 380

Asn Ala Asp Gly Ser Gly Val Gly Ile Arg Asp Tyr Gly Thr Arg Asn
385                 390                 395                 400

Thr Ile Ser Lys Cys Arg Val Glu Tyr Asn Lys Phe Gly Ile Ser Leu
            405                 410                 415

Glu Gly Lys Asp Gly Trp Val Leu Gly Asn Tyr Val Ser Asn His Tyr
            420                 425                 430

Arg Met Ser Ser Glu Ala Lys Pro Trp Asp Asp Thr Ser Asn Tyr Trp
            435                 440                 445

Asp Gly Ile Val Gly Gly Gly Glu Trp Leu Gly Val Ala Thr Gly Tyr
            450                 455                 460

Leu Ile Asp Gly Asn Glu Phe Glu Asp Asn Gly Gln Ser Gly Ile Tyr
465                 470                 475                 480

Ala Gly Gly Asn Gly Gly Ile Phe Ala Lys Asn Arg Ile Thr Asn Asn
                485                 490                 495

His Ile His Gly Asn Trp Asn Arg Gly Ile Asp Phe Gly Val Val Gln
                500                 505                 510

Arg Leu Ala Asn Ser Asp Val Tyr Glu Asn Ile Ile Thr Asp Asn Ile
            515                 520                 525

Val His Asn Asn Arg Ala Ala Asn Ile Trp Leu Ala Gly Val Arg Asp
    530                 535                 540

Ser Ile Ile Asn Asn Asn Asn Ser Trp Phe Thr Asp Asp Tyr Arg Ser
545                 550                 555                 560

Met Phe Ala Gly Asn Phe Asp Ala Cys Val Cys Leu Thr Leu Ala Asp
                565                 570                 575

Gly Gly Glu Lys Ala Ala Pro Thr Gly Asn Gln Val Asn Gly Asn Arg
                580                 585                 590

Cys Lys Thr Leu Glu Ser Asp Asp Gln Ile Ser Gly Phe Thr Leu Asn
            595                 600                 605

Ile Thr Asp Thr Ala Arg Gly Asn Gln Val Arg Asp Asn Val Leu Ser
    610                 615                 620

Pro Ile Gly Glu Ala Tyr Ile Pro Asn Pro Glu Leu Tyr Ala Val Asn
625                 630                 635                 640

Asn Ile Asp Ile Pro Thr Glu Phe Ala Phe Thr Pro Gln Leu Ile Gly
                645                 650                 655

Gly Ser Gly Val Thr Leu Gly Asn Ser Ser Gly Lys Leu Thr Ala Asn
                660                 665                 670

Gly Asn Val Phe Ser Leu Ser Leu Ser Ile Ser Ala Gln Ser Val Ser
```

```
                675                 680                 685
Ser Pro Ser Gly Ser Leu Thr Ile Gly Tyr Ile Pro Gly Leu Ser Gly
    690                 695                 700

Thr Ser Val Arg His His Asn Val Arg Thr Glu Phe Tyr Asn Asn Leu
705                 710                 715                 720

Asn Thr Thr Met Gln Arg Ala Gln Pro Tyr Val Asn Ile Gly Asp Ser
                725                 730                 735

Ala Asp Gln Leu Arg Val Tyr Arg Leu Ala Asp Gly Leu Ser Lys Asp
            740                 745                 750

Asp Leu Leu Glu Tyr Phe Met Ser Asn Ser Asp Leu Arg Met Val Gly
        755                 760                 765

Asp Ile Glu Ile Glu Pro Tyr Asn Phe Ser Arg Ser Val Thr Val Val
    770                 775                 780

Gly His Ser Phe Cys Thr Ser Asp Val Met Ser Thr Glu Leu Asn Arg
785                 790                 795                 800

Leu Leu Gly Thr Asp Ile Tyr Asn Phe Ala Arg Gly Gly Ala Ser Asp
                805                 810                 815

Val Glu Val Ala Met Ser Gln Glu Ala Ile Thr Arg Gln Tyr Ala Pro
            820                 825                 830

Val Gly Gly Ser Ile Pro Ala Ser Gly Ser Val Ala Leu Thr Pro Thr
        835                 840                 845

Glu Val Gly Ile Phe Trp Asn Gly Ala Thr Gly Lys Cys Ile Phe Gly
    850                 855                 860

Gly Ile Asp Gly Thr Phe Ser Thr Thr Leu Val Asn Ala Gly Thr Gly
865                 870                 875                 880

Glu Thr Gln Leu Val Phe Thr Arg Asp Ser Ala Gly Ser Ala Val Ser
                885                 890                 895

Val Ser Thr Thr Ala Thr Phe Ala Met Arg Pro Tyr Thr Arg Phe Asn
            900                 905                 910

Thr Asn Thr Ile Pro Ala Gly Arg Lys His Ser Leu His Arg Asp Asp
        915                 920                 925

Ile Tyr Ile Val Trp Gly Gly Arg Asn Ser Thr Asp Tyr Thr Arg Tyr
    930                 935                 940

Val Ser Glu Leu His Thr Met Val Ala Asn Met His Thr Gln Arg Phe
945                 950                 955                 960

Val Ile Cys Pro Glu Phe Pro Tyr Asp Thr Glu Thr Gly Thr Thr
                965                 970                 975

Gly Ala Thr Asn Leu Ala Ala Leu Asn Asn Asn Leu Lys Ala Asp Phe
            980                 985                 990

Pro Asp Asn Tyr Cys Gln Ile Ser Gly Val Asp Leu Leu Gln Asn Phe
        995                 1000                1005

Lys Ser Lys Tyr Asn Pro Ala Tyr Ala Gly Asp Val Thr Asp Ile
    1010                1015                1020

Ala Asn Gly Ile Thr Pro Arg Ser Leu Arg Glu Asp Asn Leu His
    1025                1030                1035

Pro Ser Glu Thr Leu Gln Pro Asn Gly Leu Tyr Ile Gly Ala Lys
    1040                1045                1050

Val Asn Ala Asp Phe Ile Ala Gln Phe Ile Lys Ser Lys Gly Trp
    1055                1060                1065

Gly Gly
    1070

<210> SEQ ID NO 56
<211> LENGTH: 851
```

<210> TYPE: PRT
<213> ORGANISM: Artificial sequence
<220> FEATURE:
<223> OTHER INFORMATION: modified bacteriophage protein

<400> SEQUENCE: 56

```
Met Leu Ile Glu Leu Ala Lys Pro Ser Gly Ser Gly Leu Val Gly Phe
1               5                   10                  15

Ser His Ser Asn Asn Tyr Asn Pro Gly Met Val Gly Glu Lys Leu Gln
            20                  25                  30

Asn Val Val Tyr Pro Thr Asp Ala Pro Phe Tyr Ala Pro Thr Asp Gly
        35                  40                  45

Thr Ser Asp Ala Thr Thr Ala Leu Gln Ser Ala Ile Thr His Cys Glu
50                  55                  60

Gly Lys Asn Ala Val Leu Cys Ile Asn Lys Ser Phe Ser Val Ser Asp
65                  70                  75                  80

Ser Leu Ser Ile Ser Ser Pro Leu Cys Val Phe Ala Met Asn Glu Gln
                85                  90                  95

Cys Gly Ile Val Ser Ser Ala Pro Ala Gly His Ala Ala Val Ile Phe
                100                 105                 110

Asn Gly Asp Asn Ile Cys Trp Asn Gly Phe Ile Arg Gly Leu Asn
            115                 120                 125

Gln Pro Ser Ser Ser Thr Ile Arg Gln Asp Gly Val Leu Leu Asn Gly
130                 135                 140

Asn Asp Cys Val Leu Asp Asn Val Ser Ile Asn Gly Phe Phe Ala Lys
145                 150                 155                 160

Gly Leu His Thr Ser Asn Ala Asp Gly Ser Gly Val Gly Ile Arg Asp
                165                 170                 175

Tyr Gly Thr Arg Asn Thr Ile Ser Lys Cys Arg Val Glu Tyr Asn Lys
            180                 185                 190

Phe Gly Ile Ser Leu Glu Gly Lys Asp Gly Trp Val Leu Gly Asn Tyr
        195                 200                 205

Val Ser Asn His Tyr Arg Met Ser Ser Glu Ala Lys Pro Trp Asp Asp
210                 215                 220

Thr Ser Asn Tyr Trp Asn Gly Ile Val Gly Gly Glu Trp Leu Gly
225                 230                 235                 240

Val Ala Thr Gly Tyr Leu Ile Asp Gly Asn Glu Phe Glu Asp Asn Gly
                245                 250                 255

Gln Ser Gly Ile Tyr Ala Gly Gly Asn Gly Ile Phe Ala Lys Asn
            260                 265                 270

Arg Ile Thr Asn Asn His Ile His Gly Asn Trp Asn Arg Gly Ile Asp
        275                 280                 285

Phe Gly Val Val Gln Arg Leu Ala Asn Ser Asp Val Tyr Glu Asn Ile
        290                 295                 300

Ile Thr Asp Asn Ile Val His Asn Asn Arg Ala Ala Asn Ile Trp Leu
305                 310                 315                 320

Ala Gly Val Arg Asp Ser Ile Ile Asn Asn Asn Ser Trp Phe Thr
                325                 330                 335

Asp Asp Tyr Arg Ser Met Phe Ala Gly Asn Phe Asp Ala Cys Val Cys
            340                 345                 350

Leu Thr Leu Ala Asp Gly Gly Glu Lys Ala Ala Pro Thr Gly Asn Gln
        355                 360                 365

Val Asn Gly Asn Arg Cys Lys Thr Leu Glu Ser Asp Asp Gln Ile Ser
370                 375                 380

Gly Phe Thr Leu Asn Ile Thr Asp Thr Ala Arg Gly Asn Gln Val Arg
```

-continued

```
            385                 390                 395                 400
Asp Asn Val Leu Ser Pro Ile Gly Glu Ala Tyr Ile Pro Asn Pro Glu
                    405                 410                 415

Leu Tyr Ala Val Asn Asn Ile Asp Ile Pro Thr Glu Phe Ala Phe Thr
                    420                 425                 430

Pro Gln Leu Ile Gly Gly Ser Gly Val Thr Leu Gly Asn Ser Ser Gly
                    435                 440                 445

Lys Leu Thr Ala Asn Gly Asn Val Phe Ser Leu Ser Leu Ser Ile Ser
    450                 455                 460

Ala Gln Ser Val Ser Ser Pro Ser Gly Ser Leu Thr Ile Gly Tyr Ile
465                 470                 475                 480

Pro Gly Leu Ser Gly Thr Ser Val Arg His His Asn Val Arg Thr Glu
                    485                 490                 495

Phe Tyr Asn Asn Leu Asn Thr Thr Met Gln Arg Ala Gln Pro Tyr Val
                    500                 505                 510

Asn Ile Gly Asp Ser Ala Asp Gln Leu Arg Val Tyr Arg Leu Ala Asp
                    515                 520                 525

Gly Leu Ser Lys Asp Asp Leu Leu Glu Tyr Phe Met Ser Asn Ser Asp
                    530                 535                 540

Leu Arg Met Val Gly Asp Ile Glu Ile Glu Pro Tyr Asn Phe Ser Arg
545                 550                 555                 560

Ser Val Thr Val Val Gly His Ser Phe Cys Thr Ser Asp Val Met Ser
                    565                 570                 575

Thr Glu Leu Asn Arg Leu Leu Gly Thr Asp Ile Tyr Asn Phe Ala Arg
                    580                 585                 590

Gly Gly Ala Ser Asp Val Glu Val Ala Met Ser Gln Glu Ala Ile Thr
                    595                 600                 605

Arg Gln Tyr Ala Pro Val Gly Gly Ser Ile Pro Ala Ser Gly Ser Val
                    610                 615                 620

Ala Leu Thr Pro Thr Glu Val Gly Ile Phe Trp Asn Gly Ala Thr Gly
625                 630                 635                 640

Lys Cys Ile Phe Gly Gly Ile Asp Gly Thr Phe Ser Thr Thr Leu Val
                    645                 650                 655

Asn Ala Gly Thr Gly Glu Thr Gln Leu Val Phe Thr Arg Asp Ser Ala
                    660                 665                 670

Gly Ser Ala Val Ser Val Ser Thr Thr Ala Thr Phe Ala Met Arg Pro
                    675                 680                 685

Tyr Thr Arg Phe Asn Thr Asn Thr Ile Pro Ala Gly Arg Lys His Ser
                    690                 695                 700

Leu His Arg Asp Asp Ile Tyr Ile Val Trp Gly Gly Arg Asn Ser Thr
705                 710                 715                 720

Asp Tyr Thr Arg Tyr Val Ser Glu Leu His Thr Met Val Ala Asn Met
                    725                 730                 735

His Thr Gln Arg Phe Val Ile Cys Pro Glu Phe Pro Tyr Asp Thr Glu
                    740                 745                 750

Thr Thr Gly Thr Thr Gly Ala Thr Asn Leu Ala Ala Leu Asn Asn Asn
                    755                 760                 765

Leu Lys Ala Asp Phe Pro Asp Asn Tyr Cys Gln Ile Ser Gly Val Asp
                    770                 775                 780

Leu Leu Gln Asn Phe Lys Ser Lys Tyr Asn Pro Ala Tyr Ala Gly Asp
785                 790                 795                 800

Val Thr Asp Ile Ala Asn Gly Ile Thr Pro Arg Ser Leu Arg Glu Asp
                    805                 810                 815
```

```
Asn Leu His Pro Ser Glu Thr Leu Gln Pro Asn Gly Leu Tyr Ile Gly
            820                 825                 830

Ala Lys Val Asn Ala Asp Phe Ile Ala Gln Phe Ile Lys Ser Lys Gly
        835                 840                 845

Trp Gly Gly
    850

<210> SEQ ID NO 57
<211> LENGTH: 1938
<212> TYPE: DNA
<213> ORGANISM: Bacteriophage

<400> SEQUENCE: 57
atgacagaca ttacagccaa tgtgatcgta tcgatgcctt cgcaactctt cactatggcg      60
cgttctttta aagcggttgc caatggcaaa atttatatcg gaaaaattga cactgacccg     120
gtaaaccctg aaaaccagat tcaggtttat gtggagaacg aagatggctc tcacgttcct     180
gtttcgcaac caatcatcat taacgctgct ggttacccgg tatataacgg acagattgcc     240
aagttcgtaa ctgtgcaagg ccattctatg gctgtttatg atgcatacgg tgcgcagcag     300
ttttattttc ctaatgtgtt gaagtacgac cctgaccaat aagacaaga gctagcggat      360 ccaaatggat atcttctaat cccatcgatg gatcagcata ttaaaattca gcagtggaga     420
gaagagggtg acattcgcgg atggggtgct attgatggag agttcaacga tgctgctgta     480
tccgctgcat tagactctga atctcctagc gttaaacttg gtggcgtcgg attcgtttca     540
aaacttcgct cacctattaa ccacaaaagt aataaagtga tgcatagcgg gtcattaaac     600
tttcaatttg atggcggaac tcagcaagag aaatccggga tacttatggc taacatctcc     660
aacgccaaag tgattgatgt tgatataaca ggcaccctgg atggaggaat tcgtgggtac     720
ggtggcagca atatcgttat agacggcgtg aatgttcacg atattggaat ttcaatgcta     780
tccggtgagt gcggcatagg aatatggttc ggtgattatg caaactacga tgtacagacg     840
gatgggctgt taattcaaaa ttgtaatatc aaaaatattg gtggtgtagg gatgcagcgt     900
ggtgatggca tcctggttta aacgcgaaaa aattcaagg taaggcataa ccatcatcat     960
acaaccaata ggatgggtat tgcagccgga agtgatacta ggcagtttga gattcatgga    1020
aactacatag gtgatacgct attagctggt atagatattg aacccgacga aggtcacacc    1080
gcttcaaatt tcaaggtata taataacaat attatcggat ttgctgcacg atacttcatt    1140
caaggcgctg gtgttggtca aacctttggc atagatactc atgccaatac ctcgtatggc    1200
aaagtgtaca agaacatatt gtcggcaggt cagtatggaa cagaagcatt tcatatagga    1260
aaccatgcgg atgagattga aattacggat aacgacctga tcggcggtgc tgttgtaatc    1320
ccattattca tcaagacata tgatggtagc ggtagtaagc gcatcaaaat aaaccgcaac    1380
agggcaaagg gaacatgtaa atcatttgca gatgtatata tgtctgaaga tgtttatatt    1440
tctgaaaatg tattctctgg taacagctct gctgatagtt ttttcctaag attttcaata    1500
atatcagggc ttaatgttga ctacaaccgg tccagtgaca caacaaactt cattaaggca    1560
ggtgacgctg gaaacacatc aaacgtgaag gtcactaata ataacatctc tactctttta    1620
gatggtatag acatactaac ttctggttcc ctggctggtt ttattgcttc tggcaacact    1680
attttatgtc cagcatccaa caaggaatt tcacttgaag tgtatggcgc aggttctatt    1740
tcagacctta ggcttcgcgg aaacataatt tataatgcta caaccaaaat atatgtgtca    1800
ccagctgcca cggatgggga tatgttaacc acaaatacca ggtttgatct gtctggagtt    1860
caaaatggca ctcagctatt tgaactatca agaaatagag ttacacagtt tcttaacaat    1920
```

```
gcttggtatg atggttag                                                    1938
```

<210> SEQ ID NO 58
<211> LENGTH: 539
<212> TYPE: PRT
<213> ORGANISM: Artificial sequence
<220> FEATURE:
<223> OTHER INFORMATION: modified bacteriophage protein

<400> SEQUENCE: 58

```
Met Lys Tyr Asp Pro Asp Gln Leu Arg Gln Glu Leu Ala Asp Pro Asn
1               5                   10                  15

Gly Tyr Leu Leu Ile Pro Ser Met Asp Gln His Ile Lys Ile Gln Gln
            20                  25                  30

Trp Arg Glu Glu Gly Asp Ile Arg Gly Trp Gly Ala Ile Asp Gly Glu
        35                  40                  45

Phe Asn Asp Ala Ala Val Ser Ala Ala Leu Asp Ser Glu Ser Pro Ser
50                  55                  60

Val Lys Leu Gly Gly Val Gly Phe Val Ser Lys Leu Arg Ser Pro Ile
65                  70                  75                  80

Asn His Lys Ser Asn Lys Val Met His Ser Gly Ser Leu Asn Phe Gln
                85                  90                  95

Phe Asp Gly Gly Thr Gln Gln Glu Lys Ser Gly Ile Leu Met Ala Asn
            100                 105                 110

Ile Ser Asn Ala Lys Val Ile Asp Val Asp Ile Thr Gly Thr Leu Asp
        115                 120                 125

Gly Gly Ile Arg Gly Tyr Gly Gly Ser Asn Ile Val Ile Asp Gly Val
    130                 135                 140

Asn Val His Asp Ile Gly Ile Ser Met Leu Ser Gly Glu Cys Gly Ile
145                 150                 155                 160

Gly Ile Trp Phe Gly Asp Tyr Ala Asn Tyr Asp Val Gln Thr Asp Gly
                165                 170                 175

Leu Leu Ile Gln Asn Cys Asn Ile Lys Asn Ile Gly Gly Val Gly Met
            180                 185                 190

Gln Arg Gly Asn Gly Ile Leu Val Tyr Asn Ala Lys Asn Phe Lys Val
        195                 200                 205

Arg His Asn Thr Ile Ile Thr Thr Asn Arg Met Gly Ile Ala Ala Gly
    210                 215                 220

Ser Asp Thr Arg Gln Phe Glu Ile His Gly Asn Tyr Ile Gly Asp Thr
225                 230                 235                 240

Leu Leu Ala Gly Ile Asp Ile Gln Pro Asp Gln Gly His Thr Ala Ser
                245                 250                 255

Asn Phe Lys Val Tyr Asn Asn Ile Ile Gly Phe Ala Ala Arg Tyr
            260                 265                 270

Phe Ile Gln Gly Ala Gly Val Gly Gln Thr Phe Gly Ile Asp Thr His
        275                 280                 285

Ala Asn Thr Ser Tyr Gly Lys Val Tyr Lys Asn Ile Leu Ser Ala Gly
    290                 295                 300

Gln Tyr Gly Thr Glu Ala Phe His Ile Gly Asn His Ala Asp Glu Ile
305                 310                 315                 320

Glu Ile Thr Asp Asn Asp Leu Ile Gly Gly Ala Val Ile Pro Leu
                325                 330                 335

Phe Ile Lys Thr Tyr Asp Gly Ser Gly Ser Lys Arg Ile Lys Ile Asn
            340                 345                 350

Arg Asn Arg Ala Lys Gly Thr Cys Lys Ser Phe Ala Asp Val Tyr Met
```

```
                    355                 360                 365
Ser Glu Asp Val Tyr Ile Ser Glu Asn Val Phe Ser Gly Asn Ser Ser
    370                 375                 380

Ala Asp Ser Phe Phe Leu Arg Phe Ser Ile Ile Ser Gly Leu Asn Val
385                 390                 395                 400

Asp Tyr Asn Arg Ser Ser Asp Thr Thr Asn Phe Ile Lys Ala Gly Asp
                405                 410                 415

Ala Gly Asn Thr Ser Asn Val Lys Val Thr Asn Asn Ile Ser Thr
                420                 425                 430

Leu Leu Asp Gly Ile Asp Ile Leu Thr Ser Gly Ser Leu Ala Gly Phe
            435                 440                 445

Ile Ala Ser Gly Asn Thr Ile Leu Cys Pro Ala Ser Asn Lys Gly Ile
    450                 455                 460

Ser Leu Glu Val Tyr Gly Ala Gly Ser Ile Ser Asp Leu Arg Leu Arg
465                 470                 475                 480

Gly Asn Ile Ile Tyr Asn Ala Thr Thr Lys Ile Tyr Val Ser Pro Ala
                485                 490                 495

Ala Thr Gly Trp Asp Met Leu Thr Thr Asn Thr Arg Phe Asp Leu Ser
            500                 505                 510

Gly Val Gln Asn Gly Thr Gln Leu Phe Glu Leu Ser Arg Asn Arg Val
    515                 520                 525

Thr Gln Phe Leu Asn Asn Ala Trp Tyr Asp Gly
    530                 535

<210> SEQ ID NO 59
<211> LENGTH: 2094
<212> TYPE: DNA
<213> ORGANISM: Bacteriophage

<400> SEQUENCE: 59
atgacggtct caaccgaagt tgaccacaac gaatacaccg gtaacggtgt tacaacgaca      60
ttcccttata ccttcaggat tttccagaaa tctgatttag tagtgcaggt tgttgacctg     120
aacgagaaca tcacagagct gattcttgac actgattaca tagttactgg ggctggagga     180
tacaatggtg gcaatataat tctgtcgaag gcattggtta gcggttatct gatttctata     240
tcacgagagc tcccggttac gcaggaaact gatttgcgta atcagggtaa gttcttgca     300 gaagtgcatg aggatgcttt tgataagcta acgatgctga tccagcaggt tcgaagttgg     360
tttagcttgg cgctgcgtaa gccgtcattc gtggcaaatt attatgatgc gcttaacaat     420
tacatcagaa acttacgcga tccttcaacc ccccaagatg cagccactaa aaattatgtt     480
gatacacagc tcagttctaa cctggggtgt actttgcgcg ttcaggagca gataccgcaa     540
cttcctgatg ctgcctcccg cgcaaacaag atgcctgctt tcgataacga tggtaaccct     600
attgttgtgc ttcctccatc agggtctgcg tctgacgtat tgatcgagct agccaagcca     660
actggatctg acttggttgg ttatgggtca cagacggtta aagcaaccct tgatagcctg     720
aatagcatgc gggaggagct tcttgataaa acaggattta atgcgctggg gcgcttcctt     780
aatctttcag agcttcgctc ctgtgttccg gaggaggcag gcagattgt atacgtagca     840 tcagcagcta gcactacaca tgctgaaaac caccttggtg gcggcttttt cgagtctgtt     900
gataacattc aggcgtgggc tgatgatggt ggaattgtaa tcaagccaga aactggaacg     960
atggtatgga gacgaattaa ttttaccact tacgacatgc aattttgggg ggtgaaacct    1020
gacggagtca cagataacgc aacagctata actcttgcaa ctaactttgc tcgctcaaac    1080
aaatgcattc tagaggctcc tgctggaaac ataaatacat caaaaacaat cccaatttat    1140
```

```
gacaatatgg gaattagagg acagggaaag gctgaagcga cagttttta taaaacaaca    1200 aatgacaaaa tagatctcac aaaaaatgga gaagtaattc ttcaggtgga tgcattatgt    1260
gcttttatac caaagcaatg ggatctaaca gataactcaa ttagttcatt ttgtgttaac    1320
ggtagagttg aaaactgcat gtttagaagg cttggcttaa cacagaaaaa tgtagattct    1380
tatagaaatt attacggact gttttagga aaatcagcag caccagttat cagacagtca    1440 attttgaat gtgcttatat cggatgcttc tcttatgtgc cgttctctgg cgtaatggaa    1500
atggtcggtt tcccacaata tccagggaaa ggatatgctg gagttttgtt tgaagatttt    1560
agggatggtc aaataaaagt aattggcact tctatggata tgcgccttgt tcaagttaat    1620
ggttaccagt tgtcatttag aatgtccggg atgcaatata ctaccatgac caattgtaca    1680
gctgaaaact gcacgccaat ggatgggaa tcaacttgct acgcatttga ttttgtaaat    1740
ccgtattgca ttgtcatgaa tacttgtgca acagaatttg ttaaagggg gcaattgcgt    1800 gttagcgttc agggaaaccc atcattccgc ccatctatta ttgtcaatgg ctttctacca    1860
attgaccaac aaagtccagt agtgcaaaca cctataattg atattgacaa tggtggtgtt    1920
gttgaaatga gtgtcatatt gaatggtggt gattgggcaa taaatccatc ggctgtaaat    1980
ttaacttctc caaaagcaag tggtaatggg ttgaaggtaa gattgatcgg tgtaaatggc    2040
tctccttctt cggtgtggag tgcgtcttct ggtgcagaag taagggagtt ctaa        2094

<210> SEQ ID NO 60
<211> LENGTH: 697
<212> TYPE: PRT
<213> ORGANISM: Bacteriophage

<400> SEQUENCE: 60

Met Thr Val Ser Thr Glu Val Asp His Asn Glu Tyr Thr Gly Asn Gly
1               5                   10                  15

Val Thr Thr Thr Phe Pro Tyr Thr Phe Arg Ile Phe Gln Lys Ser Asp
            20                  25                  30

Leu Val Val Gln Val Val Asp Leu Asn Glu Asn Ile Thr Glu Leu Ile
        35                  40                  45

Leu Asp Thr Asp Tyr Ile Val Thr Gly Ala Gly Tyr Asn Gly Gly
    50                  55                  60

Asn Ile Ile Leu Ser Lys Ala Leu Val Ser Gly Tyr Leu Ile Ser Ile
65                  70                  75                  80

Ser Arg Glu Leu Pro Val Thr Gln Glu Thr Asp Leu Arg Asn Gln Gly
            85                  90                  95

Lys Phe Phe Ala Glu Val His Glu Asp Ala Phe Asp Lys Leu Thr Met
            100                 105                 110

Leu Ile Gln Gln Val Arg Ser Trp Phe Ser Leu Ala Leu Arg Lys Pro
        115                 120                 125

Ser Phe Val Ala Asn Tyr Tyr Asp Ala Leu Asn Asn Tyr Ile Arg Asn
    130                 135                 140

Leu Arg Asp Pro Ser Thr Pro Gln Asp Ala Ala Thr Lys Asn Tyr Val
145                 150                 155                 160

Asp Thr Gln Leu Ser Ser Asn Leu Gly Cys Thr Leu Arg Val Gln Glu
            165                 170                 175

Gln Ile Pro Gln Leu Pro Asp Ala Ala Ser Arg Ala Asn Lys Met Pro
        180                 185                 190

Ala Phe Asp Asn Asp Gly Asn Pro Ile Val Val Leu Pro Pro Ser Gly
    195                 200                 205
```

-continued

```
Ser Ala Ser Asp Val Leu Ile Glu Leu Ala Lys Pro Thr Gly Ser Asp
    210                 215                 220
Leu Val Gly Tyr Gly Ser Gln Thr Val Lys Ala Thr Leu Asp Ser Leu
225                 230                 235                 240
Asn Ser Met Arg Glu Glu Leu Leu Asp Lys Thr Gly Phe Asn Ala Leu
                245                 250                 255
Gly Arg Phe Leu Asn Leu Ser Glu Leu Arg Ser Cys Val Pro Glu Glu
                260                 265                 270
Ala Gly Gln Ile Val Tyr Val Ala Ser Ala Ser Thr Thr His Ala
                275                 280                 285
Glu Asn His Leu Gly Gly Phe Phe Glu Ser Val Asp Asn Ile Gln
    290                 295                 300
Ala Trp Ala Asp Asp Gly Gly Ile Val Ile Lys Pro Glu Thr Gly Thr
305                 310                 315                 320
Met Val Trp Arg Arg Ile Asn Phe Thr Thr Tyr Asp Met Gln Phe Trp
                325                 330                 335
Gly Val Lys Pro Asp Gly Val Thr Asp Asn Ala Thr Ala Ile Thr Leu
                340                 345                 350
Ala Thr Asn Phe Ala Arg Ser Asn Lys Cys Ile Leu Glu Ala Pro Ala
                355                 360                 365
Gly Asn Ile Asn Thr Ser Lys Thr Ile Pro Ile Tyr Asp Asn Met Gly
                370                 375                 380
Ile Arg Gly Gln Gly Lys Ala Glu Ala Thr Val Phe Tyr Lys Thr Thr
385                 390                 395                 400
Asn Asp Lys Ile Asp Leu Thr Lys Asn Gly Glu Val Ile Leu Gln Val
                405                 410                 415
Asp Ala Leu Cys Ala Phe Ile Pro Lys Gln Trp Asp Leu Thr Asp Asn
                420                 425                 430
Ser Ile Ser Ser Phe Cys Val Asn Gly Arg Val Glu Asn Cys Met Phe
                435                 440                 445
Arg Arg Leu Gly Leu Thr Gln Glu Asn Val Asp Ser Tyr Arg Asn Tyr
    450                 455                 460
Tyr Gly Leu Phe Leu Gly Lys Ser Ala Ala Pro Val Ile Arg Gln Ser
465                 470                 475                 480
Ile Phe Glu Cys Ala Tyr Ile Gly Cys Phe Ser Tyr Val Pro Phe Ser
                485                 490                 495
Gly Val Met Glu Met Val Gly Phe Pro Gln Tyr Pro Gly Lys Gly Tyr
                500                 505                 510
Ala Gly Val Leu Phe Glu Asp Phe Arg Asp Gly Gln Ile Lys Val Ile
                515                 520                 525
Gly Thr Ser Met Asp Met Arg Leu Val Gln Val Asn Gly Tyr Gln Leu
    530                 535                 540
Ser Phe Arg Met Ser Gly Met Gln Tyr Thr Thr Met Thr Asn Cys Thr
545                 550                 555                 560
Ala Glu Asn Cys Thr Pro Met Asp Gly Glu Ser Thr Cys Tyr Ala Phe
                565                 570                 575
Asp Phe Val Asn Pro Tyr Cys Ile Val Met Asn Thr Cys Ala Thr Glu
                580                 585                 590
Phe Val Lys Gly Gly Gln Leu Arg Val Ser Val Gln Gly Asn Pro Ser
                595                 600                 605
Phe Arg Pro Ser Ile Ile Val Asn Gly Phe Leu Pro Ile Asp Gln Gln
    610                 615                 620
Ser Pro Val Val Gln Thr Pro Ile Ile Asp Ile Asp Asn Gly Gly Val
625                 630                 635                 640
```

```
Val Glu Met Ser Val Ile Leu Asn Gly Gly Asp Trp Ala Ile Asn Pro
            645                 650                 655

Ser Ala Val Asn Leu Thr Ser Pro Lys Ala Ser Gly Asn Gly Leu Lys
            660                 665                 670

Val Arg Leu Ile Gly Val Asn Gly Ser Pro Ser Val Trp Ser Ala
            675                 680                 685

Ser Ser Gly Ala Glu Val Arg Glu Phe
        690                 695

<210> SEQ ID NO 61
<211> LENGTH: 2094
<212> TYPE: DNA
<213> ORGANISM: Bacteriophage

<400> SEQUENCE: 61
atgacggtct caaccgaagt tgaccacaac gaatacaccg gtaacggtgt tacaacgaca      60
ttcccttata ccttcagaat tttccagaaa tctgatttag tagtgcaggt tgttgacctg     120
aacgagaaca tcacagagct gattcttgac actgattaca tagttactgg ggctggagga     180
tacaatggtg gcaatataat tctgtcgaag gaattggtta gcggttatca gatttctata     240
tcacgagagc tcccggttac gcaggaaact gatttgcgta atcagggtaa gttctttgca     300
gaagtgcatg aggatgcttt tgataagcta acgatgctga tccagcaagt tcgaagttgg     360
tttagcttgg cgctgcgtaa gccgtcattc gtggcaaatt attatgatgc gcttaacaat     420
tacatcagaa acttacgcga tccttcaacc ccccaagatg cagccactaa aaattatgtt     480
gatacacagc tcagttctaa cctggggtgt actttgcgcg ttcaggagca gataccgcaa     540
cttcctgatg ctgcctcccg cgcaaacaag atgcctgctt cgataacga tggtaaccct     600
attgttgtgc ttcctccatc agggtctgcg tctgacgtat tgatcgagct agccaagcca     660
actggatctg acttggttgg ttatgggtca cagacggtta aagcaaccct tgatagcctg     720
aatagcatgc gggaggagct tcttgataaa acaggattta atgcgctggg gcgcttcctt     780
aatctttcag agcttcgctc ctgtgttccg gaggaggcag ggcagattgt atacgtagca     840
tcagcagcta gcactacaca tgctgaaaac caccttggtg gcggcttttt cgagtctgtt     900
gataacattc aggcatgggc tgatgatggt ggaattgtaa tcaagccaga aactggaacg     960
atggtatgga gacgaattaa ttttaccact tacgacatgc aattttgggg ggtgaaacct    1020
gacggagtca cagataacgc aacagctata actcttgcaa ctaactttgc tcgctcaaac    1080
aaatgcattc tagaggctcc tgctggaaac ataaatacat caaaaacaat cccaatttat    1140
gacaatatgg gaattagagg acagggaaag gctgaagcga cagttttttta taaaacaaca    1200
aatgacaaaa tagatctcac aaaaaatgga gaagtaattc ttcaggtgga tgcattatgt    1260
gcttttatac caaagcaatg ggatctaaca gataactcaa tgagttcatt ttgtgttaac    1320
ggtagagttg aaaactgcat gtttagaagg cttggcttaa cacaagaaaa tgtagattct    1380
tatagaaatt attacggact gttttttagga aaatcagcag caccagttat cagacagtca    1440
attttgaat gtgcttatat cggatgcttc tcttatgtgc cgttctctgg cgtaatggaa    1500
atggtcggtt tcccacaata tccagggaaa ggatatgctg gagttttgtt tgaagatttt    1560
agggatggtc aaataaaagt aattggcact tctatggata tgcgccttgt tcaagttaat    1620
ggttaccagt tgtcatttag aatgtccggg atgcaatata ctaccatgac caattgtaca    1680
gctgaaaact gcacgccaat ggatgggaa tcaacttgct acgcatttga ttttgtaaat    1740
ccgtattgca ttgtcatgaa tacttgtgca acagaatttg ttaaagggg gcaattgcgt    1800
```

```
gttagcgttc agggaaaccc atcattccgc ccatctatta ttgtcaatgg ctttctacca    1860
attgaccaac aaagtccagt agtgcaaaca cctataattg atattgacaa tggtggtgtt    1920
gttgaaatga gtgtcatatt gaatggtggt gattgggcaa taaatccatc ggctgtaaat    1980
ttaacttctc caaaagcaag tggtaatggg ttgaaggtaa gattgatcgg tgtaaatggc    2040
tctccttctt cggtgtggag tgcgtcttct ggtgcagaag taagggagtt ctaa          2094

<210> SEQ ID NO 62
<211> LENGTH: 697
<212> TYPE: PRT
<213> ORGANISM: Bacteriophage

<400> SEQUENCE: 62

Met Thr Val Ser Thr Glu Val Asp His Asn Glu Tyr Thr Gly Asn Gly
1               5                   10                  15

Val Thr Thr Thr Phe Pro Tyr Thr Phe Arg Ile Phe Gln Lys Ser Asp
            20                  25                  30

Leu Val Val Gln Val Val Asp Leu Asn Glu Asn Ile Thr Glu Leu Ile
        35                  40                  45

Leu Asp Thr Asp Tyr Ile Val Thr Gly Ala Gly Gly Tyr Asn Gly Gly
    50                  55                  60

Asn Ile Ile Leu Ser Lys Glu Leu Val Ser Gly Tyr Gln Ile Ser Ile
65                  70                  75                  80

Ser Arg Glu Leu Pro Val Thr Gln Glu Thr Asp Leu Arg Asn Gln Gly
                85                  90                  95

Lys Phe Phe Ala Glu Val His Glu Asp Ala Phe Asp Lys Leu Thr Met
            100                 105                 110

Leu Ile Gln Gln Val Arg Ser Trp Phe Ser Leu Ala Leu Arg Lys Pro
        115                 120                 125

Ser Phe Val Ala Asn Tyr Tyr Asp Ala Leu Asn Asn Tyr Ile Arg Asn
    130                 135                 140

Leu Arg Asp Pro Ser Thr Pro Gln Asp Ala Ala Thr Lys Asn Tyr Val
145                 150                 155                 160

Asp Thr Gln Leu Ser Ser Asn Leu Gly Cys Thr Leu Arg Val Gln Glu
                165                 170                 175

Gln Ile Pro Gln Leu Pro Asp Ala Ala Ser Arg Ala Asn Lys Met Pro
            180                 185                 190

Ala Phe Asp Asn Asp Gly Asn Pro Ile Val Val Leu Pro Pro Ser Gly
        195                 200                 205

Ser Ala Ser Asp Val Leu Ile Glu Leu Ala Lys Pro Thr Gly Ser Asp
    210                 215                 220

Leu Val Gly Tyr Gly Ser Gln Thr Val Lys Ala Thr Leu Asp Ser Leu
225                 230                 235                 240

Asn Ser Met Arg Glu Glu Leu Leu Asp Lys Thr Gly Phe Asn Ala Leu
                245                 250                 255

Gly Arg Phe Leu Asn Leu Ser Glu Leu Arg Ser Cys Val Pro Glu Glu
            260                 265                 270

Ala Gly Gln Ile Val Tyr Val Ala Ser Ala Ser Thr Thr His Ala
        275                 280                 285

Glu Asn His Leu Gly Gly Gly Phe Phe Glu Ser Val Asp Asn Ile Gln
    290                 295                 300

Ala Trp Ala Asp Asp Gly Gly Ile Val Ile Lys Pro Glu Thr Gly Thr
305                 310                 315                 320

Met Val Trp Arg Arg Ile Asn Phe Thr Thr Tyr Asp Met Gln Phe Trp
```

```
                                325                 330                 335
Gly Val Lys Pro Asp Gly Val Thr Asp Asn Ala Thr Ala Ile Thr Leu
                340                 345                 350

Ala Thr Asn Phe Ala Arg Ser Asn Lys Cys Ile Leu Glu Ala Pro Ala
                355                 360                 365

Gly Asn Ile Asn Thr Ser Lys Thr Ile Pro Ile Tyr Asp Asn Met Gly
            370                 375                 380

Ile Arg Gly Gln Gly Lys Ala Glu Ala Thr Val Phe Tyr Lys Thr Thr
385                 390                 395                 400

Asn Asp Lys Ile Asp Leu Thr Lys Asn Gly Glu Val Ile Leu Gln Val
                405                 410                 415

Asp Ala Leu Cys Ala Phe Ile Pro Lys Gln Trp Asp Leu Thr Asp Asn
                420                 425                 430

Ser Met Ser Ser Phe Cys Val Asn Gly Arg Val Glu Asn Cys Met Phe
            435                 440                 445

Arg Arg Leu Gly Leu Thr Gln Glu Asn Val Asp Ser Tyr Arg Asn Tyr
        450                 455                 460

Tyr Gly Leu Phe Leu Gly Lys Ser Ala Ala Pro Val Ile Arg Gln Ser
465                 470                 475                 480

Ile Phe Glu Cys Ala Tyr Ile Gly Cys Phe Ser Tyr Val Pro Phe Ser
                485                 490                 495

Gly Val Met Glu Met Val Gly Phe Pro Gln Tyr Pro Lys Gly Tyr
                500                 505                 510

Ala Gly Val Leu Phe Glu Asp Phe Arg Asp Gly Gln Ile Lys Val Ile
            515                 520                 525

Gly Thr Ser Met Asp Met Arg Leu Val Gln Val Asn Gly Tyr Gln Leu
        530                 535                 540

Ser Phe Arg Met Ser Gly Met Gln Tyr Thr Thr Met Thr Asn Cys Thr
545                 550                 555                 560

Ala Glu Asn Cys Thr Pro Met Asp Gly Glu Ser Thr Cys Tyr Ala Phe
                565                 570                 575

Asp Phe Val Asn Pro Tyr Cys Ile Val Met Asn Thr Cys Ala Thr Glu
            580                 585                 590

Phe Val Lys Gly Gly Gln Leu Arg Val Ser Val Gln Gly Asn Pro Ser
        595                 600                 605

Phe Arg Pro Ser Ile Ile Val Asn Gly Phe Leu Pro Ile Asp Gln Gln
            610                 615                 620

Ser Pro Val Val Gln Thr Pro Ile Ile Asp Ile Asp Asn Gly Gly Val
625                 630                 635                 640

Val Glu Met Ser Val Ile Leu Asn Gly Gly Asp Trp Ala Ile Asn Pro
                645                 650                 655

Ser Ala Val Asn Leu Thr Ser Pro Lys Ala Ser Gly Asn Gly Leu Lys
            660                 665                 670

Val Arg Leu Ile Gly Val Asn Gly Ser Pro Ser Val Trp Ser Ala
        675                 680                 685

Ser Ser Gly Ala Glu Val Arg Glu Phe
690                 695

<210> SEQ ID NO 63
<211> LENGTH: 2055
<212> TYPE: DNA
<213> ORGANISM: Bacteriophage

<400> SEQUENCE: 63
atgacggtct caaccgaagt tgaccacaac gaatacaccg gtaacggtgt tacaacgaca    60
```

```
ttcccttata ccttcaggat tttccagaaa tctgatttag tagtgcaggt tgttgacctg    120
aacgagaaca tcacagagct gattcttgac actgattaca tagttactgg ggctggagga    180
tacaatggtg gcaatataat tctgtcgaag gcattggtta gcggttatca gatttctata    240
tcacgagagc tcccggttac gcaggaaact gatttgcgta atcagggtaa gttctttgca    300
gaagtgcatg aggatgcttt tgataagcta acgatgctga tccagcaggt tcgaagttgg    360
tttagcttgg cgctgcgtaa gccgtcattc gtggcaaatt attatgatgc gcttaacaat    420
tacatcagaa acttacgcga tccttcaacc ccccaagatg cagccactaa aaattatgtt    480
gatacacagc tcagttctaa cctggggtgt actttgcgcg ttcaggagca gataccgcaa    540
cttcctgatg ctgcctcccg cgcaaacaag atgcctgctt cgataacga tggtaaccct    600 attgttgtgc ttcctccatc agggtctgcg tctgacgtat tgatcgagct agccaagcca    660
actggatctg acttggttgg ttatgggtca cagacggtta aagcaaccct tgatagcctg    720
aatagcatgc gggaggagct tcttgataaa acaggattta atgcgctggg gcgcttcctt    780
aatctttcag agcttcgctc ctgtgttccg gaggaggcag ggcagattgt atacgtagca    840
tcagcagcta gcactacaca tgctgaaaac caccttggtg gcggcttttt cgagtctgtt    900
gataacattc aggcgtgggc tgatgatggt ggaattgtaa tcaagccaga aactggaacg    960
atggtatgga gacgaattaa tttaccact tacatgcaat tttgggggt gaaacctgac   1020 ggagtcacag ataacgcaac agctataact cttgcaacta actttgctcg ctcaaacaaa   1080
tgcattctag aggctcctgc tggaaacata aatacatcaa aaacaatccc aatttatgac   1140
aatatgggaa ttagaggaca gggaaaggct gaagcgacag tttttttataa aacaacaaat   1200 gacaaaatag atctcacaaa aaatggagaa gtaattcttc aggtggatgc attatgtgct   1260
tttataccaa agcaatggga tctaacagat aactcaatga gttcatttg tgttaacggt   1320 agagttgaaa actgcatgtt tagaaggctt ggcttaacac aagaaaatgt agattcttat   1380
agaaattatt acggactgtt tttaggaaaa tcagcagcac cagttatcag acagtcaatt   1440
tttgaatgtg cttatatcgg atgcttctct tatgtgccgt tctctggcgt aatggaaatg   1500
gtcggtttcc cacaatatcc agggaaagga tatgctggag ttttgtttga agattttagg   1560
gatggtcaaa taaagtaat tggcacttct atggatatgc gccttgttca agttaatggt   1620
taccagttgt catttagaat gtccgggatg caatatacta ccatgaccaa ttgtacagct   1680
gaaaactgca cgccaatgga tggggaatca acttgctacg catttgattt tgtaaatccg   1740
tattgcattg tcatgaatac ttgtgcaaca gaatttgtta aaggggggca attgcgtgtt   1800
agcgttcagg gaaacccatc attccgccca tctattattg tcaatggctt tctaccaatt   1860
gaccaacaaa gtccagtagt gcaaacacct ataattgata ttgacaatgg tgattgggca   1920
ataaatccat cggctgtaaa tttaacttct ccaaaagcaa gtggtaatgg gttgaaggta   1980
agattgatcg gtgtaaatgg ctctccttct tcggtgtgga gtgcgtcttc tggtgcagaa   2040
gtaagggagt tctaa                                                    2055
```

<210> SEQ ID NO 64
<211> LENGTH: 684
<212> TYPE: PRT
<213> ORGANISM: Bacteriophage

<400> SEQUENCE: 64

```
Met Thr Val Ser Thr Glu Val Asp His Asn Glu Tyr Thr Gly Asn Gly
1               5                   10                  15
```

-continued

Val Thr Thr Thr Phe Pro Tyr Thr Phe Arg Ile Phe Gln Lys Ser Asp
            20                  25                  30

Leu Val Val Gln Val Val Asp Leu Asn Glu Asn Ile Thr Glu Leu Ile
        35                  40                  45

Leu Asp Thr Asp Tyr Ile Val Thr Gly Ala Gly Tyr Asn Gly Gly
50                      55                  60

Asn Ile Ile Leu Ser Lys Ala Leu Val Ser Gly Tyr Gln Ile Ser Ile
65                  70                  75                  80

Ser Arg Glu Leu Pro Val Thr Gln Glu Thr Asp Leu Arg Asn Gln Gly
                85                  90                  95

Lys Phe Phe Ala Glu Val His Glu Asp Ala Phe Asp Lys Leu Thr Met
            100                 105                 110

Leu Ile Gln Gln Val Arg Ser Trp Phe Ser Leu Ala Leu Arg Lys Pro
        115                 120                 125

Ser Phe Val Ala Asn Tyr Tyr Asp Ala Leu Asn Asn Tyr Ile Arg Asn
    130                 135                 140

Leu Arg Asp Pro Ser Thr Pro Gln Asp Ala Ala Thr Lys Asn Tyr Val
145                 150                 155                 160

Asp Thr Gln Leu Ser Ser Asn Leu Gly Cys Thr Leu Arg Val Gln Glu
                165                 170                 175

Gln Ile Pro Gln Leu Pro Asp Ala Ala Ser Arg Ala Asn Lys Met Pro
            180                 185                 190

Ala Phe Asp Asn Asp Gly Asn Pro Ile Val Val Leu Pro Pro Ser Gly
        195                 200                 205

Ser Ala Ser Asp Val Leu Ile Glu Leu Ala Lys Pro Thr Gly Ser Asp
    210                 215                 220

Leu Val Gly Tyr Gly Ser Gln Thr Val Lys Ala Thr Leu Asp Ser Leu
225                 230                 235                 240

Asn Ser Met Arg Glu Glu Leu Leu Asp Lys Thr Gly Phe Asn Ala Leu
                245                 250                 255

Gly Arg Phe Leu Asn Leu Ser Glu Leu Arg Ser Cys Val Pro Glu Glu
            260                 265                 270

Ala Gly Gln Ile Val Tyr Val Ala Ser Ala Ala Ser Thr Thr His Ala
        275                 280                 285

Glu Asn His Leu Gly Gly Gly Phe Glu Ser Val Asp Asn Ile Gln
    290                 295                 300

Ala Trp Ala Asp Asp Gly Gly Ile Val Ile Lys Pro Glu Thr Gly Thr
305                 310                 315                 320

Met Val Trp Arg Arg Ile Asn Phe Thr Thr Tyr Met Gln Phe Trp Gly
                325                 330                 335

Val Lys Pro Asp Gly Val Thr Asp Asn Ala Thr Ala Ile Thr Leu Ala
            340                 345                 350

Thr Asn Phe Ala Arg Ser Asn Lys Cys Ile Leu Glu Ala Pro Ala Gly
        355                 360                 365

Asn Ile Asn Thr Ser Lys Thr Ile Pro Ile Tyr Asp Asn Met Gly Ile
    370                 375                 380

Arg Gly Gln Gly Lys Ala Glu Ala Thr Val Phe Tyr Lys Thr Thr Asn
385                 390                 395                 400

Asp Lys Ile Asp Leu Thr Lys Asn Gly Glu Val Ile Leu Gln Val Asp
                405                 410                 415

Ala Leu Cys Ala Phe Ile Pro Lys Gln Trp Asp Leu Thr Asp Asn Ser
            420                 425                 430

Met Ser Ser Phe Cys Val Asn Gly Arg Val Glu Asn Cys Met Phe Arg
        435                 440                 445

Arg Leu Gly Leu Thr Gln Glu Asn Val Asp Ser Tyr Arg Asn Tyr Tyr
    450                 455                 460

Gly Leu Phe Leu Gly Lys Ser Ala Ala Pro Val Ile Arg Gln Ser Ile
465                 470                 475                 480

Phe Glu Cys Ala Tyr Ile Gly Cys Phe Ser Tyr Val Pro Phe Ser Gly
                485                 490                 495

Val Met Glu Met Val Gly Phe Pro Gln Tyr Pro Gly Lys Gly Tyr Ala
            500                 505                 510

Gly Val Leu Phe Glu Asp Phe Arg Asp Gly Gln Ile Lys Val Ile Gly
            515                 520                 525

Thr Ser Met Asp Met Arg Leu Val Gln Val Asn Gly Tyr Gln Leu Ser
        530                 535                 540

Phe Arg Met Ser Gly Met Gln Tyr Thr Thr Met Thr Asn Cys Thr Ala
545                 550                 555                 560

Glu Asn Cys Thr Pro Met Asp Gly Glu Ser Thr Cys Tyr Ala Phe Asp
                565                 570                 575

Phe Val Asn Pro Tyr Cys Ile Val Met Asn Thr Cys Ala Thr Glu Phe
            580                 585                 590

Val Lys Gly Gly Gln Leu Arg Val Ser Val Gln Gly Asn Pro Ser Phe
            595                 600                 605

Arg Pro Ser Ile Ile Val Asn Gly Phe Leu Pro Ile Asp Gln Gln Ser
610                 615                 620

Pro Val Val Gln Thr Pro Ile Ile Asp Ile Asp Asn Gly Asp Trp Ala
625                 630                 635                 640

Ile Asn Pro Ser Ala Val Asn Leu Thr Ser Pro Lys Ala Ser Gly Asn
                645                 650                 655

Gly Leu Lys Val Arg Leu Ile Gly Val Asn Gly Ser Pro Ser Ser Val
            660                 665                 670

Trp Ser Ala Ser Ser Gly Ala Glu Val Arg Glu Phe
        675                 680

<210> SEQ ID NO 65
<211> LENGTH: 2136
<212> TYPE: DNA
<213> ORGANISM: Bacteriophage

<400> SEQUENCE: 65
atgacggtct caaccgaagt tgaccacaac gaatacaccg gtaacggtgt tacaacgaca      60
ttcccttata ccttcaggat tttccagaaa tctgatttag tagtgcaggt tgttgacctg     120
aacgagaaca tcacagagct gattcttgac actgattaca tagttactgg ggctggagga     180
tacaatggtg gcaatataat tctgtcgaag gcattggtta gcggttatca gatttctata     240
tcacgagagc tcccggttac gcaggaaact gatttgcgta atcaggggaa gttctttgca     300
gaagtgcatg aggatgcttt tgataagcta acgatgctga tccagcaggt tcgaagttgg     360
tttagcttgg cgctgcgtaa gccgtcattc gtggcaaact actatgatgc catgaacaac     420
tacattcgta acctgaaaga ccctcgcgat ccacaggacg ctgcaacgaa gaactatgtg     480
gatacgcttt ccactagcaa cctgaacagg acgttgcgtg tacctgaagt tattccttca     540
ttgccagacg cagcagcaag ggccaataag atcgtcgcct cgatggtgc gggtaatcca     600 tttgttatcc ttcctccttc cggttctgct tcagatgttt tcattgagct ggcaaaatct     660
accggggcgg gacttattgg aaccgcttct ggtgaaaatg ctcaatatga gttcgattct     720
ttgcataaat cagtggacac cattccgagt aagttcaggg ctatatattc tgaacccatt     780

```
gtgggctctg ataatgctca agggctttct gaaaacgaca actattactt tatgagttat    840
gacaactcag ggatttccca tgtaaagcgc ttcaaaaaag acgacttttc ctatgttgat    900
agcggcccat tggtatctgc gcacccgcaa ggaatcgcag tgctaagtga tgatgatata    960
ttaatcactg tgcccaaca taacgaaatg gtaaggtttt cctttgccac tatgacttat   1020
agtatcgtta caattcaggg gattagaaaa gattatccta tatcatttta tgataataaa   1080
atttatcagc cacaaaatat aaactccgca atatctaccg cagaattcga atacttattc   1140
atttatgata tggatactca gacatcaagt aaaagtgaaa tgtatagagg aaagttgcgg   1200
gagggcgcag tacaaggcgt atcagttcac aatggacagt tggtgttttt tactggtgga   1260
agttatacag gtggcgggggc tggcaactca atattgcca gtctttataa aacatcactc   1320
tttggtacgc tcatagatgc aaagcaattc ttgaaatctt ctttcatttc tcagttcgga   1380
aacggggttc cttattattt cgagtcgcaa gggattagtt tttataaaaa caaattgacg   1440
ttgcaatgtt atataaatga taaggttttt ttactggttg aggatgacat taccggcctt   1500
cctgtagaat acacgtacag gttaaacaat gtaaaatttt atggaattag tgaggtcgga   1560
ttaactgatt cacaacttaa cgctatggat ccaatatctt caattgtttc gaagatgata   1620
gacaacagtt cattgattca ggcgattggc ccggatacgc cgaaacttca ggcattcatc   1680
ggtcattcaa atggatattt ggaaataagt agaataaata ccaataaatc atttagtaaa   1740
ttttattctt tattatcatc ttcaagtcca ctggagggag tttcttacac aagagatggg   1800
gtttcaacta aattttattt tcacaagata tcaagaatgg tttctccttc tctttactct   1860
tcctcttcag tggcagttgt aggaaagata actatagatg gtctgtcttt attaaataaa   1920
ataactattt gcatggctcc agtatctgcg actaatgccg ttgtgaaagt atctttcgac   1980
tatgatgaag ttcaccagtt tatgaataca agtcgtcctc taaacctgat caatggaaca   2040
gcaagtgtgg tgctaagatt ctcatcggat ggtaatggta tagatattct ttctgcatca   2100
ggatcaccga taataacttc tattactgga tcatga                             2136
```

<210> SEQ ID NO 66
<211> LENGTH: 711
<212> TYPE: PRT
<213> ORGANISM: Bacteriophage

<400> SEQUENCE: 66

```
Met Thr Val Ser Thr Glu Val Asp His Asn Glu Tyr Thr Gly Asn Gly
1               5                   10                  15

Val Thr Thr Thr Phe Pro Tyr Thr Phe Arg Ile Phe Gln Lys Ser Asp
            20                  25                  30

Leu Val Val Gln Val Val Asp Leu Asn Glu Asn Ile Thr Glu Leu Ile
        35                  40                  45

Leu Asp Thr Asp Tyr Ile Val Thr Gly Ala Gly Tyr Asn Gly Gly
    50                  55                  60

Asn Ile Ile Leu Ser Lys Ala Leu Val Ser Gly Tyr Gln Ile Ser Ile
65                  70                  75                  80

Ser Arg Glu Leu Pro Val Thr Gln Glu Thr Asp Leu Arg Asn Gln Gly
                85                  90                  95

Lys Phe Phe Ala Glu Val His Glu Asp Ala Phe Asp Lys Leu Thr Met
            100                 105                 110

Leu Ile Gln Gln Val Arg Ser Trp Phe Ser Leu Ala Leu Arg Lys Pro
        115                 120                 125

Ser Phe Val Ala Asn Tyr Tyr Asp Ala Met Asn Asn Tyr Ile Arg Asn
    130                 135                 140
```

```
Leu Lys Asp Pro Arg Asp Pro Gln Asp Ala Ala Thr Lys Asn Tyr Val
145                 150                 155                 160

Asp Thr Leu Ser Thr Ser Asn Leu Asn Arg Thr Leu Arg Val Pro Glu
            165                 170                 175

Val Ile Pro Ser Leu Pro Asp Ala Ala Arg Ala Asn Lys Ile Val
        180                 185                 190

Ala Phe Asp Gly Ala Gly Asn Pro Phe Val Ile Leu Pro Pro Ser Gly
        195                 200                 205

Ser Ala Ser Asp Val Phe Ile Glu Leu Ala Lys Ser Thr Gly Ala Gly
        210                 215                 220

Leu Ile Gly Thr Ala Ser Gly Glu Asn Ala Gln Tyr Glu Phe Asp Ser
225                 230                 235                 240

Leu His Lys Ser Val Asp Thr Ile Pro Ser Lys Phe Arg Ala Ile Tyr
            245                 250                 255

Ser Glu Pro Ile Val Gly Ser Asp Asn Ala Gln Gly Leu Ser Glu Asn
            260                 265                 270

Asp Asn Tyr Tyr Phe Met Ser Tyr Asp Asn Ser Gly Ile Ser His Val
            275                 280                 285

Lys Arg Phe Lys Lys Asp Asp Phe Ser Tyr Val Asp Ser Gly Pro Leu
290                 295                 300

Val Ser Ala His Pro Gln Gly Ile Ala Val Leu Ser Asp Asp Ile
305                 310                 315                 320

Leu Ile Thr Gly Ala Gln His Asn Glu Met Val Arg Phe Ser Phe Ala
            325                 330                 335

Thr Met Thr Tyr Ser Ile Val Thr Ile Gln Gly Ile Arg Lys Asp Tyr
            340                 345                 350

Pro Ile Ser Phe Tyr Asp Asn Lys Ile Tyr Gln Pro Gln Asn Ile Asn
            355                 360                 365

Ser Ala Ile Ser Thr Ala Glu Phe Glu Tyr Leu Phe Ile Tyr Asp Met
        370                 375                 380

Asp Thr Gln Thr Ser Ser Lys Ser Glu Met Tyr Arg Gly Lys Leu Arg
385                 390                 395                 400

Glu Gly Ala Val Gln Gly Val Ser Val His Asn Gly Gln Leu Val Phe
                405                 410                 415

Phe Thr Gly Gly Ser Tyr Thr Gly Gly Ala Gly Asn Ser Asn Ile
            420                 425                 430

Ala Ser Leu Tyr Lys Thr Ser Leu Phe Gly Thr Leu Ile Asp Ala Lys
        435                 440                 445

Gln Phe Leu Lys Ser Ser Phe Ile Ser Gln Phe Gly Asn Gly Val Pro
450                 455                 460

Tyr Tyr Phe Glu Ser Gln Gly Ile Ser Phe Tyr Lys Asn Lys Leu Thr
465                 470                 475                 480

Leu Gln Cys Tyr Ile Asn Asp Lys Val Phe Leu Leu Val Glu Asp Asp
            485                 490                 495

Ile Thr Gly Leu Pro Val Glu Tyr Thr Tyr Arg Leu Asn Asn Val Lys
            500                 505                 510

Phe Tyr Gly Ile Ser Glu Val Gly Leu Thr Asp Ser Gln Leu Asn Ala
        515                 520                 525

Met Asp Pro Ile Ser Ser Ile Val Ser Lys Met Ile Asp Asn Ser Ser
        530                 535                 540

Leu Ile Gln Ala Ile Gly Pro Asp Thr Pro Lys Leu Gln Ala Phe Ile
545                 550                 555                 560

Gly His Ser Asn Gly Tyr Leu Glu Ile Ser Arg Ile Asn Thr Asn Lys
```

-continued

```
                565                 570                 575
Ser Phe Ser Lys Phe Tyr Ser Leu Leu Ser Ser Ser Pro Leu Glu
            580                 585                 590

Gly Val Ser Tyr Thr Arg Asp Gly Val Ser Thr Lys Phe Tyr Phe His
            595                 600                 605

Lys Ile Ser Arg Met Val Ser Pro Ser Leu Tyr Ser Ser Ser Ser Val
            610                 615                 620

Ala Val Val Gly Lys Ile Thr Ile Asp Gly Leu Ser Leu Leu Asn Lys
625                 630                 635                 640

Ile Thr Ile Cys Met Ala Pro Val Ser Ala Thr Asn Ala Val Val Lys
                645                 650                 655

Val Ser Phe Asp Tyr Asp Glu Val His Gln Phe Met Asn Thr Ser Arg
                660                 665                 670

Pro Leu Asn Leu Ile Asn Gly Thr Ala Ser Val Val Leu Arg Phe Ser
                675                 680                 685

Ser Asp Gly Asn Gly Ile Asp Ile Leu Ser Ala Ser Gly Ser Pro Ile
                690                 695                 700

Ile Thr Ser Ile Thr Gly Ser
705                 710

<210> SEQ ID NO 67
<211> LENGTH: 1665
<212> TYPE: DNA
<213> ORGANISM: Bacteriophage

<400> SEQUENCE: 67
atggctagct ggagccaccc gcagttcgaa aaaggcgcca ccatggctaa gtatgaccct      60
gaccaattaa gacaagagct agcgggtcca aatggatatc ttctaatccc atcgatggat     120
cagcatatta aaattcagca gtggagagaa gagggtgaca ttcgcggatg gggtgctatt     180
gatggagagt tcaacgatgc tgctgtatcc gctgcattag actctgaatc tcctagcgtt     240
aaacttggtg gcgtcggatt cgtttcaaaa cttcgctcac ctattaacca caaaagtaat     300
aaagtgatgc atagcgggtc attaaacttt caatttgatg gcggaactca gcaagagaaa     360
tccgggatac ttatggctaa catctccaac gccaaagtga ttgatgttga taacaggc       420 accctggatg gaggaattcg tgggtacggt ggcagcaata tcgttataga cggcgtgaat     480
gttcacgata ttggaatttc aacgctatcc ggtgagtgcg gcataggaat atggttcggt     540
gattatgcaa actacgatgt acagacggat gggctgttaa ttcaaaattg taatatcaaa     600
aatattggag gtgtagggat acagcgtggg gatggcatcc tggtttataa cgcgaaaaat     660
ttcaaggtaa ggtataacac catcattaca accaatagga tggctattgc agctggaagt     720
gatactaggc agtttgagat tcatggaaac tacataggtg atacgctatt agctggtata     780
gatattgagc tgacgaagg ttacactgct tcaaatttca agatatacaa taacaatatt     840
atcggatttg ctgcacgata cttcactcaa ggatctggtg ttggtcaaac ctttggtata     900
gatactcatg ctaataccte atatggcaaa gtgtataaaa acacattgtc tgcaggacag     960
tatggaacag aagcatttca tataggaaac catgcggatg agattgaagt tacgataaac    1020
aacctgattg gcggtgctgt tgtaatccca ttattcatca agacatatga tggtagtggt    1080
agtaaacaca tcaaaataaa ccgcaacagg gcaaaggga cgtgtaagtc atttgcagat    1140
gtagccatgt ctgaagatgt ttatatttct gaaaatgtat tctctggcaa tagttctaat    1200
gatagttatt tcctgagagc gtcaacaata gcagggctta atgttgacta caaccggtca    1260
agcaacacaa ccaatttcat caagtctggt gacgctggaa acacgtcaag cgtgaaggtc    1320
```

-continued

```
actaataata acgcttctac cctttcagat ggtatagaca tgctaacgtc gggttccatg    1380
actggtttta ttgcttctgg caacactatt ttatgtccag catccaacaa aggaatttca    1440
ctggaagtag caggttcagg ttctatttca gacattagtc tccgtggcaa cataattat    1500 aatgctacaa ccaaaatata tgtatcacca gctgccacgg gatgggatat gttaaccaaa    1560
aataccaggt ttgatctgtc tggagttcaa aatggcactc agctatttga actatcaaga    1620
aatagagtta cacagtttct taacaatgct tggtatgatg gctag                    1665
```

<210> SEQ ID NO 68
<211> LENGTH: 554
<212> TYPE: PRT
<213> ORGANISM: Bacteriophage

<400> SEQUENCE: 68

```
Met Ala Ser Trp Ser His Pro Gln Phe Glu Lys Gly Ala Thr Met Ala
1               5                   10                  15

Lys Tyr Asp Pro Asp Gln Leu Arg Gln Glu Leu Ala Gly Pro Asn Gly
            20                  25                  30

Tyr Leu Leu Ile Pro Ser Met Asp Gln His Ile Lys Ile Gln Gln Trp
        35                  40                  45

Arg Glu Glu Gly Asp Ile Arg Gly Trp Gly Ala Ile Asp Gly Glu Phe
    50                  55                  60

Asn Asp Ala Ala Val Ser Ala Leu Asp Ser Glu Ser Pro Ser Val
65                  70                  75                  80

Lys Leu Gly Gly Val Gly Phe Val Ser Lys Leu Arg Ser Pro Ile Asn
                85                  90                  95

His Lys Ser Asn Lys Val Met His Ser Gly Ser Leu Asn Phe Gln Phe
            100                 105                 110

Asp Gly Gly Thr Gln Gln Glu Lys Ser Gly Ile Leu Met Ala Asn Ile
        115                 120                 125

Ser Asn Ala Lys Val Ile Asp Val Asp Ile Thr Gly Thr Leu Asp Gly
    130                 135                 140

Gly Ile Arg Gly Tyr Gly Gly Ser Asn Ile Val Ile Asp Gly Val Asn
145                 150                 155                 160

Val His Asp Ile Gly Ile Ser Thr Leu Ser Gly Glu Cys Gly Ile Gly
                165                 170                 175

Ile Trp Phe Gly Asp Tyr Ala Asn Tyr Asp Val Gln Thr Asp Gly Leu
            180                 185                 190

Leu Ile Gln Asn Cys Asn Ile Lys Asn Ile Gly Gly Val Gly Ile Gln
        195                 200                 205

Arg Gly Asp Gly Ile Leu Val Tyr Asn Ala Lys Asn Phe Lys Val Arg
    210                 215                 220

Tyr Asn Thr Ile Ile Thr Thr Asn Arg Met Ala Ile Ala Ala Gly Ser
225                 230                 235                 240

Asp Thr Arg Gln Phe Glu Ile His Gly Asn Tyr Ile Gly Asp Thr Leu
                245                 250                 255

Leu Ala Gly Ile Asp Ile Glu Pro Asp Glu Gly Tyr Thr Ala Ser Asn
            260                 265                 270

Phe Lys Ile Tyr Asn Asn Asn Ile Ile Gly Phe Ala Ala Arg Tyr Phe
        275                 280                 285

Thr Gln Gly Ser Gly Val Gly Gln Thr Phe Gly Ile Asp Thr His Ala
    290                 295                 300

Asn Thr Ser Tyr Gly Lys Val Tyr Lys Asn Thr Leu Ser Ala Gly Gln
305                 310                 315                 320
```

Tyr Gly Thr Glu Ala Phe His Ile Gly Asn His Ala Asp Glu Ile Glu
              325                 330                 335

Val Thr Asp Asn Asn Leu Ile Gly Gly Ala Val Val Ile Pro Leu Phe
          340                 345                 350

Ile Lys Thr Tyr Asp Gly Ser Gly Lys His Ile Lys Ile Asn Arg
      355                 360                 365

Asn Arg Ala Lys Gly Thr Cys Lys Ser Phe Ala Asp Val Ala Met Ser
370                 375                 380

Glu Asp Val Tyr Ile Ser Glu Asn Val Phe Ser Gly Asn Ser Ser Asn
385                 390                 395                 400

Asp Ser Tyr Phe Leu Arg Ala Ser Thr Ile Ala Gly Leu Asn Val Asp
              405                 410                 415

Tyr Asn Arg Ser Ser Asn Thr Thr Asn Phe Ile Lys Ser Gly Asp Ala
          420                 425                 430

Gly Asn Thr Ser Ser Val Lys Val Thr Asn Asn Ala Ser Thr Leu
      435                 440                 445

Ser Asp Gly Ile Asp Met Leu Thr Ser Gly Ser Met Thr Gly Phe Ile
450                 455                 460

Ala Ser Gly Asn Thr Ile Leu Cys Pro Ala Ser Asn Lys Gly Ile Ser
465                 470                 475                 480

Leu Glu Val Ala Gly Ser Gly Ser Ile Ser Asp Ile Ser Leu Arg Gly
              485                 490                 495

Asn Ile Ile Tyr Asn Ala Thr Thr Lys Ile Tyr Val Ser Pro Ala Ala
          500                 505                 510

Thr Gly Trp Asp Met Leu Thr Lys Asn Thr Arg Phe Asp Leu Ser Gly
      515                 520                 525

Val Gln Asn Gly Thr Gln Leu Phe Glu Leu Ser Arg Asn Arg Val Thr
530                 535                 540

Gln Phe Leu Asn Asn Ala Trp Tyr Asp Gly
545                 550

<210> SEQ ID NO 69
<211> LENGTH: 2625
<212> TYPE: DNA
<213> ORGANISM: Bacteriophage

<400> SEQUENCE: 69
atgacggtct caaccgaagt tgaccacaac gaatacaccg gtaacggtgt tacaacgaca      60 ttccctata ccttcaggat ttttaagaag tctgatctgg tagtccaggt tgtagacctg      120
aacgataaca tcactgttct gacgctagat actgactaca cagtaaccgg cgcaggtggg      180
tatgtaggtg gtaatgtaat actggcaaca gctcttgcta atggttacca gatttccata      240
tcacgtgaat tgccggttac gcaggaaacg gatctccgta ccagggtaa gttctttgct      300 gaggtgcatg aggatgcgct tgataagttg acaatgttga ttcagcaggt tcgtagttgg      360
tttagcctgg cgctacgtaa gccgtcattt gctgctaact attacgacgc aatggacaac      420
tatattcgta atcttcgtgc cccatccagg ccgaaagacg cagcaacgaa agattatgtt      480
gatattcttt ctggtgccag cctaagcaga agcttgagag tacctgaatc gtttataaat      540
gagttacctg atgcggatgg agaaagaat aaaacactga ttttgataa ttctggatca      600 ccgcttcttc ttgatcctga agtagtgggg ttatggggat attcccttat tgattcgttt      660
caggatggtg cttcaataac aactagattt caggcacttc actggaaacg tcctgatgga      720
aatggcgagt actaccgttg ggatggatct ttaccaaaag atgttcctga gaattcaacc      780

| | |
|---|---|
| cctgaatcaa caggtggggt ttcccttggt gcctgggtat ctgtagggga tgcatcgttg | 840 |
| cggagcgacc tgattagtca agagacagat aaaggctcct caatagttac atataccct | 900 |
| aaatttaatg atgccgtctc gatgtcggta tatgaaaaac tttctgtaga tttggtgaca | 960 |
| ctttcagact acggatttaa agttggcaac accggtgctc agaacaaagc ggcgtttcag | 1020 |
| aaggctattg atgatgctac gttgccaact gagattgtta taccagaggg ggtgttcatt | 1080 |
| gttgaccctg gtattacgat taagaatact gtcaccatga tacgaggtgc tggcgcatat | 1140 |
| cagtccagaa ttttctctac gggtacagcg gcaccgataa tcacgcaaca agatggagta | 1200 |
| attacgttct gcgagttcag ggactttggt cttgacggaa atggctacgc agctaacggc | 1260 |
| atcagtctta ctgaagccaa ccacattaaa atagaaaata ttgacgtggt taatactaat | 1320 |
| aacaacgcaa tattagttaa cggttactcc attgacatca ttgggtgccg attgtttcaa | 1380 |
| aacaccggta acggtattaa tgttggtggc cactgcaata atattaatat aatcaacaac | 1440 |
| cgtatctatg gtaacggagc cggtggagtt ttacttacgc cagcttacgc tgagggcggt | 1500 |
| atgagcgtca gagttaatgg caacgatata gagcaaaata agttctacgg acttttggct | 1560 |
| tacggggtta aaggccttaa ccttgatgct aactattggg aacgaacgg tgagattggt | 1620 |
| tacccgtata gtgtacctga gtctattaca gtacgtgcgg atatccacct tatcgcgaac | 1680 |
| aattttacat taattcctga cctttcaaaa attaatgata ccgtatctat tcgcgggaat | 1740 |
| cagcagaccg cgattggcta cgccagcgcg ctacctaacc aagacggatt tattttcacg | 1800 |
| aactatgcga aaaacctgac gattgaaaat aatcagttat tagacgcatc gaaagtgaat | 1860 |
| aatttattag caatgtacca caataatctt tcgtccaaag ttactgacag gctatatctt | 1920 |
| gccaacaaca cagtgaactc cataggatac gttggtagtt atgacccggc gacacaaaac | 1980 |
| cctgacactg cgcatttaat agatattgcg aacagagagt taactgctaa ctatcttgat | 2040 |
| cgaaatatgt tgctctggac cgcggcatct ggaaccacag gaacattgat aaaaactcaa | 2100 |
| aacatctatg ctggtaatta ttcattctta gttacgacag gagatagagt ttggggacga | 2160 |
| acgatagacc tcaacaaatc accagaacta aaagggaaat ttgtatggtt tggtgcgtgg | 2220 |
| gtaaatgacc agggaacagc gtcaaaactt atgtttatag ttaatggtgc aggacaaaca | 2280 |
| gactctacag cacctttagc tggtaatggg aaatggcgct atgttagttg tggtgtgtat | 2340 |
| atatacgaaa ctgatacagc tataaatgtt ggtataagaa attatggttc aggaaatgta | 2400 |
| ctcataaact caccttctct atgtgtatat ggaatgccat caaatgcgtt acaagttgaa | 2460 |
| aaaacaacat tttatctttc gtcagtacct acatccggtt tctgggatat aggcgaacgc | 2520 |
| gttatcaata gcgcacctgc ttcaggacaa ccaaaggcat ggacatgcaa tattccaggt | 2580 |
| gggcccggga tttacagctt cctttctgag gggaattatt aataa | 2625 |

<210> SEQ ID NO 70
<211> LENGTH: 873
<212> TYPE: PRT
<213> ORGANISM: Bacteriophage

<400> SEQUENCE: 70

Met Thr Val Ser Thr Glu Val Asp His Asn Glu Tyr Thr Gly Asn Gly
1               5                   10                  15

Val Thr Thr Thr Phe Pro Tyr Thr Phe Arg Ile Phe Lys Lys Ser Asp
            20                  25                  30

Leu Val Val Gln Val Val Asp Leu Asn Asp Asn Ile Thr Val Leu Thr
        35                  40                  45

Leu Asp Thr Asp Tyr Thr Val Thr Gly Ala Gly Gly Tyr Val Gly Gly

-continued

```
                50                  55                  60
Asn Val Ile Leu Ala Thr Ala Leu Ala Asn Gly Tyr Gln Ile Ser Ile
 65                  70                  75                  80

Ser Arg Glu Leu Pro Val Thr Gln Glu Thr Asp Leu Arg Asn Gln Gly
                     85                  90                  95

Lys Phe Phe Ala Glu Val His Glu Asp Ala Leu Asp Lys Leu Thr Met
                    100                 105                 110

Leu Ile Gln Gln Val Arg Ser Trp Phe Ser Leu Ala Leu Arg Lys Pro
                    115                 120                 125

Ser Phe Ala Ala Asn Tyr Tyr Asp Ala Met Asp Asn Tyr Ile Arg Asn
130                 135                 140

Leu Arg Ala Pro Ser Arg Pro Lys Asp Ala Ala Thr Lys Asp Tyr Val
145                 150                 155                 160

Asp Ile Leu Ser Gly Ala Ser Leu Ser Arg Ser Leu Arg Val Pro Glu
                    165                 170                 175

Ser Phe Ile Asn Glu Leu Pro Asp Ala Asp Gly Arg Lys Asn Lys Thr
                    180                 185                 190

Leu Ser Phe Asp Asn Ser Gly Ser Pro Leu Leu Asp Pro Glu Ser
                    195                 200                 205

Ser Gly Leu Trp Gly Tyr Ser Leu Ile Asp Ser Phe Gln Asp Gly Ala
210                 215                 220

Ser Ile Thr Thr Arg Phe Gln Ala Leu His Trp Lys Arg Pro Asp Gly
225                 230                 235                 240

Asn Gly Glu Tyr Tyr Arg Trp Asp Gly Ser Leu Pro Lys Asp Val Pro
                    245                 250                 255

Glu Asn Ser Thr Pro Glu Ser Thr Gly Gly Val Ser Leu Gly Ala Trp
                    260                 265                 270

Val Ser Val Gly Asp Ala Ser Leu Arg Ser Asp Leu Ile Ser Gln Glu
                    275                 280                 285

Thr Asp Lys Gly Ser Ser Ile Val Thr Tyr Thr Pro Lys Phe Asn Asp
                    290                 295                 300

Ala Val Ser Met Ser Val Tyr Glu Lys Leu Ser Val Asp Leu Val Thr
305                 310                 315                 320

Leu Ser Asp Tyr Gly Phe Lys Val Gly Asn Thr Gly Ala Gln Asn Lys
                    325                 330                 335

Ala Ala Phe Gln Lys Ala Ile Asp Asp Ala Thr Leu Pro Thr Glu Ile
                    340                 345                 350

Val Ile Pro Glu Gly Val Phe Ile Val Asp Pro Gly Ile Thr Ile Lys
                    355                 360                 365

Asn Thr Val Thr Met Ile Arg Gly Ala Gly Ala Tyr Gln Ser Arg Ile
370                 375                 380

Phe Ser Thr Gly Thr Ala Ala Pro Ile Ile Thr Gln Gln Asp Gly Val
385                 390                 395                 400

Ile Thr Phe Cys Glu Phe Arg Asp Phe Gly Leu Asp Gly Asn Gly Tyr
                    405                 410                 415

Ala Ala Asn Gly Ile Ser Leu Thr Glu Ala Asn His Ile Lys Ile Glu
                    420                 425                 430

Asn Ile Asp Val Val Asn Thr Asn Asn Ala Ile Leu Val Asn Gly
                    435                 440                 445

Tyr Ser Ile Asp Ile Ile Gly Cys Arg Leu Phe Gln Asn Thr Gly Asn
                    450                 455                 460

Gly Ile Asn Val Gly Gly His Cys Asn Asn Ile Asn Ile Ile Asn Asn
465                 470                 475                 480
```

Arg Ile Tyr Gly Asn Gly Ala Gly Gly Val Leu Leu Thr Pro Ala Tyr
              485                 490                 495

Ala Glu Gly Gly Met Ser Val Arg Val Asn Gly Asn Asp Ile Glu Gln
        500                 505                 510

Asn Lys Phe Tyr Gly Leu Leu Ala Tyr Gly Val Lys Gly Leu Asn Leu
        515                 520                 525

Asp Ala Asn Tyr Trp Glu Arg Asn Gly Glu Ile Gly Tyr Pro Tyr Ser
        530                 535                 540

Val Pro Glu Ser Ile Thr Val Arg Ala Asp Ile His Leu Ile Ala Asn
545                 550                 555                 560

Asn Phe Thr Leu Ile Pro Asp Leu Ser Lys Ile Asn Asp Thr Val Ser
                565                 570                 575

Ile Arg Gly Asn Gln Gln Thr Ala Ile Gly Tyr Ala Ser Ala Leu Pro
                580                 585                 590

Asn Gln Asp Gly Phe Ile Phe Thr Asn Tyr Ala Lys Asn Leu Thr Ile
                595                 600                 605

Glu Asn Asn Gln Leu Leu Asp Ala Ser Lys Val Asn Asn Leu Leu Ala
610                 615                 620

Met Tyr His Asn Leu Ser Ser Lys Val Thr Asp Arg Leu Tyr Leu
625                 630                 635                 640

Ala Asn Asn Thr Val Asn Ser Ile Gly Tyr Val Gly Ser Tyr Asp Pro
                645                 650                 655

Ala Thr Gln Asn Pro Asp Thr Ala His Leu Ile Asp Ile Ala Asn Arg
                660                 665                 670

Glu Leu Thr Ala Asn Tyr Leu Asp Arg Asn Met Leu Leu Trp Thr Ala
                675                 680                 685

Ala Ser Gly Thr Thr Gly Thr Leu Ile Lys Thr Gln Asn Ile Tyr Ala
        690                 695                 700

Gly Asn Tyr Ser Phe Leu Val Thr Thr Gly Asp Arg Val Trp Gly Arg
705                 710                 715                 720

Thr Ile Asp Leu Asn Lys Ser Pro Glu Leu Lys Gly Lys Phe Val Trp
                725                 730                 735

Phe Gly Ala Trp Val Asn Asp Gln Gly Thr Ala Ser Lys Leu Met Phe
                740                 745                 750

Ile Val Asn Gly Ala Gly Gln Thr Asp Ser Thr Ala Pro Leu Ala Gly
                755                 760                 765

Asn Gly Lys Trp Arg Tyr Val Ser Cys Gly Val Tyr Ile Tyr Glu Thr
        770                 775                 780

Asp Thr Ala Ile Asn Val Gly Ile Arg Asn Tyr Gly Ser Gly Asn Val
785                 790                 795                 800

Leu Ile Asn Ser Pro Ser Leu Cys Val Tyr Gly Met Pro Ser Asn Ala
                805                 810                 815

Leu Gln Val Glu Lys Thr Thr Phe Tyr Leu Ser Ser Val Pro Thr Ser
                820                 825                 830

Gly Phe Trp Asp Ile Gly Glu Arg Val Ile Asn Ser Ala Pro Ala Ser
                835                 840                 845

Gly Gln Pro Lys Ala Trp Thr Cys Asn Ile Pro Gly Gly Pro Gly Ile
        850                 855                 860

Tyr Ser Phe Leu Ser Glu Gly Asn Tyr
865                 870

<210> SEQ ID NO 71
<211> LENGTH: 2160
<212> TYPE: DNA
<213> ORGANISM: Bacteriophage

```
<400> SEQUENCE: 71
atgtcagata tcaccgcaaa tgttgtggtc agcatgcctt cgcaactctt cactatgtct    60
cgctctttta aagccgtagc caatggaaaa atttatatcg gtaaaattga cactgacccg   120
gtaaatccag aaaaccagat tcaggtttat gtggaaaacg aagacggttc tcacgttcct   180
gtttcgcaac caatcatcat taacgctgct ggttaccctg tatataacgg acagattgcc   240
aagttcgtaa ctgtgcaagg ccattctatg gctgtttatg atgcatacgg tgcgcagcag   300
ttctattttc cgaatgtgct aaagtatgat ccagatcagt ttaagggcaa tctcctgagc   360
gaagatcact cacttggcga ctctctagtc atgcataacc cacagtttgt cgatagcaca   420
tcgaccattc tctcaaaaaa gctaactatc gacctgagga cgcttacaga ctacgggttt   480
gctgagggaa acaccggtgc tcagaacaaa gctgcatttc agaaggctat tgatgatgct   540
acgttgccaa ctgagattgt tataccagag ggggcgttca ttgttgaccc tggtattacg   600
attaagaata ctgtcaccat gatacgaggt gctggcgcat atcagtccag aattttctct   660
acgggtacag cggcaccgat aatcacgcaa caagatgggg taattacgtt ctgcgagttc   720
agggactttg tcttgacgg aaatggctac gcagctaacg gcatcagtct tactgaagcc   780
aaccacatta aaatagaaaa tattgacgtg gttaatacta ataacaacgc aatattagtt   840
aacggttact ccattgacat cattgggtgc cggttgtttc aaaacgccgg taacggtatt   900
aatgttggtg gttactgcaa taatattaat ataatcaaca gccgtatcta tggtaacgga   960
gccggtggag ttttacttac gccagcttac gctgagggcg tatgagcgt cagagttaat  1020 ggcaacaata tagagcaaaa taagttctac ggacttttgg cttacggggt taaaggcctt  1080
aaccttgatg ctaactattg ggaacgcaac ggtgagattg gttacccgta tagtgtacct  1140
gagtctatta cagtacgtgc ggatatccac cttatcgcga caatttttac attaattcct  1200
gaccttttca aaattaatga taccgtatct attcgcggga atcagcagac cgcgattggc  1260
tacgccagcg cgctacctaa ccaagacgga tttatttca cgaactatgc gaaaaacctg  1320
acgattgaaa ataatcagtt attagacgca tcgaaagtga ataatttatt agcaatgtac  1380
cacaataatc tttcgtccaa agttactgac aggctatatc ttgccaacaa cacagtgaac  1440
tccatcggat acgttggtag ttatgacccg gcgacacaaa accctgacac tgcgcattta  1500
atagatattg cgaacagaga gttaactgct aactatcttg atcgaaatat gttgctctgg  1560
actgcggcat ctggaactac aggaacattg ataaaaactc aaaacatcta tgctggtaat  1620
tattcattct tagttacgac aggagataga gtttggggac gaacgataga cctcaacaaa  1680
tcaccagaac taaagggaa atttgtatgg tttggtgcgt gggtcaatga ccagggatca  1740
gcgtcaaaac ttatgtttat aattaatggt gcaggacaaa cagactctac agcacctta  1800 gctggtaatg ggaaatggag ctatgttagt tgtggtgtgt atatatacga aactgataca  1860
gctataaatg ttggtataag aaattatggt tcaggaaatg tactcataaa ctcacctttct  1920 ctatgtgcat atggaatgcc atcaaacgcg ttgcaagttg aaaaaacaac atttatctt  1980 tcgtcagtac ctacatccgg tttctgggat ataggtgagc gtgttatcaa tagcgcacct  2040
gcttcaggac aaccaaaggc atggacatgc aatattccag gtgggccagg aacctattct  2100
ttcttatcag agggaaactt ttaccagccc gggccgtcga ccacgcgtgc cctatagtga  2160
```

<210> SEQ ID NO 72
<211> LENGTH: 718
<212> TYPE: PRT
<213> ORGANISM: Bacteriophage

<400> SEQUENCE: 72

```
Met Ser Asp Ile Thr Ala Asn Val Val Ser Met Pro Ser Gln Leu
1               5                   10                  15

Phe Thr Met Ser Arg Ser Phe Lys Ala Val Ala Asn Gly Lys Ile Tyr
            20                  25                  30

Ile Gly Lys Ile Asp Thr Asp Pro Val Asn Pro Glu Asn Gln Ile Gln
            35                  40                  45

Val Tyr Val Glu Asn Glu Asp Gly Ser His Val Pro Val Ser Gln Pro
    50                  55                  60

Ile Ile Ile Asn Ala Ala Gly Tyr Pro Val Tyr Asn Gly Gln Ile Ala
65                  70                  75                  80

Lys Phe Val Thr Val Gln Gly His Ser Met Ala Val Tyr Asp Ala Tyr
                85                  90                  95

Gly Ala Gln Gln Phe Tyr Phe Pro Asn Val Leu Lys Tyr Asp Pro Asp
            100                 105                 110

Gln Phe Lys Gly Asn Leu Leu Ser Glu Asp His Ser Leu Gly Asp Ser
        115                 120                 125

Leu Val Met His Asn Pro Gln Phe Val Asp Ser Thr Ser Thr Ile Leu
    130                 135                 140

Ser Lys Lys Leu Thr Ile Asp Leu Arg Thr Leu Thr Asp Tyr Gly Phe
145                 150                 155                 160

Ala Glu Gly Asn Thr Gly Ala Gln Asn Lys Ala Ala Phe Gln Lys Ala
                165                 170                 175

Ile Asp Asp Ala Thr Leu Pro Thr Glu Ile Val Ile Pro Glu Gly Ala
            180                 185                 190

Phe Ile Val Asp Pro Gly Ile Thr Ile Lys Asn Thr Val Thr Met Ile
        195                 200                 205

Arg Gly Ala Gly Ala Tyr Gln Ser Arg Ile Phe Ser Thr Gly Thr Ala
    210                 215                 220

Ala Pro Ile Ile Thr Gln Gln Asp Gly Val Ile Thr Phe Cys Glu Phe
225                 230                 235                 240

Arg Asp Phe Gly Leu Asp Gly Asn Gly Tyr Ala Ala Asn Gly Ile Ser
                245                 250                 255

Leu Thr Glu Ala Asn His Ile Lys Ile Glu Asn Ile Asp Val Val Asn
            260                 265                 270

Thr Asn Asn Asn Ala Ile Leu Val Asn Gly Tyr Ser Ile Asp Ile Ile
        275                 280                 285

Gly Cys Arg Leu Phe Gln Asn Ala Gly Asn Gly Ile Asn Val Gly Gly
    290                 295                 300

Tyr Cys Asn Asn Ile Asn Ile Ile Asn Ser Arg Ile Tyr Gly Asn Gly
305                 310                 315                 320

Ala Gly Gly Val Leu Leu Thr Pro Ala Tyr Ala Glu Gly Gly Met Ser
                325                 330                 335

Val Arg Val Asn Gly Asn Asn Ile Glu Gln Asn Lys Phe Tyr Gly Leu
            340                 345                 350

Leu Ala Tyr Gly Val Lys Gly Leu Asn Leu Asp Ala Asn Tyr Trp Glu
        355                 360                 365

Arg Asn Gly Glu Ile Gly Tyr Pro Tyr Ser Val Pro Glu Ser Ile Thr
    370                 375                 380

Val Arg Ala Asp Ile His Leu Ile Ala Asn Asn Phe Thr Leu Ile Pro
385                 390                 395                 400

Asp Leu Ser Lys Ile Asn Asp Thr Val Ser Ile Arg Gly Asn Gln Gln
                405                 410                 415
```

Thr Ala Ile Gly Tyr Ala Ser Ala Leu Pro Asn Gln Asp Gly Phe Ile
            420                 425                 430

Phe Thr Asn Tyr Ala Lys Asn Leu Thr Ile Glu Asn Gln Leu Leu
        435                 440                 445

Asp Ala Ser Lys Val Asn Leu Leu Ala Met Tyr His Asn Asn Leu
        450                 455                 460

Ser Ser Lys Val Thr Asp Arg Leu Tyr Leu Ala Asn Asn Thr Val Asn
465                 470                 475                 480

Ser Ile Gly Tyr Val Gly Ser Tyr Asp Pro Ala Thr Gln Asn Pro Asp
                485                 490                 495

Thr Ala His Leu Ile Asp Ile Ala Asn Arg Glu Leu Thr Ala Asn Tyr
                500                 505                 510

Leu Asp Arg Asn Met Leu Leu Trp Thr Ala Ala Ser Gly Thr Thr Gly
            515                 520                 525

Thr Leu Ile Lys Thr Gln Asn Ile Tyr Ala Gly Asn Tyr Ser Phe Leu
        530                 535                 540

Val Thr Thr Gly Asp Arg Val Trp Gly Arg Thr Ile Asp Leu Asn Lys
545                 550                 555                 560

Ser Pro Glu Leu Lys Gly Lys Phe Val Trp Phe Gly Ala Trp Val Asn
                565                 570                 575

Asp Gln Gly Ser Ala Ser Lys Leu Met Phe Ile Ile Asn Gly Ala Gly
                580                 585                 590

Gln Thr Asp Ser Thr Ala Pro Leu Ala Gly Asn Gly Lys Trp Ser Tyr
            595                 600                 605

Val Ser Cys Gly Val Tyr Ile Tyr Glu Thr Asp Thr Ala Ile Asn Val
        610                 615                 620

Gly Ile Arg Asn Tyr Gly Ser Gly Asn Val Leu Ile Asn Ser Pro Ser
625                 630                 635                 640

Leu Cys Ala Tyr Gly Met Pro Ser Asn Ala Leu Gln Val Glu Lys Thr
                645                 650                 655

Thr Phe Tyr Leu Ser Ser Val Pro Thr Ser Gly Phe Trp Asp Ile Gly
                660                 665                 670

Glu Arg Val Ile Asn Ser Ala Pro Ala Ser Gly Gln Pro Lys Ala Trp
            675                 680                 685

Thr Cys Asn Ile Pro Gly Gly Pro Gly Thr Tyr Ser Phe Leu Ser Glu
        690                 695                 700

Gly Asn Phe Tyr Gln Pro Gly Pro Ser Thr Thr Arg Ala Leu
705                 710                 715

<210> SEQ ID NO 73
<211> LENGTH: 2124
<212> TYPE: DNA
<213> ORGANISM: Bacteriophage

<400> SEQUENCE: 73
atgtcagata tcaccgcaaa tgttgtggtc agcatgcctt cgcaactctt cactatgtct     60
cgctctttta aagccgtagc caatggaaaa atttatatcg gtaaaattga cactgacccg    120
gtaaatccag aaaaccagat tcaggtttat gtggaaaacg aagtcggttc tcacgttcct    180
gtttcgcaac caatcatcat taacgctgct ggttaccctg tatataacgg acagattgcc    240
aagttcgtaa ctgtgcaagg ccattctatg gctgtttatg atgcatacgg tgcgcagcag    300
ttctattttc cgaatgtgct aaagtatgat ccagatcagt taagggcaa tctcctgagc    360 gaagatcact cacttggcga ctctctagtc atgcataacc cacagtttgt cgatagcaca    420

```
tcgaccattc tctcaaaaaa gctaactatc gacctgagga cgcttacaga ctacgggttt    480
gctgagggaa acaccggtgc tcagaacaaa gctgcatttc agaaggctat tgatgatgct    540
acgttgccaa ctgagattgt tataccagag ggggcgttca ttgttgaccc tggtattacg    600
attaagaata ctgtcaccat gatacagagg gctggcgcat atcagtccag aattttctct    660
acgggtacag cggcaccgat aatcacgcaa caagatgggg taattacgtt ctgcgagttc    720
agggactttg gtcttgacgg aaatggctac gcagctaacg gcatcagtct tactgaagcc    780
aaccacatta aaatagaaaa tattgacgtg gttaatacta ataacaacgc aatattagtt    840
aacggttact ccattgacat cattgggtgc cggttgtttc aaaacgccgg taacggtatt    900
aatgttggtg gttactgcaa taatattaat ataatcaaca gccgtatcta tggtaacgga    960
gccggtggag ttttacttac gccagcttac gctgagggcg tatgagcgt cagagttaat    1020 ggcaacaata tagagcaaaa taagttctac ggacttttgg cttacggggt taaaggcctt    1080
aaccttgatg ctaactattg ggaacgcaac ggtgagattg ttacccgta tagtgtacct    1140 gagtctatta cagtacgtgc ggatatccac cttatcgcga caatttttac attaattcct    1200 gaccttttcaa aaattaatga taccgtatct attcgcggga atcagcagac cgcgattggc    1260
tacgccagcg cgctacctaa ccaagacgga tttatttttca cgaactatgc gaaaaacctg    1320
acgattgaaa ataatcagtt attagacgca tcgaaagtga ataatttatt agcaatgtac    1380
cacaataatc tttcgtccaa agttactgac aggctatatc ttgccaacaa cacagtgaac    1440
tccatcggat acgttggtag ttatgacccg gcgacacaaa accctgacac tgcgcattta    1500
atagatattg cgaacagaga gttaactgct aactatcttg atcgaaatat gttgctctgg    1560
actgcggcat ctggaactac aggaacattg ataaaaactc aaaacatcta tgctggtaat    1620
tattcattct tagttacgac aggagataga gtttggggac gaacgataga cctcaacaaa    1680
tcaccagaac taaagggaa atttgtatgg tttggtgcgt gggtcaatga ccagggatca    1740
gcgtcaaaac ttatgtttat aattaatggt gcaggacaaa cagactctac agcacccttta    1800 gctggtaatg ggaaatggag ctatgttagt tgtggtgtgt atatatacga aactgataca    1860
gctataaatg ttggtataag aaattatggt tcaggaaatg tactcataaa ctcacccttct    1920 ctatgtgcat atggaatgcc atcaaacgcg ttgcaagttg aaaaaacaac atttatctt    1980 tcgtcagtac ctacatccgg tttctgggat ataggtgagc gtgttatcaa tagcgcacct    2040
gcttcaggac aaccaaaggc atggacatgc aatattccag gtgggccagg aacctattct    2100
ttcttatcag agggaaactt ttaa                                             2124
```

<210> SEQ ID NO 74
<211> LENGTH: 707
<212> TYPE: PRT
<213> ORGANISM: bacteriophage

<400> SEQUENCE: 74

Met Ser Asp Ile Thr Ala Asn Val Val Ser Met Pro Ser Gln Leu
1               5                   10                  15

Phe Thr Met Ser Arg Ser Phe Lys Ala Val Ala Asn Gly Lys Ile Tyr
                20                  25                  30

Ile Gly Lys Ile Asp Thr Asp Pro Val Asn Pro Glu Asn Gln Ile Gln
            35                  40                  45

Val Tyr Val Glu Asn Glu Val Gly Ser His Val Pro Val Ser Gln Pro
        50                  55                  60

Ile Ile Ile Asn Ala Ala Gly Tyr Pro Val Tyr Asn Gly Gln Ile Ala
65                  70                  75                  80

-continued

```
Lys Phe Val Thr Val Gln Gly His Ser Met Ala Val Tyr Asp Ala Tyr
                85                  90                  95

Gly Ala Gln Gln Phe Tyr Phe Pro Asn Val Leu Lys Tyr Asp Pro Asp
            100                 105                 110

Gln Phe Lys Gly Asn Leu Leu Ser Glu Asp His Ser Leu Gly Asp Ser
        115                 120                 125

Leu Val Met His Asn Pro Gln Phe Val Asp Ser Thr Ser Thr Ile Leu
    130                 135                 140

Ser Lys Lys Leu Thr Ile Asp Leu Arg Thr Leu Thr Asp Tyr Gly Phe
145                 150                 155                 160

Ala Glu Gly Asn Thr Gly Ala Gln Asn Lys Ala Ala Phe Gln Lys Ala
                165                 170                 175

Ile Asp Asp Ala Thr Leu Pro Thr Glu Ile Val Ile Pro Glu Gly Ala
            180                 185                 190

Phe Ile Val Asp Pro Gly Ile Thr Ile Lys Asn Thr Val Thr Met Ile
        195                 200                 205

Arg Gly Ala Gly Ala Tyr Gln Ser Arg Ile Phe Ser Thr Gly Thr Ala
    210                 215                 220

Ala Pro Ile Ile Thr Gln Gln Asp Gly Val Ile Thr Phe Cys Glu Phe
225                 230                 235                 240

Arg Asp Phe Gly Leu Asp Gly Asn Gly Tyr Ala Ala Asn Gly Ile Ser
                245                 250                 255

Leu Thr Glu Ala Asn His Ile Lys Ile Glu Asn Ile Asp Val Val Asn
            260                 265                 270

Thr Asn Asn Asn Ala Ile Leu Val Asn Gly Tyr Ser Ile Asp Ile Ile
        275                 280                 285

Gly Cys Arg Leu Phe Gln Asn Ala Gly Asn Gly Ile Asn Val Gly Gly
    290                 295                 300

Tyr Cys Asn Asn Ile Asn Ile Ile Asn Ser Arg Ile Tyr Gly Asn Gly
305                 310                 315                 320

Ala Gly Gly Val Leu Leu Thr Pro Ala Tyr Ala Glu Gly Gly Met Ser
                325                 330                 335

Val Arg Val Asn Gly Asn Asn Ile Glu Gln Asn Lys Phe Tyr Gly Leu
            340                 345                 350

Leu Ala Tyr Gly Val Lys Gly Leu Asn Leu Asp Ala Asn Tyr Trp Glu
        355                 360                 365

Arg Asn Gly Glu Ile Gly Tyr Pro Tyr Ser Val Pro Glu Ser Ile Thr
    370                 375                 380

Val Arg Ala Asp Ile His Leu Ile Ala Asn Asn Phe Thr Leu Ile Pro
385                 390                 395                 400

Asp Leu Ser Lys Ile Asn Asp Thr Val Ser Ile Arg Gly Asn Gln Gln
                405                 410                 415

Thr Ala Ile Gly Tyr Ala Ser Ala Leu Pro Asn Gln Asp Gly Phe Ile
            420                 425                 430

Phe Thr Asn Tyr Ala Lys Asn Leu Thr Ile Glu Asn Asn Gln Leu Leu
        435                 440                 445

Asp Ala Ser Lys Val Asn Asn Leu Leu Ala Met Tyr His Asn Asn Leu
    450                 455                 460

Ser Ser Lys Val Thr Asp Arg Leu Tyr Leu Ala Asn Asn Thr Val Asn
465                 470                 475                 480

Ser Ile Gly Tyr Val Gly Ser Tyr Asp Pro Ala Thr Gln Asn Pro Asp
                485                 490                 495

Thr Ala His Leu Ile Asp Ile Ala Asn Arg Glu Leu Thr Ala Asn Tyr
```

-continued

```
                500               505                510
Leu Asp Arg Asn Met Leu Leu Trp Thr Ala Ala Ser Gly Thr Thr Gly
        515                 520                 525

Thr Leu Ile Lys Thr Gln Asn Ile Tyr Ala Gly Asn Tyr Ser Phe Leu
        530                 535                 540

Val Thr Thr Gly Asp Arg Val Trp Gly Arg Thr Ile Asp Leu Asn Lys
545                 550                 555                 560

Ser Pro Glu Leu Lys Gly Lys Phe Val Trp Phe Gly Ala Trp Val Asn
                565                 570                 575

Asp Gln Gly Ser Ala Ser Lys Leu Met Phe Ile Ile Asn Gly Ala Gly
                580                 585                 590

Gln Thr Asp Ser Thr Ala Pro Leu Ala Gly Asn Gly Lys Trp Ser Tyr
        595                 600                 605

Val Ser Cys Gly Val Tyr Ile Tyr Glu Thr Asp Thr Ala Ile Asn Val
        610                 615                 620

Gly Ile Arg Asn Tyr Gly Ser Gly Asn Val Leu Ile Asn Ser Pro Ser
625                 630                 635                 640

Leu Cys Ala Tyr Gly Met Pro Ser Asn Ala Leu Gln Val Glu Lys Thr
                645                 650                 655

Thr Phe Tyr Leu Ser Ser Val Pro Thr Ser Gly Phe Trp Asp Ile Gly
                660                 665                 670

Glu Arg Val Ile Asn Ser Ala Pro Ala Ser Gly Gln Pro Lys Ala Trp
        675                 680                 685

Thr Cys Asn Ile Pro Gly Gly Pro Gly Thr Tyr Ser Phe Leu Ser Glu
        690                 695                 700

Gly Asn Phe
705
```